(12) United States Patent
Burkart et al.

(10) Patent No.: US 11,203,588 B2
(45) Date of Patent: Dec. 21, 2021

(54) ANTI-CANCER AND SPLICE MODULATING COMPOUNDS AND METHODS

(71) Applicant: The Regents of the University of California, Oakland, CA (US)

(72) Inventors: Michael D. Burkart, San Diego, CA (US); James J. La Clair, San Diego, CA (US); Sachin Dhar, Pleasanton, CA (US); Justin C. Hammons, San Diego, CA (US); Brian Leon, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 503 days.

(21) Appl. No.: 16/083,419

(22) PCT Filed: Mar. 10, 2017

(86) PCT No.: PCT/US2017/021897
§ 371 (c)(1),
(2) Date: Sep. 7, 2018

(87) PCT Pub. No.: WO2017/156454
PCT Pub. Date: Sep. 14, 2017

(65) Prior Publication Data
US 2020/0299279 A1   Sep. 24, 2020

Related U.S. Application Data

(60) Provisional application No. 62/306,562, filed on Mar. 10, 2016.

(51) Int. Cl.
*C07D 405/06* (2006.01)
*C07D 309/10* (2006.01)
*C07F 7/18* (2006.01)
*C12Q 1/6876* (2018.01)
*G01N 33/50* (2006.01)

(52) U.S. Cl.
CPC ......... *C07D 405/06* (2013.01); *C07D 309/10* (2013.01); *C07F 7/1804* (2013.01); *C12Q 1/6876* (2013.01); *G01N 33/502* (2013.01)

(58) Field of Classification Search
CPC ........................ C07D 405/06; C07D 309/10
See application file for complete search history.

(56) References Cited

U.S. PATENT DOCUMENTS

| | | | |
|---|---|---|---|
| 9,604,973 B2* | 3/2017 | Burkart | C07D 313/00 |
| 2011/0086909 A1 | 4/2011 | Koide et al. | |
| 2014/0134193 A1 | 5/2014 | Subramanyam et al. | |
| 2015/0133535 A1 | 5/2015 | Burkart et al. | |

OTHER PUBLICATIONS

Kakeya; The Journal of Antibiotics 2016, 69, 121-123. Published online Sep. 9, 2015. (Year: 2015).*
Dhar; Journal of the American Chemical Society 2016, 138, 5063-5068. (Year: 2016).*
Gundluru; Med. Chem. Commun., 2011, 2, 904-908. (Year: 2011).*
Lagisetti; ACS Chem. Biol. 2014, 9, 3, 643-648. (Year: 2014).*
Villa; J. Med. Chem. 2013, 56, 17, 6576-6582. (Year: 2013).*
International Search Report of International application No. PCT/US17/21897 dated Aug. 14, 2017, 5 pages.
Written Opinion of International application No. PCT/US17/21897 dated Aug. 14, 2017, 10 pages.

* cited by examiner

*Primary Examiner* — Daniel R Carcanague
(74) *Attorney, Agent, or Firm* — Mintz Levin Cohn Ferris Glovsky and Popeo, P.C.; Kenneth E. Jenkins; Joohee Lee

(57) ABSTRACT

There are provided inter alia stable anti-cancer compounds and splice modulators and methods of synthesis and use thereof.

18 Claims, 8 Drawing Sheets
Specification includes a Sequence Listing.

ANTI-CANCER AND SPLICE MODULATING COMPOUNDS AND METHODS

CROSS-REFERENCES TO RELATED APPLICATIONS

This application is the U.S. national phase of International Application No. PCT/US17/21897, filed Mar. 10, 2017, which claims the benefit of U.S. Provisional Application No. 62/306,562, filed Mar. 10, 2016, the contents of which are incorporated herein in their entirety and for all purposes.

STATEMENT AS TO RIGHTS TO INVENTIONS MADE UNDER FEDERALLY SPONSORED RESEARCH AND DEVELOPMENT

This invention was made with Government support under grant numbers NIH P01-CA081534 and NIH IRACDA K12 GM068524, awarded by National Institutes of Health. The Government has certain rights in this invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 048537-572N01US_ST25.TXT, created on Sep. 7, 2018, 6,327 bytes, machine format IBM-PC, MS-Windows operating system, is hereby incorporated by reference.

BACKGROUND

Splicing modulators are recognized as a new lead for the treatment of a number of diseases including cancer. There is provided herein preparation of a stable splice modulator with improved pharmacological properties. These new analogs provide benefits over known natural products (e.g., FD-895) based splice modulators including spliceostatins, pladienolides, and herboxadiene as well as the current synthetic derivatives sudemycins and pladienolide analogs (i.e., E7107 or 6-deoxypladienolide B).

Solutions to the problems inter alia of enhanced biological activity and stability are provided herein.

SUMMARY

Herein are provided, inter alia, compounds capable of modulating or inhibiting splicing and methods of using the same.

In an aspect is provided a compound with structure of Formula (I):

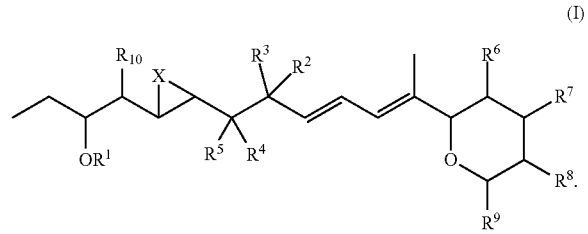

(I)

X is —O— or —C($R^{26}$)($R^{27}$)—. $R^{26}$ is hydrogen, halogen, substituted or unsubstituted alkyl, substituted or unsubstituted aryl, —$OR^{28}$, —OC(O)$R^{28}$, —OC(O)O$R^{28}$, or —OC(O)N$R^{28}R^{29}$. $R^{27}$ is hydrogen, halogen, substituted or unsubstituted alkyl, substituted or unsubstituted aryl, —$OR^{30}$, —OC(O)$R^{30}$, —OC(O)O$R^{30}$, or —OC(O)N$R^{30}R^{31}$. $R^1$ is hydrogen, substituted or unsubstituted alkyl, —C(O)$R^{11}$, or —C(O)O$R^{11}$. $R^2$ is hydrogen, halogen, substituted or unsubstituted alkyl, —$OR^{12}$, —OC(O)$R^{12}$, —OC(O)O$R^{12}$, or —OC(O)N$R^{12}R^{13}$. $R^3$ is hydrogen, halogen, substituted or unsubstituted alkyl, —$OR^{14}$, —OC(O)$R^{14}$, —OC(O)O$R^{14}$, or —OC(O)N$R^{14}R^{15}$. $R^4$ is hydrogen, halogen, substituted or unsubstituted alkyl, —$OR^{16}$, —OC(O)$R^{16}$, —OC(O)O$R^{16}$, or —OC(O)N$R^{16}R^{17}$. $R^5$ is hydrogen, halogen, substituted or unsubstituted alkyl, —$OR^{18}$, —OC(O)$R^{18}$, —OC(O)O$R^{18}$, or —OC(O)N$R^{18}R^{19}$. $R^6$ is hydrogen, —$OR^{20}$, —C(O)$R^{20}$, —C(O)O$R^{20}$, —OC(O)$R^2$, or —OC(O)O$R^{20}$. $R^7$ is hydrogen, —$OR^{21}$, —C(O)$R^{21}$, —C(O)O$R^{21}$, —OC(O)$R^{21}$, Or —OC(O)O$R^{21}$. $R^8$ is hydrogen, —$OR^{22}$, —C(O)$R^{22}$, —C(O)O$R^{22}$, —OC(O)$R^{22}$, or —OC(O)O$R^{22}$. $R^9$ is hydrogen, —$OR^{23}$, —C(O)$R^{23}$, —C(O)O$R^{23}$, —OC(O)$R^{23}$, or —OC(O)O$R^{23}$. $R^{10}$ is hydrogen, substituted or unsubstituted alkyl, —$OR^{24}$, —OC(O)$R^{24}$, —OC(O)O$R^{24}$, or —OC(O)N$R^{24}R^{25}$. $R^{11}$ 12, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{28}$, $R^{29}$, $R^{30}$, and $R^{31}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, X is —O—; $R^1$ is hydrogen or unsubstituted $C_1$-$C_4$ alkyl; and $R^{10}$ is hydrogen or unsubstituted $C_1$-$C_4$ alkyl. In embodiments, $R^1$ is hydrogen or —$CH_3$; and $R^{10}$ is hydrogen or —$CH_3$. In embodiments, the compound having a structure of Formula (IIA):

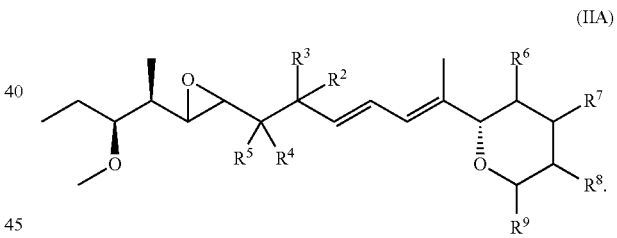

(IIA)

In embodiments, the compound having a structure of Formula (IIB):

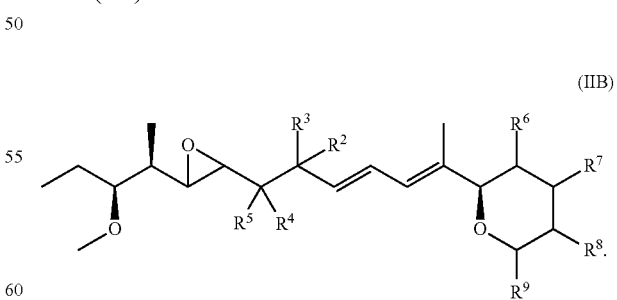

(IIB)

In embodiments, X is —C($R^{26}$)($R^{27}$)—; $R^1$ is hydrogen or unsubstituted $C_1$-$C_4$ alkyl; and $R^{10}$ is hydrogen or unsubstituted $C_1$-$C_4$ alkyl. In embodiments, $R^1$ is hydrogen or —$CH_3$; and $R^{10}$ is hydrogen or —$CH_3$. In embodiments, the compound having a structure of Formula (IIIA):

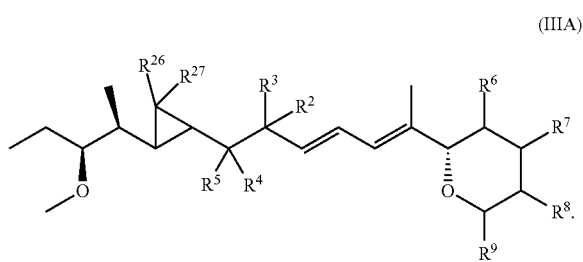

(IIIA)

In embodiments, the compound having a structure of Formula (IIIB):

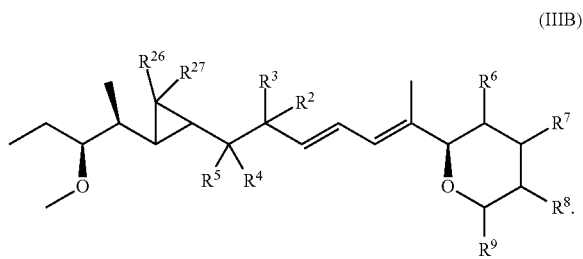

(IIIB)

In embodiments, one of $R^4$ and $R^5$ is hydrogen and the other one of $R^4$ and $R^5$ is —OH. In embodiments, a chiral carbon where $R^4$ and $R^5$ are attached has (S) stereochemistry. In embodiments, a chiral carbon where $R^4$ and $R^5$ are attached has (R) stereochemistry. In embodiments, one of $R^2$ and $R^3$ is hydrogen and the other one of $R^2$ and $R^3$ is —$CH_3$. In embodiments, a chiral carbon where $R^2$ and $R^3$ are attached has (S) stereochemistry. In embodiments, a chiral carbon where $R^2$ and $R^3$ are attached has (R) stereochemistry. In embodiments, $R^6$ is hydrogen, —$OR^{20}$ or —C(O)$OR^{20}$; $R^7$ is hydrogen, —$OR^{21}$ or —C(O)$OR^{21}$; $R^8$ is hydrogen, —$OR^{22}$ or —C(O)$OR^{22}$; $R^9$ is hydrogen, —$OR^{23}$ or —C(O)$OR^{23}$; and $R^{20}$, $R^{21}$, $R^{22}$, and $R^{23}$ are each independently hydrogen or unsubstituted $C_1$-$C_4$ alkyl. In embodiments, $R^{20}$, $R^{21}$, $R^{22}$, and $R^{23}$ are each independently hydrogen or —$CH_3$. In embodiments, at least one of $R^6$, $R^7$, $R^8$, and $R^9$ is —$OCH_3$. In embodiments, at least two of $R^6$, $R^7$, $R^8$, and $R^9$ are —$OCH_3$. In embodiments, $R^6$, $R^7$, $R^8$ and $R^9$ are —$OCH_3$. In embodiments, $R^6$ is —$OCH_3$; $R^7$ is hydrogen; $R^8$ is hydrogen; and $R^9$ is-$OCH_3$.

In another aspect provided is a pharmaceutical composition comprising a compound described herein, or pharmaceutically acceptable salt thereof, and a pharmaceutically acceptable excipient.

In another aspect provided is a method of treating cancer. The method includes administering to a subject in need thereof a therapeutically effective amount of a compound of described herein. In embodiments, the cancer is leukemia, lymphoma, metastatic cancer, or bone cancer. In embodiments, the cancer is chronic lymphocytic leukemia (CLL).

In another aspect provided is a method of detecting splicesome inhibition with a test compound as described herein. The method includes (i) contacting a cell with a test compound; (ii) extracting an mRNA from said cell thereby producing an extracted mRNA; (iii) reverse transcribing said extracted mRNA using intron-specific primers thereby forming an intron cDNA; (iv) amplifying said intron cDNA thereby forming a plurality of amplified intron cDNAs; and (v) detecting the presence of said amplified intron cDNAs thereby detecting spliceosome inhibition with said test compound. In embodiments, the cell is derived from a patient. In embodiments, the cell is a cancer cell. In embodiments, the extracting in the method includes lysing the cell.

BRIEF DESCRIPTION OF THE DRAWINGS

FIG. 2A) A derived solution structure of the FD-895 core motif as determined by evaluation of $^1$H coupling constants and NOE interactions. NOE interactions were observed both on the top face and bottom face. Data shown was collected from $^1$H, $^1$H NOESY spectral data of 1a in $CDCl_3$ and $C_6D_6$ at 23° C. FIG. 2B) Model depicting the structure of 1a superimposed on the surface of 1c. FIG. 2C) Model depicting the structure of 1c superimposed on the surface of 1a. FIG. 2D) Models depicting the structure of 1a superimposed on the surface of 2. FIG. 2E) Model depicting the structure of 2 superimposed on the surface of 1a. The structure of the core motif in 1a was determined via NMR spectroscopy. Structures of 1b and 1c were modeled by energy minimization [17].

FIG. 3A) An expanded LC-MS trace via UV monitoring at 288 nm depicting the reaction product from treatment of 19 with VO(acac)$_2$/tBuOOH. FIG. 3B) Comparable LC-MS trace depicting the formation of two isomers by m-CBPA epoxidation. FIG. 3C) An expansion of the $^1$H NMR spectra of epoxide 2 from VO(acac)$_2$/tBuOOH in $CDCl_3$. FIG. 3D) An expansion of the $^1$H NMR spectra of epoxide 20 in $CDCl_3$ from m-CBPA. Traces of 2 denoted by an asterisk could not be completely removed from 20, due to close retention times.

DETAILED DESCRIPTION

I. Definitions

Figure 1:
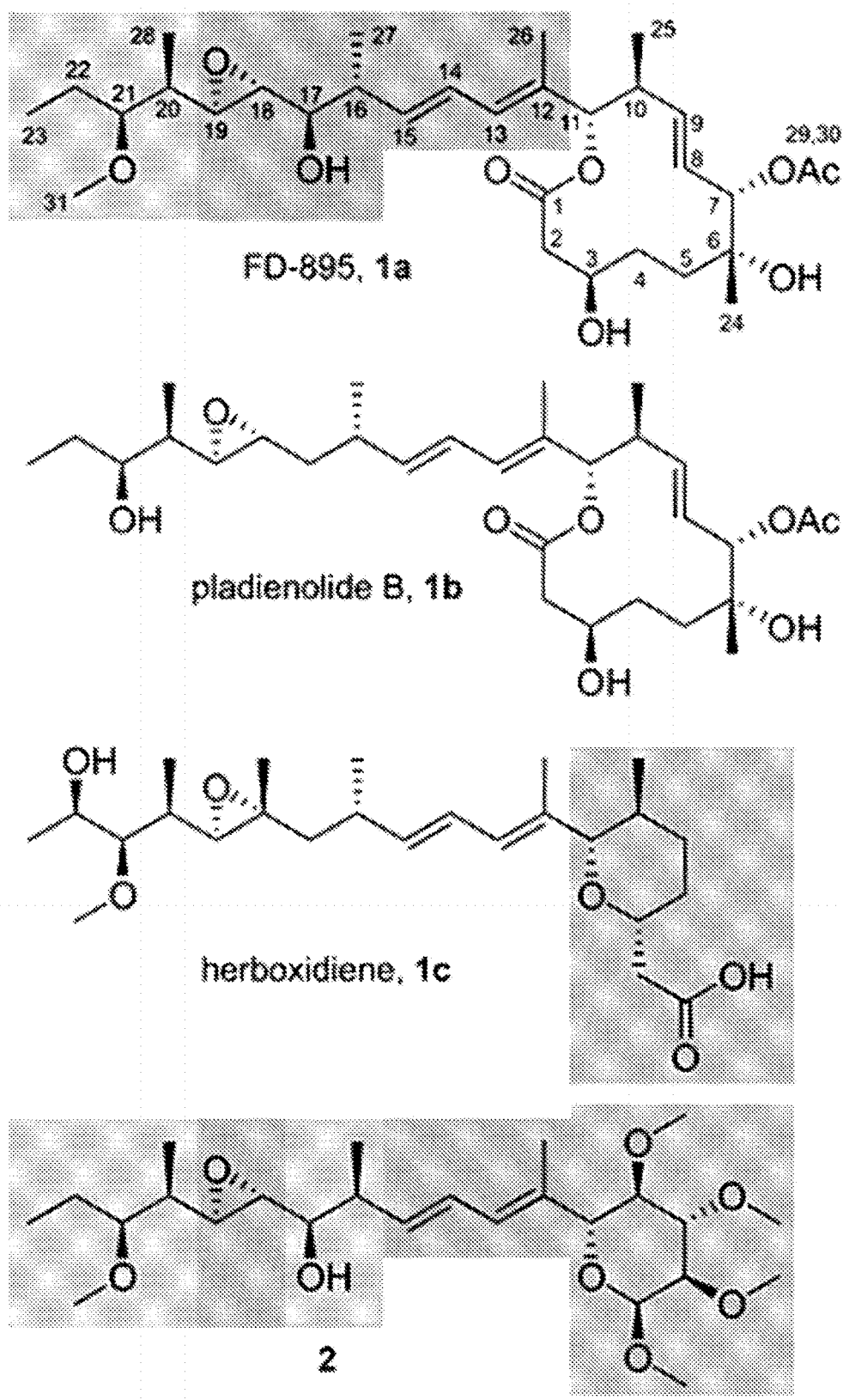
FIG. 1 depicts structures of FD-895 (1a), pladienolide B (1b), and herboxidiene (1c) and carbohydrate-derived splicing modulator 2. Compound 2 contains the terminus of 1a, the epoxide and diene of 1a, and a core derived from 1c.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Alkyl is not cyclized. Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds (e.g. alkene, alkyne). Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, or S), and wherein the nitrogen and sulfur atoms may optionally be oxidized, and the nitrogen heteroatom may optionally be quaternized. The heteroatom(s) (e.g., O, N, P, S, B, As, or Si) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded ("=O") to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"')=NR"', —S(O)R', —S(O)$_2$R', —S(O)$_2$N(R)('R"—NRS$O_2$R'), —CN, and —$NO_2$ in a number ranging from zero to (2m'+1), where m' is the total number of carbon atoms in such radical. R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', NR"C(O)$_2$R', NRC(NR'R")=NR"', S(O)R', —S(O)$_2$R', —S(O)$_2$N(R')(R", —NRSO$_2$R'), —CN, —NO$_2$, —R', —N$_3$, —CH(Ph)$_2$, fluoro(C$_1$-C$_4$)alkoxy, and fluoro (C$_1$-C$_4$)alkyl, in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R"', and R"" groups when more than one of these groups is present.

Where a moiety is substituted with an R substituent, the group may be referred to as "R-substituted." Where a moiety is R-substituted, the moiety is substituted with at least one R substituent and each R substituent is optionally different. For example, where a moiety herein is $R^{14}$-substituted or unsubstituted alkyl, a plurality of $R^{14}$ substituents may be attached to the alkyl moiety wherein each $R^{14}$ substituent is optionally different. Where an R-substituted moiety is substituted with a plurality R substituents, each of the R-substituents may be differentiated herein using a prime symbol (') such as R', R", etc. For example, where a moiety is $R^{14}$-substituted or unsubstituted alkyl, and the moiety is substituted with a plurality of $R^{14}$ substituents, the plurality of $R^{14}$ substituents may be differentiated as $R^{14'}$, $R^{14''}$, $R^{14'''}$, etc. In some embodiments, the plurality of R substituents is 3. In some embodiments, the plurality of R substituents is 2.

In embodiments, a compound as described herein may include multiple instances of $R^1$, $R^2$, and/or other substituents and variables. In such embodiments, each variable may optional be different and be appropriately labeled to distinguish each group for greater clarity. For example, where each $R^{64}$ is different, they may be referred to, for example, as $R^{64.1}$, $R^{64.2}$, $R^{64.3}$, or $R^{64.4}$, respectively, wherein the definition of $R^{64}$ is assumed by $R^{64.1}$, $R^{64.2}$, $R^{64.3}$, and/or $R^{64.4}$. The variables used within a definition of $R^1$, $R^2$, and/or other variables that appear at multiple instances and are different may similarly be appropriately labeled to distinguish each group for greater clarity.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In embodiments, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R"')$_d$—, where variables s and d are independently integers of from 0 to 3, and X' is —O—, —NR'—, —S—, —S(O)—, —S(O)$_2$—, or —S(O)$_2$NR'—. The substituents R, R', R", and R"' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In embodiments, each substituted group described in the compounds herein is substituted with at least one substituent group. More specifically, In embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In embodiments herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In embodiments, the compound is a chemical species set forth in the Examples section below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject, in a cell, in the extracellular space near a cell).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present invention, whether radioactive or not, are encompassed within the scope of the present invention.

The symbol "⌇" denotes the point of attachment of a chemical moiety to the remainder of a molecule or chemical formula.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "therapeutically effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g. infectious disease, hyperproliferative disease, cancer) means that the disease is caused by (in whole or in part), or a symptom of the disease is caused by (in whole or in part) the substance or substance activity or function. As used herein, what is described as being associated with a disease, if a causative agent, could be a target for treatment of the disease. For example, a disease associated with infection may be treated with an agent (e.g. compound as described herein) effective as an antibiotic.

As used herein, the term "cancer" refers to all types of cancer, neoplasm, or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and Medulloblastoma. Additional examples include, metastatic bone cancer, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "lymphoma" refers broadly to a group of blood cell tumors that develop from cells of the immune system found in lymph, i.e. lymphocytes (e.g. natural killer cells (NK cells), T cells, and B cells). Lymphoma is typically classified into Hodgkin's lymphomas (HL) and the non-Hodgkin lymphomas (NHL) or based on whether it develops in B-lymphocytes (B-cells) or T-lymphocytes (T-cells). Exemplary lymphomas (Hodgkin's lymphomas and non-Hodgkin's lymphomas) that may be treated with a compound or method provided herein include, for example, nodular-sclerosis classical Hodgkin lymphoma, mixed cellularity classical Hodgkin lymphoma, lymphocyte-rich classical Hodgkin lymphoma, lymphocyte-depleted classical Hodgkin lymphoma, aggressive NHL, transformed NHL, indolent NHL, relapsed NHL, refractory NHL, low grade non-Hodgkin's Lymphoma, follicular lymphoma, large cell lymphoma, B-cell lymphoma, T-cell lymphoma, Mantle cell lymphoma, Burkitt's lymphoma, NK cell lymphoma, diffuse large B-cell lymphoma, and acute lymphoblastic lymphoma.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The terms "DNA" and "RNA" refer to deoxyribonucleic acid and ribonucleic acid, respectively.

Where a method disclosed herein refers to "amplifying" a nucleic acid, the term "amplifying" refers to a process in which the nucleic acid is exposed to at least one round of extension, replication, or transcription in order to increase (e.g., exponentially increase) the number of copies (including complimentary copies) of the nucleic acid. The process can be iterative including multiple rounds of extension, replication, or transcription. Various nucleic acid amplification techniques are known in the art, such as PCR amplification or rolling circle amplification.

A "primer" as used herein refers to a nucleic acid that is capable of hybridizing to a complimentary nucleic acid sequence in order to facilitate enzymatic extension, replication or transcription.

The words "complementary" or "complementarity" refer to the ability of a nucleic acid in a polynucleotide to form a base pair with another nucleic acid in a second polynucleotide. For example, the sequence 3'-A-G-T-C-5' is complementary to the sequence 3'-G-A-C-T-5'. Complementarity may be partial, in which only some of the nucleic acids match according to base pairing, or complete, where all the nucleic acids match according to base pairing.

The terms "identical" or percent "identity," in the context of two or more nucleic acids, refer to two or more sequences or subsequences that are the same or have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI web site at ncbi.nlm.nih.gov/BLAST. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

A variety of methods of specific DNA and RNA measurements that use nucleic acid hybridization techniques are known to those of skill in the art (see, Sambrook, Id.). Some methods involve electrophoretic separation (e.g., Southern blot for detecting DNA, and Northern blot for detecting RNA), but measurement of DNA and RNA can also be carried out in the absence of electrophoretic separation (e.g., quantitative PCR, dot blot, or array).

The sensitivity of the hybridization assays may be enhanced through use of a nucleic acid amplification system that multiplies the target nucleic acid being detected. Amplification can also be used for direct detection techniques. Examples of such systems include the polymerase chain reaction (PCR) system and the ligase chain reaction (LCR) system. Other methods include the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation. It is understood that various detection probes, including Taqman® and molecular beacon probes can be used to monitor amplification reaction products in real time.

The terms "spliceosome" or "spliceosomal" are used according to their common and ordinary meaning and refer to the component or complex in a cell involved in removal of introns from transcribed pre-mRNA. A spliceosome may include a complex of small nuclear RNA (snRNA) and protein subunits.

The term "splicing" is used according to its common and ordinary meaning and refer to a process in a cell involved in removal of introns from transcribed pre-mRNA. During the splicing, the removal of introns and joining of exons from nascent pre-mRNA occur simultaneously or sequentially. Splicing plays an important role in human biology and its relevance in developing and proliferation of cancer cells.

As defined herein, the term "inhibition", "inhibit", "inhibiting" and the like in reference to a protein-inhibitor interaction means negatively affecting (e.g., decreasing) the activity or function of the protein relative to the activity or function of the protein in the absence of the inhibitor. In some embodiments, inhibition refers to reduction of a disease or symptoms of disease. In some embodiments, inhibition refers to a reduction in the activity of a particular protein or nucleic acid target. In some embodiment, inhibition of the invention refers to an inhibition upon a splicing process in a cell, preferably in a cancer cell, using an inhibitor (e.g., antagonist, antibodies, RNAi molecules or small molecules). Thus, inhibition includes, at least in part, partially or totally blocking stimulation, decreasing, preventing, or delaying activation, or inactivating, desensitizing, or down-regulating signal transduction or enzymatic activity or the amount of a protein or protein complex (e.g. spliceosome).

A "test compound" as used herein refers to an experimental compound as described herein that can be used in a screening process to identify activity, non-activity, or other modulation of a particularized biological target or pathway.

The term "modulation", "modulate", or "modulator" are used in accordance with their plain ordinary meaning and refer to the act of changing or varying one or more properties. "Modulator" refers to a composition that increases or decreases the level of a target molecule or the function of a target molecule or the physical state of the target of the molecule. "Modulation" refers to the process of changing or varying one or more properties. For example, as applied to the effects of a modulator on a biological target, to modulate means to change by increasing or decreasing a property or function of the biological target or the amount of the biological target.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As used herein, "biomolecule" is used in its customary sense and refers to a molecule found in nature or derivatives thereof, including macromolecules such as proteins, carbohydrates, lipids, and nucleic acids, as well as small molecules such as primary metabolites, secondary metabolites, and natural products. A biomolecule may be present as a moiety attached to the remainder of a compound. A biomolecule includes but is not limited to nucleic acids (e.g. DNA and RNA), peptide nucleic acids, sugars, peptides, proteins, antibodies, lipids, small molecule affinity ligands e.g. inhibitors, biotin and haptens.

As used herein, "carbohydrate" is used in its customary sense and refers to a molecule found in nature or derivatives thereof, which comprises carbon (C), hydrogen (H) and oxygen (O) atoms and typically containing polyhydroxy aldehydes, ketones, alcohols, acids, simple derivatives thereof and polymeric forms from monomeric units (monosaccharides). A monosaccharide is used in its customary sense and refers to a basic building block of carbohydrates or disaccharide containing two units of the monosaccharides. The monosaccharide can have either linear form or cyclic (ring) form and contains at least three carbons, at least four carbons, at least five carbons, or at least six carbons. The monosaccharide as used in the invention can have a 5 to 7 membered, or preferably, 6-membered ring structure. In addition, the monosaccharide may be chemically modified, for example, by removing or adding hydrogen, oxo, halogen, —OH, —NH$_2$, —COOH, —CONH$_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered).

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a composition described herein is administered at the same time, just prior to, or just after the administration of one or more additional therapies. The compound of the invention can be administered alone or can be co-administered to the patient. Co-administration is meant to include simultaneous or sequential administration of the compound individually or in combination (more than one compound or agent). Thus, the preparations can also be combined, when desired, with other active substances (e.g. to reduce metabolic degradation).

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, J. Biomater. Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989). The compositions can also be delivered as nanoparticles.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

An "agonist," as used herein, refers to a compound capable of detectably increasing the expression or activity of a given protein or receptor. The agonist can increase expression or activity 10%, 20%, 30%, 40%, 50%, 60%, 70%, 80%, 90%, 100% or more in comparison to a control in the absence of the agonist. In embodiments, expression or activity is 1.5-fold, 2-fold, 3-fold, 4-fold, 5-fold, 10-fold or more higher than the expression or activity in the absence of the agonist.

The term "antagonist" refers to a substance capable of detectably lowering expression or activity of a given protein. The antagonist can inhibit expression or activity 10%, 20%, 30%, 40%, 50%, 60%, 70%, 80%, 90%, 100% or less in comparison to a control in the absence of the antagonist. In embodiments, the inhibition is 1.5-fold, 2-fold, 3-fold, 4-fold, 5-fold, 10-fold, or more than the expression or activity in the absence of the antagonist.

The term "nucleic acid" refers to deoxyribonucleotides or ribonucleotides and polymers thereof in either single-, double- or multiple-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including nucleic acids with a phosphothioate backbone can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amio acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, OLIGONUCLE-OTIDES AND ANALOGUES: A PRACTICAL APPROACH, Oxford University Press); and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

A "labeled nucleic acid or oligonucleotide" is one that is bound, either covalently, through a linker or a chemical bond, or noncovalently, through ionic, van der Waals, electrostatic, or hydrogen bonds to a label such that the presence of the nucleic acid may be detected by detecting the presence of the detectable label bound to the nucleic acid. Alternatively, a method using high affinity interactions may achieve the same results where one of a pair of binding partners binds to the other, e.g., biotin, streptavidin. In embodiments, the phosphorothioate nucleic acid or phosphorothioate polymer includes a detectable label, as disclosed herein and generally known in the art.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 *Molecular Cloning: A Laboratory Manual,* 18.1-18.88.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. Transgenic cells and plants are those that express a heterologous gene or coding sequence, typically as a result of recombinant methods.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

II. Compounds

In one aspect, provided is a compound with structure of Formula (I):

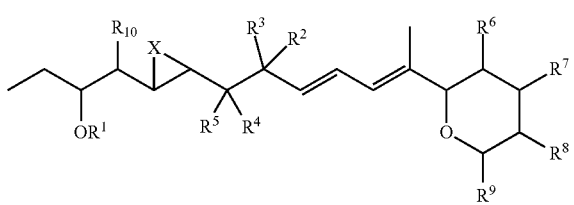

(I)

X is —O— or —C($R^{26}$)($R^{27}$)—. $R^{26}$ is hydrogen, halogen, substituted or unsubstituted alkyl, substituted or unsubstituted aryl, —O$R^{28}$, —OC(O)$R^{28}$, —OC(O)O$R^{28}$, or —OC(O)N$R^{28}R^{29}$. $R^{27}$ is hydrogen, halogen, substituted or unsubstituted alkyl, substituted or unsubstituted aryl, —O$R^{30}$, —OC(O)$R^{30}$, —OC(O)O$R^{30}$, or —OC(O)N$R^3$O$R^{31}$. $R^1$ is hydrogen, substituted or unsubstituted alkyl, —C(O)R", or —C(O)OR". $R^2$ is hydrogen, halogen, substituted or unsubstituted alkyl, —O$R^{12}$, —OC(O)$R^{12}$, —OC(O)O$R^{12}$, or —OC(O)N$R^{12}R^{13}$. $R^3$ is hydrogen, halogen, substituted or unsubstituted alkyl, —O$R^{14}$, —OC(O)$R^{14}$, —OC(O)O$R^{14}$, or —OC(O)N$R^{14}R^{15}$. $R^4$ is hydrogen, halogen, substituted or unsubstituted alkyl, —O$R^{16}$, —OC(O)$R^{16}$, —OC(O)O$R^{16}$, or —OC(O)N$R^{16}R^{17}$. $R^5$ is hydrogen, halogen, substituted or unsubstituted alkyl, —O$R^{18}$, —OC(O)$R^{18}$, —OC(O)O$R^{18}$, or —OC(O)N$R^{18}R^{19}$. $R^6$ is hydrogen, —O$R^{20}$, —C(O)$R^{20}$, —C(O)O$R^{20}$, —OC(O)$R^{20}$, or —OC(O)O$R^{20}$. $R^7$ is hydrogen, —O$R^{21}$, —C(O)$R^{21}$, —C(O)O$R^{21}$, —OC(O)$R^{21}$, or —OC(O)O$R^{21}$. $R^8$ is hydrogen, —O$R^{22}$, —C(O)R)R, —C(O)O$R^{22}$, —OC(O)$R^{22}$, Or —OC(O)O$R^{22}$. $R^9$ is hydrogen, —O$R^{23}$, —C(O)$R^{23}$, —C(O)O$R^{23}$, —OC(O)$R^{23}$, or —OC(O)O$R^{23}$. $R^{10}$ is hydrogen, substituted or unsubstituted alkyl, —O$R^{24}$, —OC(O) $R^{24}$, —OC(O)O$R^{24}$, or —OC(O)N$R^{24}R^{25}$. $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{28}$, $R^{29}$, $R^{30}$, and $R^{31}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the 6-membered ring structure in the compound may be a monosaccharide or a derivative thereof. In embodiments, the monosaccharide has a structure, which is represented by

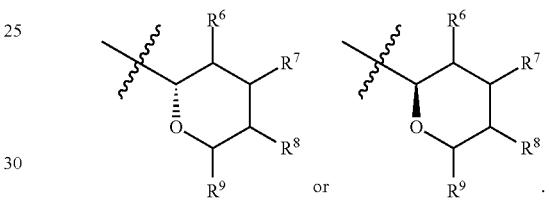

In embodiments, the compound is derived or synthesized from a monosaccharide having a 6-membered ring structure such as hexose sugar ($C_6H_{12}O_6$) including, but not limited thereto, allose, maltose, glucose, mannose, gulose, galactose, talose and iodose. In embodiments, the compound is derived or synthesized from a monosaccharide having a 6-membered ring structure such as a deoxy sugar lacking a hydroxyl group or oxygen at least one hydroxy position of the hexose sugar or the monosaccharide. Examples of the deoxy sugar include, but not limited to, deoxygalactose, deoxyglucose, deoxymannose, fucose, rhamnose and derivatives thereof. In embodiments, the compound is derived or synthesized from an acidic monosaccharide having a 6-membered ring structure, such as an acidic sugar containing at least one acidic group (e.g. carboxyl group) at least one hydroxy position of the hexose sugar or the monosaccharide. Examples of the acidic sugar include, but not limited to, uronic acid, glucuronic acid and derivatives thereof. In embodiments, the

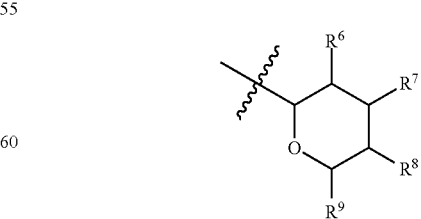

moiety in the compound has (D) or (L) configuration, which may be originated from the monosaccharide used for modification or synthesis thereof. In embodiments, the

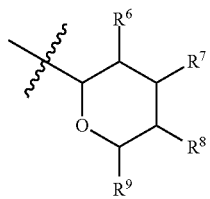

moiety in the compound has (D) configuration. In embodiments, the

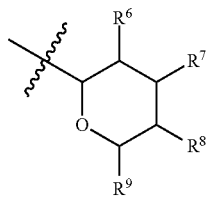

moiety in the compound has (L) configuration.

In embodiments, X is —O—. In embodiments, X together with the atoms attached thereto forms "oxirane-diyl" which refers, in the usual and customary sense, to a divalent moiety with structure:

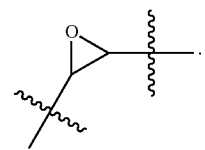 [SMILES: *C1OC1*]

In embodiments, X together with the atoms attached thereto forms

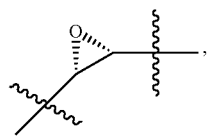

or

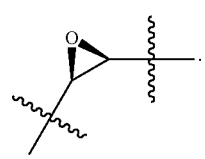 [SMILES: *[C@@H]1O[C@@H]1*]

In embodiments, X together with the atoms attached thereto forms.

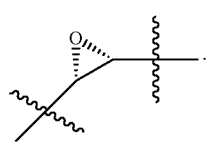 [SMILES: *[C@@H]1O[C@@H]1*]

In embodiment, X together with the atoms attached thereto forms

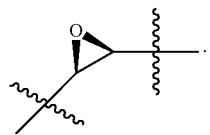 [SMILES: *[C@@H]1O[C@@H]1*]

In embodiments, X is —C(R$^{26}$)(R$^{27}$)—. In embodiments, X is —C(R$^{26}$)(R$^{27}$)—, wherein R$^{26}$ and R$^{27}$ are independently hydrogen, or substituted or unsubstituted alkyl, wherein R$^{26}$ and R$^{27}$ are independently hydrogen, or substituted or unsubstituted C$^1$-C$^4$ alkyl, wherein R$^{26}$ and R$^{27}$ are independently hydrogen or —CH$_3$, or R$^{26}$ and R$^{27}$ are hydrogen. In embodiments, X is —CH$_2$—.

In embodiments, X together with the atoms attached thereto forms substituted or unsubstituted "cyclopropane", to a divalent moiety with structure:

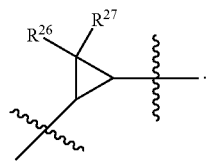

In embodiments, X together with the atoms attached thereto forms

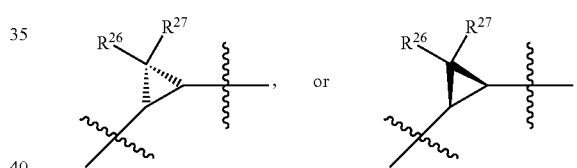

In embodiments, X together with the atoms attached thereto forms.

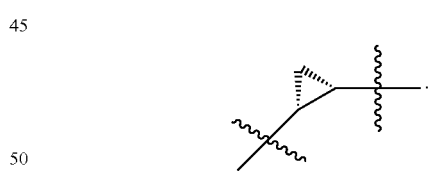

In embodiment, X together with the atoms attached thereto forms

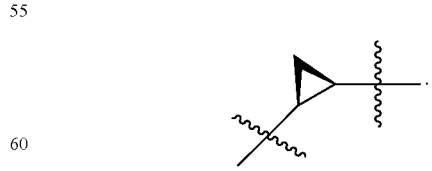

In embodiments, R$^1$ is hydrogen, substituted or unsubstituted alkyl (e.g., C$_1$-C$_8$, C$_1$-C$_6$, C$_1$-C$_4$, or C$_1$-C$_2$), —C(O)R$^{11}$, or —C(O)OR$^{11}$. In embodiments, R$^1$ is hydrogen, substituted or unsubstituted C$_1$-C$_4$ alkyl, —OH, —OCH$_3$, —C(O)H, —C(O)CH$_3$, —C(O)OH, or —C(O)OCH$_3$. In embodiments, $R^1$ is hydrogen, unsubstituted $C_1$-$C_4$ alkyl, —OH, —OCH$_3$, —C(O)H, —C(O)CH$_3$, —C(O)OH, or —C(O)OCH$_3$. In embodiments, $R^1$ is hydrogen, —CH$_3$, —CH$_2$CH$_3$, —OH, —OCH$_3$, —C(O)H, —C(O)CH$_3$, —C(O)OH, or —C(O)OCH$_3$. In embodiments, $R^1$ is hydrogen, —CH$_3$, —CH$_2$CH$_3$, —OH, or —OCH$_3$. In embodiments, $R^1$ is hydrogen, —CH$_3$ or —CH$_2$CH$_3$. In embodiments, $R^1$ is hydrogen. In embodiments, $R^1$ is —CH$_3$. In embodiments, $R^1$ is —CH$_2$CH$_3$.

In embodiments, a chiral carbon where —OR$^1$ is attached has (S) stereochemistry. In embodiments, a chiral carbon where —OR$^1$ is attached has (R) stereochemistry.

In embodiments, $R^{10}$ is hydrogen, substituted or unsubstituted alkyl (e.g., $C_1$-$C_8$, $C_1$-$C_6$, $C_1$-$C_4$, or $C_1$-$C_2$), —OR$^{24}$, —OC(O)R$^{24}$, —OC(O)OR$^{24}$, or —OC(O)NR$^{24}$R$^{25}$. In embodiments, $R^{10}$ is hydrogen, substituted or unsubstituted $C_1$-$C_6$ alkyl, OH, —OCH$_3$, —OC(O)H, —OC(O)CH$_3$, —OC(O)OH, —OC(O)OCH$_3$, —OC(O)NH$_2$, or —OC(O)NHCH$_3$. In embodiments, $R^{10}$ is hydrogen, substituted or unsubstituted $C_1$-$C_4$ alkyl, —OH, —OCH$_3$, —OC(O)H, —OC(O)CH$_3$, —OC(O)OH, or —OC(O)OCH$_3$. In embodiments, $R^{10}$ is hydrogen, unsubstituted $C_1$-$C_4$ alkyl, —OH, —OCH$_3$, —OC(O)H, —OC(O)CH$_3$, —OC(O)OH, or —OC(O)OCH$_3$. In embodiments, $R^{10}$ is hydrogen, unsubstituted $C_1$-$C_4$ alkyl, —OH, —OCH$_3$, —OC(O)H, or —OC(O)CH$_3$. In embodiments, $R^{10}$ is hydrogen, —CH$_3$, —CH$_2$CH$_3$, —OH, or —OCH$_3$. In embodiments, $R^{10}$ is hydrogen, —CH$_3$, or —CH$_2$CH$_3$. In embodiments, $R^{10}$ is hydrogen. In embodiments, $R^{10}$ is —CH$_3$. In embodiments, $R^{10}$ is —CH$_2$CH$_3$.

In embodiments, when $R^{10}$ is not hydrogen, a chiral carbon where $R^{10}$ is attached has (S) stereochemistry. In embodiments, when $R^{10}$ is not hydrogen, a chiral carbon where $R^{10}$ is attached has (R) stereochemistry.

In embodiments, X is —O—; $R^1$ is hydrogen or unsubstituted $C_1$-$C_4$ alkyl; and $R^{10}$ is hydrogen or unsubstituted $C_1$-$C_4$ alkyl. In embodiments, X is —O—; $R^1$ is hydrogen, —CH$_3$, or —CH$_2$CH$_3$; and $R^{10}$ is hydrogen, —CH$_3$, or —CH$_2$CH$_3$. In embodiments, X is —O—; $R^1$ is hydrogen or —CH$_3$; and $R^{10}$ is hydrogen or —CH$_3$. In embodiments, X is —O—; $R^1$ is hydrogen; and $R^{10}$ is hydrogen. In embodiments, X is —O—; $R^1$ is hydrogen; and $R^{10}$ is —CH$_3$. In embodiments, X is —O—; $R^1$ is —CH$_3$; and $R^{10}$ is hydrogen. In embodiments, X is —O—; $R^1$ is —CH$_3$; and $R^{10}$ is —CH$_3$. In embodiments, the compound has a structure of Formula (II):

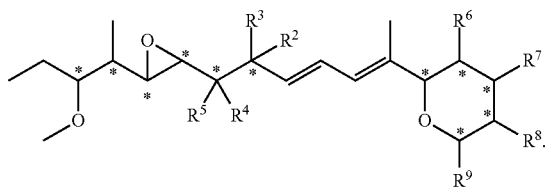

(II)

In embodiments, the compounds of Formula (II) may have chiral centers denoted by a "*" in the following structure, where stereochemical modification or variation can be made:

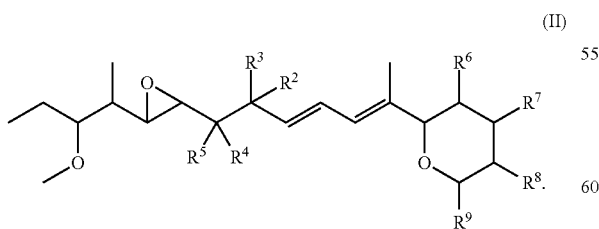

In embodiments, the compound has a structure of Formula (IIA) or Formula (IIB).

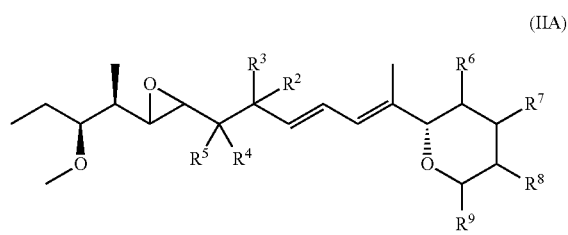

(IIA)

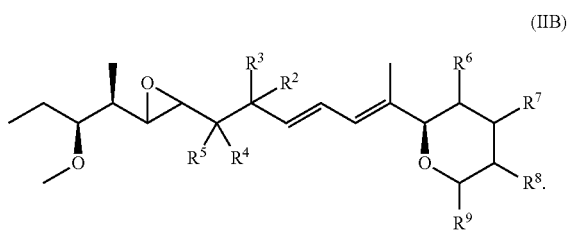

(IIB)

In embodiments, the compound has the structure of Formula (IIA). In embodiments, the compound has the structure of Formula (IIB).

In embodiments, the compound has a structure of Formula (IIA-1) or Formula (IIA-2).

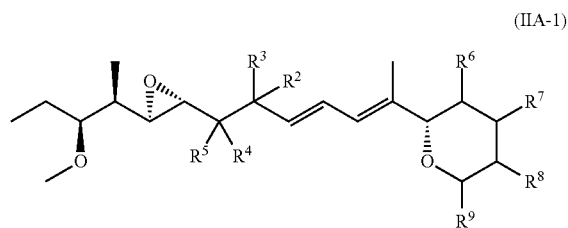

(IIA-1)

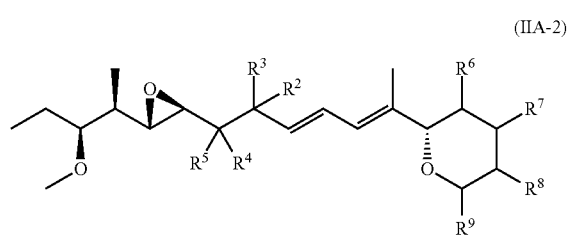

(IIA-2)

In embodiments, the compound has a structure of Formula (IIA-1). In embodiments, the compound has a structure of Formula (IIA-2).

In embodiments, the compound has a structure of Formula (IIB-1) or Formula (IIB-2).

(IIB-1)

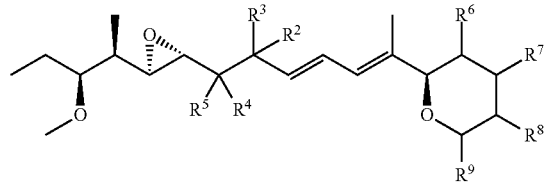

(IIB-2)

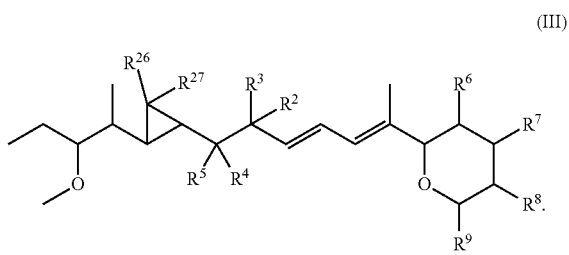

In embodiments, the compound has a structure of Formula (IIB-1). In embodiments, the compound has a structure of Formula (IIB-2).

In embodiments, X is —C(R$^{26}$)(R$^{27}$)—; R$^1$ is hydrogen or unsubstituted C$_1$-C$_4$ alkyl; and R$^{10}$ is hydrogen or unsubstituted C$_1$-C$_4$ alkyl. In embodiments, X is —C(R$^{26}$)(R$^{27}$)—; R$^1$ is hydrogen, —CH$_3$, or —CH$_2$CH$_3$; and R$^{10}$ is hydrogen, —CH$_3$, or —CH$_2$CH$_3$. In embodiments, X is —C(R$^{26}$)(R$^{27}$)—; R$^1$ is hydrogen or —CH$_3$; and R$^{10}$ is hydrogen or —CH$_3$. In embodiments, X is —C(R$^{26}$)(R$^{27}$)—; R$^1$ is hydrogen; and R$^{10}$ is hydrogen. In embodiments, X is —C(R$^{26}$)(R$^{27}$)—; R$^1$ is hydrogen; and R$^{10}$ is —CH$_3$. In embodiments, X is —C(R$^{26}$)(R$^{27}$)—; R$^1$ is —CH$_3$; and R$^{10}$ is hydrogen. In embodiments, X is —C(R$^{26}$)(R$^{27}$)—; R$^1$ is —CH$_3$; and R$^{10}$ is —CH$_3$.

In embodiments, the compound has a structure of Formula (III), (III)

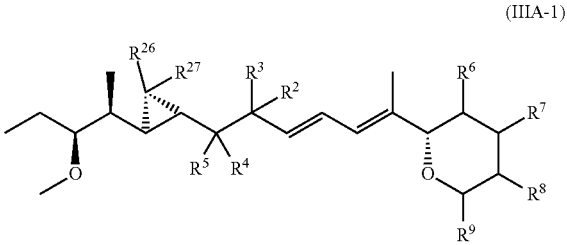

In embodiments, the compounds of Formula (III) may have chiral centers denoted by a "*" in the following structure, where stereochemical modification or variation can be made:

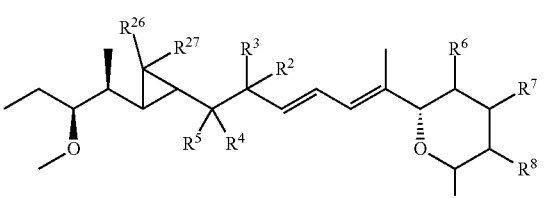

In embodiments, the compound has a structure of Formula (IIIA) or Formula (IIIB).

(IIIA)

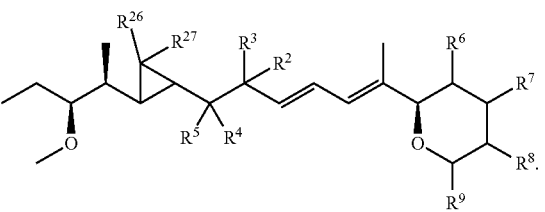

(IIIB)

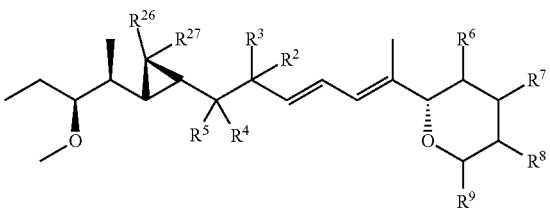

In embodiments, the compound has the structure of Formula (IIIA). In embodiments, the compound has the structure of Formula (IIIB).

In embodiments, the compound has a structure of Formula (IIIA-1) or Formula (IIIA-2).

(IIIA-1)

(IIIA-2)

In embodiments, the compound has a structure of Formula (IIIA-1). In embodiments, the compound has a structure of Formula (IIIA-2).

In embodiments, the compound has a structure of Formula (IIIB-1) or Formula (IIIB-2).

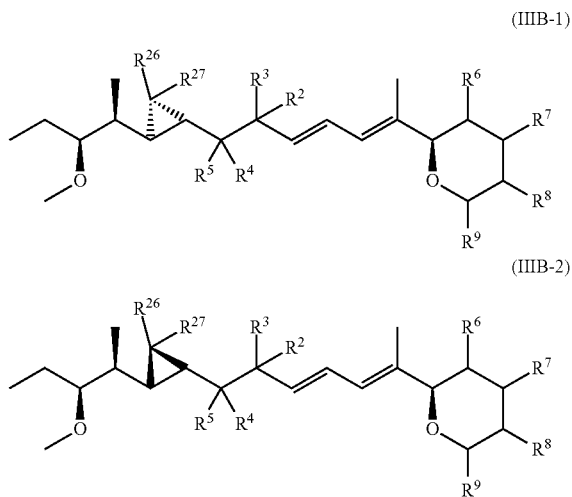

(IIIB-1)

(IIIB-2)

In embodiments, the compound has a structure of Formula (IIIB-1). In embodiments, the compound has a structure of Formula (IIIB-2).

In embodiments, $R^{26}$ is hydrogen, halogen (e.g. —F, —Cl, or —Br), substituted or unsubstituted $C_1$-$C_6$ alkyl, substituted or unsubstituted aryl (e.g. phenyl), —OH, —OCH$_3$, —OC(O)H, —OC(O)CH$_3$, —OC(O)OH, —OC(O)OCH$_3$, —OC(O)NH$_2$, or —OC(O)NHCH$_3$. In embodiments, $R^{26}$ is hydrogen, halogen (e.g. —F, —Cl, or —Br), substituted or unsubstituted $C_1$-$C_4$ alkyl, —OH, —OCH$_3$, —OC(O)H, —OC(O)CH$_3$, —OC(O)OH, —OC(O)OCH$_3$, —OC(O)NH$_2$, or —OC(O)NHCH$_3$. In embodiments, $R^{26}$ is hydrogen, halogen (e.g. —F, —Cl, or —Br), substituted or unsubstituted $C_1$-$C_4$ alkyl, —OH, or —OCH$_3$. In embodiments, $R^{26}$ is hydrogen, halogen (e.g. —F, —Cl, or —Br), unsubstituted $C_1$-$C_4$ alkyl, —OH, or —OCH$_3$. In embodiments, $R^{26}$ is hydrogen, halogen (e.g. —F, —Cl, or —Br), —CH$_3$, —CH$_2$CH$_3$, —OH, or —OCH$_3$. In embodiments, $R^{26}$ is hydrogen. In embodiments, $R^{26}$ is —F, —Cl, or —Br. In embodiments, $R^{26}$ is —CH$_3$ or —CH$_2$CH$_3$. In embodiments, $R^{26}$ is —OH, or —OCH$_3$.

In embodiments, $R^{27}$ is hydrogen, halogen (e.g. —F, —Cl, or —Br), substituted or unsubstituted $C_1$-$C_6$ alkyl, substituted or unsubstituted aryl (e.g. phenyl), —OH, —OCH$_3$, —OC(O)H, —OC(O)CH$_3$, —OC(O)OH, —OC(O)OCH$_3$, —OC(O)NH$_2$, or —OC(O)NHCH$_3$. In embodiments, $R^{27}$ is hydrogen, halogen (e.g. —F, —Cl, or —Br), substituted or unsubstituted $C_1$-$C_4$ alkyl, —OH, —OCH$_3$, —OC(O)H, —OC(O)CH$_3$, —OC(O)OH, —OC(O)OCH$_3$, —OC(O)NH$_2$, or —OC(O)NHCH$_3$. In embodiments, $R^{27}$ is hydrogen, halogen (e.g. —F, —Cl, or —Br), substituted or unsubstituted $C_1$-$C_4$ alkyl, —OH, or —OCH$_3$. In embodiments, $R^{27}$ is hydrogen, halogen (e.g. —F, —Cl, or —Br), unsubstituted $C_1$-$C_4$ alkyl, —OH, or —OCH$_3$. In embodiments, $R^{27}$ is hydrogen, halogen (e.g. —F, —Cl, or —Br), —CH$_3$, —CH$_2$CH$_3$, —OH, or —OCH$_3$. In embodiments, $R^{27}$ is hydrogen. In embodiments, $R^{27}$ is-F, —Cl, or —Br. In embodiments, $R^{27}$ is —CH$_3$ or —CH$_2$CH$_3$. In embodiments, $R^{27}$ is —OH, or —OCH$_3$.

In embodiments, the chiral carbon where $R^{26}$ and $R^{27}$ are attached has (S) stereochemistry. In embodiments, the chiral carbon where $R^{26}$ and $R^{27}$ are attached has (R) stereochemistry.

In embodiments, one of $R^4$ and $R^5$ is hydrogen and the other one of $R^4$ and $R^5$ is not hydrogen. In embodiments, $R^4$ is hydrogen and $R^5$ is substituted or unsubstituted alkyl (e.g., $C_1$-$C_8$, $C_1$-$C_6$, $C_1$-$C_4$, or $C_1$-$C_2$), —OR, —OC(O)R$^{18}$, —OC(O)OR$^{18}$, or —OC(O)NR$^{18}$R$^{19}$ (e.g. —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$). In embodiments, $R^4$ is hydrogen and $R^5$ is substituted or unsubstituted $C_1$-$C_6$ alkyl, or —OR$^8$. In embodiments, $R^4$ is hydrogen and $R^5$ is substituted or unsubstituted $C_1$-$C_4$ alkyl, or —OH, —OCH$_3$, —OCH$_2$CH$_3$. In embodiments, $R^4$ is hydrogen and $R^5$ is —CH$_3$, —OH, —OCH$_3$, or —OCH$_2$CH$_3$. In embodiments, $R^4$ is hydrogen and $R^5$ is —CH$_3$ or —OH. In embodiments, $R^4$ is hydrogen and $R^5$ is —OH.

In embodiments, $R^5$ is hydrogen and $R^4$ is substituted or unsubstituted alkyl (e.g., $C_1$-$C_8$, $C_1$-$C_6$, $C_1$-$C_4$, or $C_1$-$C_2$), —OR$^{16}$, —OC(O)R$^{16}$, —OC(O)OR$^{16}$, or —OC(O)NR$^{16}$R$^{17}$ (e.g. —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$). In embodiments, $R^5$ is hydrogen and $R^4$ is substituted or unsubstituted $C_1$-$C_6$ alkyl, or —OR$^{16}$. In embodiments, $R^5$ is hydrogen and $R^4$ is substituted or unsubstituted $C_1$-$C_4$ alkyl, or —OH, —OCH$_3$, —OCH$_2$CH$_3$. In embodiments, $R^5$ is hydrogen and $R^4$ is —CH$_3$, —OH, —OCH$_3$, or —OCH$_2$CH$_3$. In embodiments, $R^5$ is hydrogen and $R^4$ is —CH$_3$ or —OH. In embodiments, $R^5$ is hydrogen and $R^4$ is-OH. In embodiments, $R^5$ is hydrogen and $R^4$ is —CH$_3$.

In embodiments, the chiral carbon where $R^4$ and $R^5$ are attached has (S) stereochemistry. In embodiments, the chiral carbon where $R^4$ and $R^5$ are attached has (R) stereochemistry.

In embodiments, one of $R^2$ and $R^3$ is hydrogen and the other one of $R^2$ and $R^3$ is not hydrogen. In embodiments, $R^2$ is hydrogen and $R^3$ is substituted or unsubstituted alkyl (e.g., $C_1$-$C_8$, $C_1$-$C_6$, $C_1$-$C_4$, or $C_1$-$C_2$), —OR$^{14}$, —OC(O)R$^{14}$, —OC(O)OR$^{14}$, or —OC(O)NR$^{14}$R$^{15}$ (e.g. —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$). In embodiments, $R^2$ is hydrogen and $R^3$ is substituted or unsubstituted $C_1$-$C_6$ alkyl, or —OR$^{14}$ (e.g. —OH, —OCH$_3$, or —OCH$_2$CH$_3$). In embodiments, $R^2$ is hydrogen and $R^3$ is $C_1$-$C_4$ unsubstituted alkyl. In embodiments, $R^2$ is hydrogen and $R^3$ is —CH$_3$ or —CH$_2$CH$_3$. In embodiments, $R^2$ is hydrogen and $R^3$ is —CH$_3$.

In embodiments, $R^3$ is hydrogen and $R^2$ is substituted or unsubstituted alkyl (e.g., $C_1$-$C_8$, $C_1$-$C_6$, $C_1$-$C_4$, or $C_1$-$C_2$), —OR$^{12}$, —OC(O)R$^{12}$, —OC(O)OR$^{12}$, or —OC(O)NR$^{12}$R$^{13}$ (e.g. —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$). In embodiments, $R^3$ is hydrogen and $R^2$ is substituted or unsubstituted $C_1$-$C_6$ alkyl, or —OR$^{12}$ (e.g. —OH, —OCH$_3$, or —OCH$_2$CH$_3$). In embodiments, $R^3$ is hydrogen and $R^2$ is $C_1$-$C_4$ unsubstituted alkyl. In embodiments, $R^3$ is hydrogen and $R^2$ is —CH$_3$ or —CH$_2$CH$_3$. In embodiments, $R^3$ is hydrogen and $R^2$ is —CH$_3$.

In embodiments, the chiral carbon where $R^2$ and $R^3$ are attached has (S) stereochemistry. In embodiments, the chiral carbon where $R^2$ and $R^3$ are attached has (R) stereochemistry.

In embodiments, $R^6$ is hydrogen, —OR$^{20}$, —C(O)R$^{20}$, —C(O)OR$^{20}$, —OC(O)R$^{20}$, or —OC(O)OR$^{20}$. In embodiments, $R^6$ is hydrogen, —OR$^{20}$, —C(O)R$^{20}$, or —C(O)OR$^{20}$. In embodiments, $R^6$ is hydrogen, —OR$^{20}$, or —C(O)OR$^{20}$. In embodiments, $R^6$ is hydrogen. In embodiments, $R^6$ is —OR$^{20}$. In embodiments, $R^6$ is —C(O)OR$^{20}$.

In embodiments, $R^{20}$ is independently hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{20}$ is independently hydrogen, substituted or unsubstituted $C_1$-$C_4$ alkyl, substituted or unsubstituted 2 to 6 membered heteroalkyl, substituted or unsubstituted $C_3$-$C_6$ cycloalkyl, or substituted or unsubstituted 3 to 6 membered heterocycloalkyl. In embodiments, $R^{20}$ is independently hydrogen, substituted or unsubstituted $C_1$-$C_4$ alkyl, or substituted or unsubstituted 2 to 6 membered heteroalkyl. In embodiments, $R^{20}$ is independently hydrogen, or substituted or unsubstituted $C_1$-$C_4$ alkyl. In embodiments, $R^{20}$ is substituted or unsubstituted $C_1$-$C_2$ alkyl. In embodiments, $R^{20}$ is unsubstituted $C_1$-$C_2$ alkyl. In embodiments, $R^{20}$ is —$CH_3$ or —$CH_2CH_3$. In embodiments, $R^{20}$ is hydrogen.

In embodiments, $R^6$ is hydrogen, —OH, —$OCH_3$, —$OCH_2CH_3$, —C(O)H, —C(O)$CH_3$, —C(O)OH, —C(O)$OCH_3$, —OC(O)H, —OC(O)$CH_3$, —OC(O)OH, or —OC(O)$OCH_3$. In embodiments, $R^6$ is hydrogen, —OH, —$OCH_3$, —$OCH_2CH_3$, —C(O)H, —C(O)$CH_3$, —C(O)OH, —C(O)$OCH_3$, —OC(O)H, or —OC(O)$CH_3$. In embodiments, $R^6$ is hydrogen, —OH, —$OCH_3$, —$OCH_2CH_3$, —C(O)H, —C(O)$CH_3$, —C(O)OH, or —C(O)$OCH_3$. In embodiments, $R^6$ is hydrogen, —OH, —$OCH_3$, —$OCH_2CH_3$, —C(O)H, or —C(O)$CH_3$. In embodiments, $R^6$ is hydrogen, —OH, or —$OCH_3$. In embodiments, $R^6$ is hydrogen. In embodiments, $R^6$ is —OH. In embodiments, $R^6$ is —$OCH_3$. In embodiments, $R^6$ is —C(O)H. In embodiments, $R^6$ is —C(O)$CH_3$. In embodiments, $R^6$ is —C(O)OH. In embodiments, $R^6$ is —C(O)$OCH_3$.

In embodiments, the chiral carbon where $R^6$ is attached has (S) stereochemistry. In embodiments, the chiral carbon where $R^6$ is attached has (R) stereochemistry.

In embodiments, $R^7$ is hydrogen, —$OR^{21}$, —C(O)$R^{21}$, —C(O)$OR^{21}$, —OC(O)$R^{21}$, or —OC(O)$OR^{21}$. In embodiments, $R^7$ is hydrogen, —$OR^{21}$, —C(O)$R^{21}$, or —C(O)$OR^{21}$. In embodiments, $R^7$ is hydrogen, —$OR^{21}$, or —C(O)$OR^{21}$. In embodiments, $R^7$ is hydrogen. In embodiments, $R^7$ is —$OR^{21}$. In embodiments, $R^7$ is —C(O)$OR^{21}$.

In embodiments, $R^{21}$ is independently hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{21}$ is independently hydrogen, substituted or unsubstituted $C_1$-$C_4$ alkyl, substituted or unsubstituted 2 to 6 membered heteroalkyl, substituted or unsubstituted $C_3$-$C_6$ cycloalkyl, or substituted or unsubstituted 3 to 6 membered heterocycloalkyl. In embodiments, $R^{21}$ is independently hydrogen, substituted or unsubstituted $C_1$-$C_4$ alkyl, or substituted or unsubstituted 2 to 6 membered heteroalkyl. In embodiments, $R^{21}$ is independently hydrogen, or substituted or unsubstituted $C_1$-$C_4$ alkyl. In embodiments, $R^{21}$ is substituted or unsubstituted $C_1$-$C_2$ alkyl. In embodiments, $R^{21}$ is unsubstituted $C_1$-$C_2$ alkyl. In embodiments, $R^{21}$ is —$CH_3$ or —$CH_2CH_3$. In embodiments, $R^{21}$ is hydrogen.

In embodiments, $R^7$ is hydrogen, —OH, —$OCH_3$, —$OCH_2CH_3$, —C(O)H, —C(O)$CH_3$, —C(O)OH, —C(O)$OCH_3$, —OC(O)H, —OC(O)$CH_3$, —OC(O)OH, or —OC(O)$OCH_3$. In embodiments, $R^7$ is hydrogen, —OH, —$OCH_3$, —$OCH_2CH_3$, —C(O)H, —C(O)$CH_3$, —C(O)OH, —C(O)$OCH_3$, —OC(O)H, or —OC(O)$CH_3$. In embodiments, $R^7$ is hydrogen, —OH, —$OCH_3$, —$OCH_2CH_3$, —C(O)H, —C(O)$CH_3$, —C(O)OH, or —C(O)$OCH_3$. In embodiments, $R^7$ is hydrogen, —OH, —$OCH_3$, —$OCH_2CH_3$, —C(O)H, or —C(O)$CH_3$. In embodiments, $R^7$ is hydrogen, —OH, or —$OCH_3$. In embodiments, $R^7$ is hydrogen. In embodiments, $R^7$ is —OH. In embodiments, $R^7$ is —$OCH_3$. In embodiments, $R^7$ is —C(O)H. In embodiments, $R^7$ is —C(O)$CH_3$. In embodiments, $R^7$ is —C(O)OH. In embodiments, $R^7$ is —C(O)$OCH_3$.

In embodiments, the chiral carbon where $R^7$ is attached has (S) stereochemistry. In embodiments, the chiral carbon where $R^7$ is attached has (R) stereochemistry.

In embodiments, $R^8$ is hydrogen, —$OR^{22}$, —C(O)$R^{22}$, —C(O)$OR^{22}$, —OC(O)$R^{22}$, or —OC(O)$OR^{22}$. In embodiments, $R^8$ is hydrogen, —$OR^{22}$, —C(O)$R^{22}$, or —C(O)$OR^{22}$. In embodiments, $R^8$ is hydrogen, —$OR^{22}$, or —C(O)$OR^{22}$. In embodiments, $R^8$ is hydrogen. In embodiments, $R^8$ is —$OR^{22}$. In embodiments, $R^8$ is —C(O)$OR^{22}$.

In embodiments, $R^{22}$ is independently hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{22}$ is independently hydrogen, substituted or unsubstituted $C_1$-$C_4$ alkyl, substituted or unsubstituted 2 to 6 membered heteroalkyl, substituted or unsubstituted $C_3$-$C_6$ cycloalkyl, or substituted or unsubstituted 3 to 6 membered heterocycloalkyl. In embodiments, $R^{22}$ is independently hydrogen, substituted or unsubstituted $C_1$-$C_4$ alkyl, or substituted or unsubstituted 2 to 6 membered heteroalkyl. In embodiments, $R^{22}$ is independently hydrogen, or substituted or unsubstituted $C_1$-$C_4$ alkyl. In embodiments, $R^{22}$ is substituted or unsubstituted $C_1$-$C_2$ alkyl. In embodiments, $R^{22}$ is unsubstituted $C_1$-$C_2$ alkyl. In embodiments, $R^{22}$ is —$CH_3$ or —$CH_2CH_3$. In embodiments, $R^{22}$ is hydrogen.

In embodiments, $R^8$ is hydrogen, —OH, —$OCH_3$, —$OCH_2CH_3$, —C(O)H, —C(O)$CH_3$, —C(O)OH, —C(O)$OCH_3$, —OC(O)H, —OC(O)$CH_3$, —OC(O)OH or —OC(O)$OCH_3$. In embodiments, $R^8$ is hydrogen, —OH, —$OCH_3$, —$OCH_2CH_3$, —C(O)H, —C(O)$CH_3$, —C(O)OH, —C(O)$OCH_3$, —OC(O)H, or —OC(O)$CH_3$. In embodiments, $R^8$ is hydrogen, —OH, —$OCH_3$, —$OCH_2CH_3$, —C(O)H, —C(O)$CH_3$, —C(O)OH, or —C(O)$OCH_3$. In embodiments, $R^8$ is hydrogen, —OH, —$OCH_3$, —$OCH_2CH_3$, —C(O)H, or —C(O)$CH_3$. In embodiments, $R^8$ is hydrogen, —OH, or —$OCH_3$. In embodiments, $R^8$ is hydrogen. In embodiments, $R^8$ is —OH. In embodiments, $R^8$ is —$OCH_3$. In embodiments, $R^8$ is —C(O)H. In embodiments, $R^8$ is —C(O)$CH_3$. In embodiments, $R^8$ is —C(O)OH. In embodiments, $R^8$ is —C(O)$OCH_3$.

In embodiments, the chiral carbon where $R^8$ is attached has (S) stereochemistry. In embodiments, the chiral carbon where $R^8$ is attached has (R) stereochemistry.

In embodiments, $R^9$ is hydrogen, —$OR^{23}$, —C(O)$R^{23}$, —C(O)$OR^{23}$, —OC(O)$R^{23}$, or —OC(O)$OR^{23}$. In embodiments, $R^9$ is hydrogen, —$OR^{23}$, —C(O)$R^{23}$, or —C(O)$OR^{23}$. In embodiments, $R^9$ is hydrogen, —$OR^{23}$, or —C(O)$OR^{23}$. In embodiments, $R^9$ is hydrogen. In embodiments, $R^9$ is —$OR^{23}$. In embodiments, $R^9$ is —C(O)$OR^{23}$.

In embodiments, $R^{23}$ is independently hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{23}$ is independently hydrogen, substituted or unsubstituted $C_1$-$C_4$ alkyl, substituted or unsubstituted 2 to 6 membered heteroalkyl, substituted or unsubstituted $C_3$-$C_6$ cycloalkyl, or substituted or unsubstituted 3 to 6 membered heterocycloalkyl. In embodiments, $R^{23}$ is independently hydrogen, substituted or unsubstituted $C_1$-$C_4$ alkyl, or substituted or unsubstituted 2 to 6 membered heteroalkyl. In embodiments, $R^{23}$ is independently hydrogen, or substituted or unsubstituted $C_1$-$C_4$ alkyl. In embodiments, $R^{23}$ is substituted or unsubstituted $C_1$-$C_2$ alkyl. In embodiments, $R^{23}$ is unsubstituted $C_1$-$C_2$ alkyl. In embodiments, $R^{23}$ is —$CH_3$ or —$CH_2CH_3$. In embodiments, $R^{23}$ is hydrogen.

In embodiments, $R^9$ is hydrogen, —OH, —$OCH_3$, —$OCH_2CH_3$, —C(O)H, —C(O)$CH_3$, —C(O)OH, —C(O)$OCH_3$, —OC(O)H, —OC(O)$CH_3$, —OC(O)OH or —OC(O)$OCH_3$. In embodiments, $R^9$ is hydrogen, —OH, —$OCH_3$, —$OCH_2CH_3$, —C(O)H, —C(O)$CH_3$, —C(O)OH, —C(O)$OCH_3$, —OC(O)H, or —OC(O)$CH_3$. In embodiments, $R^9$ is hydrogen, —OH, —$OCH_3$, —$OCH_2CH_3$, —C(O)H, —C(O)$CH_3$, —C(O)OH, or —C(O)$OCH_3$. In embodiments, $R^9$ is hydrogen, —OH, —$OCH_3$, —$OCH_2CH_3$, —C(O)H, or —C(O)$CH_3$. In embodiments, $R^9$ is hydrogen, —OH, or —$OCH_3$. In embodiments, $R^9$ is hydrogen. In embodiments, $R^9$ is —OH. In embodiments, $R^9$ is —$OCH_3$. In embodiments, $R^9$ is —C(O)H. In embodiments, $R^9$ is —C(O)$CH_3$. In embodiments, $R^9$ is —C(O)OH. In embodiments, $R^9$ is —C(O)$OCH_3$.

In embodiments, the chiral carbon where $R^9$ is attached has (S) stereochemistry. In embodiments, the chiral carbon where $R^9$ is attached has (R) stereochemistry.

In embodiments, $R^{20}$, $R^{21}$, $R^{22}$, and $R^{23}$ are each independently hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{20}$, $R^{21}$, $R^{22}$, and $R^{23}$ are each independently hydrogen, or substituted or unsubstituted $C_1$-$C_6$ alkyl. In embodiments, $R^{20}$, $R^{21}$, $R^{22}$, and $R^{23}$ are each independently hydrogen or substituted or unsubstituted $C_1$-$C_4$ alkyl. In embodiments, $R^{20}$, $R^{21}$, $R^{22}$, and $R^{23}$ are each independently hydrogen or unsubstituted $C_1$-$C_4$ alkyl. In embodiments, $R^{20}$, $R^{21}$, $R^{22}$, and $R^{23}$ are each independently hydrogen or unsubstituted $C_1$-$C_2$ alkyl. In embodiments, $R^{20}$, $R^{21}$, $R^{22}$, and $R^{23}$ are each independently hydrogen, —$CH_3$ or —$CH_2CH_3$. In embodiments, $R^{20}$, $R^{21}$, $R^{22}$, and $R^{23}$ are each independently hydrogen, or —$CH_3$. In embodiments, $R^{20}$, $R^{21}$, $R^{22}$, and $R^{23}$ are hydrogen. In embodiments, $R^{20}$, $R^{21}$, $R^{22}$, and $R^{23}$ are —$CH_3$.

In embodiments, at least one of $R^6$, $R^7$, $R^8$, and $R^9$ is —$OCH_3$. In embodiments, $R^6$, R and $R^8$ are hydrogen and $R^9$ is —$OCH_3$. In embodiments, $R^6$, $R^7$ and $R^9$ are hydrogen and $R^8$ is —$OCH_3$. In embodiments, $R^6$, $R^8$ and $R^9$ are hydrogen and $R^7$ is —$OCH_3$. In embodiments, $R^7$, $R^8$ and $R^9$ are hydrogen and $R^6$ is-$OCH_3$. In embodiments, at least one of $R^6$, $R^7$, $R^8$, and $R^9$ is hydrogen. In embodiments, $R^6$, $R^7$ and $R^8$ are —$OCH_3$ and $R^9$ is hydrogen. In embodiments, $R^6$, $R^7$ and $R^9$ are —$OCH_3$ and $R^8$ is hydrogen. In embodiments, $R^6$, $R^8$ and $R^9$ are —$OCH_3$ and $R^7$ is hydrogen. In embodiments, $R^7$, $R^8$ and $R^9$ are —$OCH_3$ and $R^6$ is hydrogen. In embodiments, at least two of $R^6$, $R^7$, $R^8$ and $R^9$ are —$OCH_3$ and the others are hydrogen. In embodiments, $R^6$ and $R^7$ are —$OCH_3$ and $R^8$ and $R^9$ are hydrogen. In embodiments, $R^6$ and $R^8$ are —$OCH_3$ and $R^7$ and $R^9$ are hydrogen. In embodiments, $R^6$ and $R^9$ are —$OCH_3$ and $R^7$ and $R^8$ are hydrogen. In embodiments, $R^7$ and $R^8$ are —$OCH_3$ and $R^6$ and $R^9$ are hydrogen. In embodiments, $R^8$ and $R^9$ are —$OCH_3$ and $R^6$ and $R^7$ are hydrogen. In embodiments, $R^6$, $R^7$, $R^8$ and $R^9$ are —$OCH_3$. In embodiments, $R^6$, $R^7$, $R^8$ and $R^9$ are hydrogen. In embodiments, at least one of $R^6$, $R^7$, $R^8$ and $R^9$ is —OH. In embodiments, at least two of $R^6$, $R^7$, $R^8$ and $R^9$ are —OH. In embodiments, at least one of $R^6$, $R^7$, $R^8$ and $R^9$ is hydrogen. In embodiments, at least two of $R^6$, $R^7$, $R^8$ and $R^9$ are hydrogen.

In embodiments, $R^1$ is hydrogen, $R^{1A}$-substituted or unsubstituted alkyl (e.g., $C_1$-$C_8$, $C_1$-$C_6$, $C_1$-$C_4$, or $C_1$-$C_2$), —C(O)$R^{11}$, or —C(O)OR", (e.g. —C(O)H, —C(O)$CH_3$, —C(O)OH, or —C(O)$OCH_3$). In embodiments, $R^1$ is hydrogen, $R^{1A}$-substituted or unsubstituted $C_1$-$C_6$ alkyl, —C(O)$R^{11}$, or —C(O)OR$^{11}$ (e.g. —C(O)H, —C(O)$CH_3$, —C(O)OH, or —C(O)$OCH_3$). In embodiments, $R^1$ is hydrogen, $R^{1A}$-substituted or unsubstituted $C_1$-$C_4$ alkyl, —C(O)H, —C(O)$CH_3$, —C(O)OH, or —C(O)$OCH_3$. In embodiments, $R^1$ is hydrogen, unsubstituted $C_1$-$C_4$ alkyl, —C(O)H, —C(O)$CH_3$, —C(O)OH, or —C(O)$OCH_3$.

$R^{1A}$ is independently oxo, halogen, —$CX^{1A}_3$, —$CHX^{1A}_2$, —$CH_2X^{1A}$, —$OCX^{1A}_3$, —$OCH_2X^{1A}$, —$OCHX^{1A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{1B}$-substituted or unsubstituted alkyl (e.g., $C_1$-$C_8$, $C_1$-$C_6$, $C_1$-$C_4$, or $C_1$-$C_2$), $R^{1B}$-substituted or unsubstituted heteroalkyl (e.g., 2 to 8 membered, 2 to 6 membered, 4 to 6 membered, 2 to 3 membered, or 4 to 5 membered), $R^{1B}$-substituted or unsubstituted cycloalkyl (e.g., $C_3$-$C_8$, $C_3$-$C_6$, $C_4$-$C_6$, or $C_5$-$C_6$), $R^{1B}$-substituted or unsubstituted heterocycloalkyl (e.g., 3 to 8 membered, 3 to 6 membered, 4 to 6 membered, 4 to 5 membered, or 5 to 6 membered), $R^{1B}$-substituted or unsubstituted aryl (e.g., $C_6$-$C_{12}$, $C_6$-$C_{10}$, or phenyl), or $R^{1B}$-substituted or unsubstituted heteroaryl (e.g., 5 to 12 membered, 5 to 10 membered, 5 to 9 membered, or 5 to 6 membered). $X^{1A}$ is independently —F, —Cl, —Br, or —I. In embodiments, $R^{1A}$ is independently oxo, halogen, —$CX^{1A}_3$, —$CHX^{1A}_2$, —$CH_2X^{1A}$, —$OCX^{1A}_3$, —$OCH_2X^{1A}$, —$OCHX^{1A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{1A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{1B}$-substituted or unsubstituted $C_1$-$C_6$ alkyl, $R^{1B}$-substituted or unsubstituted 2 to 6 membered heteroalkyl, $R^{1B}$-substituted or unsubstituted $C_3$-$C_6$ cycloalkyl, $R^{1B}$-substituted or unsubstituted 3 to 6 membered heterocycloalkyl, $R^{1B}$-substituted or unsubstituted phenyl, or $R^{1B}$-substituted or unsubstituted 5 to 6 membered heteroaryl. In embodiments, $R^{1A}$ is independently oxo, halogen, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl.

In embodiments, $R^2$ is hydrogen, halogen (e.g. —F, —Cl, —Br, or —I), $R^{2A}$-substituted or unsubstituted alkyl (e.g., C$_1$-C$_8$, C$_1$-C$_6$, C$_1$-C$_4$, or C$_1$-C$_2$), —OR$^{12}$, —OC(O)R$^{12}$, —OC(O)OR$^{12}$, or —OC(O)NR$^{12}$R$^{13}$ (e.g. —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$). In embodiments, $R^2$ is hydrogen, halogen (e.g. —F, —Cl, —Br, or —I), unsubstituted alkyl (e.g., C$_1$-C$_8$, C$_1$-C$_6$, C$_1$-C$_4$, or C$_1$-C$_2$), —OR$^{12}$, —OC(O)R$^{12}$, —OC(O)OR$^{12}$, or —OC(O)NR$^{12}$R (e.g. —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$). In embodiments, $R^2$ is hydrogen, halogen, $R^{2A}$-substituted or unsubstituted C$_1$-C$_6$ alkyl, —OR$^{12}$, —OC(O)R$^{12}$, —OC(O)OR$^{12}$, or —OC(O)NR$^{12}$R$^{13}$ (e.g. —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$). In embodiments, $R^2$ is hydrogen, halogen (e.g. —F, —Cl, —Br, or —I), $R^{2A}$-substituted or unsubstituted C$_1$-C$_4$ alkyl, —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$. In embodiments, $R^2$ is hydrogen, halogen (e.g. —F, —Cl, —Br, or —I), unsubstituted C$_1$-C$_4$ alkyl, —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$.

$R^{2A}$ is independently oxo, halogen, —CX$^{2A}_3$, —CHX$^{2A}_2$, —CH$_2$X$^{2A}$, —OCX$^{2A}_3$, —OCH$_2$X$^{2A}$, —OCHX$^{2A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, $R^{2B}$-substituted or unsubstituted alkyl (e.g., C$_1$-C$_8$, C$_1$-C$_6$, C$_1$-C$_4$, or C$_1$-C$_2$), $R^{2B}$-substituted or unsubstituted heteroalkyl (e.g., 2 to 8 membered, 2 to 6 membered, 4 to 6 membered, 2 to 3 membered, or 4 to 5 membered), $R^{2B}$-substituted or unsubstituted cycloalkyl (e.g., C$_3$-C$_8$, C$_3$-C$_6$, C$_4$-C$_6$, or C$_5$-C$_6$), $R^{2B}$-substituted or unsubstituted heterocycloalkyl (e.g., 3 to 8 membered, 3 to 6 membered, 4 to 6 membered, 4 to 5 membered, or 5 to 6 membered), $R^{2B}$-substituted or unsubstituted aryl (e.g., C$_6$-C$_{12}$, C$_6$-C$_{10}$, or phenyl), or $R^{2B}$-substituted or unsubstituted heteroaryl (e.g., 5 to 12 membered, 5 to 10 membered, 5 to 9 membered, or 5 to 6 membered). $X^{2A}$ is independently —F, —Cl, —Br, or —I. In embodiments, $R^{2A}$ is independently oxo, halogen, —CX$^{2A}_3$, —CHX$^{2A}_2$, —CH$_2$X$^{2A}$, —OCX$^{2A}_3$, —OCH$_2$X$^{2A}$, —OCHX$^{2A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). In embodiments, $R^{2A}$ is independently oxo, halogen, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, $R^{2B}$-substituted or unsubstituted C$_1$-C$_6$ alkyl, $R^{2B}$-substituted or unsubstituted 2 to 6 membered heteroalkyl, $R^{2B}$-substituted or unsubstituted C$_3$-C$_6$ cycloalkyl, $R^{2B}$-substituted or unsubstituted 3 to 6 membered heterocycloalkyl, $R^{2B}$-substituted or unsubstituted phenyl, or $R^{2B}$-substituted or unsubstituted 5 to 6 membered heteroaryl. In embodiments, $R^{2A}$ is independently oxo, halogen, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl.

In embodiments, $R^3$ is hydrogen, halogen (e.g. —F, —Cl, —Br, or —I), $R^{3A}$-substituted or unsubstituted alkyl (e.g., C$_1$-C$_8$, C$_1$-C$_6$, C$_1$-C$_4$, or C$_1$-C$_2$), —OR$^{14}$, —OC(O)R$^{14}$, —OC(O)OR$^{14}$, or —OC(O)NR$^{14}$R$^{15}$ (e.g. —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$). In embodiments, $R^3$ is hydrogen, halogen (e.g. —F, —Cl, —Br, or —I), unsubstituted alkyl (e.g., C$_1$-C$_8$, C$_1$-C$_6$, C$_1$-C$_4$, or C$_1$-C$_2$), —OR$^4$, —OC(O)R$^{14}$, —OC(O)OR$^{14}$, or —OC(O)NR$^{14}$R$^{15}$ (e.g. —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$). In embodiments, $R^3$ is hydrogen, halogen (e.g. —F, —Cl, —Br, or —I), $R^{3A}$-substituted or unsubstituted C$_1$-C$_6$ alkyl, —OR$^{14}$, —OC(O)R$^{14}$, —OC(O)OR$^{14}$, or —OC(O)NR$^{14}$R$^{15}$ (e.g. —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$). In embodiments, $R^3$ is hydrogen, halogen (e.g. —F, —Cl, —Br, or —I), $R^{3A}$-substituted or unsubstituted C$_1$-C$_4$ alkyl, —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$. In embodiments, $R^3$ is hydrogen, halogen (e.g. —F, —Cl, —Br, or —I), unsubstituted C$_1$-C$_4$ alkyl, —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$.

$R^{3A}$ is independently oxo, halogen, —CX$^{3A}_3$, —CHX$^{3A}_2$, —CH$_2$X$^{3A}$, —OCX$^{3A}_3$, —OCH$_2$X$^{3A}$, —OCHX$^{3A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, $R^{3B}$-substituted or unsubstituted alkyl (e.g., $C_1$-$C_8$, $C_1$-$C_6$, $C_1$-$C_4$, or $C_1$-$C_2$), $R^{3B}$-substituted or unsubstituted heteroalkyl (e.g., 2 to 8 membered, 2 to 6 membered, 4 to 6 membered, 2 to 3 membered, or 4 to 5 membered), $R^{3B}$-substituted or unsubstituted cycloalkyl (e.g., $C_3$-$C_8$, $C_3$-$C_6$, $C_4$-$C_6$, or $C_5$-$C_6$), $R^{3B}$-substituted or unsubstituted heterocycloalkyl (e.g., 3 to 8 membered, 3 to 6 membered, 4 to 6 membered, 4 to 5 membered, or 5 to 6 membered), $R^{3B}$-substituted or unsubstituted aryl (e.g., $C_6$-$C_{12}$, $C_6$-$C_{10}$, or phenyl), or $R^{3B}$-substituted or unsubstituted heteroaryl (e.g., 5 to 12 membered, 5 to 10 membered, 5 to 9 membered, or 5 to 6 membered). $X^{3A}$ is independently —F, —Cl, —Br, or —I. In embodiments, $R^{3A}$ is independently oxo, halogen, —$CX^{3A}_3$, —$CHX^{3A}_2$, —$CH_2X^{3A}$, —$OCX^{3A}_3$, —$OCH_2X^{3A}$, —$OCHX^{3A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{3A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{3B}$-substituted or unsubstituted $C_1$-$C_6$ alkyl, $R^{3B}$-substituted or unsubstituted 2 to 6 membered heteroalkyl, $R^{3B}$-substituted or unsubstituted $C_3$-$C_6$ cycloalkyl, $R^{3B}$-substituted or unsubstituted 3 to 6 membered heterocycloalkyl, $R^{3B}$-substituted or unsubstituted phenyl, or $R^{3B}$-substituted or unsubstituted 5 to 6 membered heteroaryl. In embodiments, $R^{3A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, $R^4$ is hydrogen, halogen (e.g. —F, —Cl, —Br, or —I), $R^{4A}$-substituted or unsubstituted alkyl (e.g., $C_1$-$C_8$, $C_1$-$C_6$, $C_1$-$C_4$, or $C_1$-$C_2$), —$OR^{16}$, —$OC(O)R^{16}$, —$OC(O)OR^{16}$, or —$OC(O)NR^{16}R^{17}$ (e.g. —OH, —$OCH_3$, —$OCH_2CH_3$, —$OC(O)H$, —$OC(O)CH_3$, —$OC(O)OH$, —$OC(O)OCH_3$, —$OC(O)NH_2$ or —$OC(O)NHCH_3$). In embodiments, $R^4$ is hydrogen, halogen (e.g. —F, —Cl, —Br, or —I), unsubstituted alkyl (e.g., $C_1$-$C_8$, $C_1$-$C_6$, $C_1$-$C_4$, or $C_1$-$C_2$), —$OR^{16}$, —$OC(O)R^{16}$, —$OC(O)OR^{16}$, or —$OC(O)NR^{16}R^{17}$ (e.g. —OH, —$OCH_3$, —$OCH_2CH_3$, —$OC(O)H$, —$OC(O)CH_3$, —$OC(O)OH$, —$OC(O)OCH_3$, —$OC(O)NH_2$ or —$OC(O)NHCH_3$). In embodiments, $R^4$ is hydrogen, halogen (e.g. —F, —Cl, —Br, or —I), $R^{4A}$-substituted or unsubstituted $C_1$-$C_6$ alkyl, —$OR^{16}$, —$OC(O)R^{16}$, —$OC(O)OR^{16}$, or —$OC(O)NR^{16}R^{17}$ (e.g. —OH, —$OCH_3$, —$OCH_2CH_3$, —$OC(O)H$, —$OC(O)CH_3$, —$OC(O)OH$, —$OC(O)OCH_3$, —$OC(O)NH_2$ or —$OC(O)NHCH_3$). In embodiments, $R^4$ is hydrogen, halogen (e.g. —F, —Cl, —Br, or —I), $R^{4A}$-substituted or unsubstituted $C_1$-$C_4$ alkyl, —OH, —$OCH_3$, —$OCH_2CH_3$, —$OC(O)H$, —$OC(O)CH_3$, —$OC(O)OH$, —$OC(O)OCH_3$, —$OC(O)NH_2$ or —$OC(O)NHCH_3$. In embodiments, $R^4$ is hydrogen, halogen (e.g. —F, —Cl, —Br, or —I), unsubstituted $C_1$-$C_4$ alkyl, —OH, —$OCH_3$, —$OCH_2CH_3$, —$OC(O)H$, —$OC(O)CH_3$, —$OC(O)OH$, —$OC(O)OCH_3$, —$OC(O)NH_2$ or —$OC(O)NHCH_3$.

$R^{4A}$ is independently oxo, halogen, —$CX^{4A}_3$, —$CHX^{4A}_2$, —$CH_2X^{4A}$, —$OCX^{4A}_3$, —$OCH_2X^{4A}$, —$OCHX^{4A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{4B}$-substituted or unsubstituted alkyl (e.g., $C_1$-$C_8$, $C_1$-$C_6$, $C_1$-$C_4$, or $C_1$-$C_2$), $R^{4B}$-substituted or unsubstituted heteroalkyl (e.g., 2 to 8 membered, 2 to 6 membered, 4 to 6 membered, 2 to 3 membered, or 4 to 5 membered), $R^{4B}$-substituted or unsubstituted cycloalkyl (e.g., $C_3$-$C_8$, $C_3$-$C_6$, $C_4$-$C_6$, or $C_5$-$C_6$), $R^{4B}$-substituted or unsubstituted heterocycloalkyl (e.g., 3 to 8 membered, 3 to 6 membered, 4 to 6 membered, 4 to 5 membered, or 5 to 6 membered), $R^{4B}$-substituted or unsubstituted aryl (e.g., $C_6$-$C_{12}$, $C_6$-$C_{10}$, or phenyl), or $R^{4B}$-substituted or unsubstituted heteroaryl (e.g., 5 to 12 membered, 5 to 10 membered, 5 to 9 membered, or 5 to 6 membered). $X^{4A}$ is independently —F, —Cl, —Br, or —I. In embodiments, $R^{4A}$ is independently oxo, halogen, —$CX^{4A}_3$, —$CHX^{4A}_2$, —$CH_2X^{4A}$, —$OCX^{4A}_3$, —$OCH_2X^{4A}$, —$OCHX^{4A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{4A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{4B}$-substituted or unsubstituted $C_1$-$C_6$ alkyl, $R^{4B}$-substituted or unsubstituted 2 to 6 membered heteroalkyl, $R^{4B}$-substituted or unsubstituted $C_3$-$C_6$ cycloalkyl, $R^{4B}$-substituted or unsubstituted 3 to 6 membered heterocycloalkyl, $R^{4B}$-substituted or unsubstituted phenyl, or $R^{4B}$-substituted or unsubstituted 5 to 6 membered heteroaryl. In embodiments, $R^{4A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl.

In embodiments, R$^5$ is hydrogen, halogen (e.g. —F, —Cl, —Br, or —I), R$^{5A}$-substituted or unsubstituted alkyl (e.g., C$_1$-C$_8$, C$_1$-C$_6$, C$_1$-C$_4$, or C$_1$-C$_2$), —OR$^8$, —OC(O)R$^8$, —OC(O)OR$^{18}$, or —OC(O)NR$^8$R$^{19}$ (e.g. —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$). In embodiments, R$^5$ is hydrogen, halogen (e.g. —F, —Cl, —Br, or —I), unsubstituted alkyl (e.g., C$_1$-C$_8$, C$_1$-C$_6$, C$_1$-C$_4$, or C$_1$-C$_2$), —OR$^8$, —OC(O)R$^{18}$, —OC(O)OR$^{18}$, or —OC(O)NR$^{18}$R$^{19}$ (e.g. —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$). In embodiments, R$^5$ is hydrogen, halogen (e.g. —F, —Cl, —Br, or —I), R$^{5A}$-substituted or unsubstituted C$_1$-C$_6$ alkyl, —OR$^8$, —OC(O)R$^{18}$, —OC(O)OR$^{18}$, or —OC(O)NR$^{18}$R$^{19}$ (e.g. —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$). In embodiments, R$^5$ is hydrogen, halogen (e.g. —F, —Cl, —Br, or —I), R$^{5A}$-substituted or unsubstituted C$_1$-C$_4$ alkyl, —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$. In embodiments, R$^5$ is hydrogen, halogen (e.g. —F, —Cl, —Br, or —I), unsubstituted C$_1$-C$_4$ alkyl, —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$.

R$^{5A}$ is independently oxo, halogen, —CX$^{5A}_3$, —CHX$^{5A}_2$, —CH$_2$X$^{5A}$, —OCX$^{5A}_3$, —OCH$_2$X$^{5A}$, —OCHX$^{5A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{5B}$-substituted or unsubstituted alkyl (e.g., C$_1$-C$_8$, C$_1$-C$_6$, C$_1$-C$_4$, or C$_1$-C$_2$), R$^{5B}$-substituted or unsubstituted heteroalkyl (e.g., 2 to 8 membered, 2 to 6 membered, 4 to 6 membered, 2 to 3 membered, or 4 to 5 membered), R$^{5B}$-substituted or unsubstituted cycloalkyl (e.g., C$_3$-C$_8$, C$_3$-C$_6$, C$_4$-C$_6$, or C$_5$-C$_6$), R$^{5B}$-substituted or unsubstituted heterocycloalkyl (e.g., 3 to 8 membered, 3 to 6 membered, 4 to 6 membered, 4 to 5 membered, or 5 to 6 membered), R$^{5B}$-substituted or unsubstituted aryl (e.g., C$_6$-C$_{12}$, C$_6$-C$_{10}$, or phenyl), or R$^{5B}$-substituted or unsubstituted heteroaryl (e.g., 5 to 12 membered, 5 to 10 membered, 5 to 9 membered, or 5 to 6 membered). X$^{5A}$ is independently —F, —Cl, —Br, or —I. In embodiments, R$^{5A}$ is independently oxo, halogen, —CX$^{5A}_3$, —CHX$^{5A}_2$, —CH$_2$X$^{5A}$, —OCX$^{5A}_3$, —OCH$_2$X$^{5A}$, —OCHX$^{5A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). In embodiments, R$^{5A}$ is independently oxo, halogen, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, R$^{5B}$-substituted or unsubstituted C$_1$-C$_6$ alkyl, R$^{5B}$-substituted or unsubstituted 2 to 6 membered heteroalkyl, R$^{5B}$-substituted or unsubstituted C$_3$-C$_6$ cycloalkyl, R$^{5B}$-substituted or unsubstituted 3 to 6 membered heterocycloalkyl, R$^{5B}$-substituted or unsubstituted phenyl, or R$^{5B}$-substituted or unsubstituted 5 to 6 membered heteroaryl. In embodiments, R$^{5A}$ is independently oxo, halogen, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl.

In embodiments, R$^{10}$ is independently hydrogen, R$^{10A}$-substituted or unsubstituted alkyl (e.g., C$_1$-C$_8$, C$_1$-C$_6$, C$_1$-C$_4$, or C$_1$-C$_2$), —OR$^{24}$, —OC(O)R$^{24}$, —OC(O)OR$^{24}$, or —OC(O)NR$^{24}$R$^{25}$ (e.g. —OH, —OCH$_3$, —OC(O)H, —OC(O)CH$_3$, —OC(O)OH, —OC(O)OCH$_3$, —OC(O)NH$_2$, or —OC(O)NHCH$_3$). In embodiments, R$^{10}$ is independently hydrogen, R$^{10A}$-substituted or unsubstituted C$_1$-C$_6$ alkyl, —OR$^{24}$, —OC(O)R$^{24}$, —OC(O)OR$^{24}$, or —OC(O)NR$^{24}$R$^{25}$ (e.g. —OH, —OCH$_3$, —OC(O)H, —OC(O)CH$_3$, —OC(O)OH, —OC(O)OCH$_3$, —OC(O)NH$_2$, or —OC(O)NHCH$_3$). In embodiments, R$^{10}$ is independently hydrogen, R$^{10A}$-substituted or unsubstituted C$_1$-C$_4$ alkyl, OH, —OCH$_3$, —C(O)H, —C(O)CH$_3$, —C(O)OH, —C(O)OCH$_3$, —OC(O)H, —OC(O)CH$_3$, —OC(O)NH$_2$, or —OC(O)NHCH$_3$). In embodiments, R$^{10}$ is independently hydrogen, unsubstituted C$_1$-C$_4$ alkyl, —OH, —OCH$_3$, —OC(O)H, —OC(O)CH$_3$, —OC(O)OH, —OC(O)OCH$_3$, —OC(O)NH$_2$, or —OC(O)NHCH$_3$.

R$^{10A}$ is independently oxo, halogen, —CX$^{10A}_3$, —CHX$^{10A}_2$, —CH$_2$X$^{10A}$, —OCX$^{1A}_3$, —OCH$_2$X$^{10A}$, —OCHX$^{10A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{10B}$-substituted or unsubstituted alkyl (e.g., C$_1$-C$_8$, C$_1$-C$_6$, C$_1$-C$_4$, or C$_1$-C$_2$), R$^{10B}$-substituted or unsubstituted heteroalkyl (e.g., 2 to 8 membered, 2 to 6 membered, 4 to 6 membered, 2 to 3 membered, or 4 to 5 membered), R$^{10B}$-substituted or unsubstituted cycloalkyl (e.g., C$_3$-C$_8$, C$_3$-C$_6$, C$_4$-C$_6$, or C$_5$-C$_6$), R$^{10B}$-substituted or unsubstituted heterocycloalkyl (e.g., 3 to 8 membered, 3 to 6 membered, 4 to 6 membered, 4 to 5 membered, or 5 to 6 membered), R$^{10B}$-substituted or unsubstituted aryl (e.g., C$_6$-C$_{12}$, C$_6$-C$_{10}$, or phenyl), or R$^{10B}$-substituted or unsubstituted heteroaryl (e.g., 5 to 12 membered, 5 to 10 membered, 5 to 9 membered, or 5 to 6 membered). $X^{10A}$ is independently —F, —Cl, —Br, or —I. In embodiments, $R^{10A}$ is independently oxo, halogen, —$CX^{10A}_3$, —$CHX^{10A}_2$, —$CH_2X^{10A}$, —$OCX^{10A}_3$, —$OCH_2X^{10A}$, —$OCHX^{10A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{10A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC (O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{10B}$-substituted or unsubstituted $C_1$-$C_6$ alkyl, $R^{10B}$-substituted or unsubstituted 2 to 6 membered heteroalkyl, $R^{10B}$-substituted or unsubstituted $C_3$-$C_6$ cycloalkyl, $R^{10B}$-substituted or unsubstituted 3 to 6 membered heterocycloalkyl, $R^{10B}$-substituted or unsubstituted phenyl, or $R^{10B}$-substituted or unsubstituted 5 to 6 membered heteroaryl. In embodiments, $R^{10A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, $R^{11}$ is independently hydrogen, $R^{11A}$-substituted or unsubstituted alkyl (e.g., $C_1$-$C_8$, $C_1$-$C_6$, $C_1$-$C_4$, or $C_1$-$C_2$), $R^{11A}$-substituted or unsubstituted heteroalkyl (e.g., 2 to 8 membered, 2 to 6 membered, 4 to 6 membered, 2 to 3 membered, or 4 to 5 membered), $R^{11A}$-substituted or unsubstituted cycloalkyl (e.g., $C_3$-$C_8$, $C_3$-$C_6$, $C_4$-$C_6$, or $C_5$-$C_6$), $R^{11A}$-substituted or unsubstituted heterocycloalkyl (e.g., 3 to 8 membered, 3 to 6 membered, 4 to 6 membered, 4 to 5 membered, or 5 to 6 membered), $R^{11A}$-substituted or unsubstituted aryl (e.g., $C_6$-$C_{12}$, $C_6$-$C_{10}$, or phenyl), or $R^{11A}$-substituted or unsubstituted heteroaryl (e.g., 5 to 12 membered, 5 to 10 membered, 5 to 9 membered, or 5 to 6 membered). In embodiments, $R^{11}$ is independently hydrogen, unsubstituted $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{11}$ is independently hydrogen, $R^{11A}$-substituted or unsubstituted $C_1$-$C_6$ alkyl, $R^{11A}$-substituted or unsubstituted 2 to 6 membered heteroalkyl, $R^{11A}$-substituted or unsubstituted $C_3$-$C_6$ cycloalkyl, $R^{11A}$-substituted or unsubstituted 3 to 6 membered heterocycloalkyl, $R^{11A}$-substituted or unsubstituted phenyl, or $R^{11A}$-substituted or unsubstituted 5 to 6 membered heteroaryl. In embodiments, $R^{11}$ is independently hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. $R^{11A}$ is independently oxo, halogen, —$CX^{11A}_3$, —$CHX^{11A}_2$, —$CH_2X^{11A}$, —$OCX^{11A}_3$, —$OCH_2X^{11A}$, —$OCHX^{11A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{11B}$-substituted or unsubstituted alkyl (e.g., $C_1$-$C_8$, $C_1$-$C_6$, $C_1$-$C_4$, or $C_1$-$C_2$), $R^{11B}$-substituted or unsubstituted heteroalkyl (e.g., 2 to 8 membered, 2 to 6 membered, 4 to 6 membered, 2 to 3 membered, or 4 to 5 membered), $R^{11B}$-substituted or unsubstituted cycloalkyl (e.g., $C_3$-$C_8$, $C_3$-$C_6$, $C_4$-$C_6$, or $C_5$-$C_6$), $R^{11B}$-substituted or unsubstituted heterocycloalkyl (e.g., 3 to 8 membered, 3 to 6 membered, 4 to 6 membered, 4 to 5 membered, or 5 to 6 membered), $R^{11B}$-substituted or unsubstituted aryl (e.g., $C_6$-$C_{12}$, $C_6$-$C_{10}$, or phenyl), or $R^{11B}$-substituted or unsubstituted heteroaryl (e.g., 5 to 12 membered, 5 to 10 membered, 5 to 9 membered, or 5 to 6 membered). $X^{11A}$ is independently —F, —Cl, —Br, or —I. In embodiments, $R^{11A}$ is independently oxo, halogen, —$CX^{11A}_3$, —$CHX^{11A}_2$, —$CH_2X^{11A}$, —$OCX^{11A}_3$, —$OCH_2X^{11A}$, —$OCHX^{11A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{11A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{11B}$-substituted or unsubstituted $C_1$-$C_6$ alkyl, $R^{11B}$-substituted or unsubstituted 2 to 6 membered heteroalkyl, $R^{11B}$-substituted or unsubstituted $C_3$-$C_6$ cycloalkyl, $R^{11B}$-substituted or unsubstituted 3 to 6 membered heterocycloalkyl, $R^{11B}$-substituted or unsubstituted phenyl, or $R^{11B}$-substituted or unsubstituted 5 to 6 membered heteroaryl. In embodiments, $R^{11A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl.

In embodiments, R$^{12}$ is independently hydrogen, R$^{12A}$-substituted or unsubstituted alkyl (e.g., C$_1$-C$_8$, C$_1$-C$_6$, C$_1$-C$_4$, or C$_1$-C$_2$), R$^{12A}$-substituted or unsubstituted heteroalkyl (e.g., 2 to 8 membered, 2 to 6 membered, 4 to 6 membered, 2 to 3 membered, or 4 to 5 membered), R$^{12A}$-substituted or unsubstituted cycloalkyl (e.g., C$_3$-C$_8$, C$_3$-C$_6$, C$_4$-C$_6$, or C$_5$-C$_6$), R$^{12A}$-substituted or unsubstituted heterocycloalkyl (e.g., 3 to 8 membered, 3 to 6 membered, 4 to 6 membered, 4 to 5 membered, or 5 to 6 membered), R$^{12A}$-substituted or unsubstituted aryl (e.g., C$_6$-C$_{12}$, C$_6$-C$_{10}$, or phenyl), or R$^{12A}$-substituted or unsubstituted heteroaryl (e.g., 5 to 12 membered, 5 to 10 membered, 5 to 9 membered, or 5 to 6 membered). In embodiments, R$^{12}$ is independently hydrogen, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). In embodiments, R$^{12}$ is independently hydrogen, R$^{12A}$-substituted or unsubstituted C$_1$-C$_6$ alkyl, R$^{12A}$-substituted or unsubstituted 2 to 6 membered heteroalkyl, R$^{12A}$-substituted or unsubstituted C$_3$-C$_6$ cycloalkyl, R$^{12A}$-substituted or unsubstituted 3 to 6 membered heterocycloalkyl, R$^{12A}$-substituted or unsubstituted phenyl, or R$^{12A}$-substituted or unsubstituted 5 to 6 membered heteroaryl. In embodiments, R$^{12}$ is independently hydrogen, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl.

R$^{12A}$ is independently oxo, halogen, —CX$^{12A}_3$, —CHX$^{12A}_2$, —CH$_2$X$^{12A}$, —OCX$^{12A}_3$, —OCH$_2$X$^{12A}$, —OCHX$^{12A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{12B}$-substituted or unsubstituted alkyl (e.g., C$_1$-C$_8$, C$_1$-C$_6$, C$_1$-C$_4$, or C$_1$-C$_2$), R$^{12B}$-substituted or unsubstituted heteroalkyl (e.g., 2 to 8 membered, 2 to 6 membered, 4 to 6 membered, 2 to 3 membered, or 4 to 5 membered), R$^{12B}$-substituted or unsubstituted cycloalkyl (e.g., C$_3$-C$_8$, C$_3$-C$_6$, C$_4$-C$_6$, or C$_5$-C$_6$), R$^{12B}$-substituted or unsubstituted heterocycloalkyl (e.g., 3 to 8 membered, 3 to 6 membered, 4 to 6 membered, 4 to 5 membered, or 5 to 6 membered), R$^{12B}$-substituted or unsubstituted aryl (e.g., C$_6$-C$_{12}$, C$_6$-C$_{10}$, or phenyl), or R$^{12B}$-substituted or unsubstituted heteroaryl (e.g., 5 to 12 membered, 5 to 10 membered, 5 to 9 membered, or 5 to 6 membered). X$^{12A}$ is independently —F, —Cl, —Br, or —I. In embodiments, R$^{12A}$ is independently oxo, halogen, —CX$^{12A}_3$, —CHX$^{12A}_2$, —CH$_2$X$^{12A}$, —OCX$^{12A}_3$, —OCH$_2$X$^{12A}$, —OCHX$^{12A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). In embodiments, R$^{12A}$ is independently oxo, halogen, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, R$^{12B}$-substituted or unsubstituted C$_1$-C$_6$ alkyl, R$^{12B}$-substituted or unsubstituted 2 to 6 membered heteroalkyl, R$^{12B}$-substituted or unsubstituted C$_3$-C$_6$ cycloalkyl, R$^{12B}$-substituted or unsubstituted 3 to 6 membered heterocycloalkyl, R$^{12B}$ substituted or unsubstituted phenyl, or R$^{12B}$-substituted or unsubstituted 5 to 6 membered heteroaryl. In embodiments, R$^{12A}$ is independently oxo, halogen, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl.

In embodiments, R$^{13}$ is independently hydrogen, R$^{13A}$-substituted or unsubstituted alkyl (e.g., C$_1$-C$_8$, C$_1$-C$_6$, C$_1$-C$_4$, or C$_1$-C$_2$), R$^{13A}$-substituted or unsubstituted heteroalkyl (e.g., 2 to 8 membered, 2 to 6 membered, 4 to 6 membered, 2 to 3 membered, or 4 to 5 membered), R$^{13A}$-substituted or unsubstituted cycloalkyl (e.g., C$_3$-C$_8$, C$_3$-C$_6$, C$_4$-C$_6$, or C$_5$-C$_6$), R$^{13A}$-substituted or unsubstituted heterocycloalkyl (e.g., 3 to 8 membered, 3 to 6 membered, 4 to 6 membered, 4 to 5 membered, or 5 to 6 membered), R$^{13A}$-substituted or unsubstituted aryl (e.g., C$_6$-C$_{12}$, C$_6$-C$_{10}$, or phenyl), or R$^{13A}$-substituted or unsubstituted heteroaryl (e.g., 5 to 12 membered, 5 to 10 membered, 5 to 9 membered, or 5 to 6 membered). In embodiments, R$^{13}$ is independently hydrogen, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). In embodiments, R$^{13}$ is independently hydrogen, R$^{13A}$-substituted or unsubstituted C$_1$-C$_6$ alkyl, R$^{13A}$-substituted or unsubstituted 2 to 6 membered heteroalkyl, R$^{13A}$-substituted or unsubstituted C$_3$-C$_6$ cycloalkyl, R$^{13A}$-substituted or unsubstituted 3 to 6 membered heterocycloalkyl, R$^{13A}$-substituted or unsubstituted phenyl, or R$^{13A}$-substituted or unsubstituted 5 to 6 membered heteroaryl. In embodiments, R$^{13}$ is independently hydrogen, unsubstituted C$_1$-C$_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

$R^{13A}$ is independently oxo, halogen, $-CX^{13A}_3$, $-CHX^{13A}_2$, $-CH_2X^{13A}$, $-OCX^{13A}_3$, $-OCH_2X^{13A}$, $-OCHX^{13A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{13B}$-substituted or unsubstituted alkyl (e.g., $C_1$-$C_8$, $C_1$-$C_6$, $C_1$-$C_4$, or $C_1$-$C_2$), $R^{13B}$-substituted or unsubstituted heteroalkyl (e.g., 2 to 8 membered, 2 to 6 membered, 4 to 6 membered, 2 to 3 membered, or 4 to 5 membered), $R^{13B}$-substituted or unsubstituted cycloalkyl (e.g., $C_3$-$C_8$, $C_3$-$C_6$, $C_4$-$C_6$, or $C_5$-$C_6$), $R^{13B}$-substituted or unsubstituted heterocycloalkyl (e.g., 3 to 8 membered, 3 to 6 membered, 4 to 6 membered, 4 to 5 membered, or 5 to 6 membered), $R^{13B}$-substituted or unsubstituted aryl (e.g., $C_6$-$C_{12}$, $C_6$-$C_{10}$, or phenyl), or $R^{13B}$-substituted or unsubstituted heteroaryl (e.g., 5 to 12 membered, 5 to 10 membered, 5 to 9 membered, or 5 to 6 membered). $X^{13A}$ is independently $-F$, $-Cl$, $-Br$, or $-I$. In embodiments, $R^{13A}$ is independently oxo, halogen, $-CX^{13A}_3$, $-CHX^{13A}_2$, $-CH_2X^{13A}$, $-OCX^{13A}_3$, $-OCH_2X^{13A}$, $-OCHX^{13A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{13A}$ is independently oxo, halogen, $-CF_3$, $-CHF_2$, $-CH_2F$, $-CCl_3$, $-CHCl_2$, $-CH_2Cl$, $-CBr_3$, $-CHBr_2$, $-CH_2Br$, $-CI_3$, $-CHI_2$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $R^{13B}$-substituted or unsubstituted $C_1$-$C_6$ alkyl, $R^{13B}$-substituted or unsubstituted 2 to 6 membered heteroalkyl, $R^{13B}$-substituted or unsubstituted $C_3$-$C_6$ cycloalkyl, $R^{13B}$-substituted or unsubstituted 3 to 6 membered heterocycloalkyl, $R^{13B}$-substituted or unsubstituted phenyl, or $R^{13B}$-substituted or unsubstituted 5 to 6 membered heteroaryl. In embodiments, $R^{13A}$ is independently oxo, halogen, $-CF_3$, $-CHF_2$, $-CH_2F$, $-CCl_3$, $-CHCl_2$, $-CH_2Cl$, $-CBr_3$, $-CHBr_2$, $-CH_2Br$, $-CI_3$, $-CHI_2$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, $R^{14}$ is independently hydrogen, $R^{14A}$-substituted or unsubstituted alkyl (e.g., $C_1$-$C_8$, $C_1$-$C_6$, $C_1$-$C_4$, or $C_1$-$C_2$), $R^{14A}$-substituted or unsubstituted heteroalkyl (e.g., 2 to 8 membered, 2 to 6 membered, 4 to 6 membered, 2 to 3 membered, or 4 to 5 membered), $R^{14A}$-substituted or unsubstituted cycloalkyl (e.g., $C_3$-$C_8$, $C_3$-$C_6$, $C_4$-$C_6$, or $C_5$-$C_6$), $R^{14A}$-substituted or unsubstituted heterocycloalkyl (e.g., 3 to 8 membered, 3 to 6 membered, 4 to 6 membered, 4 to 5 membered, or 5 to 6 membered), $R^{14A}$-substituted or unsubstituted aryl (e.g., $C_6$-$C_{12}$, $C_6$-$C_{10}$, or phenyl), or $R^{14A}$-substituted or unsubstituted heteroaryl (e.g., 5 to 12 membered, 5 to 10 membered, 5 to 9 membered, or 5 to 6 membered). In embodiments, $R^{14}$ is independently hydrogen, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{14}$ is independently hydrogen, $R^{14A}$-substituted or unsubstituted $C_1$-$C_6$ alkyl, $R^{14A}$-substituted or unsubstituted 2 to 6 membered heteroalkyl, $R^{14A}$-substituted or unsubstituted $C_3$-$C_6$ cycloalkyl, $R^{14A}$-substituted or unsubstituted 3 to 6 membered heterocycloalkyl, $R^{14A}$-substituted or unsubstituted phenyl, or $R^{14A}$-substituted or unsubstituted 5 to 6 membered heteroaryl. In embodiments, $R^{14}$ is independently hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

$R^{14A}$ is independently oxo, halogen, $-CX^{14A}_3$, $-CHX^{14A}_2$, $-CH_2X^{14A}$, $-OCX^{14A}_3$, $-OCH_2X^{14A}$, $-OCHX^{14A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{14B}$-substituted or unsubstituted alkyl (e.g., $C_1$-$C_8$, $C_1$-$C_6$, $C_1$-$C_4$, or $C_1$-$C_2$), $R^{14B}$-substituted or unsubstituted heteroalkyl (e.g., 2 to 8 membered, 2 to 6 membered, 4 to 6 membered, 2 to 3 membered, or 4 to 5 membered), $R^{14B}$-substituted or unsubstituted cycloalkyl (e.g., $C_3$-$C_8$, $C_3$-$C_6$, $C_4$-$C_6$, or $C_5$-$C_6$), $R^{14B}$-substituted or unsubstituted heterocycloalkyl (e.g., 3 to 8 membered, 3 to 6 membered, 4 to 6 membered, 4 to 5 membered, or 5 to 6 membered), $R^{14B}$-substituted or unsubstituted aryl (e.g., $C_6$-$C_{12}$, $C_6$-$C_{10}$, or phenyl), or $R^{14B}$-substituted or unsubstituted heteroaryl (e.g., 5 to 12 membered, 5 to 10 membered, 5 to 9 membered, or 5 to 6 membered). $X^{14A}$ is independently $-F$, $-Cl$, $-Br$, or $-I$. In embodiments, $R^{14A}$ is independently oxo, halogen, $-CX^{14A}_3$, $-CHX^{14A}_2$, $-CH_2X^{14A}$, $-OCX^{14A}_3$, $-OCH_2X^{14A}$, $-OCHX^{14A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{14A}$ is independently oxo, halogen, $-CF_3$, $-CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{14B}$-substituted or unsubstituted $C_1$-$C_6$ alkyl, $R^{14B}$-substituted or unsubstituted 2 to 6 membered heteroalkyl, $R^{14B}$-substituted or unsubstituted $C_3$-$C_6$ cycloalkyl, $R^{14B}$-substituted or unsubstituted 3 to 6 membered heterocycloalkyl, $R^{14B}$-substituted or unsubstituted phenyl, or $R^{14B}$-substituted or unsubstituted 5 to 6 membered heteroaryl. In embodiments, $R^{14A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, $R^{15}$ is independently hydrogen, $R^{15A}$-substituted or unsubstituted alkyl (e.g., $C_1$-$C_8$, $C_1$-$C_6$, $C_1$-$C_4$, or $C_1$-$C_2$), $R^{15A}$-substituted or unsubstituted heteroalkyl (e.g., 2 to 8 membered, 2 to 6 membered, 4 to 6 membered, 2 to 3 membered, or 4 to 5 membered), $R^{15A}$-substituted or unsubstituted cycloalkyl (e.g., $C_3$-$C_8$, $C_3$-$C_6$, $C_4$-$C_6$, or $C_5$-$C_6$), $R^{15A}$-substituted or unsubstituted heterocycloalkyl (e.g., 3 to 8 membered, 3 to 6 membered, 4 to 6 membered, 4 to 5 membered, or 5 to 6 membered), $R^{15A}$-substituted or unsubstituted aryl (e.g., $C_6$-$C_{12}$, $C_6$-$C_{10}$, or phenyl), or $R^{15A}$-substituted or unsubstituted heteroaryl (e.g., 5 to 12 membered, 5 to 10 membered, 5 to 9 membered, or 5 to 6 membered). In embodiments, $R^{15}$ is independently hydrogen, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{15}$ is independently hydrogen, $R^{15A}$-substituted or unsubstituted $C_1$-$C_6$ alkyl, $R^{15A}$-substituted or unsubstituted 2 to 6 membered heteroalkyl, $R^{15A}$-substituted or unsubstituted $C_3$-$C_6$ cycloalkyl, $R^{15A}$-substituted or unsubstituted 3 to 6 membered heterocycloalkyl, $R^{15A}$-substituted or unsubstituted phenyl, or $R^{15A}$-substituted or unsubstituted 5 to 6 membered heteroaryl. In embodiments, $R^{15}$ is independently hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

$R^{15A}$ is independently oxo, halogen, —$CX^{15A}_3$, —$CHX^{15A}_2$, —$CH_2X^{15A}$, —$OCX^{15A}_3$, —$OCH_2X^{15A}$, —$OCHX^{15A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{15B}$-substituted or unsubstituted alkyl (e.g., $C_1$-$C_8$, $C_1$-$C_6$, $C_1$-$C_4$, or $C_1$-$C_2$), $R^{15B}$-substituted or unsubstituted heteroalkyl (e.g., 2 to 8 membered, 2 to 6 membered, 4 to 6 membered, 2 to 3 membered, or 4 to 5 membered), $R^{15B}$-substituted or unsubstituted cycloalkyl (e.g., $C_3$-$C_8$, $C_3$-$C_6$, $C_4$-$C_6$, or $C_5$-$C_6$), $R^{15B}$-substituted or unsubstituted heterocycloalkyl (e.g., 3 to 8 membered, 3 to 6 membered, 4 to 6 membered, 4 to 5 membered, or 5 to 6 membered), $R^{15B}$-substituted or unsubstituted aryl (e.g., $C_6$-$C_{12}$, $C_6$-$C_{10}$, or phenyl), or $R^{15B}$-substituted or unsubstituted heteroaryl (e.g., 5 to 12 membered, 5 to 10 membered, 5 to 9 membered, or 5 to 6 membered). $X^{15A}$ is independently —F, —Cl, —Br, or —I. In embodiments, $R^{15A}$ is independently oxo, halogen, —$CX^{15A}_3$, —$CHX^{15A}_2$, —$CH_2X^{15A}$, —$OCX^{15A}_3$, —$OCH_2X^{15A}$, —$OCHX^{15A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{15A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{15B}$-substituted or unsubstituted $C_1$-$C_6$ alkyl, $R^{15B}$-substituted or unsubstituted 2 to 6 membered heteroalkyl, $R^{15B}$-substituted or unsubstituted $C_3$-$C_6$ cycloalkyl, $R^{15B}$-substituted or unsubstituted 3 to 6 membered heterocycloalkyl, $R^{15B}$-substituted or unsubstituted phenyl, or $R^{15B}$-substituted or unsubstituted 5 to 6 membered heteroaryl. In embodiments, $R^{15A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, $R^{16}$ is independently hydrogen, $R^{16A}$-substituted or unsubstituted alkyl (e.g., $C_1$-$C_8$, $C_1$-$C_6$, $C_1$-$C_4$, or $C_1$-$C_2$), $R^{16A}$-substituted or unsubstituted heteroalkyl (e.g., 2 to 8 membered, 2 to 6 membered, 4 to 6 membered, 2 to 3 membered, or 4 to 5 membered), $R^{16A}$-substituted or unsubstituted cycloalkyl (e.g., $C_3$-$C_8$, $C_3$-$C_6$, $C_4$-$C_6$, or $C_5$-$C_6$), $R^{16A}$-substituted or unsubstituted heterocycloalkyl (e.g., 3 to 8 membered, 3 to 6 membered, 4 to 6 membered, 4 to 5 membered, or 5 to 6 membered), $R^{16A}$-substituted or unsubstituted aryl (e.g., $C_6$-$C_{12}$, $C_6$-$C_{10}$, or phenyl), or $R^{16A}$-substituted or unsubstituted heteroaryl (e.g., 5 to 12 membered, 5 to 10 membered, 5 to 9 membered, or 5 to 6 membered). In embodiments, $R^{16}$ is independently hydrogen, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{16}$ is independently hydrogen, $R^{16A}$-substituted or unsubstituted $C_1$-$C_6$ alkyl, $R^{16A}$-substituted or unsubstituted 2 to 6 membered heteroalkyl, $R^{16A}$-substituted or unsubstituted $C_3$-$C_6$ cycloalkyl, $R^{16A}$-substituted or unsubstituted 3 to 6 membered heterocycloalkyl, $R^{16A}$-substituted or unsubstituted phenyl, or $R^{16A}$-substituted or unsubstituted 5 to 6 membered heteroaryl. In embodiments, $R^{16}$ is independently hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

$R^{16A}$ is independently oxo, halogen, $-CX^{16A}_3$, $-CHX^{16A}_2$, $-CH_2X^{16A}$, $-OCX^{16A}_3$, $-OCH_2X^{16A}$, $-OCHX^{16A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{16B}$-substituted or unsubstituted alkyl (e.g., $C_1$-$C_8$, $C_1$-$C_6$, $C_1$-$C_4$, or $C_1$-$C_2$), $R^{16B}$-substituted or unsubstituted heteroalkyl (e.g., 2 to 8 membered, 2 to 6 membered, 4 to 6 membered, 2 to 3 membered, or 4 to 5 membered), $R^{16B}$-substituted or unsubstituted cycloalkyl (e.g., $C_3$-$C_8$, $C_3$-$C_6$, $C_4$-$C_6$, or $C_5$-$C_6$), $R^{16B}$-substituted or unsubstituted heterocycloalkyl (e.g., 3 to 8 membered, 3 to 6 membered, 4 to 6 membered, 4 to 5 membered, or 5 to 6 membered), $R^{16B}$-substituted or unsubstituted aryl (e.g., $C_6$-$C_{12}$, $C_6$-$C_{10}$, or phenyl), or $R^{16B}$-substituted or unsubstituted heteroaryl (e.g., 5 to 12 membered, 5 to 10 membered, 5 to 9 membered, or 5 to 6 membered). $X^{16A}$ is independently $-F$, $-Cl$, $-Br$, or $-I$. In embodiments, $R^{16A}$ is independently oxo, halogen, $-CX^{16A}_3$, $-CHX^{16A}_2$, $-CH_2X^{16A}$, $-OCX^{16A}_3$, $-OCH_2X^{16A}$, $-OCHX^{16A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{16A}$ is independently oxo, halogen, $-CF_3$, $-CHF_2$, $-CH_2F$, $-CCl_3$, $-CHCl_2$, $-CH_2Cl$, $-CBr_3$, $-CHBr_2$, $-CH_2Br$, $-CI_3$, $-CHI_2$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $R^{16B}$-substituted or unsubstituted $C_1$-$C_6$ alkyl, $R^{16B}$-substituted or unsubstituted 2 to 6 membered heteroalkyl, $R^{16B}$-substituted or unsubstituted $C_3$-$C_6$ cycloalkyl, $R^{16B}$-substituted or unsubstituted 3 to 6 membered heterocycloalkyl, $R^{16B}$-substituted or unsubstituted phenyl, or $R^{16B}$-substituted or unsubstituted 5 to 6 membered heteroaryl. In embodiments, $R^{16A}$ is independently oxo, halogen, $-CF_3$, $-CHF_2$, $-CH_2F$, $-CCl_3$, $-CHCl_2$, $-CH_2Cl$, $-CBr_3$, $-CHBr_2$, $-CH_2Br$, $-CI_3$, $-CHI_2$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, $R^{17}$ is independently hydrogen, $R^{17A}$-substituted or unsubstituted alkyl (e.g., $C_1$-$C_8$, $C_1$-$C_6$, $C_1$-$C_4$, or $C_1$-$C_2$), $R^{17A}$-substituted or unsubstituted heteroalkyl (e.g., 2 to 8 membered, 2 to 6 membered, 4 to 6 membered, 2 to 3 membered, or 4 to 5 membered), $R^{17A}$-substituted or unsubstituted cycloalkyl (e.g., $C_3$-$C_8$, $C_3$-$C_6$, $C_4$-$C_6$, or $C_5$-$C_6$), $R^{17A}$-substituted or unsubstituted heterocycloalkyl (e.g., 3 to 8 membered, 3 to 6 membered, 4 to 6 membered, 4 to 5 membered, or 5 to 6 membered), $R^{17A}$-substituted or unsubstituted aryl (e.g., $C_6$-$C_{12}$, $C_6$-$C_{10}$, or phenyl), or $R^{17A}$-substituted or unsubstituted heteroaryl (e.g., 5 to 12 membered, 5 to 10 membered, 5 to 9 membered, or 5 to 6 membered). In embodiments, $R^{17}$ is independently hydrogen, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{17}$ is independently hydrogen, $R^{17A}$-substituted or unsubstituted $C_1$-$C_6$ alkyl, $R^{17A}$-substituted or unsubstituted 2 to 6 membered heteroalkyl, $R^{17A}$-substituted or unsubstituted $C_3$-$C_6$ cycloalkyl, $R^{17A}$-substituted or unsubstituted 3 to 6 membered heterocycloalkyl, $R^{17A}$-substituted or unsubstituted phenyl, or $R^{17A}$-substituted or unsubstituted 5 to 6 membered heteroaryl. In embodiments, $R^{17}$ is independently hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

$R^{17A}$ is independently oxo, halogen, $-CX^{17A}_3$, $-CHX^{17A}_2$, $-CH_2X^{17A}$, $-OCX^{17A}_3$, $-OCH_2X^{17A}$, $-OCHX^{17A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{17B}$-substituted or unsubstituted alkyl (e.g., $C_1$-$C_8$, $C_1$-$C_6$, $C_1$-$C_4$, or $C_1$-$C_2$), $R^{17B}$-substituted or unsubstituted heteroalkyl (e.g., 2 to 8 membered, 2 to 6 membered, 4 to 6 membered, 2 to 3 membered, or 4 to 5 membered), $R^{17B}$-substituted or unsubstituted cycloalkyl (e.g., $C_3$-$C_8$, $C_3$-$C_6$, $C_4$-$C_6$, or $C_5$-$C_6$), $R^{17B}$-substituted or unsubstituted heterocycloalkyl (e.g., 3 to 8 membered, 3 to 6 membered, 4 to 6 membered, 4 to 5 membered, or 5 to 6 membered), $R^{17B}$-substituted or unsubstituted aryl (e.g., $C_6$-$C_{12}$, $C_6$-$C_{10}$, or phenyl), or $R^{17B}$-substituted or unsubstituted heteroaryl (e.g., 5 to 12 membered, 5 to 10 membered, 5 to 9 membered, or 5 to 6 membered). $X^{17A}$ is independently —F, —Cl, —Br, or —I. In embodiments, $R^{17A}$ is independently oxo, halogen, —$CX^{17A}_3$, —$CHX^{17A}_2$, —$CH_2X^{17A}$, —$OCX^{17A}_3$, —$OCH_2X^{17A}$, —$OCHX^{17A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{17A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHOH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{17B}$-substituted or unsubstituted $C_1$-$C_6$ alkyl, $R^{17B}$-substituted or unsubstituted 2 to 6 membered heteroalkyl, $R^{17B}$-substituted or unsubstituted $C_3$-$C_6$ cycloalkyl, $R^{17B}$-substituted or unsubstituted 3 to 6 membered heterocycloalkyl, $R^{17B}$-substituted or unsubstituted phenyl, or $R^{17B}$-substituted or unsubstituted 5 to 6 membered heteroaryl. In embodiments, $R^{17A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, $R^{18}$ is independently hydrogen, $R^{18A}$-substituted or unsubstituted alkyl (e.g., $C_1$-$C_8$, $C_1$-$C_6$, $C_1$-$C_4$, or $C_1$-$C_2$), $R^{18A}$-substituted or unsubstituted heteroalkyl (e.g., 2 to 8 membered, 2 to 6 membered, 4 to 6 membered, 2 to 3 membered, or 4 to 5 membered), $R^{18A}$-substituted or unsubstituted cycloalkyl (e.g., $C_3$-$C_8$, $C_3$-$C_6$, $C_4$-$C_6$, or $C_5$-$C_6$), $R^{18A}$-substituted or unsubstituted heterocycloalkyl (e.g., 3 to 8 membered, 3 to 6 membered, 4 to 6 membered, 4 to 5 membered, or 5 to 6 membered), $R^{18A}$-substituted or unsubstituted aryl (e.g., $C_6$-$C_{12}$, $C_6$-$C_{10}$, or phenyl), or $R^{18A}$-substituted or unsubstituted heteroaryl (e.g., 5 to 12 membered, 5 to 10 membered, 5 to 9 membered, or 5 to 6 membered). In embodiments, $R^{18}$ is independently hydrogen, $R^{18A}$-substituted or unsubstituted $C_1$-$C_6$ alkyl, $R^{18A}$-substituted or unsubstituted 2 to 6 membered heteroalkyl, $R^{18A}$-substituted or unsubstituted $C_3$-$C_6$ cycloalkyl, $R^{18A}$-substituted or unsubstituted 3 to 6 membered heterocycloalkyl, $R^{18A}$-substituted or unsubstituted phenyl, or $R^{18A}$-substituted or unsubstituted 5 to 6 membered heteroaryl. In embodiments, $R^{18}$ is independently hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

$R^{18A}$ is independently oxo, halogen, —$CX^{18A}_3$, —$CHX^{18A}_2$, —$CH_2X^{18A}$, —$OCX^{18A}_3$, —$OCH_2X^{18A}$, —$OCHX^{8A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{18B}$-substituted or unsubstituted alkyl (e.g., $C_1$-$C_8$, $C_1$-$C_6$, $C_1$-$C_4$, or $C_1$-$C_2$), $R^{18B}$-substituted or unsubstituted heteroalkyl (e.g., 2 to 8 membered, 2 to 6 membered, 4 to 6 membered, 2 to 3 membered, or 4 to 5 membered), $R^{18B}$-substituted or unsubstituted cycloalkyl (e.g., $C_3$-$C_8$, $C_3$-$C_6$, $C_4$-$C_6$, or $C_5$-$C_6$), $R^{18B}$-substituted or unsubstituted heterocycloalkyl (e.g., 3 to 8 membered, 3 to 6 membered, 4 to 6 membered, 4 to 5 membered, or 5 to 6 membered), $R^{18B}$-substituted or unsubstituted aryl (e.g., $C_6$-$C_{12}$, $C_6$-$C_{10}$, or phenyl), or $R^{18B}$-substituted or unsubstituted heteroaryl (e.g., 5 to 12 membered, 5 to 10 membered, 5 to 9 membered, or 5 to 6 membered). $X^{18A}$ is independently —F, —Cl, —Br, or —I. In embodiments, $R^{18A}$ is independently oxo, halogen, —$CX^{18A}_3$, —$CHX^{18A}_2$, —$CH_2X^{18A}$, —$OCX^{18A}_3$, —$OCH_2X^{18A}$, —$OCHX^{18A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{18A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{18B}$-substituted or unsubstituted $C_1$-$C_6$ alkyl, $R^{18B}$-substituted or unsubstituted 2 to 6 membered heteroalkyl, $R^{18B}$-substituted or unsubstituted $C_3$-$C_6$ cycloalkyl, $R^{18B}$-substituted or unsubstituted 3 to 6 membered heterocycloalkyl, $R^{18B}$-substituted or unsubstituted phenyl, or $R^{18B}$-substituted or unsubstituted 5 to 6 membered heteroaryl. In embodiments, $R^{18A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl.

In embodiments, R$^{19}$ is independently hydrogen, R$^{19A}$-substituted or unsubstituted alkyl (e.g., C$_1$-C$_8$, C$_1$-C$_6$, C$_1$-C$_4$, or C$_1$-C$_2$), R$^{19A}$-substituted or unsubstituted heteroalkyl (e.g., 2 to 8 membered, 2 to 6 membered, 4 to 6 membered, 2 to 3 membered, or 4 to 5 membered), R$^{19A}$-substituted or unsubstituted cycloalkyl (e.g., C$_3$-C$_8$, C$_3$-C$_6$, C$_4$-C$_6$, or C$_5$-C$_6$), R$^{19A}$-substituted or unsubstituted heterocycloalkyl (e.g., 3 to 8 membered, 3 to 6 membered, 4 to 6 membered, 4 to 5 membered, or 5 to 6 membered), R$^{19A}$-substituted or unsubstituted aryl (e.g., C$_6$-C$_{12}$, C$_6$-C$_{10}$, or phenyl), or R$^{19A}$-substituted or unsubstituted heteroaryl (e.g., 5 to 12 membered, 5 to 10 membered, 5 to 9 membered, or 5 to 6 membered). In embodiments, R$^{19}$ is independently hydrogen, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). In embodiments, R$^{19}$ is independently hydrogen, R$^{19A}$-substituted or unsubstituted C$_1$-C$_6$ alkyl, R$^{19A}$-substituted or unsubstituted 2 to 6 membered heteroalkyl, R$^{19A}$-substituted or unsubstituted C$_3$-C$_6$ cycloalkyl, R$^{19A}$-substituted or unsubstituted 3 to 6 membered heterocycloalkyl, R$^{19A}$-substituted or unsubstituted phenyl, or R$^{19A}$-substituted or unsubstituted 5 to 6 membered heteroaryl. In embodiments, R$^{19}$ is independently hydrogen, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl.

R$^{19A}$ is independently oxo, halogen, —CX$^{19A}{}_3$, —CHX$^{19A}{}_2$, —CH$_2$X$^{19A}$, —OCX$^{19A}{}_3$, —OCH$_2$X$^{19A}$, —OCHX$^{19A}{}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{19B}$-substituted or unsubstituted alkyl (e.g., C$_1$-C$_8$, C$_1$-C$_6$, C$_1$-C$_4$, or C$_1$-C$_2$), R$^{19B}$-substituted or unsubstituted heteroalkyl (e.g., 2 to 8 membered, 2 to 6 membered, 4 to 6 membered, 2 to 3 membered, or 4 to 5 membered), R$^{19B}$-substituted or unsubstituted cycloalkyl (e.g., C$_3$-C$_8$, C$_3$-C$_6$, C$_4$-C$_6$, or C$_5$-C$_6$), R$^{19B}$-substituted or unsubstituted heterocycloalkyl (e.g., 3 to 8 membered, 3 to 6 membered, 4 to 6 membered, 4 to 5 membered, or 5 to 6 membered), R$^{19B}$-substituted or unsubstituted aryl (e.g., C$_6$-C$_{12}$, C$_6$-C$_{10}$, or phenyl), or R$^{19B}$-substituted or unsubstituted heteroaryl (e.g., 5 to 12 membered, 5 to 10 membered, 5 to 9 membered, or 5 to 6 membered). X$^{19A}$ is independently —F, —Cl, —Br, or —I. In embodiments, R$^{19A}$ is independently oxo, halogen, —CX$^{19A}{}_3$, —CHX$^{19A}{}_2$, —CH$_2$X$^{19A}$, —OCX$^{19A}{}_3$, —OCH$_2$X$^{19A}$, —OCHX$^{19A}{}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). In embodiments, R$^{19A}$ is independently oxo, halogen, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —CN, —OH, —NH$_2$, —COOH, —CONH$_2$, —NO$_2$, —SH, —SO$_3$H, —SO$_4$H, —SO$_2$NH$_2$, —NNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, R$^{19B}$-substituted or unsubstituted C$_1$-C$_6$ alkyl, R$^{19B}$-substituted or unsubstituted 2 to 6 membered heteroalkyl, R$^{19B}$-substituted or unsubstituted C$_3$-C$_6$ cycloalkyl, R$^{19B}$-substituted or unsubstituted 3 to 6 membered heterocycloalkyl, R$^{19B}$-substituted or unsubstituted phenyl, or R$^{19B}$-substituted or unsubstituted 5 to 6 membered heteroaryl. In embodiments, R$^{19A}$ is independently oxo, halogen, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl.

In embodiments, R$^{20}$ is independently hydrogen, R$^{20A}$-substituted or unsubstituted alkyl (e.g., C$_1$-C$_8$, C$_1$-C$_6$, C$_1$-C$_4$, or C$_1$-C$_2$), R$^{20A}$-substituted or unsubstituted heteroalkyl (e.g., 2 to 8 membered, 2 to 6 membered, 4 to 6 membered, 2 to 3 membered, or 4 to 5 membered), R$^{20A}$-substituted or unsubstituted cycloalkyl (e.g., C$_3$-C$_8$, C$_3$-C$_6$, C$_4$-C$_6$, or C$_5$-C$_6$), R$^{20A}$-substituted or unsubstituted heterocycloalkyl (e.g., 3 to 8 membered, 3 to 6 membered, 4 to 6 membered, 4 to 5 membered, or 5 to 6 membered), R$^{20A}$-substituted or unsubstituted aryl (e.g., C$_6$-C$_{12}$, C$_6$-C$_{10}$, or phenyl), or R$^{20A}$-substituted or unsubstituted heteroaryl (e.g., 5 to 12 membered, 5 to 10 membered, 5 to 9 membered, or 5 to 6 membered). In embodiments, R$^{20}$ is independently hydrogen, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). In embodiments, R$^{20}$ is independently hydrogen, R$^{20A}$-substituted or unsubstituted C$_1$-C$_6$ alkyl, R$^{20A}$-substituted or unsubstituted 2 to 6 membered heteroalkyl, R$^{20A}$-substituted or unsubstituted C$_3$-C$_6$ cycloalkyl, R$^{20A}$-substituted or unsubstituted 3 to 6 membered heterocycloalkyl, R$^{20A}$-substituted or unsubstituted phenyl, or R$^{20A}$-substituted or unsubstituted 5 to 6 membered heteroaryl. In embodiments, $R^{20}$ is independently hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

$R^{20A}$ is independently oxo, halogen, —$CX^{20A}_3$, —$CHX^{20A}_2$, —$CH_2X^{20A}$, —$OCX^{20A}_3$, —$OCH_2X^{20A}$, —$OCHX^{20A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{20B}$-substituted or unsubstituted alkyl (e.g., $C_1$-$C_8$, $C_1$-$C_6$, $C_1$-$C_4$, or $C_1$-$C_2$), $R^{20B}$-substituted or unsubstituted heteroalkyl (e.g., 2 to 8 membered, 2 to 6 membered, 4 to 6 membered, 2 to 3 membered, or 4 to 5 membered), $R^{20B}$-substituted or unsubstituted cycloalkyl (e.g., $C_3$-$C_8$, $C_3$-$C_6$, $C_4$-$C_6$, or $C_5$-$C_6$), $R^{20B}$-substituted or unsubstituted heterocycloalkyl (e.g., 3 to 8 membered, 3 to 6 membered, 4 to 6 membered, 4 to 5 membered, or 5 to 6 membered), $R^{20B}$-substituted or unsubstituted aryl (e.g., $C_6$-$C_{12}$, $C_6$-$C_{10}$, or phenyl), or $R^{20B}$-substituted or unsubstituted heteroaryl (e.g., 5 to 12 membered, 5 to 10 membered, 5 to 9 membered, or 5 to 6 membered). $X^{20A}$ is independently —F, —Cl, —Br, or —I. In embodiments, $R^{20A}$ is independently oxo, halogen, —$CX^{20A}_3$, —$CHX^{20A}_2$, —$CH_2X^{20A}$, —$OCX^{20A}_3$, —$OCH_2X^{20A}$, —$OCHX^{20A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{20A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{20B}$-substituted or unsubstituted $C_1$-$C_6$ alkyl, $R^{20B}$-substituted or unsubstituted 2 to 6 membered heteroalkyl, $R^{20B}$-substituted or unsubstituted $C_3$-$C_6$ cycloalkyl, $R^{20B}$-substituted or unsubstituted 3 to 6 membered heterocycloalkyl, $R^{20B}$-substituted or unsubstituted phenyl, or $R^{20B}$-substituted or unsubstituted 5 to 6 membered heteroaryl. In embodiments, $R^{20A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, $R^{21}$ is independently hydrogen, $R^{21A}$-substituted or unsubstituted alkyl (e.g., $C_1$-$C_8$, $C_1$-$C_6$, $C_1$-$C_4$, or $C_1$-$C_2$), $R^{21A}$-substituted or unsubstituted heteroalkyl (e.g., 2 to 8 membered, 2 to 6 membered, 4 to 6 membered, 2 to 3 membered, or 4 to 5 membered), $R^{21A}$-substituted or unsubstituted cycloalkyl (e.g., $C_3$-$C_8$, $C_3$-$C_6$, $C_4$-$C_6$, or $C_5$-$C_6$), $R^{21A}$-substituted or unsubstituted heterocycloalkyl (e.g., 3 to 8 membered, 3 to 6 membered, 4 to 6 membered, 4 to 5 membered, or 5 to 6 membered), $R^{21A}$-substituted or unsubstituted aryl (e.g., $C_6$-$C_{12}$, $C_6$-$C_{10}$, or phenyl), or $R^{21A}$-substituted or unsubstituted heteroaryl (e.g., 5 to 12 membered, 5 to 10 membered, 5 to 9 membered, or 5 to 6 membered). In embodiments, $R^{21}$ is independently hydrogen, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{21}$ is independently hydrogen, $R^{21A}$-substituted or unsubstituted $C_1$-$C_6$ alkyl, $R^{21A}$-substituted or unsubstituted 2 to 6 membered heteroalkyl, $R^{21A}$-substituted or unsubstituted $C_3$-$C_6$ cycloalkyl, $R^{21A}$-substituted or unsubstituted 3 to 6 membered heterocycloalkyl, $R^{21A}$-substituted or unsubstituted phenyl, or $R^{21A}$-substituted or unsubstituted 5 to 6 membered heteroaryl. In embodiments, $R^{21}$ is independently hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

$R^{21A}$ is independently oxo, halogen, —$CX^{21A}_3$, —$CHX^{21A}_2$, —$CH_2X^{21A}$, —$OCX^{21A}_3$, —$OCH_2X^{21A}$, —$OCHX^{21A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{21B}$-substituted or unsubstituted alkyl (e.g., $C_1$-$C_8$, $C_1$-$C_6$, $C_1$-$C_4$, or $C_1$-$C_2$), $R^{21B}$-substituted or unsubstituted heteroalkyl (e.g., 2 to 8 membered, 2 to 6 membered, 4 to 6 membered, 2 to 3 membered, or 4 to 5 membered), $R^{21B}$-substituted or unsubstituted cycloalkyl (e.g., $C_3$-$C_8$, $C_3$-$C_6$, $C_4$-$C_6$, or $C_5$-$C_6$), $R^{21B}$-substituted or unsubstituted heterocycloalkyl (e.g., 3 to 8 membered, 3 to 6 membered, 4 to 6 membered, 4 to 5 membered, or 5 to 6 membered), $R^{21B}$-substituted or unsubstituted aryl (e.g., $C_6$-$C_{12}$, $C_6$-$C_{10}$, or phenyl), or $R^{21B}$-substituted or unsubstituted heteroaryl (e.g., 5 to 12 membered, 5 to 10 membered, 5 to 9 membered, or 5 to 6 membered). $X^{21A}$ is independently —F, —Cl, —Br, or —I. In embodiments, $R^{21A}$ is independently oxo, halogen, —$CX^{21A}_3$, —$CHX^{21A}_2$, —$CH_2X^{21A}$, —$OCX^{21A}_3$, —$OCH_2X^{21A}$, —$OCHX^{21A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{21A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{21B}$-substituted or unsubstituted $C_1$-$C_6$ alkyl, $R^{21B}$-substituted or unsubstituted 2 to 6 membered heteroalkyl, $R^{21B}$-substituted or unsubstituted $C_3$-$C_6$ cycloalkyl, $R^{21B}$-substituted or unsubstituted 3 to 6 membered heterocycloalkyl, $R^{21B}$-substituted or unsubstituted phenyl, or $R^{21B}$-substituted or unsubstituted 5 to 6 membered heteroaryl. In embodiments, $R^{21A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, $R^{22}$ is independently hydrogen, $R^{22A}$-substituted or unsubstituted alkyl (e.g., $C_1$-$C_8$, $C_1$-$C_6$, $C_1$-$C_4$, or $C_1$-$C_2$), $R^{22A}$-substituted or unsubstituted heteroalkyl (e.g., 2 to 8 membered, 2 to 6 membered, 4 to 6 membered, 2 to 3 membered, or 4 to 5 membered), $R^{22A}$-substituted or unsubstituted cycloalkyl (e.g., $C_3$-$C_8$, $C_3$-$C_6$, $C_4$-$C_6$, or $C_5$-$C_6$), $R^{22A}$-substituted or unsubstituted heterocycloalkyl (e.g., 3 to 8 membered, 3 to 6 membered, 4 to 6 membered, 4 to 5 membered, or 5 to 6 membered), $R^{22A}$-substituted or unsubstituted aryl (e.g., $C_6$-$C_{12}$, $C_6$-$C_{10}$, or phenyl), or $R^{22A}$-substituted or unsubstituted heteroaryl (e.g., 5 to 12 membered, 5 to 10 membered, 5 to 9 membered, or 5 to 6 membered). In embodiments, $R^{22}$ is independently hydrogen, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{22}$ is independently hydrogen, $R^{22A}$-substituted or unsubstituted $C_1$-$C_6$ alkyl, $R^{22A}$-substituted or unsubstituted 2 to 6 membered heteroalkyl, $R^{22A}$-substituted or unsubstituted $C_3$-$C_6$ cycloalkyl, $R^{22A}$-substituted or unsubstituted 3 to 6 membered heterocycloalkyl, $R^{22A}$-substituted or unsubstituted phenyl, or $R^{22A}$-substituted or unsubstituted 5 to 6 membered heteroaryl. In embodiments, $R^{22}$ is independently hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

$R^{22A}$ is independently oxo, halogen, —$CX^{22A}_3$, —$CHX^{22A}_2$, —$CH_2X^{22A}$, —$OCX^{22A}_3$, —$OCH_2X^{22A}$, —$OCHX^{22A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{22B}$-substituted or unsubstituted alkyl (e.g., $C_1$-$C_8$, $C_1$-$C_6$, $C_1$-$C_4$, or $C_1$-$C_2$), $R^{22B}$-substituted or unsubstituted heteroalkyl (e.g., 2 to 8 membered, 2 to 6 membered, 4 to 6 membered, 2 to 3 membered, or 4 to 5 membered), $R^{22B}$-substituted or unsubstituted cycloalkyl (e.g., $C_3$-$C_8$, $C_3$-$C_6$, $C_4$-$C_6$, or $C_5$-$C_6$), $R^{22B}$-substituted or unsubstituted heterocycloalkyl (e.g., 3 to 8 membered, 3 to 6 membered, 4 to 6 membered, 4 to 5 membered, or 5 to 6 membered), $R^{22B}$-substituted or unsubstituted aryl (e.g., $C_6$-$C_{12}$, $C_6$-$C_{10}$, or phenyl), or $R^{22B}$-substituted or unsubstituted heteroaryl (e.g., 5 to 12 membered, 5 to 10 membered, 5 to 9 membered, or 5 to 6 membered). $X^{22A}$ is independently —F, —Cl, —Br, or —I. In embodiments, $R^{22A}$ is independently oxo, halogen, —$CX^{22A}_3$, —$CHX^{22A}_2$, —$CH_2X^{22A}$, —$OCX^{22A}_3$, —$OCH_2X^{22A}$, —$OCHX^{22A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{22A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{22B}$-substituted or unsubstituted $C_1$-$C_6$ alkyl, $R^{22B}$-substituted or unsubstituted 2 to 6 membered heteroalkyl, $R^{22B}$-substituted or unsubstituted $C_3$-$C_6$ cycloalkyl, $R^{22B}$-substituted or unsubstituted 3 to 6 membered heterocycloalkyl, $R^{22B}$-substituted or unsubstituted phenyl, or $R^{22B}$-substituted or unsubstituted 5 to 6 membered heteroaryl. In embodiments, $R^{22A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, $R^{23}$ is independently hydrogen, $R^{23A}$-substituted or unsubstituted alkyl (e.g., $C_1$-$C_8$, $C_1$-$C_6$, $C_1$-$C_4$, or $C_1$-$C_2$), $R^{23A}$-substituted or unsubstituted heteroalkyl (e.g., 2 to 8 membered, 2 to 6 membered, 4 to 6 membered, 2 to 3 membered, or 4 to 5 membered), $R^{23A}$-substituted or unsubstituted cycloalkyl (e.g., $C_3$-$C_8$, $C_3$-$C_6$, $C_4$-$C_6$, or $C_5$-$C_6$), $R^{23A}$-substituted or unsubstituted heterocycloalkyl (e.g., 3 to 8 membered, 3 to 6 membered, 4 to 6 membered, 4 to 5 membered, or 5 to 6 membered), $R^{23A}$- substituted or unsubstituted aryl (e.g., $C_6$-$C_{12}$, $C_6$-$C_{10}$, or phenyl), or $R^{23A}$-substituted or unsubstituted heteroaryl (e.g., 5 to 12 membered, 5 to 10 membered, 5 to 9 membered, or 5 to 6 membered). In embodiments, $R^{23}$ is independently hydrogen, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{23}$ is independently hydrogen, $R^{23A}$-substituted or unsubstituted $C_1$-$C_6$ alkyl, $R^{23A}$-substituted or unsubstituted 2 to 6 membered heteroalkyl, $R^{23A}$-substituted or unsubstituted $C_3$-$C_6$ cycloalkyl, $R^{23A}$-substituted or unsubstituted 3 to 6 membered heterocycloalkyl, $R^{23A}$-substituted or unsubstituted phenyl, or $R^{23A}$-substituted or unsubstituted 5 to 6 membered heteroaryl. In embodiments, $R^{23}$ is independently hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

$R^{23A}$ is independently oxo, halogen, —$CX^{23A}_3$, —$CHX^{23A}_2$, —$CH_2X^{23A}$, —$OCX^{23A}_3$, —$OCH_2X^{23A}$, —$OCHX^{23A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{23B}$-substituted or unsubstituted alkyl (e.g., $C_1$-$C_8$, $C_1$-$C_6$, $C_1$-$C_4$, or $C_1$-$C_2$), $R^{23B}$-substituted or unsubstituted heteroalkyl (e.g., 2 to 8 membered, 2 to 6 membered, 4 to 6 membered, 2 to 3 membered, or 4 to 5 membered), $R^{23B}$-substituted or unsubstituted cycloalkyl (e.g., $C_3$-$C_8$, $C_3$-$C_6$, $C_4$-$C_6$, or $C_5$-$C_6$), $R^{23B}$-substituted or unsubstituted heterocycloalkyl (e.g., 3 to 8 membered, 3 to 6 membered, 4 to 6 membered, 4 to 5 membered, or 5 to 6 membered), $R^{23B}$-substituted or unsubstituted aryl (e.g., $C_6$-$C_{12}$, $C_6$-$C_{10}$, or phenyl), or $R^{23B}$-substituted or unsubstituted heteroaryl (e.g., 5 to 12 membered, 5 to 10 membered, 5 to 9 membered, or 5 to 6 membered). $X^{23A}$ is independently —F, —Cl, —Br, or —I. In embodiments, $R^{23A}$ is independently oxo, halogen, —$CX^{23A}_3$, —$CHX^{23A}_2$, —$CH_2X^{23A}$, —$OCX^{23A}_3$, —$OCH_2X^{23A}$, —$OCHX^{23A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{23A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC (O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{23B}$-substituted or unsubstituted $C_1$-$C_6$ alkyl, $R^{23B}$-substituted or unsubstituted 2 to 6 membered heteroalkyl, $R^{23B}$-substituted or unsubstituted $C_3$-$C_6$ cycloalkyl, $R^{23B}$-substituted or unsubstituted 3 to 6 membered heterocycloalkyl, $R^{23B}$-substituted or unsubstituted phenyl, or $R^{23B}$-substituted or unsubstituted 5 to 6 membered heteroaryl. In embodiments, $R^{23A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O) $NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, $R^{24}$ is independently hydrogen, $R^{24A}$-substituted or unsubstituted alkyl (e.g., $C_1$-$C_8$, $C_1$-$C_6$, $C_1$-$C_4$, or $C_1$-$C_2$), $R^{24A}$-substituted or unsubstituted heteroalkyl (e.g., 2 to 8 membered, 2 to 6 membered, 4 to 6 membered, 2 to 3 membered, or 4 to 5 membered), $R^{24A}$-substituted or unsubstituted cycloalkyl (e.g., $C_3$-$C_8$, $C_3$-$C_6$, $C_4$-$C_6$, or $C_5$-$C_6$), $R^{24A}$-substituted or unsubstituted heterocycloalkyl (e.g., 3 to 8 membered, 3 to 6 membered, 4 to 6 membered, 4 to 5 membered, or 5 to 6 membered), $R^{24A}$-substituted or unsubstituted aryl (e.g., $C_6$-$C_{12}$, $C_6$-$C_{10}$, or phenyl), or $R^{24A}$-substituted or unsubstituted heteroaryl (e.g., 5 to 12 membered, 5 to 10 membered, 5 to 9 membered, or 5 to 6 membered). In embodiments, $R^{24}$ is independently hydrogen, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{24}$ is independently hydrogen, $R^{24A}$-substituted or unsubstituted $C_1$-$C_6$ alkyl, $R^{24A}$-substituted or unsubstituted 2 to 6 membered heteroalkyl, $R^{24A}$-substituted or unsubstituted $C_3$-$C_6$ cycloalkyl, $R^{24A}$-substituted or unsubstituted 3 to 6 membered heterocycloalkyl, $R^{24A}$-substituted or unsubstituted phenyl, or $R^{24A}$-substituted or unsubstituted 5 to 6 membered heteroaryl. In embodiments, $R^{24}$ is independently hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

$R^{24A}$ is independently oxo, halogen, —$CX^{24A}_3$, —$CHX^{24A}_2$, —$CH_2X^{24A}$, —$OCX^{24A}_3$, —$OCH_2X^{24A}$, —$OCHX^{24A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{24B}$-substituted or unsubstituted alkyl (e.g., $C_1$-$C_8$, $C_1$-$C_6$, $C_1$-$C_4$, or $C_1$-$C_2$), $R^{24B}$-substituted or unsubstituted heteroalkyl (e.g., 2 to 8 membered, 2 to 6 membered, 4 to 6 membered, 2 to 3 membered, or 4 to 5 membered), $R^{24B}$-substituted or unsubstituted cycloalkyl (e.g., $C_3$-$C_8$, $C_3$-$C_6$, $C_4$-$C_6$, or $C_5$-$C_6$), $R^{24B}$-substituted or unsubstituted heterocycloalkyl (e.g., 3 to 8 membered, 3 to 6 membered, 4 to 6 membered, 4 to 5 membered, or 5 to 6 membered), $R^{24B}$-substituted or unsubstituted aryl (e.g., $C_6$-$C_{12}$, $C_6$-$C_{10}$, or phenyl), or $R^{24B}$-substituted or unsubstituted heteroaryl (e.g., 5 to 12 membered, 5 to 10 membered, 5 to 9 membered, or 5 to 6 membered). $X^{24A}$ is independently —F, —Cl, —Br, or —I. In embodiments, $R^{24A}$ is independently oxo, halogen, —$CX^{24A}_3$, —$CHX^{24A}_2$, —$CH_2X^{24A}$, —$OCX^{24A}_3$, —$OCH_2X^{24A}$, —$OCHX^{24A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{24A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{24B}$-substituted or unsubstituted $C_1$-$C_6$ alkyl, $R^{24B}$-substituted or unsubstituted 2 to 6 membered heteroalkyl, $R^{24B}$-substituted or unsubstituted $C_3$-$C_6$ cycloalkyl, $R^{24B}$-substituted or unsubstituted 3 to 6 membered heterocycloalkyl, $R^{24B}$-substituted or unsubstituted phenyl, or $R^{24B}$-substituted or unsubstituted 5 to 6 membered heteroaryl. In embodiments, $R^{24A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, $R^{25}$ is independently hydrogen, $R^{25A}$-substituted or unsubstituted alkyl (e.g., $C_1$-$C_8$, $C_1$-$C_6$, $C_1$-$C_4$, or $C_1$-$C_2$), $R^{25A}$-substituted or unsubstituted heteroalkyl (e.g., 2 to 8 membered, 2 to 6 membered, 4 to 6 membered, 2 to 3 membered, or 4 to 5 membered), $R^{25A}$-substituted or unsubstituted cycloalkyl (e.g., $C_3$-$C_8$, $C_3$-$C_6$, $C_4$-$C_6$, or $C_5$-$C_6$), $R^{25A}$-substituted or unsubstituted heterocycloalkyl (e.g., 3 to 8 membered, 3 to 6 membered, 4 to 6 membered, 4 to 5 membered, or 5 to 6 membered), $R^{25A}$-substituted or unsubstituted aryl (e.g., $C_6$-$C_{12}$, $C_6$-$C_{10}$, or phenyl), or $R^{25A}$-substituted or unsubstituted heteroaryl (e.g., 5 to 12 membered, 5 to 10 membered, 5 to 9 membered, or 5 to 6 membered). In embodiments, $R^{25}$ is independently hydrogen, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted hetero-cycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{25}$ is independently hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. $R^{25A}$ is independently oxo, halogen, —$CX^{25A}_3$, —$CHX^{25A}_2$, —$CH_2X^{25A}$, —$OCX^{25A}_3$, —$OCH_2X^{25A}$, —$OCHX^{25A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{25B}$-substituted or unsubstituted alkyl (e.g., $C_1$-$C_8$, $C_1$-$C_6$, $C_1$-$C_4$, or $C_1$-$C_2$), $R^{25B}$-substituted or unsubstituted heteroalkyl (e.g., 2 to 8 membered, 2 to 6 membered, 4 to 6 membered, 2 to 3 membered, or 4 to 5 membered), $R^{25B}$-substituted or unsubstituted cycloalkyl (e.g., $C_3$-$C_8$, $C_3$-$C_6$, $C_4$-$C_6$, or $C_5$-$C_6$), $R^{25B}$-substituted or unsubstituted heterocycloalkyl (e.g., 3 to 8 membered, 3 to 6 membered, 4 to 6 membered, 4 to 5 membered, or 5 to 6 membered), $R^{25B}$-substituted or unsubstituted aryl (e.g., $C_6$-$C_{12}$, $C_6$-$C_{10}$, or phenyl), or $R^{25B}$-substituted or unsubstituted heteroaryl (e.g., 5 to 12 membered, 5 to 10 membered, 5 to 9 membered, or 5 to 6 membered). $X^{25A}$ is independently —F, —Cl, —Br, or —I. In embodiments, $R^{25A}$ is independently oxo, halogen, —$CX^{25A}_3$, —$CHX^{25A}_2$, —$CH_2X^{25A}$, —$OCX^{25A}_3$, —$OCH_2X^{25A}$, —$OCHX^{25A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{25A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{25B}$-substituted or unsubstituted $C_1$-$C_6$ alkyl, $R^{25B}$-substituted or unsubstituted 2 to 6 membered heteroalkyl, $R^{25B}$-substituted or unsubstituted $C_3$-$C_6$ cycloalkyl, $R^{25B}$-substituted or unsubstituted 3 to 6 membered heterocycloalkyl, $R^{25B}$-substituted or unsubstituted phenyl, or $R^{25B}$-substituted or unsubstituted 5 to 6 membered heteroaryl. In embodiments, $R^{25A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —CH$_2$Br, —CI$_3$, —CHI$_2$, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl.

In embodiments, R$^{26}$ is independently hydrogen, halogen (e.g. —F, —Cl, —Br, or —I), R$^{26A}$-substituted or unsubstituted alkyl (e.g., C$_1$-C$_8$, C$_1$-C$_6$, C$_1$-C$_4$, or C$_1$-C$_2$), R$^{26A}$-substituted or unsubstituted aryl (e.g., C$_6$-C$_{12}$, C$_6$-C$_{10}$, or phenyl), —OR$^{28}$, —OC(O)R$^{28}$, —OC(O)OR$^{28}$ or —OC(O)NR$^{28}$R$^{29}$ (e.g. —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$). In embodiments, R$^{26}$ is independently hydrogen, halogen (e.g. —F, —Cl, —Br, or —I), unsubstituted alkyl (e.g., C$_1$-C$_8$, C$_1$-C$_6$, C$_1$-C$_4$, or C$_1$-C$_2$), unsubstituted aryl (e.g., C$_6$-C$_{12}$, C$_6$-C$_{10}$, or phenyl), —OR$^{28}$, —OC(O)R$^{28}$, —OC(O)OR$^{28}$, or —OC(O)NR$^{28}$R$^{29}$ (e.g. —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$). In embodiments, R$^{26}$ is independently hydrogen, halogen (e.g. —F, —Cl, —Br, or —I), R$^{26A}$-substituted or unsubstituted C$_1$-C$_6$ alkyl, R$^{26A}$-substituted or unsubstituted phenyl, —OR$^{28}$, —OC(O)R$^{28}$, —OC(O)OR$^{28}$, or —OC(O)NR$^{28}$R$^{29}$ (e.g. —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$). In embodiments, R$^{26}$ is independently hydrogen, halogen (e.g. —F, —Cl, —Br, or —I), unsubstituted C$_1$-C$_4$ alkyl, unsubstituted phenyl, —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$.

R$^{26A}$ is independently oxo, halogen, —CX$^{26A}_3$, —CHX$^{26A}_2$, —CH$_2$X$^{26A}$, —OCX$^{26A}_3$, —OCH$_2$X$^{26A}$, —OCHX$^{26A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, R$^{26B}$-substituted or unsubstituted alkyl (e.g., C$_1$-C$_8$, C$_1$-C$_6$, C$_1$-C$_4$, or C$_1$-C$_2$), R$^{26B}$-substituted or unsubstituted heteroalkyl (e.g., 2 to 8 membered, 2 to 6 membered, 4 to 6 membered, 2 to 3 membered, or 4 to 5 membered), R$^{26B}$-substituted or unsubstituted cycloalkyl (e.g., C$_3$-C$_8$, C$_3$-C$_6$, C$_4$-C$_6$, or C$_5$-C$_6$), R$^{26B}$-substituted or unsubstituted heterocycloalkyl (e.g., 3 to 8 membered, 3 to 6 membered, 4 to 6 membered, 4 to 5 membered, or 5 to 6 membered), R$^{26B}$-substituted or unsubstituted aryl (e.g., C$_6$-C$_{12}$, C$_6$-C$_{10}$, or phenyl), or R$^{26B}$-substituted or unsubstituted heteroaryl (e.g., 5 to 12 membered, 5 to 10 membered, 5 to 9 membered, or 5 to 6 membered). X$^{26A}$ is independently —F, —Cl, —Br, or —I. In embodiments, R$^{26A}$ is independently oxo, halogen, —CX$^{26A}_3$, —CHX$^{26A}_2$, —CH$_2$X$^{26A}$, —OCX$^{26A}_3$, —OCH$_2$X$^{26A}$, —OCHX$^{26A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). In embodiments, R$^{26A}$ is independently oxo, halogen, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, R$^{26B}$-substituted or unsubstituted C$_1$-C$_6$ alkyl, R$^{26B}$-substituted or unsubstituted 2 to 6 membered heteroalkyl, R$^{26B}$-substituted or unsubstituted C$_3$-C$_6$ cycloalkyl, R$^{26B}$-substituted or unsubstituted 3 to 6 membered heterocycloalkyl, R$^{26B}$-substituted or unsubstituted phenyl, or R$^{26B}$-substituted or unsubstituted 5 to 6 membered heteroaryl. In embodiments, R$^{26A}$ is independently oxo, halogen, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl.

In embodiments, R$^{27}$ is independently hydrogen, halogen (e.g. —F, —Cl, —Br, or —I), R$^{27A}$-substituted or unsubstituted alkyl (e.g., C$_1$-C$_8$, C$_1$-C$_6$, C$_1$-C$_4$, or C$_1$-C$_2$), R$^{27A}$-substituted or unsubstituted aryl (e.g., C$_6$-C$_{12}$, C$_6$-C$_{10}$, or phenyl), —OR$^{30}$, —OC(O)R$^{30}$, —OC(O)OR$^{30}$, or —OC(O)N$^{30}$R$^{31}$ (e.g. —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$). In embodiments, R$^{27}$ is independently hydrogen, halogen (e.g. —F, —Cl, —Br, or —I), unsubstituted alkyl (e.g., C$_1$-C$_8$, C$_1$-C$_6$, C$_1$-C$_4$, or C$_1$-C$_2$), unsubstituted aryl (e.g., C$_6$-C$_{12}$, C$_6$-C$_{10}$, or phenyl), —OR$^{30}$, —OC(O)R$^{30}$, —OC(O)OR$^{30}$, or —OC(O)NR$^{30}$R$^{31}$ (e.g. —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$). In embodiments, R$^{27}$ is independently hydrogen, halogen (e.g. —F, —Cl, —Br, or —I), R$^{27A}$-substituted or unsubstituted C$_1$-C$_6$ alkyl, R$^{27A}$-substituted or unsubstituted phenyl, —OR$^{30}$, —OC(O)R$^{30}$, —OC(O)OR$^{30}$, or —OC(O)NR$^{30}$R$^{31}$ (e.g. —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$). In embodiments, R$^{27}$ is independently hydrogen, halogen (e.g. —F, —Cl, —Br, or —I), unsubstituted C$_1$-C$_4$ alkyl, unsubstituted phenyl, —OH, —OCH$_3$, —OCH$_2$CH$_3$, —OC(O)H, —OC(O)CH$_3$, —OC(O)OH, —OC(O)OCH$_3$, —OC(O)NH$_2$ or —OC(O)NHCH$_3$.

R$^{27A}$ is independently oxo, halogen, —CX$^{27A}_3$, —CHX$^{27A}_2$, —CH$_2$X$^{27A}$, —OCX$^{27A}_3$, —OCH$_2$X$^{27A}$, —OCHX$^{27A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, R$^{27B}$-substituted or unsubstituted alkyl (e.g., C$_1$-C$_8$, C$_1$-C$_6$, C$_1$-C$_4$, or C$_1$-C$_2$), R$^{27B}$-substituted or unsubstituted heteroalkyl (e.g., 2 to 8 membered, 2 to 6 membered, 4 to 6 membered, 2 to 3 membered, or 4 to 5 membered), $R^{27B}$-substituted or unsubstituted cycloalkyl (e.g., $C_3$-$C_8$, $C_3$-$C_6$, $C_4$-$C_6$, or $C_5$-$C_6$), $R^{27B}$-substituted or unsubstituted heterocycloalkyl (e.g., 3 to 8 membered, 3 to 6 membered, 4 to 6 membered, 4 to 5 membered, or 5 to 6 membered), $R^{27B}$-substituted or unsubstituted aryl (e.g., $C_6$-$C_{12}$, $C_6$-$C_{10}$, or phenyl), or $R^{27B}$-substituted or unsubstituted heteroaryl (e.g., 5 to 12 membered, 5 to 10 membered, 5 to 9 membered, or 5 to 6 membered). $X^{27A}$ is independently —F, —Cl, —Br, or —I. In embodiments, $R^{27A}$ is independently oxo, halogen, —$CX^{27A}_3$, —$CHX^{27A}_2$, —$CH_2X^{27A}$, —$OCX^{27A}_3$, —$OCH_2X^{27A}$, —$OCHX^{27A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{27A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{27B}$-substituted or unsubstituted $C_1$-$C_6$ alkyl, $R^{27B}$-substituted or unsubstituted 2 to 6 membered heteroalkyl, $R^{27B}$-substituted or unsubstituted $C_3$-$C_6$ cycloalkyl, $R^{27B}$-substituted or unsubstituted 3 to 6 membered heterocycloalkyl, $R^{27B}$-substituted or unsubstituted phenyl, or $R^{27B}$-substituted or unsubstituted 5 to 6 membered heteroaryl. In embodiments, $R^{27A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, $R^{28}$ is independently hydrogen, $R^{28A}$-substituted or unsubstituted alkyl (e.g., $C_1$-$C_8$, $C_1$-$C_6$, $C_1$-$C_4$, or $C_1$-$C_2$), $R^{28A}$-substituted or unsubstituted heteroalkyl (e.g., 2 to 8 membered, 2 to 6 membered, 4 to 6 membered, 2 to 3 membered, or 4 to 5 membered), $R^{28A}$-substituted or unsubstituted cycloalkyl (e.g., $C_3$-$C_8$, $C_3$-$C_6$, $C_4$-$C_6$, or $C_5$-$C_6$), $R^{28A}$-substituted or unsubstituted heterocycloalkyl (e.g., 3 to 8 membered, 3 to 6 membered, 4 to 6 membered, 4 to 5 membered, or 5 to 6 membered), $R^{28A}$-substituted or unsubstituted aryl (e.g., $C_6$-$C_{12}$, $C_6$-$C_{10}$, or phenyl), or $R^{28A}$-substituted or unsubstituted heteroaryl (e.g., 5 to 12 membered, 5 to 10 membered, 5 to 9 membered, or 5 to 6 membered). In embodiments, $R^{28}$ is independently hydrogen, $R^{28A}$-substituted or unsubstituted $C_1$-$C_6$ alkyl, $R^{28A}$-substituted or unsubstituted 2 to 6 membered heteroalkyl, $R^{28A}$-substituted or unsubstituted $C_3$-$C_6$ cycloalkyl, $R^{28A}$-substituted or unsubstituted 3 to 6 membered heterocycloalkyl, $R^{28A}$-substituted or unsubstituted phenyl, or $R^{28A}$-substituted or unsubstituted 5 to 6 membered heteroaryl. In embodiments, $R^{28}$ is independently hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. $R^{28A}$ is independently oxo, halogen, —$CX^{28A}_3$, —$CHX^{28A}_2$, —$CH_2X^{28A}$, —$OCX^{28A}_3$, —$OCH_2X^{28A}$, —$OCHX^{28A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{28B}$-substituted or unsubstituted alkyl (e.g., $C_1$-$C_8$, $C_1$-$C_6$, $C_1$-$C_4$, or $C_1$-$C_2$), $R^{28B}$-substituted or unsubstituted heteroalkyl (e.g., 2 to 8 membered, 2 to 6 membered, 4 to 6 membered, 2 to 3 membered, or 4 to 5 membered), $R^{28B}$-substituted or unsubstituted cycloalkyl (e.g., $C_3$-$C_8$, $C_3$-$C_6$, $C_4$-$C_6$, or $C_5$-$C_6$), $R^{28B}$-substituted or unsubstituted heterocycloalkyl (e.g., 3 to 8 membered, 3 to 6 membered, 4 to 6 membered, 4 to 5 membered, or 5 to 6 membered), $R^{28B}$-substituted or unsubstituted aryl (e.g., $C_6$-$C_{12}$, $C_6$-$C_{10}$, or phenyl), or $R^{28B}$-substituted or unsubstituted heteroaryl (e.g., 5 to 12 membered, 5 to 10 membered, 5 to 9 membered, or 5 to 6 membered). $X^{28A}$ is independently —F, —Cl, —Br, or —I. In embodiments, $R^{28A}$ is independently oxo, halogen, —$CX^{28A}_3$, —$CHX^{28A}_2$, —$CH_2X^{28A}$, —$OCX^{28A}_3$, —$OCH_2X^{28A}$, —$OCHX^{28A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{28A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{28B}$-substituted or unsubstituted $C_1$-$C_6$ alkyl, $R^{28B}$-substituted or unsubstituted 2 to 6 membered heteroalkyl, $R^{28B}$-substituted or unsubstituted $C_3$-$C_6$ cycloalkyl, $R^{28B}$-substituted or unsubstituted 3 to 6 membered heterocycloalkyl, $R^{28B}$-substituted or unsubstituted phenyl, or $R^{28B}$-substituted or unsubstituted 5 to 6 membered heteroaryl. In embodiments, $R^{28A}$ is independently oxo, halogen, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl.

In embodiments, $R^{29}$ is independently hydrogen, $R^{29A}$-substituted or unsubstituted alkyl (e.g., C$_1$-C$_8$, C$_1$-C$_6$, C$_1$-C$_4$, or C$_1$-C$_2$), $R^{29A}$-substituted or unsubstituted heteroalkyl (e.g., 2 to 8 membered, 2 to 6 membered, 4 to 6 membered, 2 to 3 membered, or 4 to 5 membered), $R^{29A}$-substituted or unsubstituted cycloalkyl (e.g., C$_3$-C$_8$, C$_3$-C$_6$, C$_4$-C$_6$, or C$_5$-C$_6$), $R^{29A}$-substituted or unsubstituted heterocycloalkyl (e.g., 3 to 8 membered, 3 to 6 membered, 4 to 6 membered, 4 to 5 membered, or 5 to 6 membered), $R^{29A}$-substituted or unsubstituted aryl (e.g., C$_6$-C$_{12}$, C$_6$-C$_{10}$, or phenyl), or $R^{29A}$-substituted or unsubstituted heteroaryl (e.g., 5 to 12 membered, 5 to 10 membered, 5 to 9 membered, or 5 to 6 membered). In embodiments, $R^{29}$ is independently hydrogen, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). In embodiments, $R^{29}$ is independently hydrogen, $R^{29A}$-substituted or unsubstituted C$_1$-C$_6$ alkyl, $R^{29A}$-substituted or unsubstituted 2 to 6 membered heteroalkyl, $R^{29A}$-substituted or unsubstituted C$_3$-C$_6$ cycloalkyl, $R^{29A}$-substituted or unsubstituted 3 to 6 membered heterocycloalkyl, $R^{29A}$-substituted or unsubstituted phenyl, or $R^{29A}$-substituted or unsubstituted 5 to 6 membered heteroaryl. In embodiments, $R^{29}$ is independently hydrogen, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl.

$R^{29A}$ is independently oxo, halogen, —CX$^{29A}_3$, —CHX$^{29A}_2$, —CH$_2$X$^{29A}$, —OCX$^{29A}_3$, —OCH$_2$X$^{29A}$, —OCHX$^{29A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, $R^{29B}$-substituted or unsubstituted alkyl (e.g., C$_1$-C$_8$, C$_1$-C$_6$, C$_1$-C$_4$, or C$_1$-C$_2$), $R^{29B}$-substituted or unsubstituted heteroalkyl (e.g., 2 to 8 membered, 2 to 6 membered, 4 to 6 membered, 2 to 3 membered, or 4 to 5 membered), $R^{29B}$-substituted or unsubstituted cycloalkyl (e.g., C$_3$-C$_8$, C$_3$-C$_6$, C$_4$-C$_6$, or C$_5$-C$_6$), $R^{29B}$-substituted or unsubstituted heterocycloalkyl (e.g., 3 to 8 membered, 3 to 6 membered, 4 to 6 membered, 4 to 5 membered, or 5 to 6 membered), $R^{29B}$-substituted or unsubstituted aryl (e.g., C$_6$-C$_{12}$, C$_6$-C$_{10}$, or phenyl), or $R^{29B}$-substituted or unsubstituted heteroaryl (e.g., 5 to 12 membered, 5 to 10 membered, 5 to 9 membered, or 5 to 6 membered). $X^{29A}$ is independently —F, —Cl, —Br, or —I. In embodiments, $R^{29A}$ is independently oxo, halogen, —CX$^{29A}_3$, —CHX$^{29A}_2$, —CH$_2$X$^{29A}$, —OCX$^{29A}_3$, —OCH$_2$X$^{29A}$, —OCHX$^{29A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered).

In embodiments, $R^{29A}$ is independently oxo, halogen, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl.

In embodiments, $R^{30}$ is independently hydrogen, $R^{30A}$-substituted or unsubstituted alkyl (e.g., C$_1$-C$_8$, C$_1$-C$_6$, C$_1$-C$_4$, or C$_1$-C$_2$), $R^{30A}$-substituted or unsubstituted heteroalkyl (e.g., 2 to 8 membered, 2 to 6 membered, 4 to 6 membered, 2 to 3 membered, or 4 to 5 membered), $R^{30A}$-substituted or unsubstituted cycloalkyl (e.g., C$_3$-C$_8$, C$_3$-C$_6$, C$_4$-C$_6$, or C$_5$-C$_6$), $R^{30A}$-substituted or unsubstituted heterocycloalkyl (e.g., 3 to 8 membered, 3 to 6 membered, 4 to 6 membered, 4 to 5 membered, or 5 to 6 membered), $R^{30A}$-substituted or unsubstituted aryl (e.g., C$_6$-C$_{12}$, C$_6$-C$_{10}$, or phenyl), or $R^{30A}$-substituted or unsubstituted heteroaryl (e.g., 5 to 12 membered, 5 to 10 membered, 5 to 9 membered, or 5 to 6 membered). In embodiments, $R^{30}$ is independently hydrogen, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). In embodiments, $R^{30}$ is independently hydrogen, $R^{30A}$-substituted or unsubstituted $C_1$-$C_6$ alkyl, $R^{30A}$-substituted or unsubstituted 2 to 6 membered heteroalkyl, $R^{30A}$-substituted or unsubstituted $C_3$-$C_6$ cycloalkyl, $R^{30A}$-substituted or unsubstituted 3 to 6 membered heterocycloalkyl, $R^{30A}$-substituted or unsubstituted phenyl, or $R^{30A}$-substituted or unsubstituted 5 to 6 membered heteroaryl. In embodiments, $R^{30}$ is independently hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

$R^{30A}$ is independently oxo, halogen, —$CX^{30A}_3$, —$CHX^{30A}_2$, —$CH_2X^{30A}$, —$OCX^{30A}_3$, —$OCH_2X^{30A}$, —$OCHX^{30A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{30B}$-substituted or unsubstituted alkyl (e.g., $C_1$-$C_8$, $C_1$-$C_6$, $C_1$-$C_4$, or $C_1$-$C_2$), $R^{30B}$-substituted or unsubstituted heteroalkyl (e.g., 2 to 8 membered, 2 to 6 membered, 4 to 6 membered, 2 to 3 membered, or 4 to 5 membered), $R^{30B}$-substituted or unsubstituted cycloalkyl (e.g., $C_3$-$C_8$, $C_3$-$C_6$, $C_4$-$C_6$, or $C_5$-$C_6$), $R^{30B}$-substituted or unsubstituted heterocycloalkyl (e.g., 3 to 8 membered, 3 to 6 membered, 4 to 6 membered, 4 to 5 membered, or 5 to 6 membered), $R^{30B}$-substituted or unsubstituted aryl (e.g., $C_6$-$C_{12}$, $C_6$-$C_{10}$, or phenyl), or $R^{30B}$-substituted or unsubstituted heteroaryl (e.g., 5 to 12 membered, 5 to 10 membered, 5 to 9 membered, or 5 to 6 membered). $X^{30A}$ is independently —F, —Cl, —Br, or —I. In embodiments, $R^{30A}$ is independently oxo, halogen, —$CX^{30A}_3$, —$CHX^{30A}_2$, —$CH_2X^{30A}$, —$OCX^{30A}_3$, —$OCH_2X^{30A}$, —$OCHX^{30A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{30A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{30B}$-substituted or unsubstituted $C_1$-$C_6$ alkyl, $R^{30B}$-substituted or unsubstituted 2 to 6 membered heteroalkyl, $R^{30B}$-substituted or unsubstituted $C_3$-$C_6$ cycloalkyl, $R^{30B}$-substituted or unsubstituted 3 to 6 membered heterocycloalkyl, $R^{30B}$-substituted or unsubstituted phenyl, or $R^{30B}$-substituted or unsubstituted 5 to 6 membered heteroaryl. In embodiments, $R^{30A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O) $NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, $R^{31}$ is independently hydrogen, $R^{31A}$-substituted or unsubstituted alkyl (e.g., $C_1$-$C_8$, $C_1$-$C_6$, $C_1$-$C_4$, or $C_1$-$C_2$), $R^{31A}$-substituted or unsubstituted heteroalkyl (e.g., 2 to 8 membered, 2 to 6 membered, 4 to 6 membered, 2 to 3 membered, or 4 to 5 membered), $R^{31A}$-substituted or unsubstituted cycloalkyl (e.g., $C_3$-$C_8$, $C_3$-$C_6$, $C_4$-$C_6$, or $C_5$-$C_6$), $R^{31A}$-substituted or unsubstituted heterocycloalkyl (e.g., 3 to 8 membered, 3 to 6 membered, 4 to 6 membered, 4 to 5 membered, or 5 to 6 membered), $R^{31A}$-substituted or unsubstituted aryl (e.g., $C_6$-$C_{12}$, $C_6$-$C_{10}$, or phenyl), or $R^{31A}$-substituted or unsubstituted heteroaryl (e.g., 5 to 12 membered, 5 to 10 membered, 5 to 9 membered, or 5 to 6 membered). In embodiments, $R^{31}$ is independently hydrogen, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{31}$ is independently hydrogen, $R^{31A}$-substituted or unsubstituted $C_1$-$C_6$ alkyl, $R^{31A}$-substituted or unsubstituted 2 to 6 membered heteroalkyl, $R^{31A}$-substituted or unsubstituted $C_3$-$C_6$ cycloalkyl, $R^{31A}$-substituted or unsubstituted 3 to 6 membered heterocycloalkyl, $R^{31A}$-substituted or unsubstituted phenyl, or $R^{31A}$-substituted or unsubstituted 5 to 6 membered heteroaryl. In embodiments, $R^{31}$ is independently hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

$R^{31A}$ is independently oxo, halogen, —$CX^{31A}_3$, —$CHX^{31A}_2$, —$CH_2X^{31A}$, —$OCX^{31A}_3$, —$OCH_2X^{31A}$, —$OCHX^{31A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{31B}$-substituted or unsubstituted alkyl (e.g., $C_1$-$C_8$, $C_1$-$C_6$, $C_1$-$C_4$, or $C_1$-$C_2$), $R^{31B}$-substituted or unsubstituted heteroalkyl (e.g., 2 to 8 membered, 2 to 6 membered, 4 to 6 membered, 2 to 3 membered, or 4 to 5 membered), $R^{31B}$-substituted or unsubstituted cycloalkyl (e.g., $C_3$-$C_8$, $C_3$-$C_6$, $C_4$-$C_6$, or $C_5$-$C_6$), $R^{31B}$-substituted or unsubstituted heterocycloalkyl (e.g., 3 to 8 membered, 3 to 6 membered, 4 to 6 membered, 4 to 5 membered, or 5 to 6 membered), $R^{31B}$-substituted or unsubstituted aryl (e.g., $C_6$-$C_{12}$, $C_6$-$C_{10}$, or phenyl), or $R^{31B}$-substituted or unsubstituted heteroaryl (e.g., 5 to 12 membered, 5 to 10 membered, 5 to 9 membered, or 5 to 6 membered). $X^{31A}$ is independently —F, —Cl, —Br, or —I. In embodiments, $R^{31A}$ is independently oxo, halogen, —$CX^{31A}_3$, —$CHX^{31A}_2$, —$CH_2X^{31A}$, —$OCX^{31A}_3$, —$OCH_2X^{31A}$, —$OCHX^{31A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{31A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{31B}$-substituted or unsubstituted $C_1$-$C_6$ alkyl, $R^{31B}$-substituted or unsubstituted 2 to 6 membered heteroalkyl, $R^{31B}$-substituted or unsubstituted $C_3$-$C_6$ cycloalkyl, $R^{31B}$-substituted or unsubstituted 3 to 6 membered heterocycloalkyl, $R^{31B}$-substituted or unsubstituted phenyl, or $R^{31B}$-substituted or unsubstituted 5 to 6 membered heteroaryl. In embodiments, $R^{31A}$ is independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

$R^{1B}$, $R^{2B}$, $R^{3B}$, $R^{4B}$, $R^{5B}$, $R^{10B}$, $R^{11B}$, $R^{12B}$, $R^{13B}$, $R^{14B}$, $R^{15B}$, $R^{16B}$, $R^{17B}$, $R^{18B}$, $R^{19B}$, $R^{20B}$, $R^{21B}$, $R^{22B}$, $R^{23B}$, $R^{24B}$, $R^{25B}$, $R^{26B}$, $R^{27B}$, $R^{28B}$, $R^{29B}$, $R^{30B}$, and $R^{31B}$ are independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^{1B}$, $R^{2B}$, $R^{3B}$, $R^{4B}$, $R^{5B}$, $R^{10B}$, $R^{11B}$, $R^{12B}$, $R^{13B}$, $R^{14B}$, $R^{15B}$, $R^{16B}$, $R^{17B}$, $R^{18B}$, $R^{19B}$, $R^{20B}$, $R^{21B}$, $R^{22B}$, $R^{23B}$, $R^{24B}$, $R^{25B}$, $R^{26B}$, $R^{27B}$, $R^{28B}$, $R^{29B}$, $R^{30B}$, and $R^{31B}$ are independently oxo, halogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, the compound is selected from:

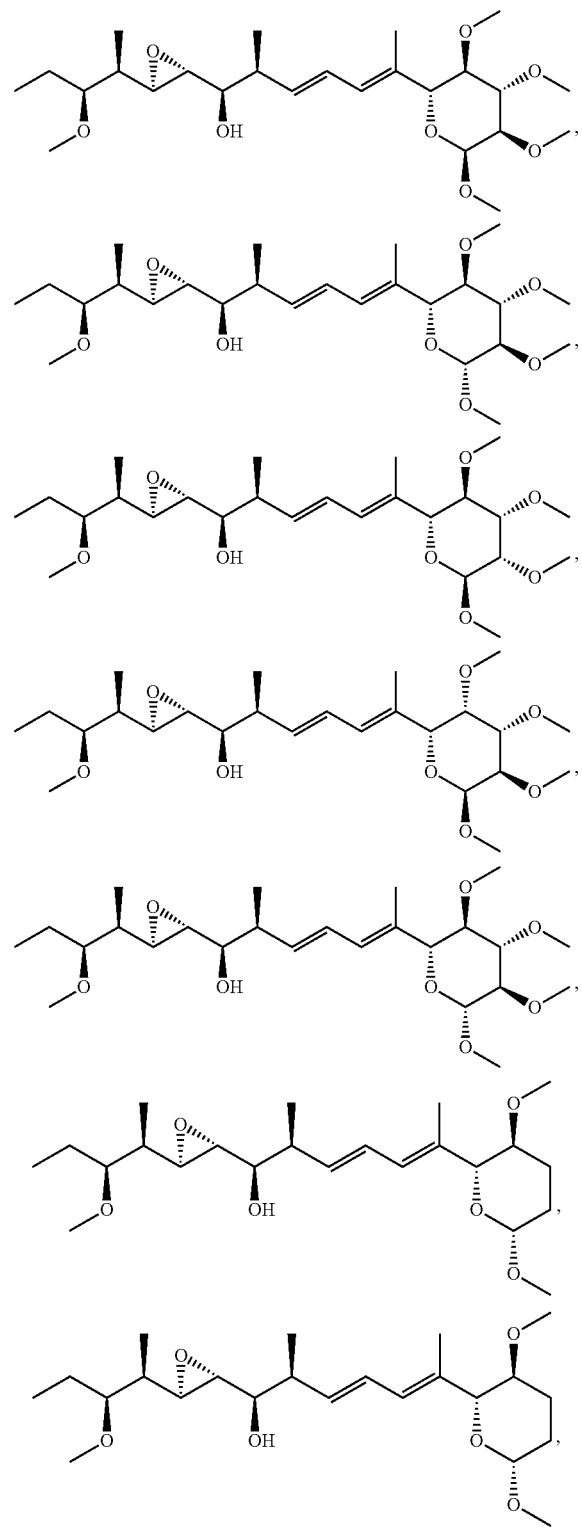

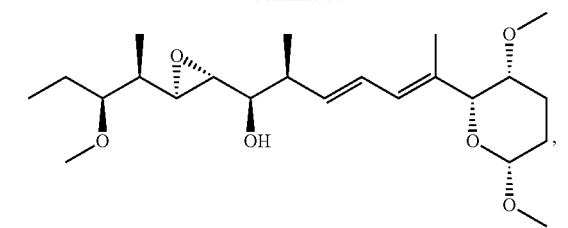
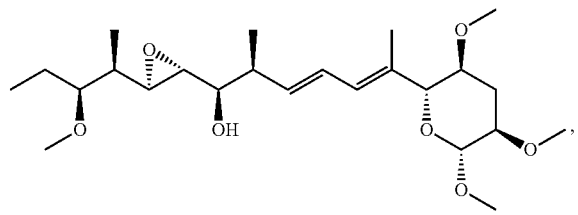
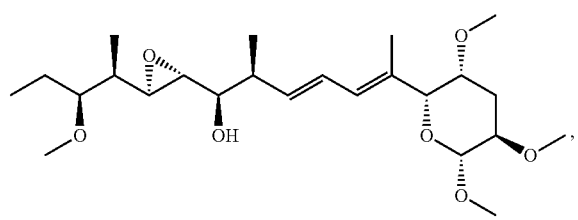
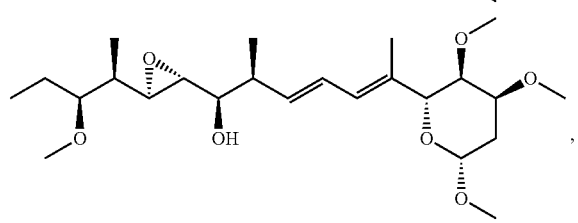
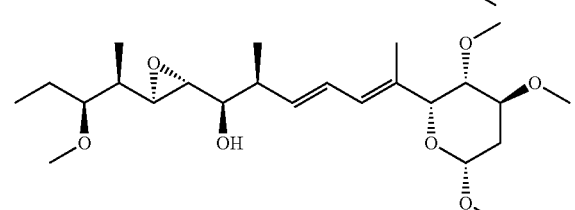
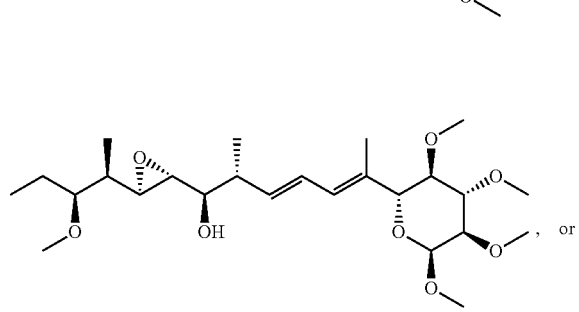, or
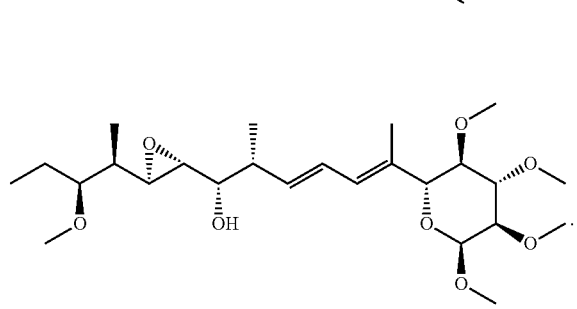
In embodiments, the compound is selected from:
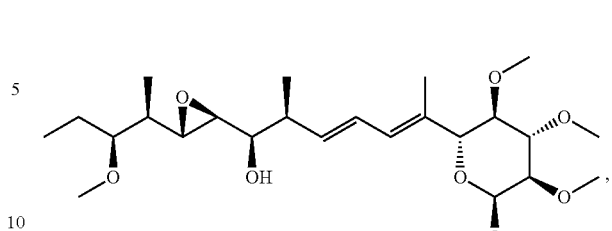
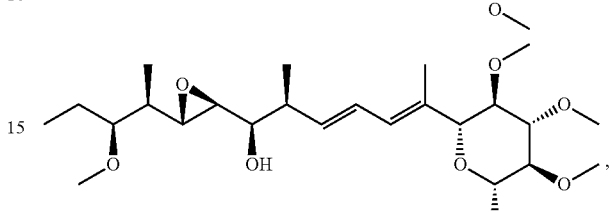
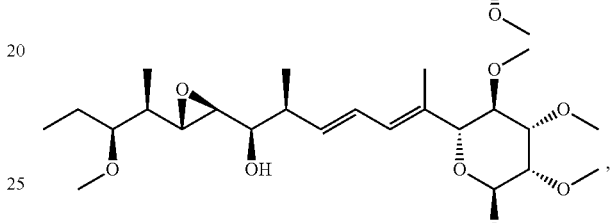
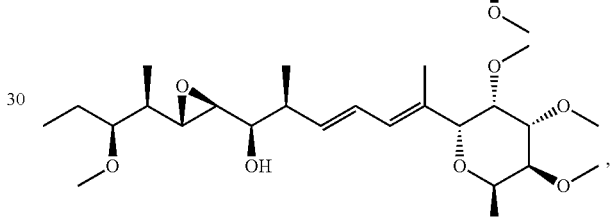
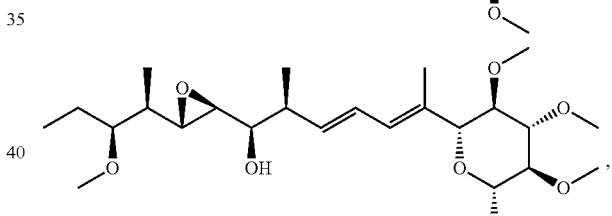
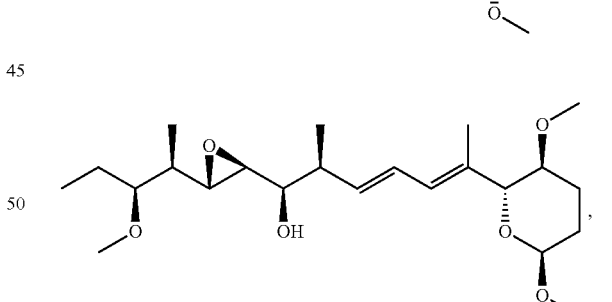
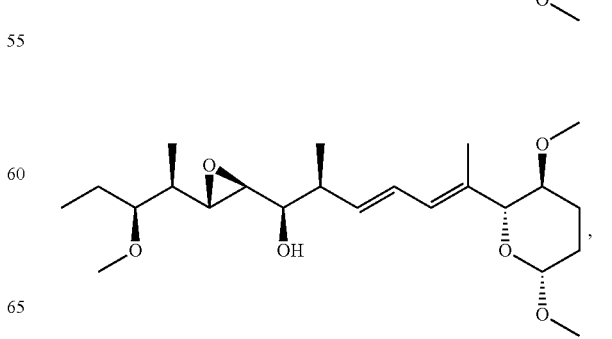

-continued
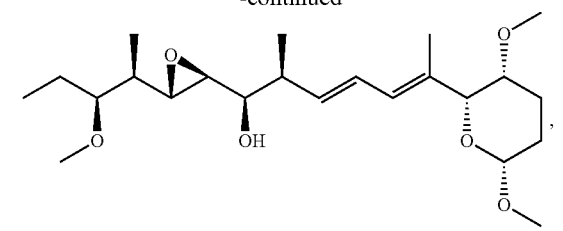
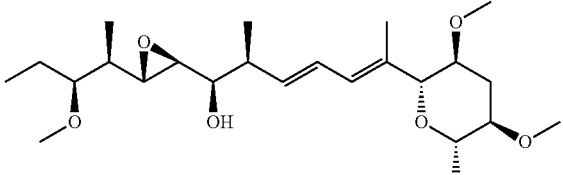
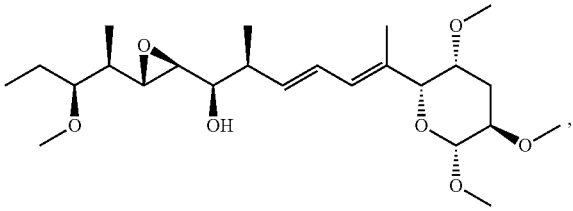
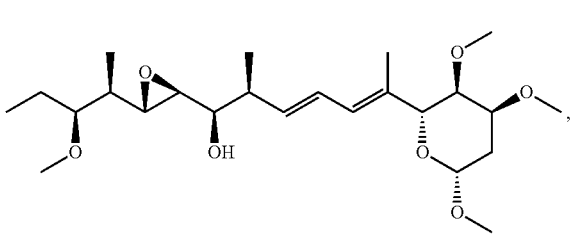
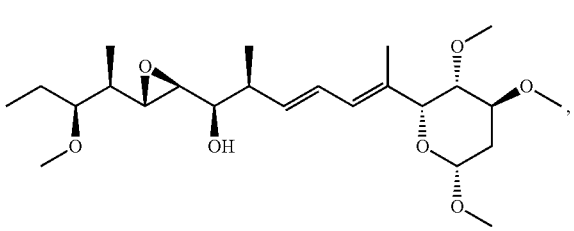
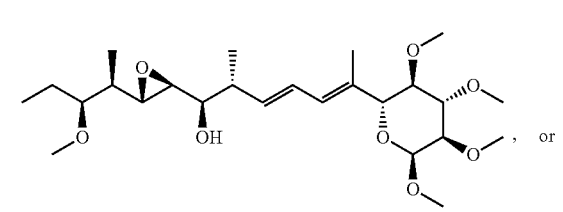
, or
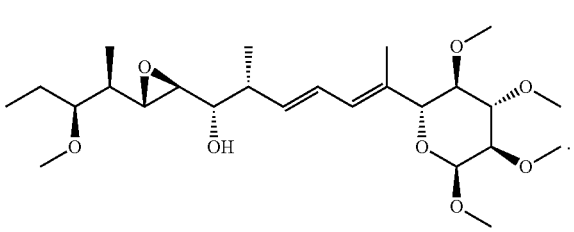
In embodiments, the compound is selected from:
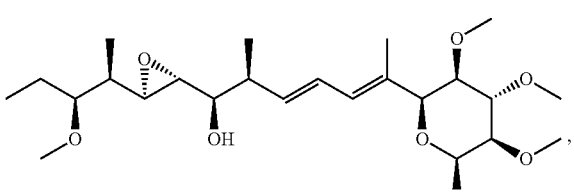
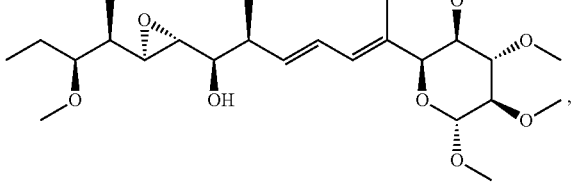
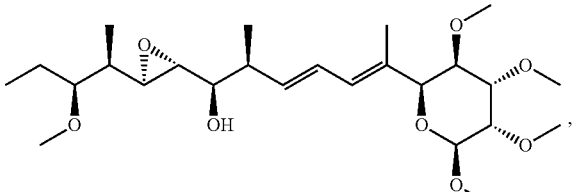
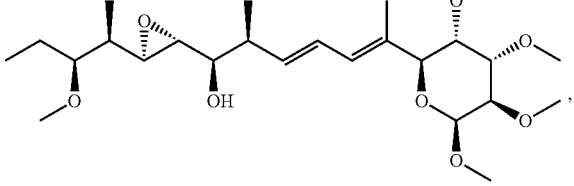
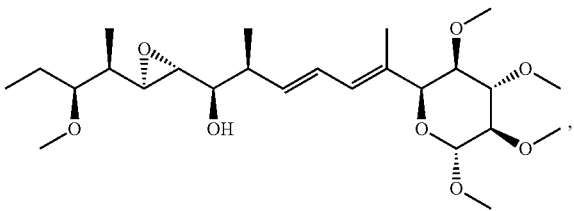
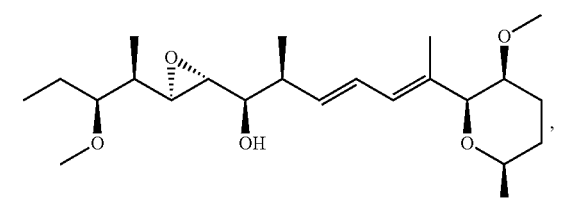
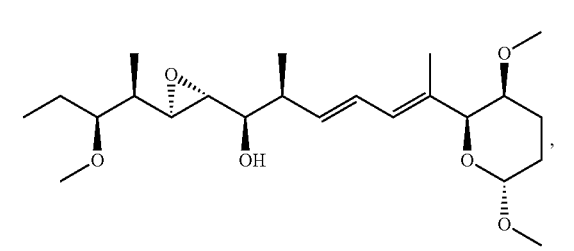

-continued
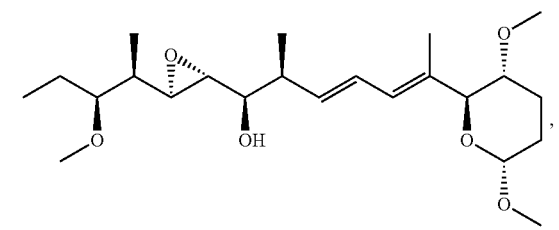
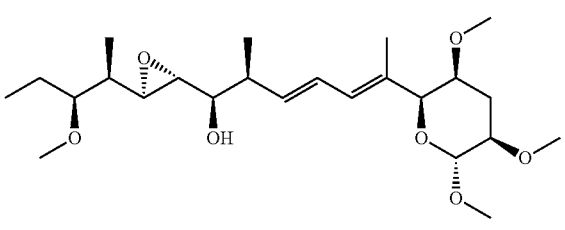
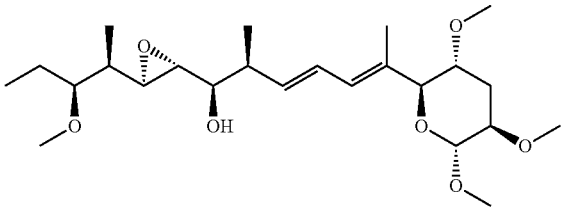
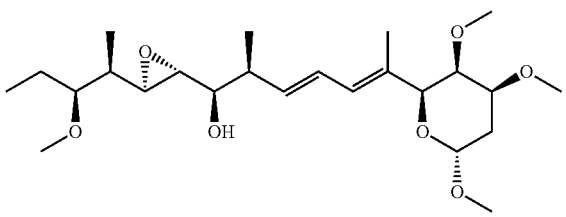
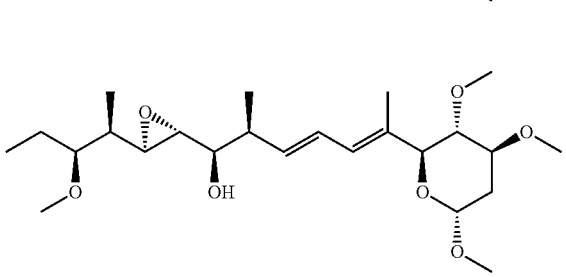
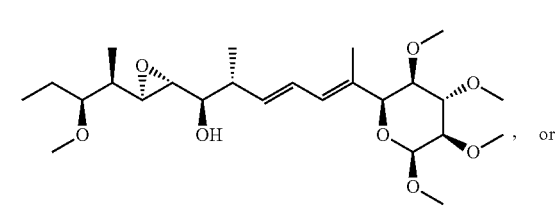, or
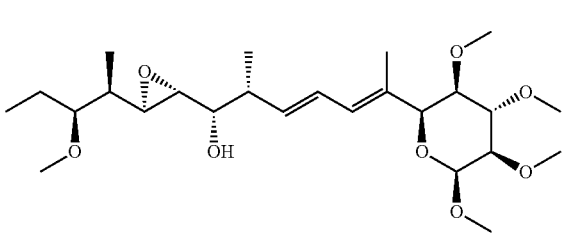
In embodiments, the compound is selected from:
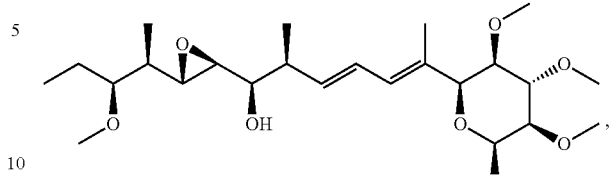
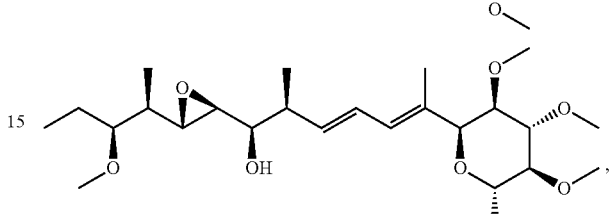
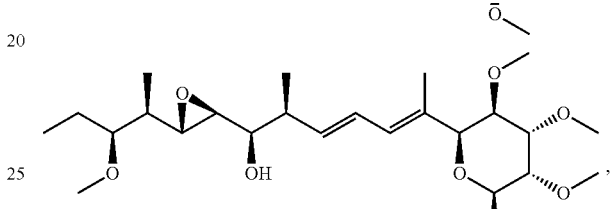
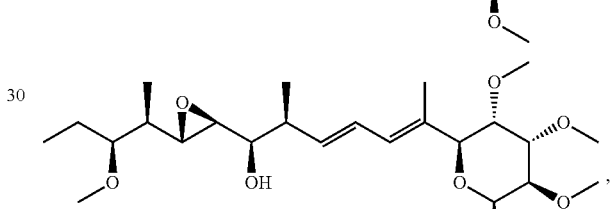
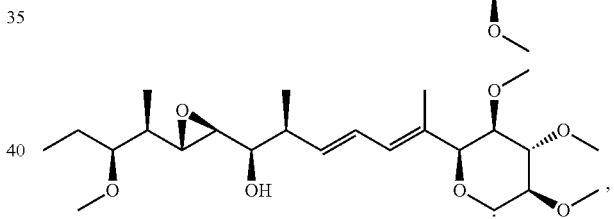
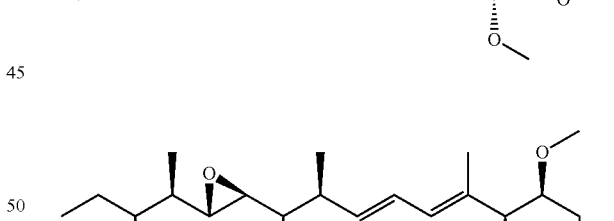
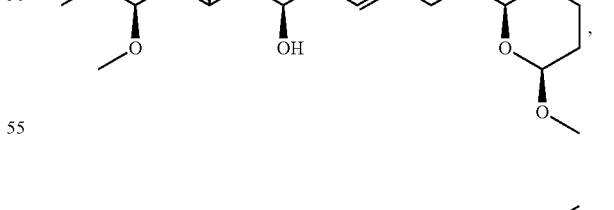
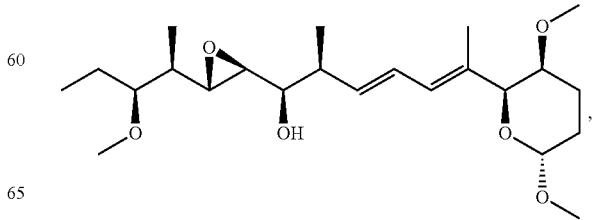

-continued
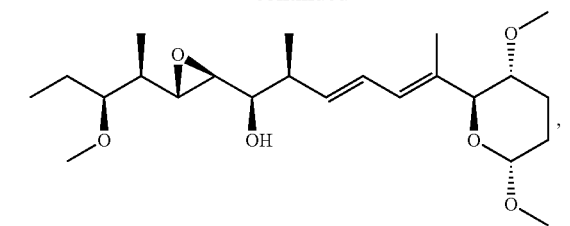
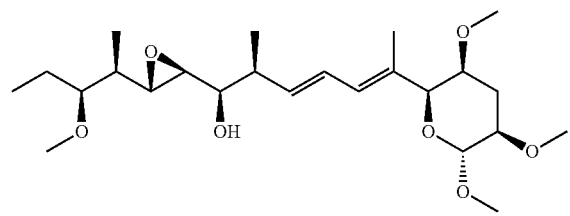
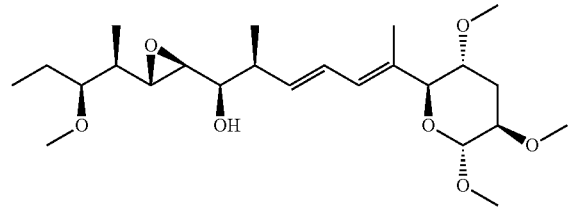
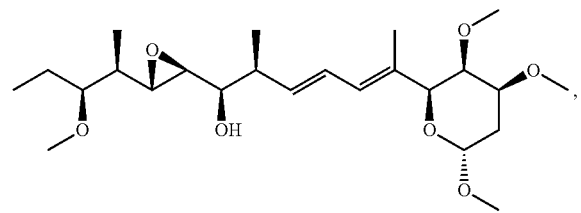
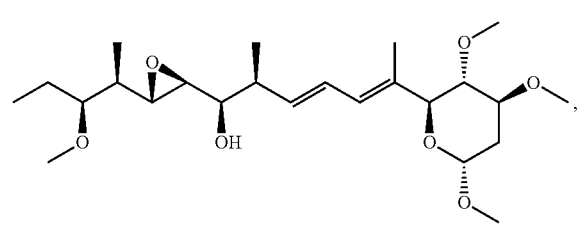
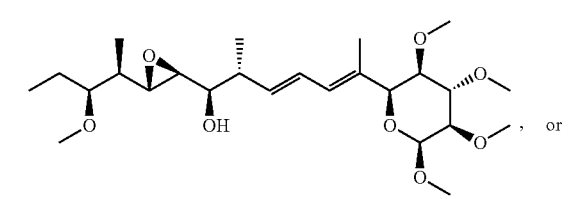, or
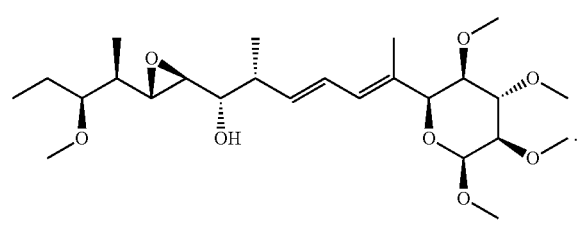.
In embodiments, the compound is selected from:
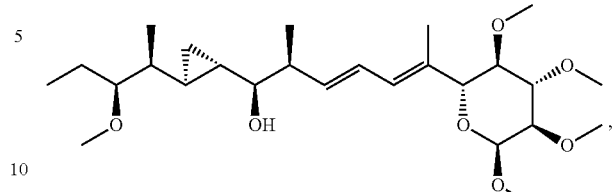
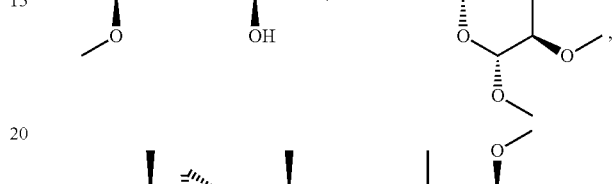
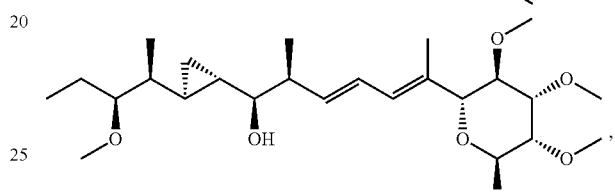
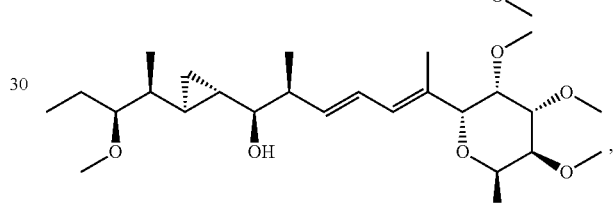
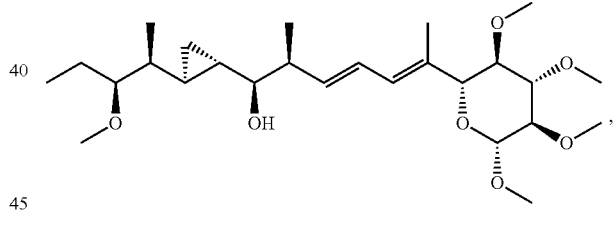
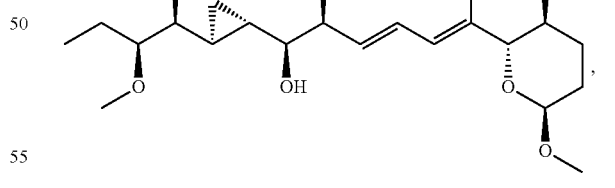
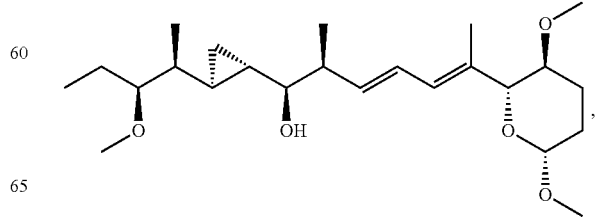

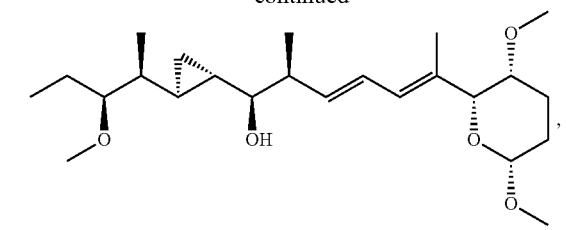
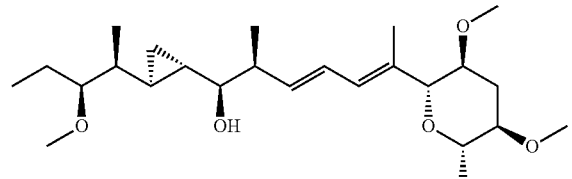
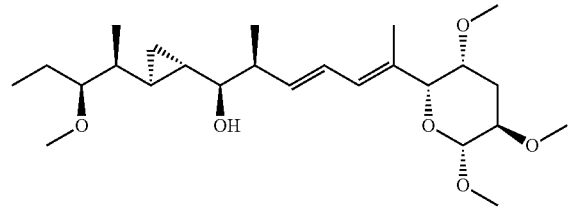
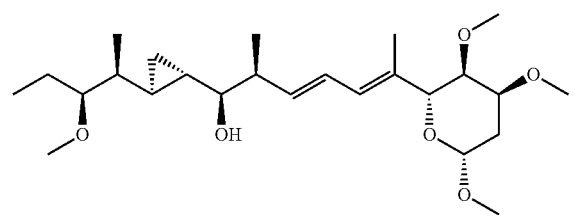
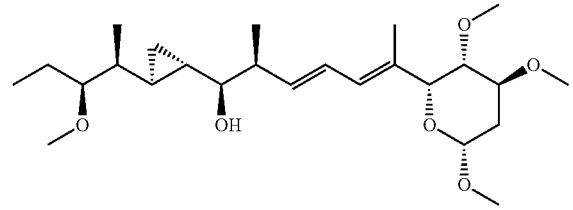
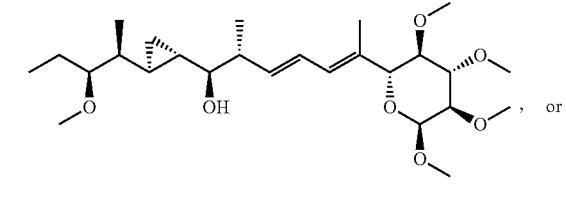, or
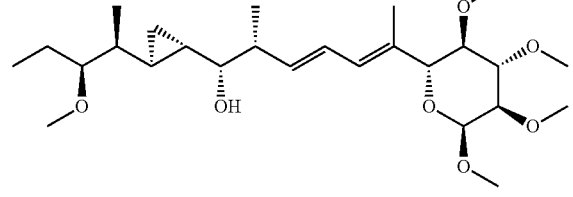
In embodiments, the compound is selected from:
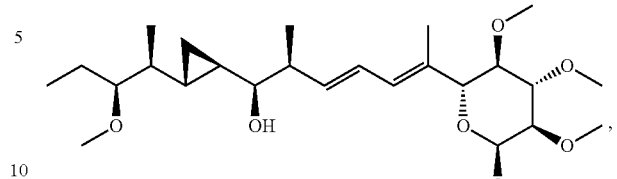
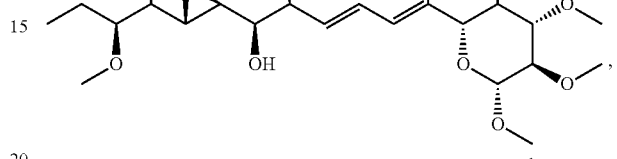
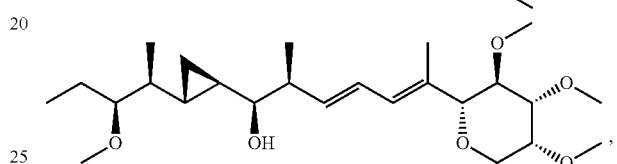
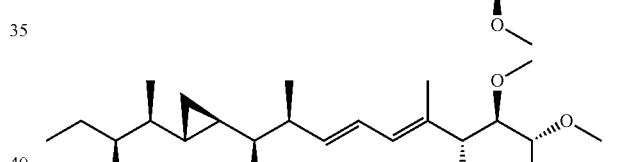
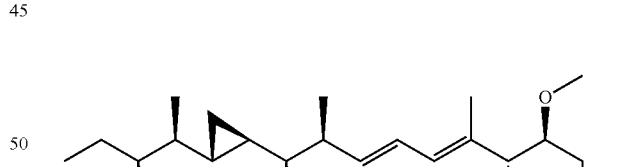
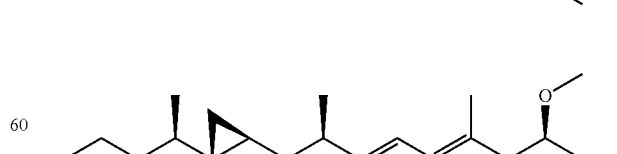
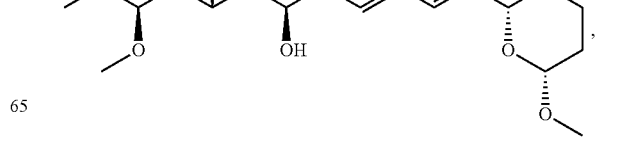

-continued
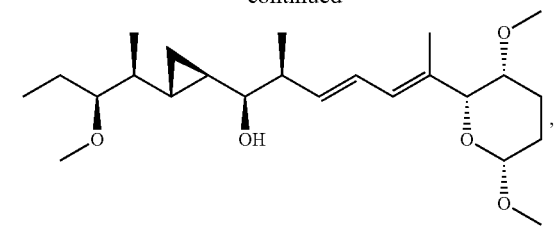
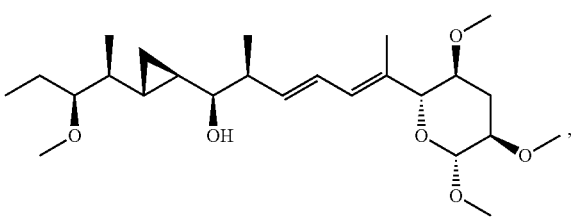
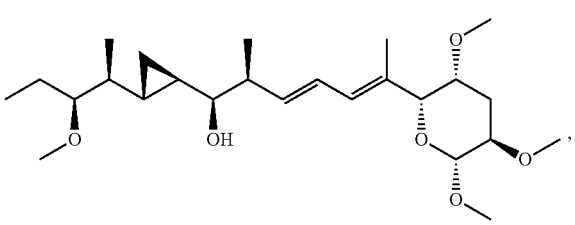
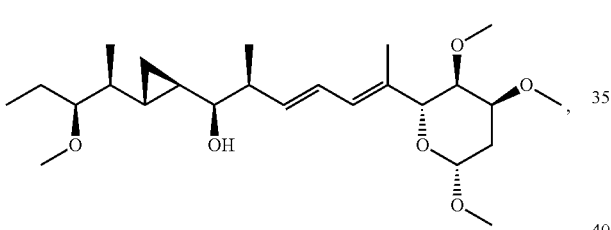
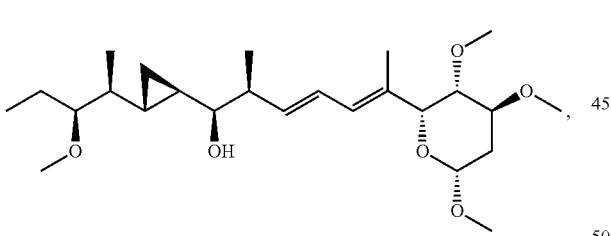
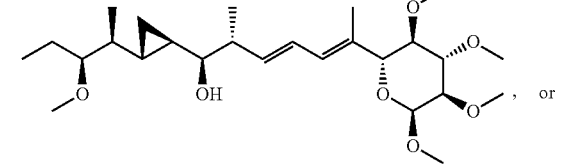, or
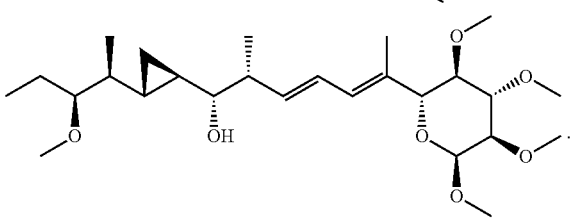
In embodiments, the compound is selected from:
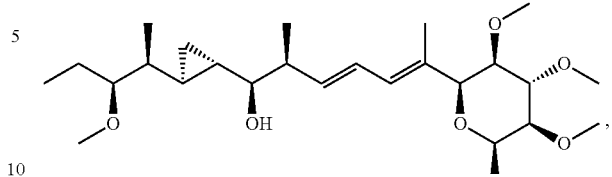
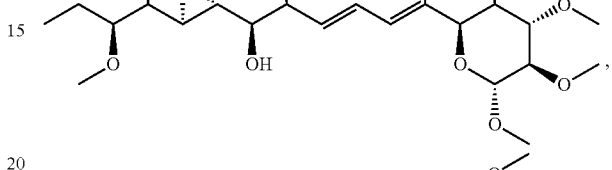
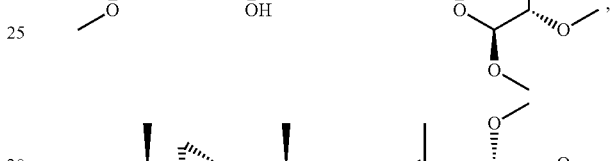
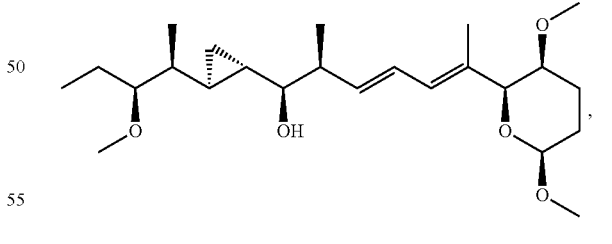
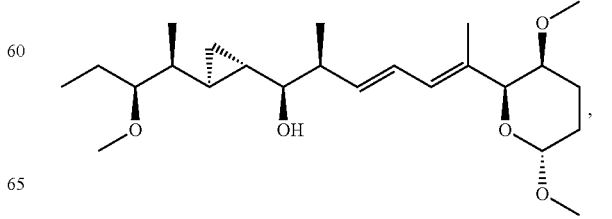

-continued
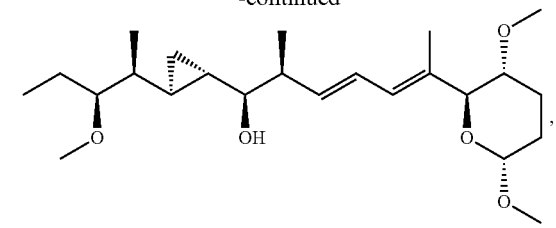
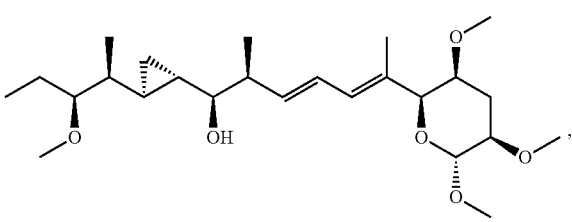
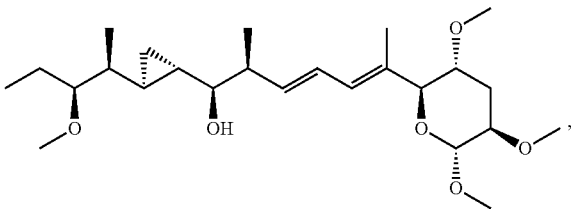
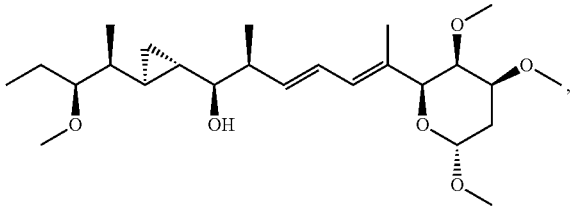
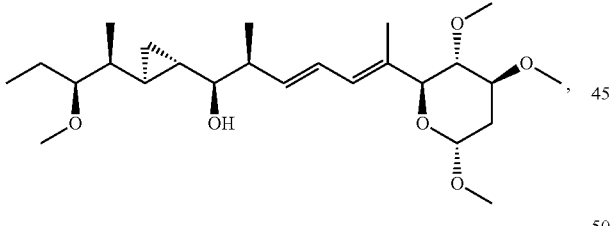
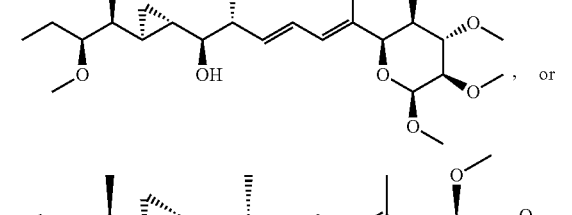, or
In embodiments, the compound is selected from:
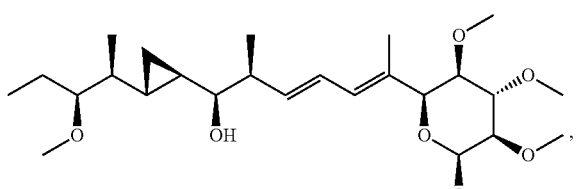
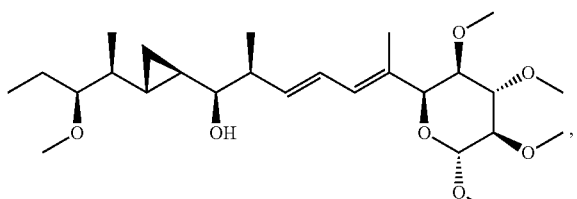
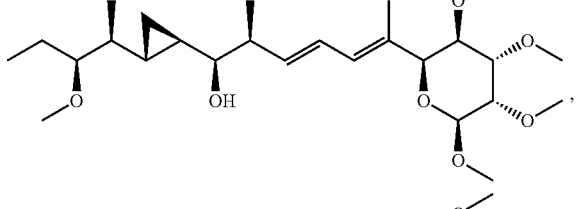
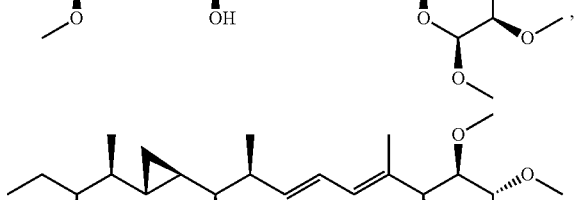
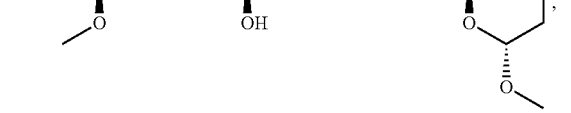

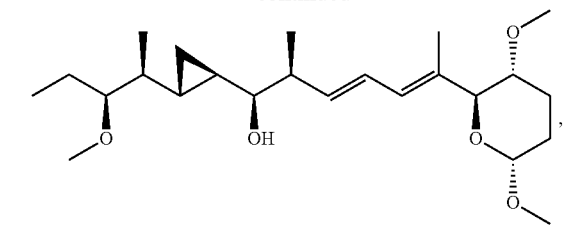
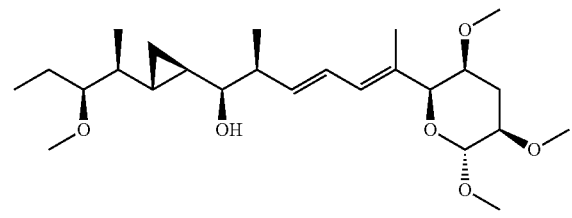
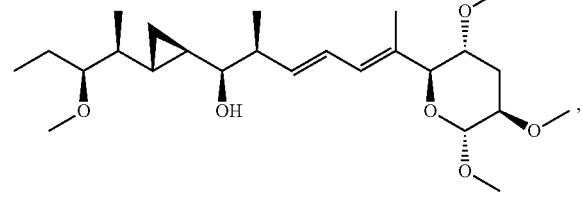
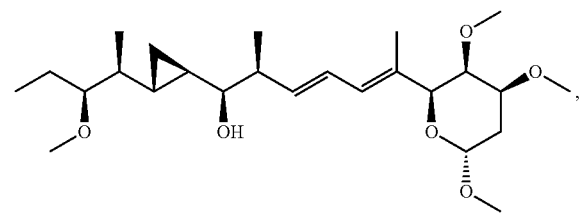
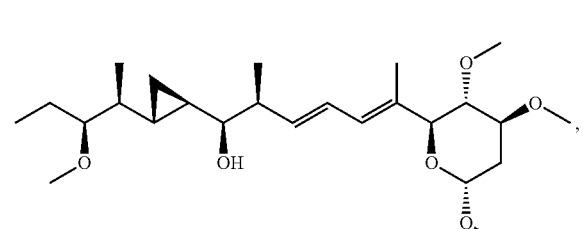
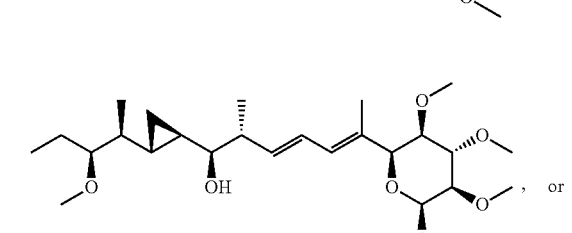, or
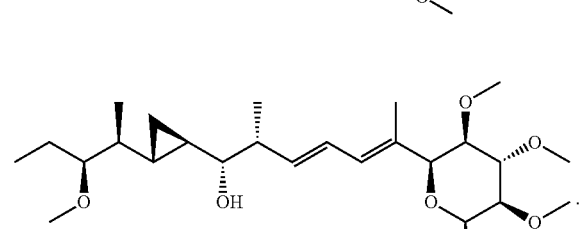
In embodiments, the compound are selected from:
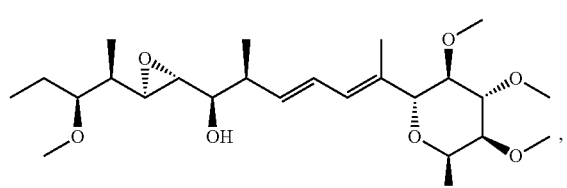
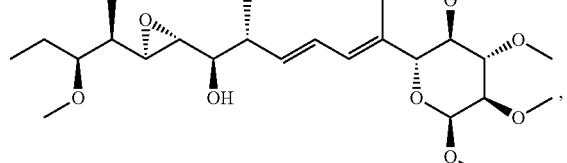
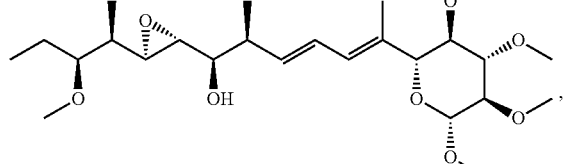
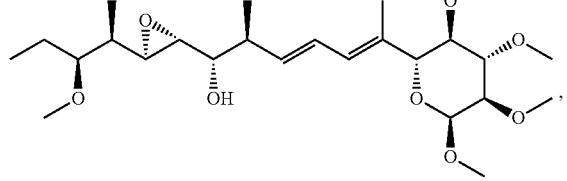
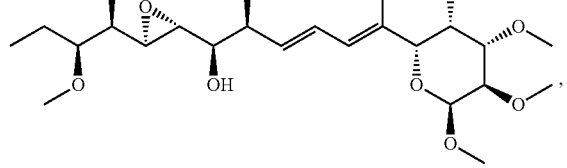
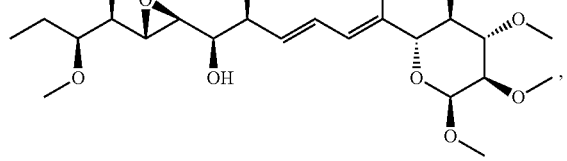
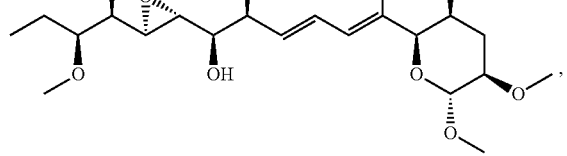
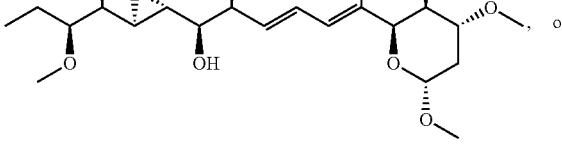, or -continued

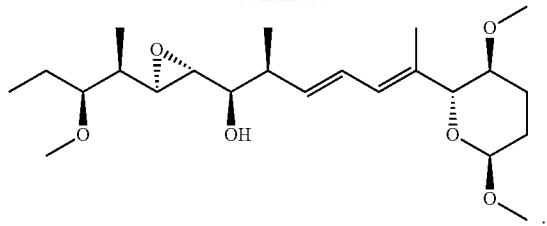

In embodiments, the compound is a compound described herein (e.g., in an aspect, embodiment, example, table, figure, scheme, appendix, or claim).

III. Pharmaceutical Compositions

Also provided herein are pharmaceutical formulations. In embodiments, the pharmaceutical formulation includes a compound (e.g. Formulae (I), (II), (IIA), (IIB), (IIA-1), (IIA-2), (IIB-1), (IIB-2), (III), (IIIA), (IIIB), (IIIA-1), (IIIA-2), (IIIB-1) and (IIIB-2)) described above (including all embodiments thereof) and a pharmaceutically acceptable excipient.

The pharmaceutical composition may contain a dosage of the compound in a therapeutically effective amount.

1. Formulations

The pharmaceutical composition may be prepared and administered in a wide variety of dosage formulations. Compounds described herein (e.g., having a structure of Formula (I), (II), (IIA), (IIB), (IIA-1), (IIA-2), (IIB-1), (IIB-2), (III), (IIIA), (IIIB), (IIIA-1), (IIIA-2), (IIIB-1), or (IIIB-2)) may be administered orally, rectally, or by injection (e.g. intravenously, intramuscularly, intracutaneously, subcutaneously, intraduodenally, or intraperitoneally).

For preparing pharmaceutical compositions from compounds described herein (e.g., having a structure of Formula (I), (II), (IIA), (IIB), (IIA-1), (IIA-2), (IIB-1), (IIB-2), (III), (IIIA), (IIIB), (IIIA-1), (IIIA-2), (IIIB-1), or (IIIB-2)), pharmaceutically acceptable carriers can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the active component may be mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The pharmaceutical compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The pharmaceutic composition may be intended for intravenous use. The pharmaceutically acceptable excipient can include buffers to adjust the pH to a desirable range for intravenous use. Many buffers including salts of inorganic acids such as phosphate, borate, and sulfate are known.

2. Effective Dosages

The pharmaceutical composition may include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat leukemia (e.g., chronic lymphocytic leukemia), such compositions will contain amounts of active ingredients effective to achieve the desired result (e.g. increasing the extent of cancer cell death in the patient).

The dosage and frequency (single or multiple doses) of compounds administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

3. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

When parenteral application is needed or desired, particularly suitable admixtures for the compounds included in the pharmaceutical composition may be injectable, sterile solutions, oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. Pharmaceutical admixtures suitable for use in the pharmaceutical compositions presented herein may include those described, for example, in Pharmaceutical Sciences (19th Ed., Mack Pub. Co., Easton, Pa.) and WO 96/05309, the teachings of both of which are hereby incorporated by reference.

IV. Methods

1. Methods of Treating Cancer

In another aspect a method of treating cancer is provided. In embodiments, the method includes administering to a subject in need thereof, a therapeutically effective amount of a compound (e.g. Formulae (I), (II), (IIA), (IIB), (IIA-1), (IIA-2), (IIB-1), (IIB-2), (III), (IIIA), (IIIB), (IIIA-1), (IIIA-2), (IIIB-1) and (IIIB-2)) described above (including all embodiments thereof). The compound may be co-administered with a pharmaceutically acceptable excipient, as addressed in previous sections. The cancer may be leukemia, lymphoma, metastatic cancer or bone cancer. The cancer may be leukemia or lymphoma. The cancer may be chronic lymphocytic leukemia (CLL).

2. Methods of Detecting Spliceosome Inhibition

In another aspect, provided is a method of detecting spliceosome inhibition using a test compound (e.g. Formulae (I), (II), (IIA), (IIB), (IIA-1), (IIA-2), (IIB-1), (IIB-2), (III), (IIIA), (IIIB), (IIIA-1), (IIIA-2), (IIIB-1) and (IIIB-2)) described above (including all embodiments thereof). In embodiments, the method includes contacting a cell with the test compound, extracting an mRNA from the cell to produce an extracted mRNA, reverse transcribing the mRNA using intron-specific primers to form an intron cDNA, amplifying the intron cDNA to form a plurality of amplified intron cDNA's, and detecting the presence of the amplified intron cDNAs to detect spliceosome inhibition resulting from the test compound.

In another aspect, provided is a method of inhibiting a spliceosome. The method includes contacting a spliceosome with a compound provided herein (e.g. Formulae (I), (II), (IIA), (IIB), (IIA-1), (IIA-2), (IIB-1), (IIB-2), (III), (IIIA), (IIIB), (IIIA-1), (IIIA-2), (IIB-1) and (IIIB-2)). In embodiments, the spliceosome is within a subject, such as a human subject or a cancer subject. In related embodiments, where the spliceosome is within a subject, the compound is provided in an amount effective to inhibit the spliceosome. In related embodiments, where the spliceosome is within a subject, the compound is provided in an amount effective to treat cancer. In other embodiments, the method is performed in vitro.

V. Embodiments

Embodiments contemplated herein include embodiments P1 to P4 following.

Embodiment P1

A compound with structure of Formula (I):

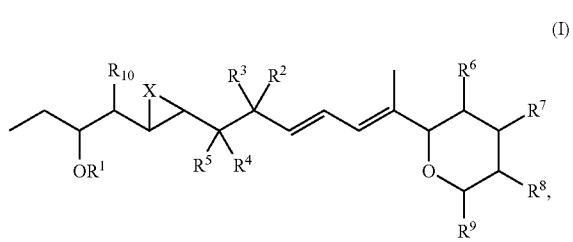
(I)

wherein X is —O— or —C($R^{26}$)($R^{27}$)—; $R^{26}$ is hydrogen, halogen, substituted or unsubstituted alkyl, substituted or unsubstituted aryl, —$OR^{28}$, —$OC(O)R^{28}$, —$OC(O)OR^{28}$, or —$OC(O)NR^{28}R^{29}$; $R^{27}$ is hydrogen, halogen, substituted or unsubstituted alkyl, substituted or unsubstituted aryl, —$OR^{30}$, —$OC(O)R^{30}$, —$OC(O)OR^{30}$, or —$OC(O)NR^{30}R^{31}$; $R^{1}$ is hydrogen, substituted or unsubstituted alkyl, —$C(O)R^{11}$, or —$C(O)OR^{11}$; $R^{2}$ is hydrogen, halogen, substituted or unsubstituted alkyl, —$OR^{12}$, —$OC(O)R^{12}$, —$OC(O)OR^{12}$, or —$OC(O)NR^{12}R^{13}$; $R^{3}$ is hydrogen, halogen, substituted or unsubstituted alkyl, —$OR^{14}$, —$OC(O)R^{14}$, —$OC(O)OR^{14}$, or —$OC(O)NR^{14}R^{15}$; $R^{4}$ is hydrogen, halogen, substituted or unsubstituted alkyl, —$OR^{16}$, —$OC(O)R^{16}$, —$OC(O)OR^{16}$, or —$OC(O)NR^{16}R^{17}$; $R^{5}$ is hydrogen, halogen, substituted or unsubstituted alkyl, —$OR^{18}$, —$OC(O)R^{8}$, —$OC(O)OR^{18}$, or —$OC(O)NR^{18}R^{19}$; $R^{6}$ is hydrogen, —$OR^{20}$, —$C(O)R^{20}$, —$C(O)OR^{20}$, —$OC(O)R^{20}$, —$OC(O)OR^{20}$; $R^{7}$ is hydrogen, —$OR^{21}$, —$C(O)R^{21}$, —$C(O)OR^{21}$, —$OC(O)R^{21}$, Or —$OC(O)OR^{21}$; $R^{8}$ is hydrogen, —$OR^{22}$, —$C(O)R^{22}$, —$C(O)OR^{22}$, —$OC(O)R^{22}$, or —$OC(O)OR^{22}$; $R^{9}$ is hydrogen, —$OR^{23}$, —$C(O)R^{23}$, —$C(O)OR^{23}$, —$OC(O)R^{23}$, or —$OC(O)OR^{23}$; $R^{10}$ is hydrogen, substituted or unsubstituted alkyl, —$OR^{24}$, —$OC(O)R^{24}$, —$OC(O)OR^{24}$ or —$OC(O)NR^{24}R^{25}$; and $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{28}$, $R^{29}$, $R^{30}$, and $R^{31}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P2

The compound of embodiment P1 with structure of Compound (2):

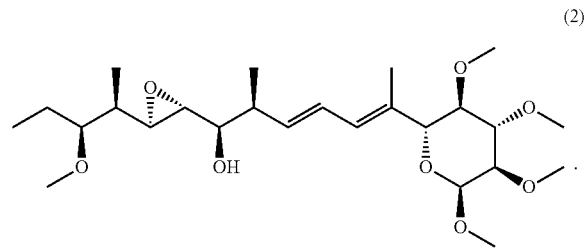 [SMILES: CC[C@H](OC)[C@@H](C)[C@H]1O[C@@H]1[C@H](O)[C@@H](C)/C=C/C=C(\C)[C@H]1O[C@H](OC)[C@H](OC)[C@@H](OC)[C@@H]1OC]
(2)

Embodiment P3

A pharmaceutical composition comprising a compound according to embodiment P1 and a pharmaceutically acceptable excipient.

Embodiment P4

A method of treating cancer comprising administering to a subject in need thereof a therapeutically effective amount of a compound of embodiment P1.

Embodiments contemplated herein include embodiments Q1 to Q12 following.

Embodiment Q1

The compound of embodiment Q1 with structure of the following compound:

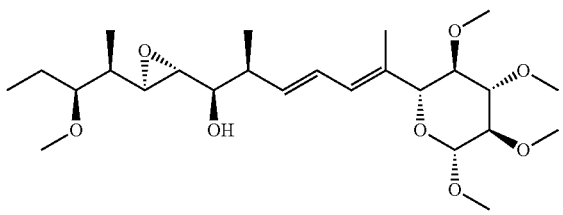 [SMILES: CC[C@H](OC)[C@@H](C)[C@H]1O[C@@H]1[C@H](O)[C@@H](C)/C=C/C=C(\C)[C@H]1O[C@@H](OC)[C@H](OC)[C@@H](OC)[C@@H]1OC]

Embodiment Q2

The compound of embodiment Q2 with structure of the following compound:

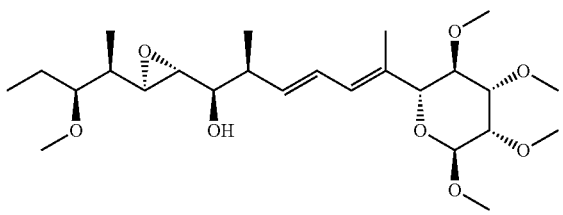 [SMILES: CC[C@H](OC)[C@@H](C)[C@H]1O[C@@H]1[C@H](O)[C@@H](C)/C=C/C=C(\C)[C@H]1O[C@H](OC)[C@@H](OC)[C@@H](OC)[C@@H]1OC]

Embodiment Q3

The compound of embodiment Q3 with structure of the following compound:

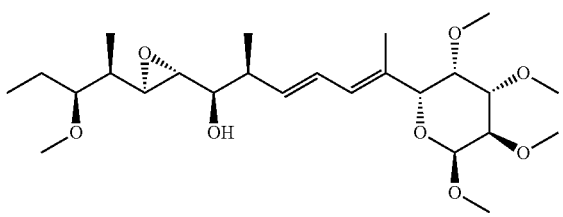 [SMILES: CC[C@H](OC)[C@@H](C)[C@H]1O[C@@H]1[C@H](O)[C@@H](C)/C=C/C=C(\C)[C@H]1O[C@H](OC)[C@H](OC)[C@@H](OC)[C@H]1OC]

Embodiment Q4

The compound of embodiment Q4 with structure of the following compound:

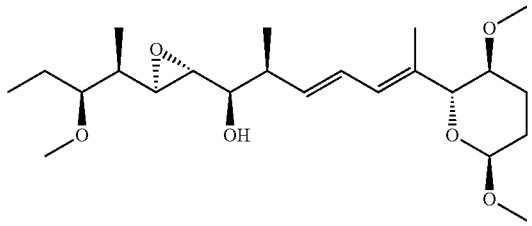 [SMILES: CC[C@H](OC)[C@@H](C)[C@H]1O[C@@H]1[C@H](O)[C@@H](C)/C=C/C=C(\C)[C@H]1O[C@H](OC)CC[C@@H]1OC]

Embodiment Q5

The compound of embodiment Q5 with structure of the following compound:

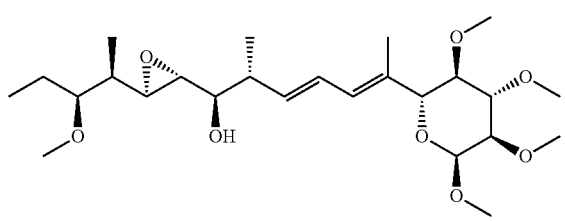 [SMILES: CC[C@H](OC)[C@@H](C)[C@H]1O[C@@H]1[C@H](O)[C@H](C)/C=C/C=C(\C)[C@H]1O[C@H](OC)[C@H](OC)[C@@H](OC)[C@@H]1OC]

Embodiment Q6

The compound of embodiment Q6 with structure of the following compound:

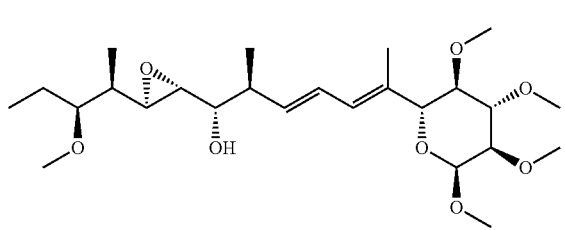 [SMILES: CC[C@H](OC)[C@@H](C)[C@H]1O[C@@H]1[C@@H](O)[C@@H](C)/C=C/C=C(\C)[C@H]1O[C@H](OC)[C@H](OC)[C@@H](OC)[C@@H]1OC]

Embodiment Q7

The compound of embodiment Q7 with structure of the following compound:

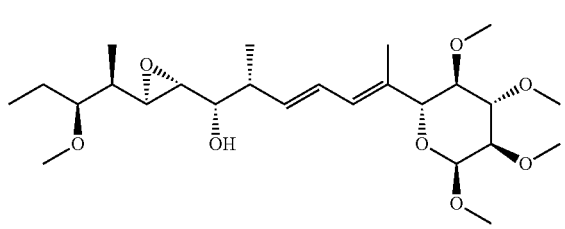 [SMILES: CC[C@H](OC)[C@@H](C)[C@H]1O[C@@H]1[C@@H](O)[C@H](C)/C=C/C=C(\C)[C@H]1O[C@H](OC)[C@H](OC)[C@@H](OC)[C@@H]1OC]

Embodiment Q8

The compound of embodiment Q8 with structure of the following compound:

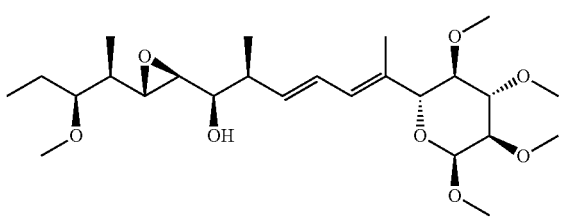 [SMILES: CC[C@H](OC)[C@@H](C)[C@@H]1O[C@H]1[C@H](O)[C@@H](C)/C=C/C=C(\C)[C@H]1O[C@H](OC)[C@H](OC)[C@@H](OC)[C@@H]1OC]

Embodiment Q9

The compound of embodiment Q9 with structure of the following compound:

Embodiment Q10

The compound of embodiment Q10 with structure of the following compound:

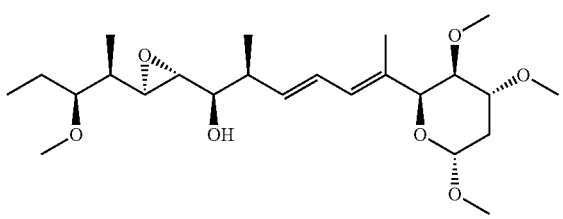 [SMILES: CC[C@H](OC)[C@@H](C)[C@H]1O[C@@H]1[C@H](O)[C@@H](C)/C=C/C=C(\C)[C@@H]1O[C@@H](OC)C[C@@H](OC)[C@@H]1OC]

Embodiment Q11

A pharmaceutical composition comprising a compound according to embodiments Q1-Q10 and a pharmaceutically acceptable excipient.

Embodiment Q12

A method of treating cancer comprising administering to a subject in need thereof a therapeutically effective amount of a compound of embodiments of Q1-Q10.

VI. Examples

Example 1—A Carbohydrate-Derived Splice Modulator

Abstract Small molecule splice modulators have recently been recognized for their clinical potential for diverse cancers. This combined with their use as tools to study the importance of splice-regulated events and their association with disease continues to fuel the discovery of new splice modulators. One of the key challenges found in the current class of materials arises from their instability, where rapid metabolic degradation can lead to off-target responses. We now describe the preparation of bench-stable splice modulators by adapting carbohydrate motifs as a central scaffold to provide rapid access to potent splice modulators.

Introduction

In 2007, two Japanese teams revealed the importance of targeting the SF3b unit of the spliceosome for anti-tumor therapy [1,2]. These breakthroughs not only forwarded the spliceosome as an important target for cancer [2], but also identified two key families of polyketide spliceosome modulators (FIG. 1), including FD-895 (1a)[2], pladienolide B (1b)[3] and herboxidiene (1c) [4]. Since these discoveries, the development of splicing assays has been instrumental in the advance of next generation splice modulators. The success of these discoveries was further marked by the translation of an analog of pladienolide D, E7101, into phase I clinical trials[5]. However, many of these natural products are subject to low stability and/or poor pharmacological properties[6]. To this end, our laboratory has been a part of a growing medicinal chemistry effort to identify next generation splice modulators with improved pharmacological properties.

An attractive proposal suggested a method of analog development through the use of a consensus motif [7]. Pursuing this approach, their team has advanced the sudemycins [8] and a pladienolide-herboxidiene hybrid [9] as next generation leads. This, along with efforts at the Eisai Co. Ltd [10], H3 Biomedicine [11], Pfizer [12], Ghosh-Jurica laboratories [13], Koide laboratory [14], and our laboratories [15], have provided a strong foundation for achieving analogs with improved pharmacological properties. We now report on an advanced new class of splice modulators that are more potent, stable and rapidly accessible analogs.

In addition to carbohydrates being ubiquitous biological scaffolds, they are also derived from the natural chiral pool, making them ideal scaffolds for medicinal chemical optimization [16]. To expand on this hypothesis, we designed and prepared carbohydrate-derived compound, i.e. an analog of FD-895 whose core was derived from D-glucose.

Results

Our design began with FD-895 (1a) due to the fact that earlier medicinal chemistry efforts in our laboratory provided derivatives with improved pharmacological properties [6a]. From these studies, we determined that manipulation of the stereochemistry at the $C_{16}$-$C_{19}$ diad (FIG. 1) provided an effective means to improve activity. From these data, we targeted a side chain that contained the exact terminus (FIG. 1), epoxide (FIG. 1), and diene groups (FIG. 1) as one of our more active analogs of FD-895 [6a]. Here, we incorporated already known SAR data to improve activity by selecting an improved $C_{16}$-$C_{19}$ stereodiad (shown in 2, FIG. 1).

Clues Obtained from the Solution Structure Analysis of FD-895 (1a).

Figure 2A:
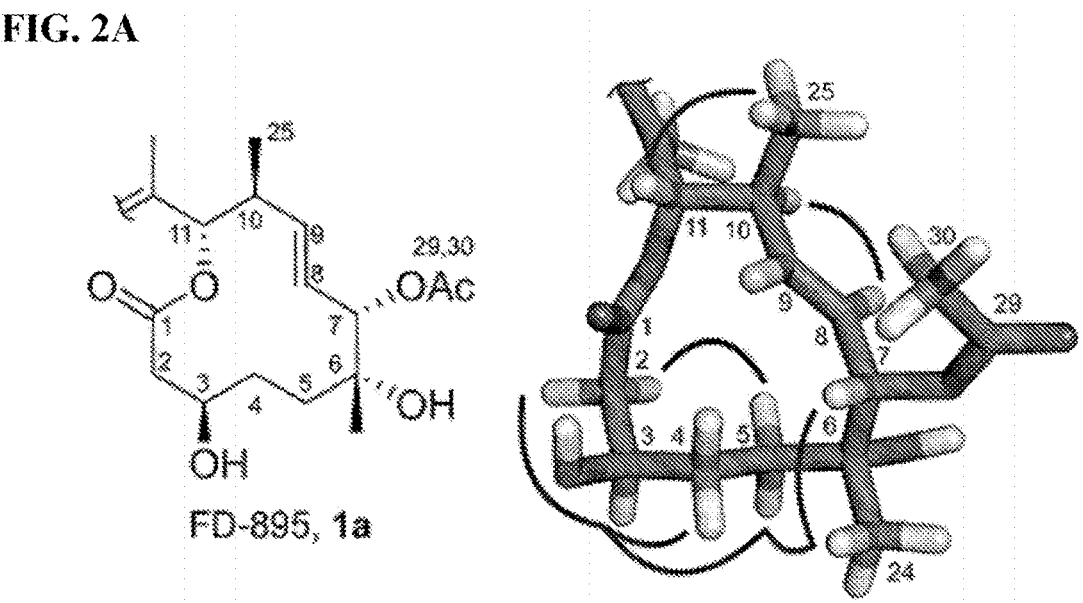
FIGS. 2A-2E. Models of FD-895 (1a), herboxadiene (1c) and carbohydrate-derived analog 2.

While structural information on the eukaryotic spliceosome has recently been published [18], representation of the binding of a splice modulator with SF3b has yet to be established. We began by exploring the solution structure of the macrolide core of FD-895 (1a). Using multiple solvents ($CDCl_3$ and $C_6D_6$) for data acquisition, we identified a series of NOE interactions that, along with coupling constant data, allowed assignment of the solution structure of the macrolide core (FIG. 2A).

Design of a Carbohydrate Core Motif.

Using this structure and analyzing its space-filling model, we began to search for motifs that accurately represented the macrolide core. Our goal was to find a structural unit that offered an improved synthetic entry and diverse means of tailoring, while also addressing previous pharmacological issues (stability and solubility). We began by inspecting the overlap between the small herboxidiene (1c) and large FD-895 (1a) cores. While a clear overlay existed, it was evident that space occupied by the $C_4$-$C_7$ unit within 1a may not be a requirement for activity. We realized that simple monosaccharides such as D-glucose or D-galactose could provide a strong overlap with these cores. After evaluating several structures, we turned our attention to explore α-methyl-2,3,4-trimethoxy-D-glucopyranoside (3) as a core mimetic [19].

Figure 2B:
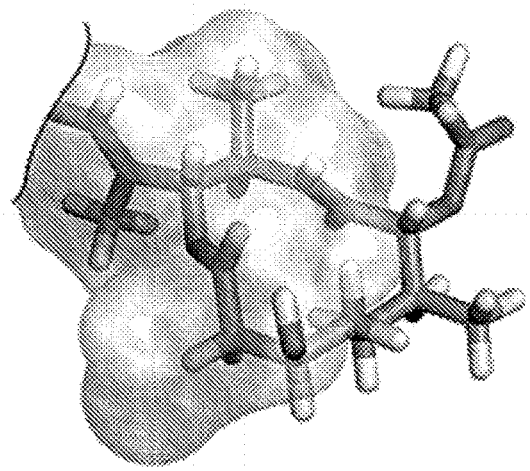
Figure 2C:
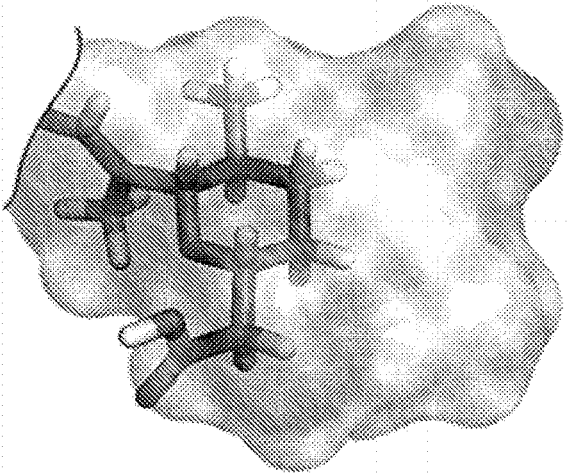
Figure 2D:
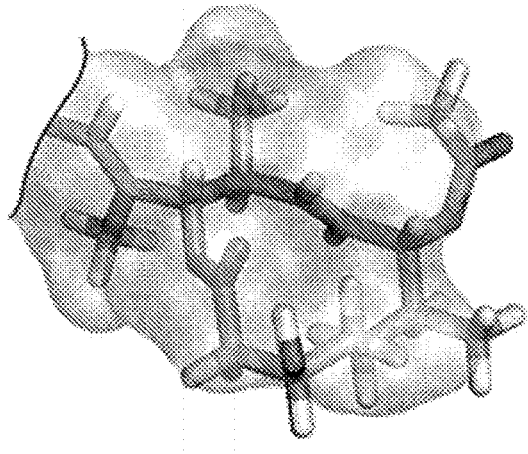
Figure 2E:
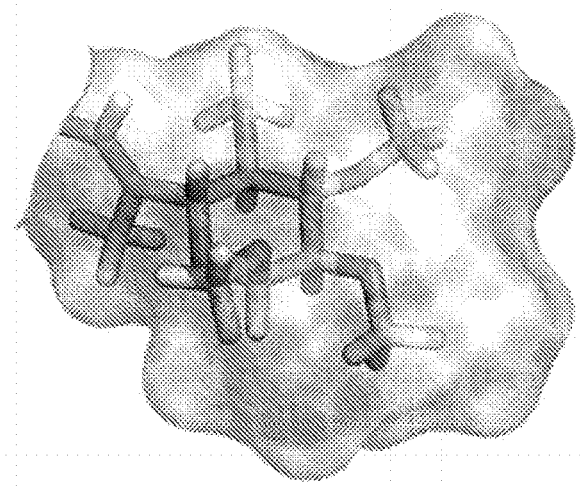

Structurally, glycoside 2 offered a functional map that lay between the core sizes of 1a and 1c (FIGS. 2A-2E). As illustrated in FIGS. 2D-2E, the C2, C3, and C4 methoxy groups in 2 provided an improved fit to 1a relative to herboxadiene (FIGS. 2B-2C). Specifically, the C2 methoxy group of 2 filled the space taken by the C24 methyl group in 1a. Likewise, the C3 methoxy of 2 was able to partially fill the space of the $C_{29}$-$C_{30}$ acetate, a region that was already shown to tolerate functional modifications [20]. With this support, we turned our attention to the synthesis and biological evaluation analog 2.

Synthetic Plan.

Our plan focused on using a late-stage Julia-Kocienski olefination to couple a side chain derived from FD-895 to the monosaccharide core (see Scheme A). Here, we envisioned that we could leverage the extensive efforts from our own laboratory for development of pladienolide/FD-895 side chain [6a,15b] as a means to probe the structure-activity relationships (SARs) of side chain incorporating analogs. We therefore set out towards preparation of core component 8 (Scheme 1) and side chain component 16 (Scheme 2).

Scheme A.
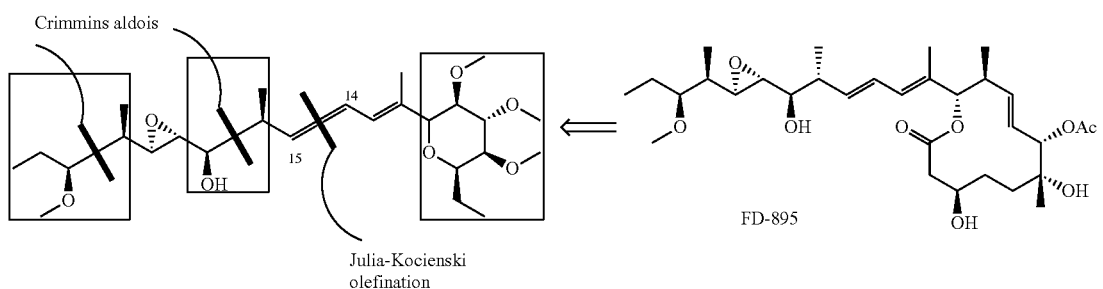
Scheme 1. Synthesis of core compound 8.
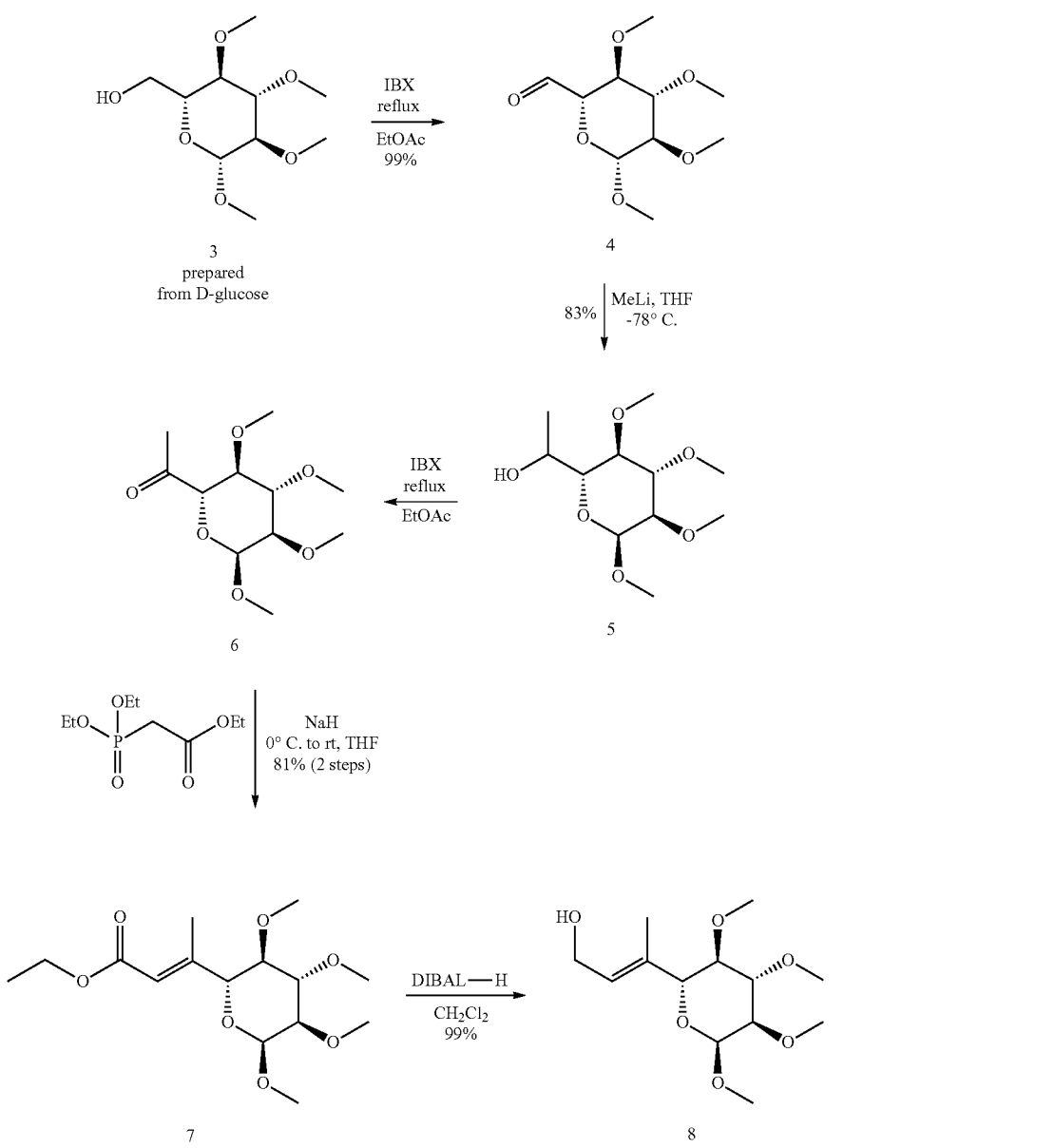

Scheme 2. Synthesis of side chain component 16

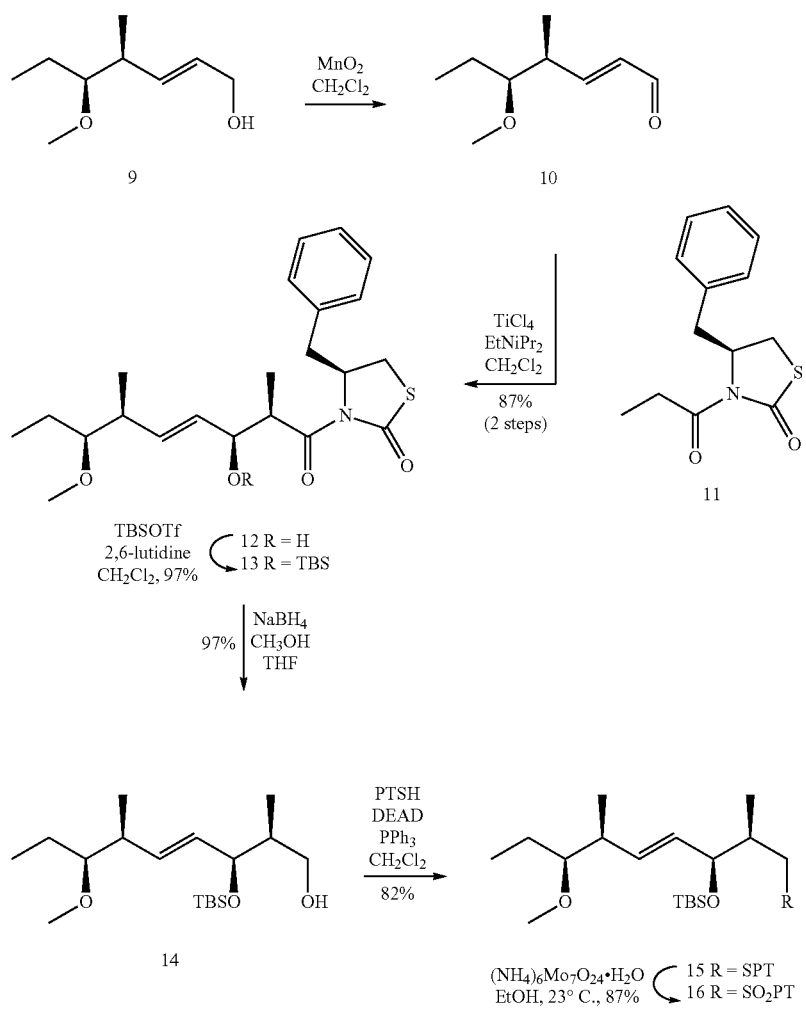

Synthesis of a Carbohydrate Core Component 8.

Synthesis of 8 was accomplished in 5 steps from 3, a monosaccharide derivative that in turn was prepared in 3 steps (54% yield) from α-methyl-D-glucopyranoside [19]. We began by oxidizing to aldehyde 4. Advantageously, we were able to reduce chromatographic purification efforts by using a combination of an IBX oxidation followed by solvent-dependent filtration through a pad of $SiO_2$. The addition of MeLi to crude 4 occurred with minimal by-product formation providing alcohol 5 in 82% yield from 3.

Repetition of the IBX oxidation procedure provided ketone 6, which could be rapidly purified by passage through a $SiO_2$ plug. While small samples of 6 were purified for characterization, the crude product was readily subjected to a Horner-Wadsworth-Emmons olefination to afford ester 7. We were able to convert 5 to 7 in two steps and 80% yield with a single purification. Finally, ester 7 was reduced with DIBAL-H to afford core unit 8, which could be stored for months at −20° C. without decomposition. Overall, this process provides access to 8 in 66% in 5 steps from 3 (36% in 8 steps from α-methyl-D-glucopyranoside).

Synthesis of the Side Chain Component 16.

The synthesis of the side chain component began with allylic alcohol 9, an intermediate that was prepared at >10 g scale for the synthesis of FD-895 (1a) [6a]. Allylic oxidation with $MnO_2$ provided aldehyde 10, which was purified through a $SiO_2$ plug and directly submitted to a Crimmins aldol condensation with auxiliary 11, to afford adduct 12 in 87% yield over two steps. NMR analyses on the crude product indicated that this reaction occurred without detectable formation of other isomeric products.

With 12 in hand, the carbinol was protected as TBS ether 13, and the auxiliary was removed by $NaBH_4$ reduction. Optimization studies indicated that a 5:1 ratio of THF: $CH_3OH$ provided a reproducibly high yield of 14. Completion of this component was accomplished by a two-step installation of the 1-phenyl-1H-tetrazol-5-yl (PT) sulfone. While Mitsunobu conditions were effective at producing sulfone 15 in 82% yield at gram scales, oxidation often provided significant quantities of the corresponding sulfoxides (incomplete oxidation by-products). Typically, samples of these sulfoxides were collected after chromatographic purification and resubmitted to the oxidation conditions to afford a combined yield of 89% of component 16. To date, we have completed the synthesis of gram quantities of 16 in 6 steps and 58% overall yield from 9 and 12 steps and 21% overall yield from auxiliary 11.

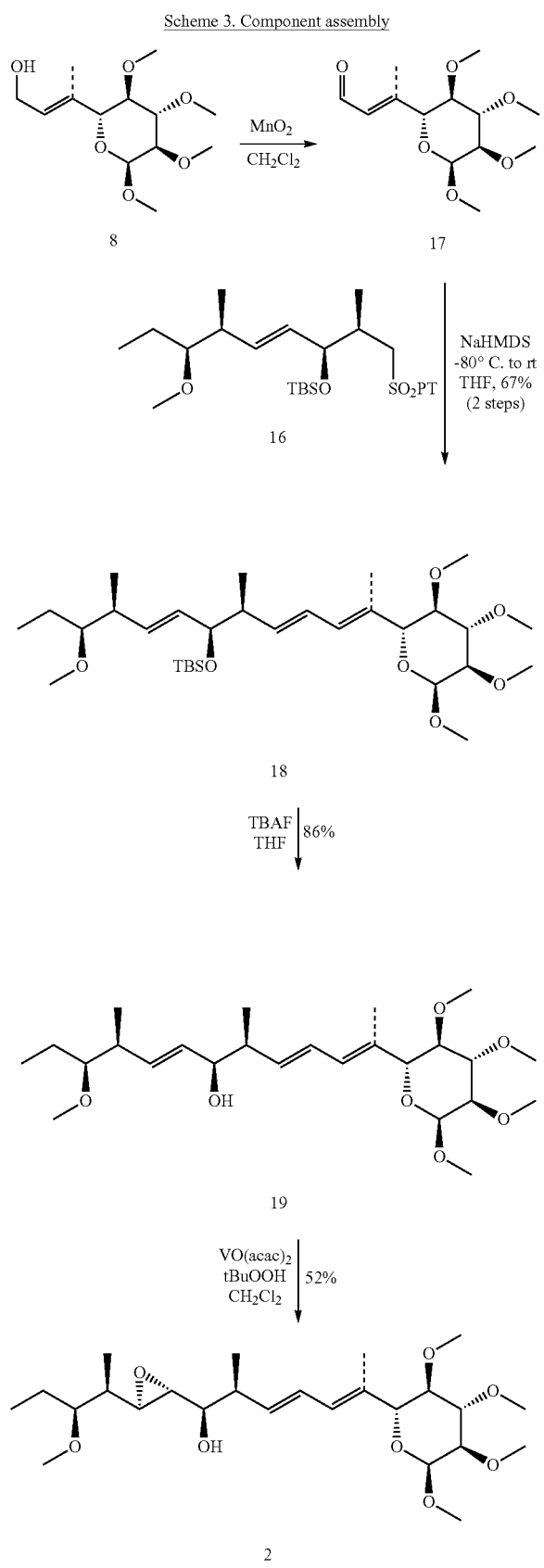

Scheme 3. Component assembly

Component Assembly and Completion of the Synthesis of 2.

With components 8 and 16 in hand, the component coupling began by oxidizing allylic alcohol 8 to the corresponding aldehyde 19. Purification via dry column vacuum chromatography using Geduran 60 silica gel was sufficient to afford pure 19 for coupling. After initial screening, we found the optimum yield (68%) of 18 was obtained when applying 1.05 eq. NaHMDS to 1.0 eq. of sulfone 8 and following this by addition of 1.1 eq. of aldehyde 19. The yield of this reaction also included recovery of 8% of sulfone 16 and 11% of the chromatographically separable cis-isomer of 18 (structure not shown). With samples of pure 18 at hand, deprotection with TBAF afforded alcohol 19.

Figure 3A:
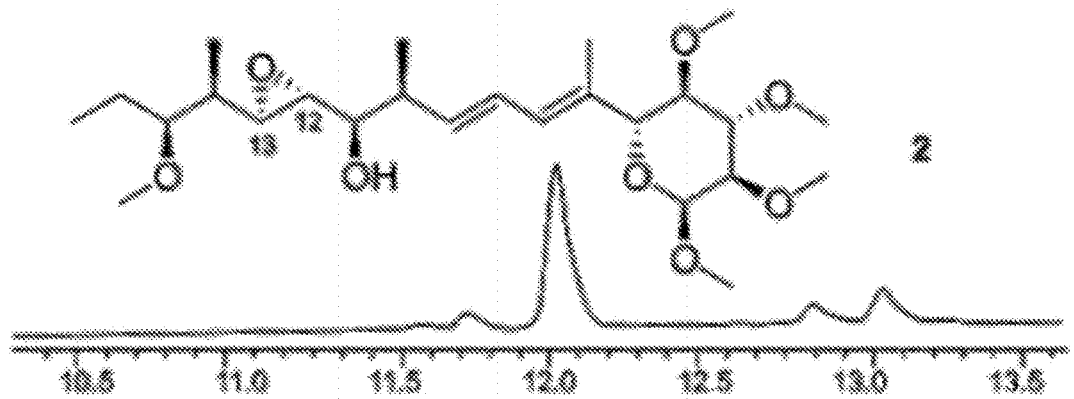
FIGS. 3A-3D. Stereoselectivity of the $C_{12}$-$C_{13}$ epoxidation.

Next, we turned to the stereoselective VO(acac)$_2$ catalyzed epoxidation of allylic alcohols[21] to install the C12-C13 epoxide. As shown in FIG. 3A, treatment of 19 with 4.5 eq. of tBuOOH and 3 eq. of VO(acac)$_2$ at −20° C. for 6 h provided the desired stereoisomer with ~4:1 diastereoselectivity. While this was the major product, over warming or not starting the reaction at −78° C. resulted in epoxidation at C8-C9. This product was not stable as the C11 carbinol was capable of attacking the C8 center of the epoxide forming the corresponding furan analog (structure not shown). While additional optimization efforts will be required, the current conditions returned 2 in 52% yield with only traces of the undesired C8-C9 epoxidation (5-10% yield).

Validation of the Structural Assignment of 2.

Figure 3B:
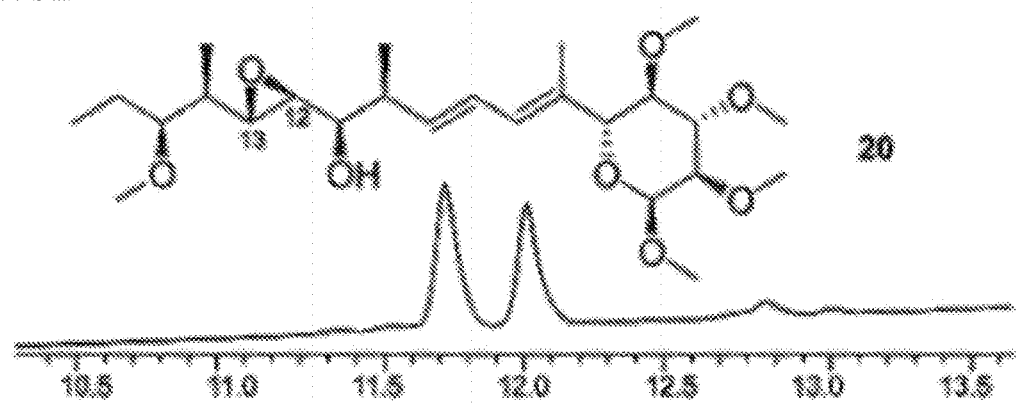

While the mechanism of the VO(acac)$_2$/tBuOOH epoxidation suggests delivery of the correct stereochemical outcome, we wanted to gain further confirmation that the product was indeed 2. We began by exploring other epoxidation conditions to prepare samples of the other isomer. Treatment of 19 with 1.2 eq. of m-CPBA at −78° C. in NaHCO$_3$ buffered CH$_2$Cl$_2$ followed by slow warming to room temperature afforded a ~1:1 mixture of both epoxides (FIG. 3B) in 62% yield. After chromatographic purification, we were able to obtain samples of both isomers.

Figure 3C:
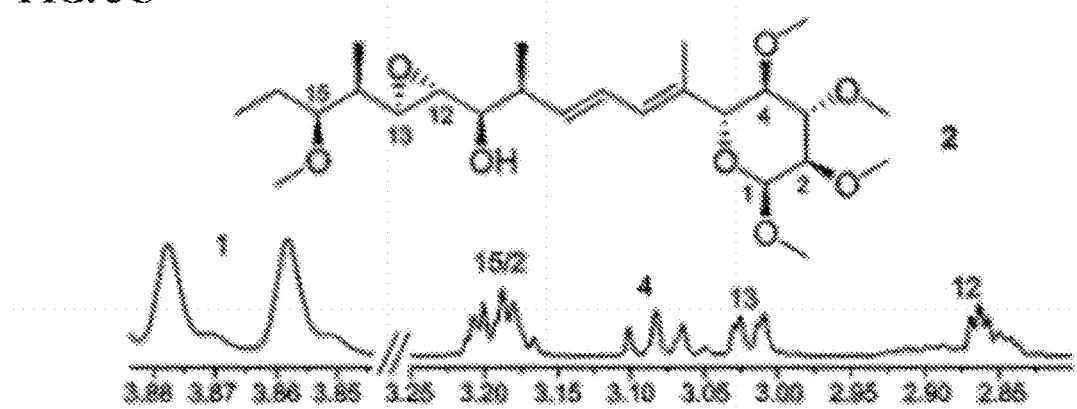
Figure 3D:
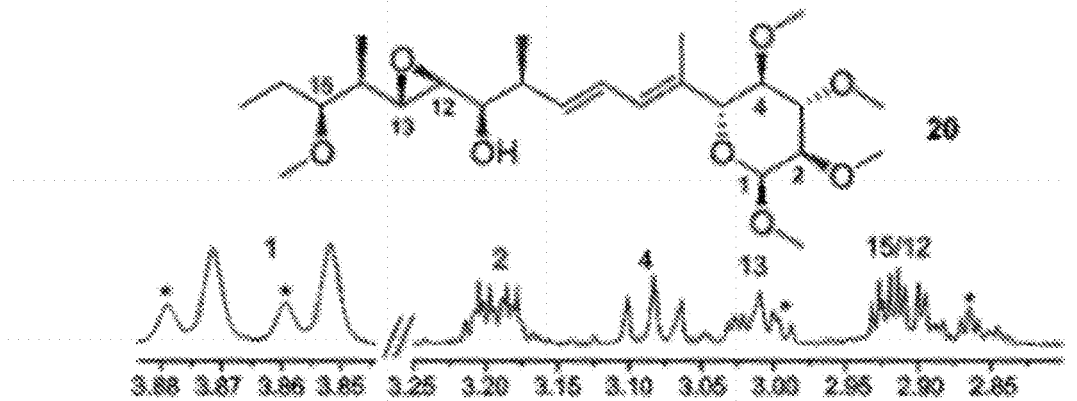
Figure 4:
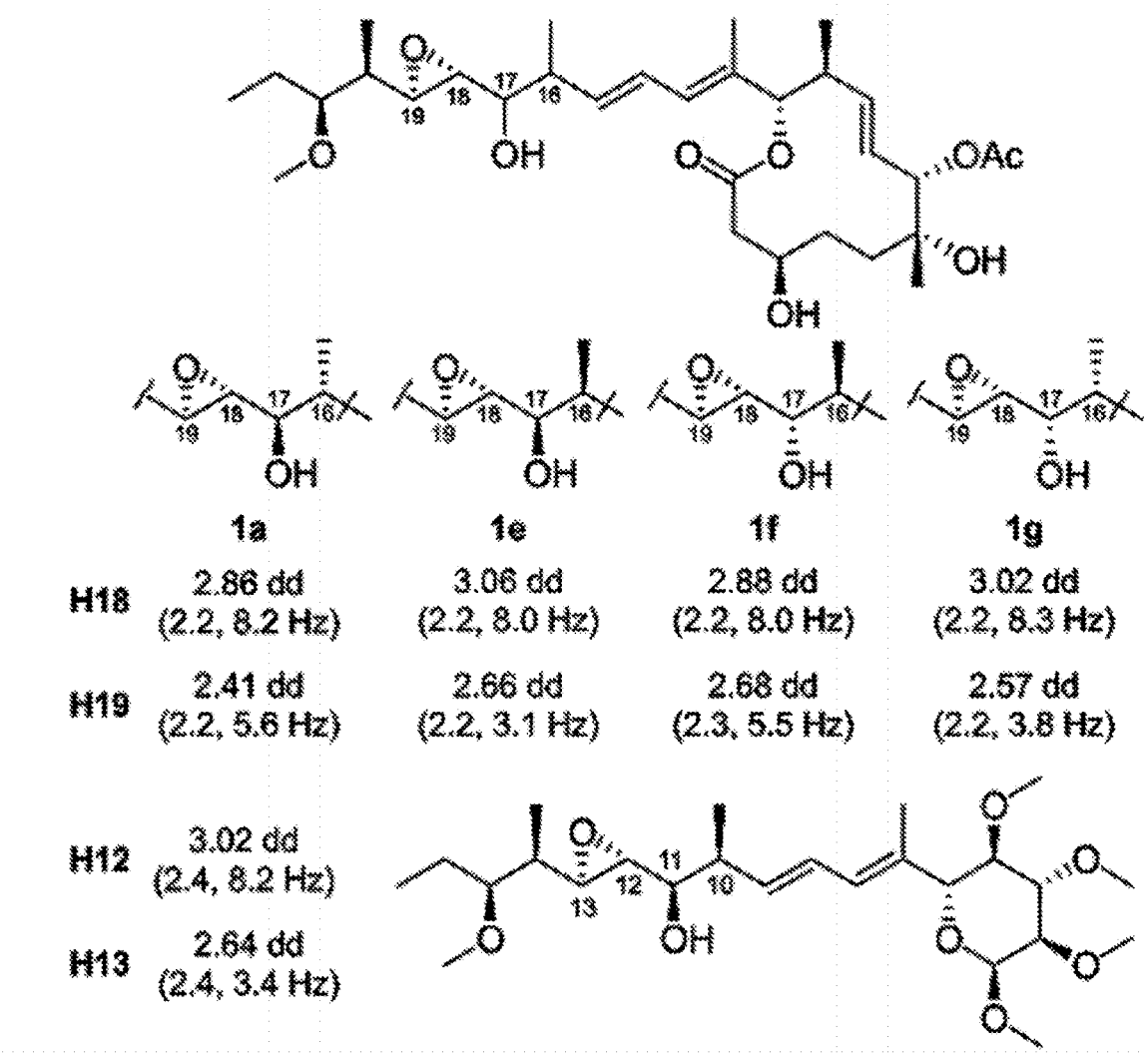
FIG. 4. Coupling constant analyses. NMR analysis in $C_6D_6$ provided a coupling pattern at C12-C13 in 2 that matched that from the corresponding FD-895 analog 1e (green) but not analogs 1a, 1f, or 1g (black) [6a,15b].

Comparative NMR analyses on the epoxides from VO(acac)$_2$/tBuOOH and m-CPBA provided a solution (FIG. 3C). Using 2D NMR data set (see Supporting Information), we were able to fully assign the proton assignments in this product. First, we identified that the chemical shift and coupling patterns of the epoxide protons at C12-C13 provided the closest match to the configuration of the corresponding C16-C19 isomer 1e (FIG. 4), with comparable chemical shifts and coupling constants.

Stability and Solubility of 2.

Early studies indicate that 2 was more soluble and stable in aqueous buffers than FD-895 (1a). Using capillary NMR and solvent $^{13}$C-satellites (QSCS) as a means of quantitation [22], we found that 2 was soluble up to 95±5 mM D$_2$O/DMSO-d$_6$ (10:1) at 23° C., while FD-895 (1a) was limited to 15±5 mM under the same conditions. Additionally, we used NMR monitoring to show that while 1a had a half-life of ~70 h in D$_2$O/DMSO-d$_6$ (10:1) at 37° C. [6a], carbohydrate-analog 2 showed no signs of decomposition even after 744 h (1 month) under the same conditions. While detailed partitioning, permeability, and metabolic stability analyses are ongoing, this initial evidence suggests that 2 offers the potential to improve pharmacological properties of this class of splice modulator.

Epoxide 2 Displays Potent Activity in Primary CLL-B Cells in Contrast to its Precursor Alkene 19.

Figure 7A:
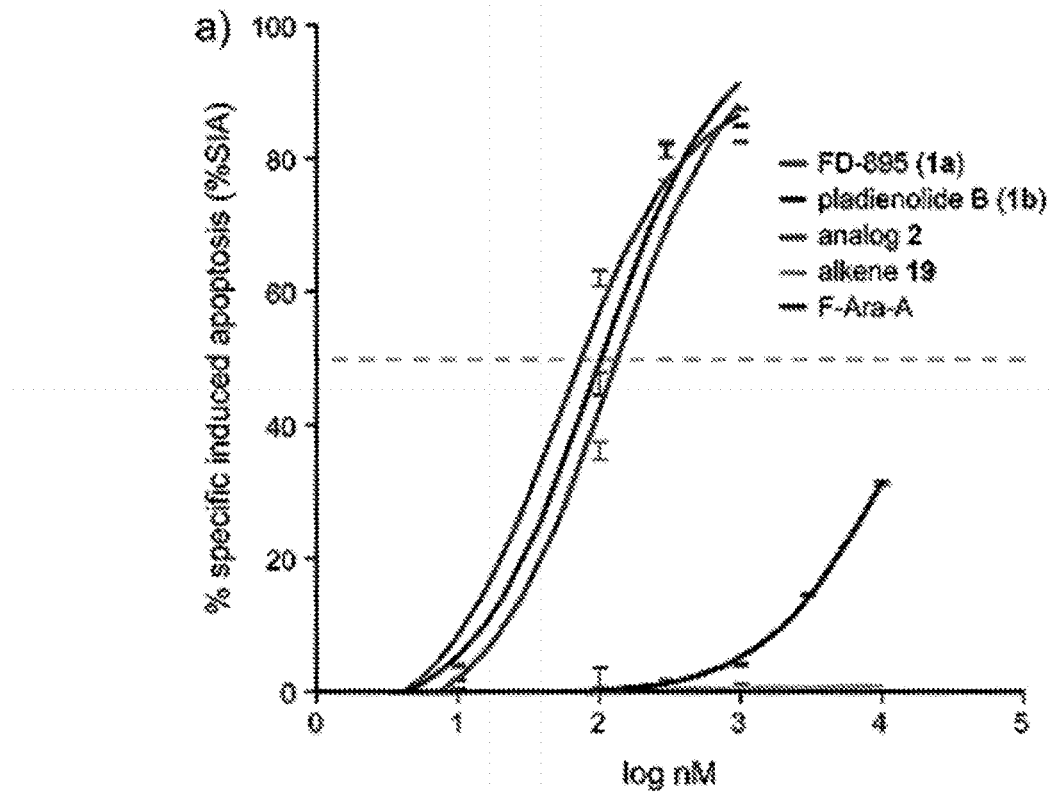
FIGS. 7A-7B. CLL-B cells cultured either alone or with stromal cell support were treated with 1a, 1b, 2, 19, or F-ara-A for 48 h at 37° C. followed by flow cytometric analysis and determination of the % SIA, as described in the experimental section. Analyses were derived from two CLL patients as indicated in the plots of FIG. 7A and FIG. 7B.
Figure 7B:
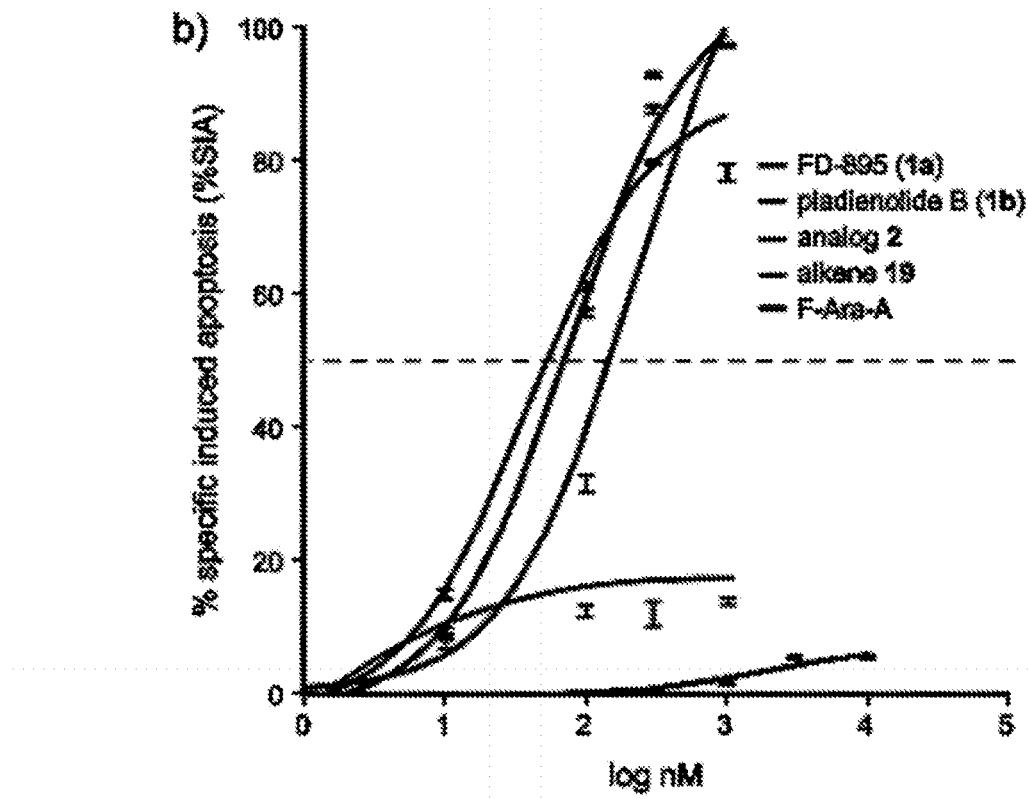

We then screened the activity of 19 and 2 in primary CLL-B cells obtained from two CLL patients, that displayed potent in vitro cytotoxic activity (FIGS. 7A-7B) measured in form of specific induced apoptosis (% SIA) of 1a ($IC_{50}$ value of 54.1±7.5 nM) and 1b ($IC_{50}$ value of 84.4±1.2 nM). Interestingly, these studies indicated that alkene 19 did not display any activity ($IC_{50}$ value >50 µM in both sets of cells). Epoxide 2, on the other hand, was active ($IC_{50}$ value of 153.0±11.8 nM) with ~3-fold loss of activity when compared to FD-895 (1a).

Compound 2 Modulates Splicing.

Figure 5:
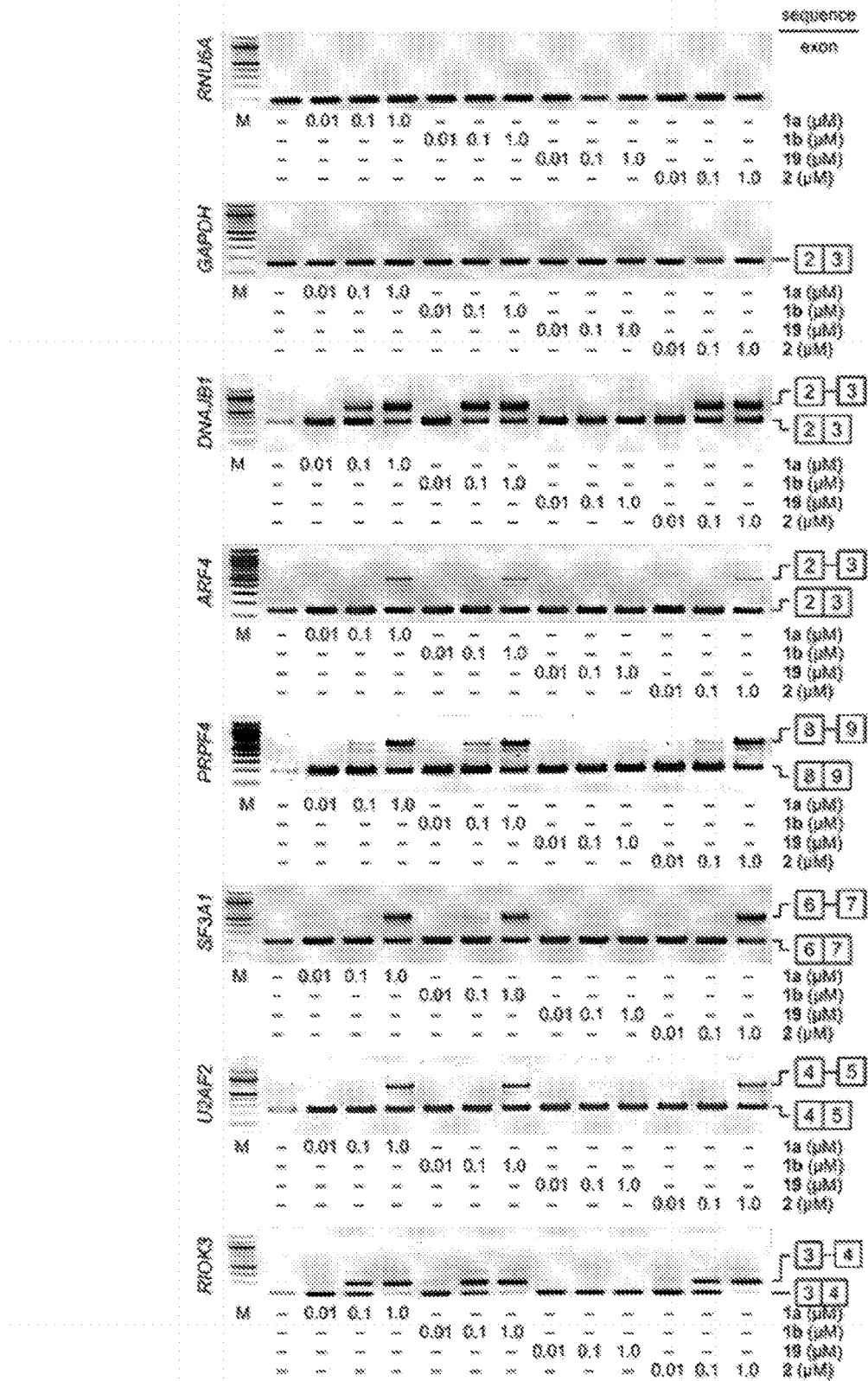
FIG. 5. Compound 2 induces splice modulation via intron retention (IR) comparable to FD-895 (1a) and pladienolide B (1b) in CLL-B cells. The alkene precursor 19, which was shown inactive in screening assays, did not induce IR. Genes GAPDH and RNU6A were used as unspliced and loading controls, respectively. Complementary qRT-PCR data has been provided in FIG. 8.
Figure 8:
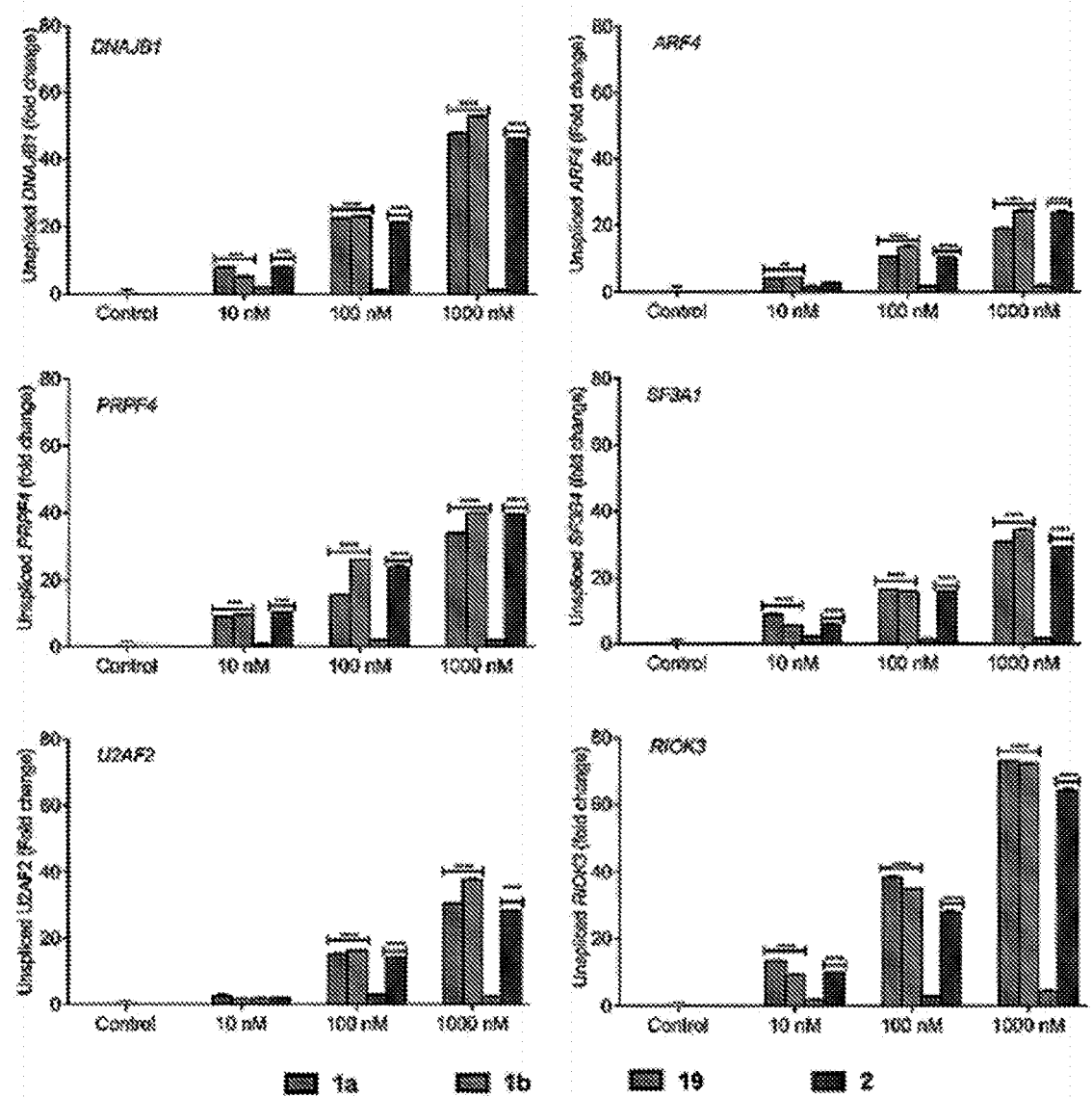
FIG. 8. The figure depicts histograms of qRT-PCR data associated with the RT-PCR data from selected genes depicted in FIG. 5. X-axis bins (left to right): control, 10 nM, 100 nM, 1000 nM. Ordering (left to right, top to bottom): DNAJB1, ARF4, PRPF4, SF3A1, U1AF2, RIOK3.

We then turned to RT-PCR analysis to determine if the activity of 2 also included a comparable splice response as 1a and 1b in CLL-B cells. Using unspliced RNU6A and unmodulated GAPDH (top, FIG. 5) as controls, we were able to obtain complementary splice modulation in all six genes selected from our prior studies to provide a diversity of intron retention (IR) response.[15a] This included comparable modification of IR in DNAJB1, ARF4, PRPF4, RIOK3, SF3A1, and U2AF2 (FIG. 4 and FIG. 8) from primary CLL-B cells. In contrast, alkene precursor 19 was inactive for all six genes (FIG. 5), indicating that the epoxide in 2 is essential for activity.

Figure 6:
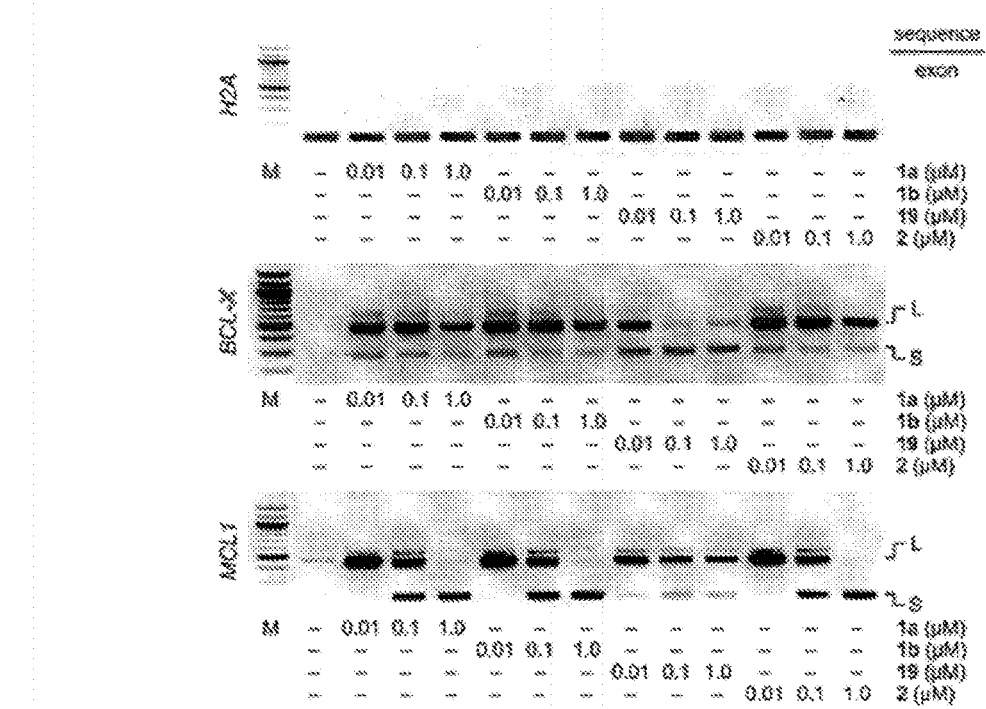
FIG. 6. Compound 2 modulates alternate splicing (AS) in CLL-B cells, which is comparable to FD-895 (1a) and pladienolide B (1b). The alkene precursor 19, which was shown inactive in screening assays, did not induce AS. H2A gene was used as unspliced loading control as depicted. S and L denote short and long isoforms, respectively.

Additionally, we were able to confirm that compound 2 also induced alternate splicing (AS) events. As shown in FIG. 6, treatment of CLL-B cells with 1a, 1b and 2 resulted in a decrease in the long (anti-apoptotic) form and increased the expression of short (pro-apoptotic) form of MCL1. Similarly, BCL-X demonstrates comparable AS events (FIG. 6). This indicates that cell death induced by 1a, 1b and 2 is not exclusively derived through AS of MCL1 but may also include other players. This fact is further supported by RNAseq analyses [15a], which implicates the involvement of other pathways. Efforts are now underway to explore the roles of IR and AS events as well as to identify structural motifs that enrich specific events.

Experimental Section

A. General Experimental Methods.

Chemical reagents were purchased from Acros, Fluka, Sigma-Aldrich, or TCI. Deuterated NMR solvents were purchased from Cambridge Isotope Laboratories. All reactions were conducted with rigorously dried anhydrous solvents that were obtained by passing through a solvent column composed of activated Al alumina. Anhydrous N,N-dimethylformamide was obtained by passage over activated molecular sieves and a subsequent NaOCN column to remove traces of dimethylamine. Triethylamine ($Et_3N$) was dried over Na and freshly distilled. Ethyl-N,N-diisopropylamine ($EtNiPr_2$) was distilled from ninhydrin, then from potassium hydroxide. Anhydrous $CH_3CN$ was obtained by distillation from $CaH_2$. All reactions were performed under positive pressure of Ar in oven-dried glassware sealed with septa, with stirring from a Teflon coated stir bars using an IKAMAG RCT-basic mechanical stirrer (IKA GmbH). Solutions were heated using either a sand or silicon oil bath. Analytical Thin Layer Chromatography (TLC) was performed on Silica Gel 60 F254 precoated glass plates (EM Sciences). Preparative TLC (pTLC) was conducted on Silica Gel 60 plates (EM Sciences). Visualization was achieved with UV light and/or an appropriate stain ($I_2$ on $SiO_2$, $KMnO_4$, bromocresol green, dinitrophenylhydrazine, ninhydrin, and ceric ammonium molybdate). Flash chromatography was carried out Geduran Silica Gel 60 (40-63 mesh) from EM Biosciences. Yields and characterization data correspond to isolated, chromatographically and spectroscopically homogeneous materials. $^1H$ NMR spectra were recorded on Varian Mercury 300, Varian Mercury 400 spectrometers, Varian Mercury Plus 400, a JEOL ECA500, or a Varian VX500 spectrometer. A majority of the $^{13}C$ NMR spectra were recorded at 125 MHz on a Varian VX500 spectrometer equipped with an Xsens Cold probe. The remaining spectra were either collected at 125 MHz on a JEOL ECA 500, 100 MHz on a Varian Mercury 400 or 100 MHz on a Varian Mercury Plus 400 spectrometer. Chemical shifts for $^1H$ NMR and $^{13}C$ NMR analyses were referenced to the reported values of Gottlieb,[1] using the signal from the residual solvent for $^1H$ spectra, or to the $^{13}C$ signal from the deuterated solvent. Chemical shift δ values for $^1H$ and $^{13}C$ spectra are reported in parts per million (ppm) relative to these referenced values, and multiplicities are abbreviated as s=singlet, d=doublet, t=triplet, q=quartet, m=multiplet, br=broad. All $^{13}C$ NMR spectra were recorded with complete proton decoupling. FID files were processed using MestraNova 6.0.2. (MestreLab Research). Electrospray (ESI) mass spectrometric analyses were performed using a ThermoFinnigan LCQ Deca spectrometer, and high-resolution analyses were conducted using a ThermoFinnigan MAT900XL mass spectrometer with electron impact (EI) ionization. A Thermo Scientific LTQ Orbitrap XL mass spectrometer was used for high-resolution electrospray ionization mass spectrometry analysis (HR-ESI-MS). FTIR spectra were obtained on a Nicolet magna 550 series II spectrometer as thin films on either KBr or NaCl discs, and peaks are reported in wavenumbers ($cm^{-1}$). Optical rotations $[\alpha]_D$ were measured using a Perkin-Elmer Model 241 polarimeter with the specified solvent and concentration and are quoted in units of deg $cm^2$ $g^{-1}$. Spectral data were collected for all new compounds.

B. Synthesis of Core Chain Component 8.

Component 8 was prepared in 8 steps in 36% overall yield from α-methyl-D-glucopyranoside (S1) as shown in Scheme 1 (above) and Scheme S1 (below). Preparation of 6-trityl-α-methyl-α-D-glucopyranoside S2 was achieved by modification of methods developed by Crich,[S1] as described below. The following section provides a complete description of the synthetic procedures and spectroscopic properties of intermediated S2-S3, 3-8 and 19.

Scheme S1 depicts the synthesis of core component 8. Preparation of 8 required three chromatographic purifications as the crude products of S2, 3, 4, and 6 could be used without additional purification. Flash chromatography was required to purify intermediates S3, 5, and 7. The final materials were stored. Aldehyde 19 was prepared immediately before the component coupling process as described in Scheme 3 and Scheme S3 following.

Scheme S1.

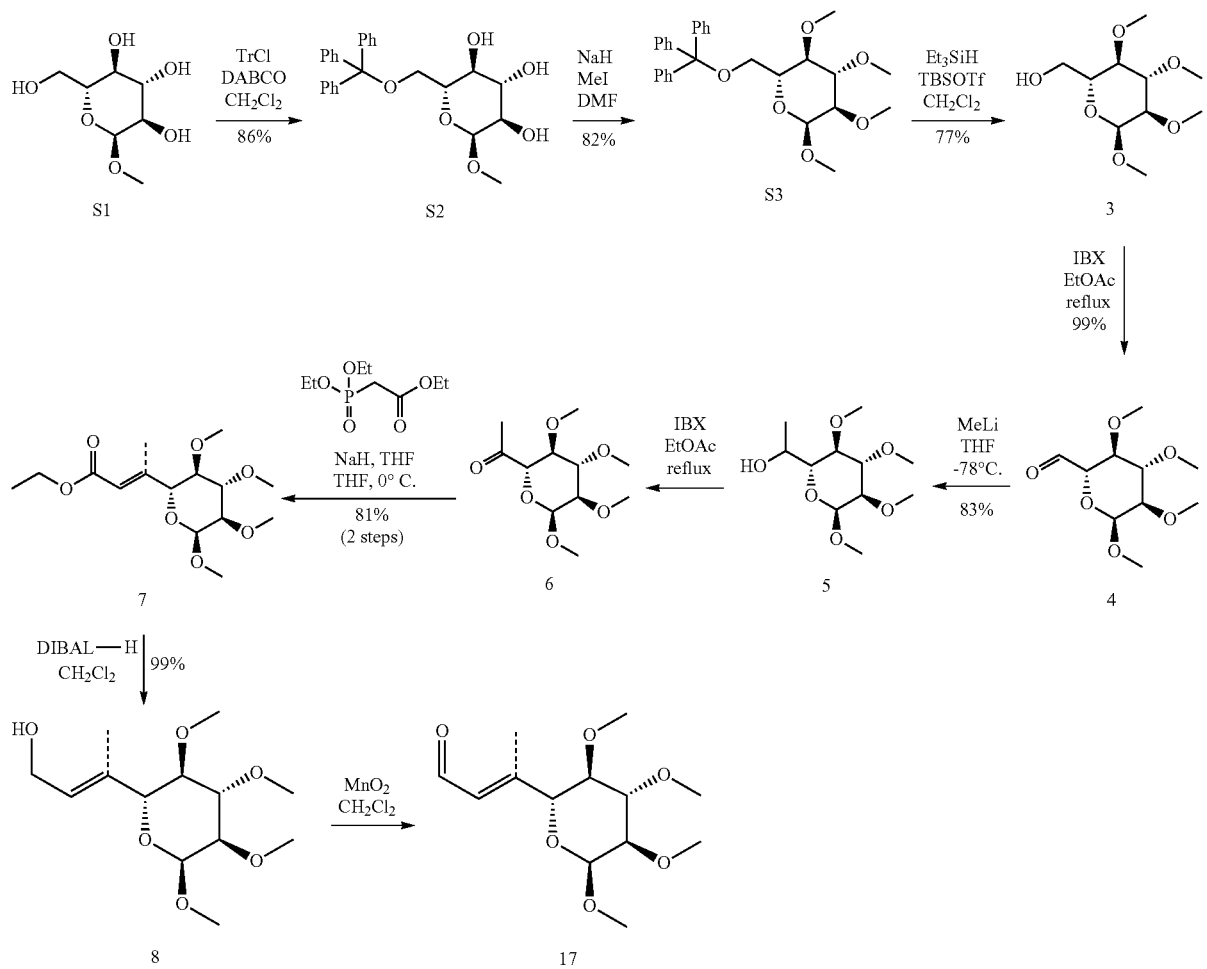

(2S,3R,4S,5R,6R)-2,3,4,5-tetramethoxy-6-((trityloxy)methyl)tetrahydro-2H-pyran (S3)

Trityl ether S2 (10.1 g, 23.2 mmol), prepared from -methyl-D-glucopyranoside (S1) according to the DABCO method of Gadakh, S1 was suspended in DMF (110 mL), placed under a strict Ar atmosphere and cooled to 0° C. NaH (4.82 g, 120.4 mmol) was added in four portions over the period of 15 min. After stirring at 0° C. for 1.5 h, MeI (11.53 mL, 185.2 mmol) was added in a drop wise fashion. The reaction was then slowly warmed to rt and stirred at rt for 12 h. In order to optimize yield, the mixture was retreated prior to work up by cooling the flask to 0° C. and adding an additional aliquot of NaH (2.41, 60.2 mmol). After 30 min, a second aliquot of MeI (5.7 mL, 92.6 mmol) was added and the mixture was warmed to rt. After 7 h at rt, satd. NH$_4$Cl (200 mL) was added in a drop wise fashion. The mixture was extracted with EtOAc (3×200 mL), washed with H$_2$O (200 mL) and satd. NH$_4$Cl (200 mL), dried over Na$_2$SO$_4$ and concentrated on a rotary evaporator. Pure S3 (9.13 g, 82%) was obtained by flash chromatography eluting with a gradient of hexanes to EtOAc.

Intermediate S3

TLC (1:1 hexanes/EtOAc): R$_f$=0.67; $^1$H NMR (CDCl$_3$, 500 MHz) δ 7.49 (m, 6H), 7.29 (m, 6H), 7.24 (m, 3H), 4.92 (d, J=3.6 Hz, 1H), 3.62 (s, 3H), 3.60 (m, 1H), 3.56 (s, 3H), 3.48 (t, J=9.2 Hz, 1H), 3.44 (s, 3H). 3.39 (dd, J=2.0, 10.0 Hz, 1H), 3.30 (m, 2H), 3.27 (s, 3H), 3.11 (dd, J=4.3, 10.0 Hz, 1H); $^{13}$C NMR (CDCl$_3$, 125 MHz) δ 144.1, 128.9, 127.9, 127.1, 97.4, 86.3, 83.8, 82.0, 80.0, 70.2, 62.5, 61.1, 60.6, 59.2, 55.1; HR-ESI-MS m/z calcd. for C$_{29}$H$_{34}$O$_6$[M+Na]$^+$: 501.2248, found 501.2249.

(2R,3R,4S,5R,6S)-3,4,5,6-tetramethoxytetrahydro-2H-pyran-2-yl)methanol (3)

Intermediate S3 (8.78 g, 18.4 mmol) was dissolved in CH$_2$Cl$_2$ (180 mL). Et$_3$SiH (5.86 mL, 36.7 mmol) was added neat followed by the addition of TBSOTf (0.04 mL, 0.2 mmol). An immediate yellow color appeared. If the CH$_2$Cl$_2$ is not sufficiently dry additional amounts of TBSOTf will be required. After 2 h, the yellow color disappeared and TLC analysis indicated that the reaction was complete. Satd. NaHCO$_3$ solution (0.1 mL) was added and the mixture was dried with Na$_2$SO$_4$ and concentrated on a rotary evaporator. Pure S3 (9.13 g, 83%) was obtained by extraction between hexanes and CH$_3$CN. Briefly, the crude product was dissolved in CH$_3$CN (100 mL) and washed with hexanes (3×200 mL). The CH$_3$CN was collected and dried via rotary evaporation to afford pure 3 (4.34 g, 77%) as a white solid.

Alcohol 3: TLC (1:1 hexanes/EtOAc): $R_f$=0.13; $^1$H NMR (CD$_3$OD, 500 MHz) δ 4.83 (d, J=3.6 Hz, 1H), 3.74 (dd, J=2.2, 11.9 Hz, 1H), 3.65 (dd, J=4.6, 11.9 Hz, 1H), 3.58 (s, 3H), 3.53 (s, 3H), 3.47 (s, 3H), 3.45 (m, 2H), 3.38 (s, 3H), 3.18 (dd, J=3.6, 9.6 Hz, 1H), 3.12 (dd, J=8.9, 10.0 Hz, 1H); $^{13}$C NMR (CDCl$_3$, 125 MHz) δ 98.4, 84.7, 83.0, 80.6, 72.5, 61.9, 61.0, 60.8. 58.8, 55.4; HR-ESI-MS m/z calcd. for C$_{10}$H$_{20}$O$_6$[M+Na]$^+$: 259.1152, found 259.1155.

1-((2S,3S,4S,5R,6S)-3,4,5,6-tetramethoxytetrahydro-2H-pyran-2-yl)ethan-1-one (5)

Alcohol 5 was prepared through a back-to-back two-step procedure without purification of intermediate aldehyde 4. Alcohol 3 (2.21 g, 9.4 mmol) was dissolved in EtOAc (120 mL). IBX (5.57 g, 20.6 mmol) was added as a solid and the mixture was brought to reflux with vigorous stirring. After 4 h, the mixture was cooled to 0° C. and flushed through a pad SiO$_2$ (200 g) washing with EtOAc (400 mL). The combined fractions were dried and submitted immediately for the next step. Aldehyde 4 (2.19 g, 9.4 mmol) was dried by azeotropic removal of toluene (3×200 mL). The resulting wax was dissolved in THF (100 mL) and cooled to −80° C. A 1.6 M solution of MeLi in ether (23.4 mL, 37.4 mmol) was added slowly to this solution. After 15 min at −80° C., the mixture was warmed to rt over 2 h and stirred at rt for an additional 1 h. Satd. NH$_4$Cl (100 mL) was added slowly. The mixture was extracted with EtOAc (3×50 mL), washed with brine (200 mL), dried over Na$_2$SO$_4$ and concentrated on a rotary evaporator. Pure 5 (1.95 g, 83%) was obtained as a ~2:1 mixtures of isomers by flash chromatography eluting with a gradient of hexanes to EtOAc.

Alcohol 5: TLC (1:1 hexanes/EtOAc): Rf=0.16; $^1$H NMR (CDCl$_3$, 500 MHz) δ 4.82 (d, J=3.6 Hz, 1H, minor), 4.78 (d, J=3.6 Hz, 1H, major), 3.98 (m, 1H, both), 3.62 (s, 3H, minor), 3.61 (s, 3H, major), 3.58 (s, 3H, both), 3.55 (m, 1H, both), 3.51 (s, 3H, minor), 3.51 (s, 3H, major), 3.46 (m, 2H, both), 3.40 (s, 3H, major), 3.38 (s, 3H, minor), 3.30 (dd, J=1.6, 9.9 Hz, 1H, minor), 3.24 (dd, J=8.6, 9.2 Hz 1H, minor), 3.16 (dd, J=3.6, 9.6 Hz, 1H, both), 3.09 (dd, J=8.8, 9.9 Hz, 1H, major), 2.75 (d, J=4.7 Hz, OH, 1H, major), 1.77 (d, J=9.7 Hz, OH, 1H, minor), 1.29 (d, J=6.6 Hz, 3H, minor), 1.23 (d, J=6.5 Hz, 3H, major); $^{13}$C NMR (CDCl$_3$, 125 MHz) δ 97.6, 97.3, 83.9, 83.9, 82.5, 82.2, 82.0, 79.9, 72.9, 72.1, 68.8, 65.5, 61.0, 60.9, 60.8, 60.4, 59.2, 59.1, 55.2, 55.2, 20.4, 18.3; HR-ESI-MS m/z calcd. for C$_{11}$H$_{22}$O$_6$[M+Na]$^+$: 273.1309, found 273.1308.

1-((2S,3S,4S,5R,6S)-3,4,5,6-tetramethoxytetrahydro-2H-pyran-2-yl)ethan-1-one (6)

Alcohol 5 (1.0 g, 4.0 mmol) was dissolved in EtOAc (50 mL). IBX (3.36 g, 12.0 mmol) was added as a solid and the mixture was brought to reflux with vigorous stirring. After 4 h, a second aliquot of IBX (3.36 g, 12.0 mmol) was added and the mixture was continued to stir at reflux for an additional 4 h. The mixture was cooled to 0° C. and flushed through a pad SiO$_2$ (200 g) washing with EtOAc (400 mL). The combined fractions were dried and used immediately as a crude product 6 (992.3 mg, 99%). Samples of pure ketone were obtained by flash chromatography eluting with a gradient of hexanes to EtOAc.

Ketone 6: TLC (1:1 hexanes/EtOAc): $R_f$=0.40; $^1$H NMR (CDCl$_3$, 500 MHz) δ 4.85 (d, J=3.5 Hz, 1H), 4.00 (d, J=10 Hz, 1H), 3.61 (s, 3H), 3.53 (t, J=9.2 Hz, 1H, 3H), 3.51 (s, 3H), 3.49 (s, 3H), 3.43 (s, 3H), 3.22 (t, J=9.8 Hz, 1H), 3.20 (dd, J=3.6, 9.7 Hz, 1H), 2.27 (s, 3H); $^{13}$C NMR (CDCl$_3$, 125 MHz) δ 205.0, 98.0, 83.5, 81.4, 80.8, 74.1, 61.2, 60.6, 59.3, 55.8, 28.3; HR-ESI-MS m/z calcd. for C$_{11}$H$_{20}$O$_6$[M+Na]$^+$: 271.1152, found 271.1149.

Ethyl (E)-3-((2R,3R,4S,5R,6S)-3,4,5,6-tetramethoxytetrahydro-2H-pyran-2-yl)but-2-enoate (7)

NaH (400 mg, 60% w/w in oil, 10.0 mmol) was suspended in THF (30 mL) and cooled to 0° C. Triethyl phosphonoacetate (2.51 g, 11.2 mmol) was added in a drop wise fashion to the suspension of NaH. After stirring for 1.5 h, crude ketone 5 (992.0 mg, 4.0 mmol) dissolved in THF (10 mL) was added. The mixture was warmed to rt. TLC analysis indicated that the reaction was complete after 3 h. Satd. NH$_4$Cl (50 mL) was added slowly. The mixture was extracted with EtOAc (3×100 mL), washed with brine (200 mL), dried over Na$_2$SO$_4$ and concentrated on a rotary evaporator. Pure 7 (0.982 g, 81%) was obtained by flash chromatography eluting with a gradient of hexanes to 1:1 hexanes/EtOAc.

Ester 7: TLC (1:1 hexanes/EtOAc): $R_f$=0.59; $^1$H NMR (CDCl$_3$, 500 MHz) δ 5.94 (dd, J=0.7, 1.5 Hz, 1H), 4.80 (d, J=3.6 Hz, 1H), 4.16 (dq, J=1.2, 7.2 Hz, 1H), 3.89 (d, J=9.8 Hz, 1H), 3.61 (s, 3H), 3.52 (s, 3H), 3.50 (dd, J=8.8, 9.6 Hz, 1H), 3.42 (s, 3H), 3.38 (s, 3H), 3.20 (dd, J=3.6, 9.6 Hz, 1H), 3.04, (dd, J=8.7, 9.8 Hz, 1H), 2.20 (d, J=2.2 Hz, 1H), 1.28 (t, J=7.1 Hz, 1H); $^{13}$C NMR (CDCl$_3$, 125 MHz) δ 166.3, 153.9, 119.7, 97.6, 83.2, 82.5, 81.5, 75.1, 61.1, 60.5, 59.9, 59.1, 55.3, 15.0, 14.3; HR-ESI-MS m/z calcd. for C$_{15}$H$_{26}$O$_7$ [M+Na]$^+$: 341.1574, found 341.1571.

Ethyl (E)-3-((2R,3R,4S,5R,6S)-3,4,5,6-tetramethoxytetrahydro-2H-pyran-2-yl)but-2-enoate (8)

Ester 7 (981.0 mg, 3.1 mmol) was dissolved in CH$_2$Cl$_2$ (40 mL) and cooled to −78° C. A 1.0 M solution of DIBAL-H in toluene (9.3 mL, 9.3 mmol) was added drop wise. After 20 min, the reaction mixture was slowly warmed to rt over 2 h and then stirred at rt for 1 h. The mixture was recooled to −78° C. and EtOAc (5 mL) was added, followed by a satd. Solution of Rochelle's salt (100 mL). The mixture was warmed to rt and stirred at rt for 5 h until the mixture provided two clear phases. The crude product was recovered by extraction EtOAc (3×100 mL), washed with brine (100 mL), drying over Na$_2$SO$_4$ and concentration on a rotary evaporator. Pure 8 (0.845 g, 99%) was obtained by flash chromatography eluting with a gradient of hexanes to 1:2 hexanes/EtOAc.

Allylic alcohol 8: TLC (1:1 hexanes/EtOAc): Rf=0.09; $^1$H NMR (CDCl$_3$, 500 MHz) δ 5.76 (dt, J=2.1, 6.8 Hz, 1H), 4.79 (d J=3.6 Hz, 1H), 4.25 (dq, J=6.3, 13.1 Hz, 1H), 3.86 (d, J=9.8 Hz, 1H), 3.62 (s, 3H), 3.52 (s, 3H), 3.50 (m, 1H), 3.44 (s, 3H), 3.39 (s, 3H), 3.19 (dd, J=3.6, 9.6 Hz, 1H), 3.05 (dd, J=8.8, 9.8 Hz, 1H), 1.73 (s, 3H); $^{13}$C NMR (CDCl$_3$, 125 MHz) δ 134.9, 130.0, 97.6, 83.3, 81.8, 81.6, 75.6, 61.2, 60.3, 59.4, 59.2, 55.4, 12.5; HR-ESI-MS m/z calcd. for C$_{13}$H$_{24}$O$_6$ [M+Na]$^+$: 299.1465, found 299.1463.

C. Synthesis of Side Chain Component 16.

Sulfone 16 was prepared in 6 steps in 58% overall yield from allylic alcohol 9, as shown in Scheme 2 (in the manuscript) and Scheme S2 (below). Gram scaled preparation of allylic alcohol 9 was accomplished in 11 steps and 27% overall yield from L-Phe.[S1] The bulk of the effort in preparing 9 arose from the preparation of auxiliary 11, which was readily recycled.[S1] The following section provides a complete description of the synthetic procedures and spectroscopic properties of intermediated 10, 12, 13, and 14-16.

(2R,3S,6S,7S,E)-1-((S)-4-Benzyl-2-thioxothiazolidin-3-yl)-3-hydroxy-7-methoxy-2,6-dimethylnon-4-en-1-one (12)

Allylic alcohol 9 [2] (1.12 g, 7.1 mmol) was dissolved in $CH_2Cl_2$ (50 mL) and $MnO_2$ (9.31 g, 107.2 mmol) was added as a powder. The slurry was vigorously stirred at rt until TLC indicated complete conversion, typically 24-36 h. The mixture was applied to a DCVC column containing 150 g $SiO_2$. The column was washed with EtOAc (3×100 mL) and dried via rotary evaporation. The resulting product, aldehyde 10 (1.12 g, 99% yield) was further dried via toluene azeotrope (3×10 mL) and used immediately without further purification. Crimmins auxiliary 11 (2.28 g, 8.6 mmol) was dissolved in $CH_2Cl_2$ (70 mL) and cooled 0° C. $TiCl_4$ (0.99 mL, 9.0 mmol) was added in a drop wise fashion. After 5 min at 0° C., $EtN^iPr_2$ (1.64 mL, 9.4 mmol) was added in a drop wise fashion. The mixture was stirred at 0° C. for 30 min and then cooled to −78° C. Aldehyde 10 (1.12, 7.2 mmol) was dissolved in $CH_2Cl_2$ (25 mL) and added in a drop wise fashion. The mixture was stirred at −78° C. for 2.5 h then slowly warmed over 1.5 h to 0° C. After 15 min at 0° C., satd. $NH_4Cl$ (50 mL) was added. The mixture was extracted with EtOAc (3×100 mL), washed with brine (50 mL), dried over $Na_2SO_4$ and concentrated on a rotary evaporator. Pure adduct 12 (2.65 g, 87%) was obtained by flash chromatography eluting with a gradient of hexanes to 1:1 hexanes/EtOAc.

Adduct 12: TLC (3:1 hexanes/EtOAc): $R_f$=0.39; $^1$H NMR (CDCl$_3$, 500 MHz) δ 7.34 (m, 2H), 7.28 (m, 3H), 5.73 (ddd, J=1.3, 7.8, 15.6 Hz, 1H), 5.51 (ddd, J=1.1, 5.8, 15.6 Hz, 1H), 5.38 (ddd, J=4.0, 7.3, 11.3 Hz, 1H), 4.79 (dq, J=3.2, 7.0 Hz, 1H), 4.60 (m, 1H), 3.38 (dd, J=4.6, 11.8 Hz, 1H), 3.35 (s, 3H), 3.24 (dd, J=4.0, 13.2 Hz, 1H), 3.04 (dd, J=10.4, 13.2 Hz, 1H), 2.92 (m, 1H), 2.89 (d, J=11.6 Hz, 1H), 2.42 (td, J=6.8, 12.1 Hz, 1H), 1.59 (s, OH, 1H), 1.53 (dqd, J=4.3, 7.5, 14.9 Hz, 1H), 1.41 (td, J=7.1, 14.1 Hz, 1H), 1.18 (d, J=7.0 Hz, 1H), 1.03 (d, J=6.8 Hz, 1H), 0.89 (t, J=7.4 Hz, 1H); $^{13}$C NMR (CDCl$_3$, 125 MHz) δ 201.8, 197.7, 136.5, 135.4, 129.6, 129.1, 128.7, 127.4, 86.3, 72.2, 69.1, 57.8, 43.4, 39.5, 37.1, 31.9, 23.8, 16.2, 11.4, 9.8; HR-ESI-MS m/z calcd. for $C_{22}H_{31}NO_3S_2[M+Na]^+$: 444.1638, found 444.1639.

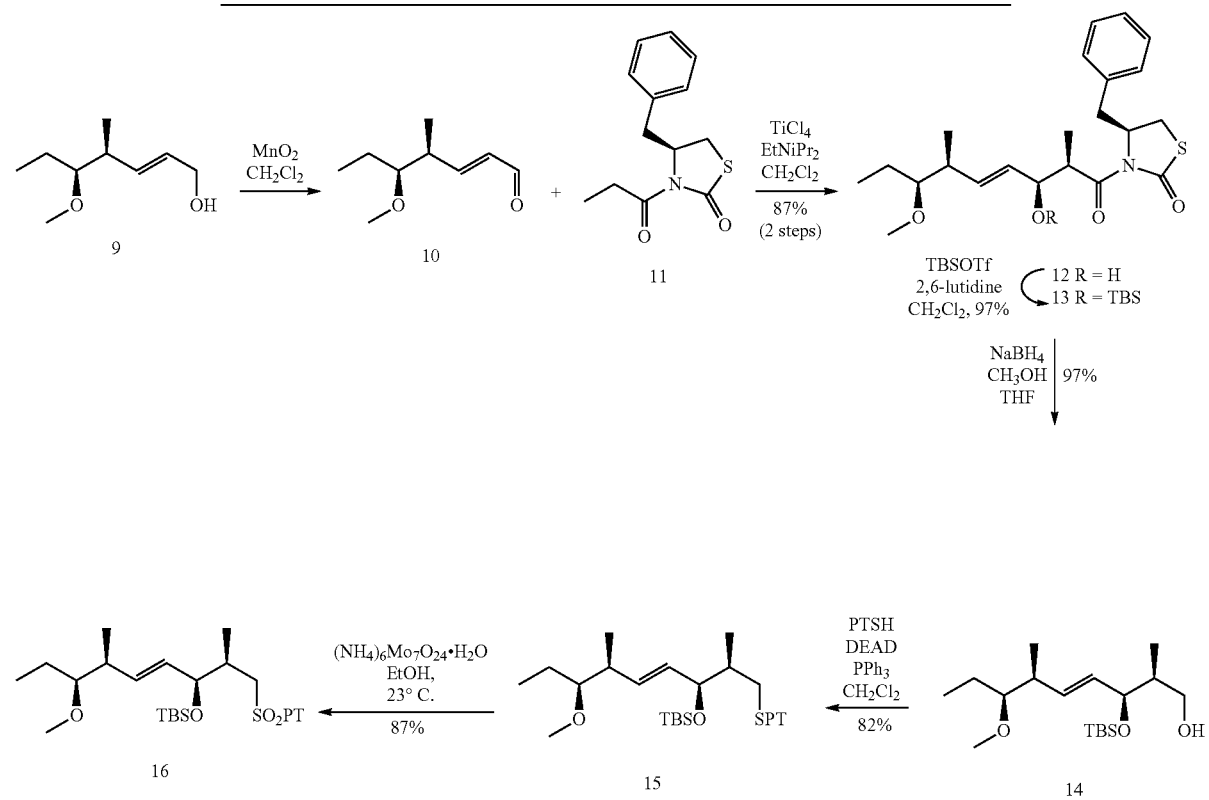

Scheme S2. Synthesis of side chain component 16. Preparation of 16 required four chromatographic purifications as the crude products of 10 and 13 could be used without additional purification. Flash chromatography was required to purify intermediates 12, 14, 15, and 16. The materials was stored at 16, and used as described in Scheme 3 and Scheme S3.

(2R,3S,6S,7S,E)-1-((S)-4-benzyl-2-thioxothiazolidin-3-yl)-3-((tert-butyldimethylsilyl)oxy)-7-methoxy-2,6-dimethylnon-4-en-1-one (13)

Adduct 12 (3.22 g, 7.64 mmol) and 2,6-lutidine (2.65 mL, 22.9 mmol) were dissolved in $CH_2Cl_2$ (125 mL) and cooled 0° C. TBSOTf (3.50 mL, 15.3 mmol) was added in a drop wise fashion. After 15 min at 0° C., the mixture was warmed to 10° C. over 2 h. After 15 min at 10° C., satd. NaHCO$_3$ (0.5 mL) was added and the mixture was stirred at rt for 30 min. The mixture was applied to a DCVC column containing 200 g SiO$_2$. The column was washed with EtOAc (3×200 mL)

and dried via rotary evaporation. The resulting product 10 (3.98 g, 97% yield) was further dried via toluene azeotrope (3×50 mL) and used as is. Pure samples of 13 were obtained for spectroscopic analyses via flash chromatography eluting with a gradient of hexanes to 1:1 hexanes/EtOAc.

Adduct 13: TLC (3:1 hexanes/EtOAc): $R_f$=0.75; $^1$H NMR (CDCl$_3$, 500 MHz) δ 7.34 (m, 2H), 7.28 (m, 3H), 5.59 (d, J=6.9 Hz, 1H), 5.57 (d, J=6.1 Hz, 1H), 5.33 (dddd, J=1.2, 3.5, 7.4, 10.8 Hz, 1H), 4.80 (t, J=6.6 Hz, 1H), 4.51 (t, J=6.5 Hz, 1H), 3.35 (m, 1H), 3.31 (m, 1H), 3.30 (s, 3H), 3.19 (dd, J=3.4, 13.1 Hz, 1H), 2.99 (dd, J=11.0, 13.2 Hz, 1H), 2.87 (dd, J=4.3, 6.7 Hz, 1H), 2.84 (d, J=11.6 Hz, 1H), 2.33 (h, J=6.7, 1H), 1.67 (m, 1H), 1.50 (ttd, J=3.6, 7.5, 14.8 Hz, 1H), 1.38 (pq, 7.1, 14.1 Hz, 1H), 1.26 (dd, J=6.5, 4.27 Hz, 1H), 1.21 (d, J=6.8 Hz, 3H), 1.00 (d, J=6.8 Hz, 3H), 0.90 (s, 9H), 0.84 (t, J=7.5 Hz, 3H), 0.06 (s, 3H), 0.03 (s, 3H); $^{13}$C NMR (CDCl$_3$, 125 MHz) δ 201.2, 196.3, 136.8, 135.1, 131.1, 129.5, 129.1, 127.3, 86.2, 75.2, 69.3, 57.6, 45.2, 39.4, 37.2, 31.6, 26.1, 25.9, 23.8, 18.4, 16.0, 14.2, 9.7, −3.7, −4.2; HR-ESI-MS m/z calcd. for $C_{28}H_{45}NO_3S_2Si$ [M+Na]$^+$: 558.2502, found 558.2503.

(2S,3S,6S,7S,E)-3-((tert-butyldimethylsilyl)oxy)-7-methoxy-2,6-dimethylnon-4-en-1-ol (14)

Adduct 13 (1.33 g, 2.5 mmol) was dissolved in a mixture of THF (53 mL) and CH$_3$OH (13 mL) and cooled to 0° C. NaBH$_4$ (159.0 mg, 19.9 mmol) was added in 3 portions over 5 min. The mixture was stirred at 0° C. for 1.5 h. If not complete via TLC analysis additional NaBH$_4$ could be added to complete the reaction. If complete, satd. NH$_4$Cl (25 mL) was added. The resulting mixture was extracted with EtOAc (3×100 mL), washed with brine (50 mL), dried over Na$_2$SO$_4$ and concentrated on a rotary evaporator. Pure alcohol 14 (802.0 mg, 97%) was obtained by flash chromatography eluting with a gradient of hexanes to 1:1 hexanes/EtOAc.

Alcohol 14: TLC (3:1 hexanes/EtOAc): $R_f$=0.55; $^1$H NMR (CDCl$_3$, 500 MHz) δ 5.51 (m, 2H), 4.13 (m, 2H), 3.62 (ddd, J=2.8, 8.6, 11.2 Hz, 1H), 3.46 (ddd, 4.2, 7.4, 11.2 Hz, 1H), 3.34 (s, 3H), 3.03 (bs, 1H), 2.89 (ddd, J=4.1, 6.1, 7.4 Hz, 1H), 2.41 (m, 1H), 1.95 (m, 1H), 1.76 (bs, 1H), 1.53 (dtd, J=4.3, 7.5, 14.8 Hz, 1H), 1.38 (ddt, J=6.7, 7.7, 13.5 Hz, 1H), 1.01 (d, J=6.9 Hz, 3H), 0.90 (t, J=7.4 Hz, 3H), 0.88 (s, 9H), 0.78 (dd, J=7.1 Hz, 3H), 0.06 (s, 3H), 0.02 (s, 3H); $^{13}$C NMR (CDCl$_3$, 125 MHz) δ 134.9, 129.9, 86.4, 78.2, 65.9, 57.6, 41.5, 39.4, 25.9, 23.5, 18.2, 16.2, 13.0, 9.8, −4.0, −4.9; HR-ESI-MS m/z calcd. for $C_{18}H_{38}NO_3Si$ [M+Na]$^+$: 353.2482, found 353.2485.

5-(((2R,3S,6S,7S,E)-3-((tert-butyldimethylsilyl)oxy)-7-methoxy-2,6-dimethylnon-4-en-1-yl)thio)-1-phenyl-1H-tetrazole (15)

Alcohol 14 (1.01 g, 3.1 mmol), 1-phenyl-1H-tetrazole-5-thiol (819.5 mg, 4.6 mmol) and PPh$_3$ (1.20 g, 4.6 mmol) were dissolved in THF (50 mL). The solution was cooled to 0° C. DEAD (720.0 μL, 4.6 mmol) was added in a drop wise fashion until a yellow color persists. Additional DEAD up to 1.2 mmol could be added if needed if the color does not persist. After 30 min, the solution was allowed to warm to rt over 30 min. After 4 h at rt, H$_2$O (20 mL) was added. The resulting mixture was extracted with EtOAc (3×50 mL), washed with brine (25 mL), dried over Na$_2$SO$_4$ and concentrated on a rotary evaporator. Pure sulfide 15 (1.24 g, 82%) was obtained by flash chromatography eluting with a gradient of hexanes to 2:1 hexanes/EtOAc.

Sulfide 15: TLC (3:1 hexanes/EtOAc): $R_f$=0.70; $^1$H NMR (CDCl$_3$, 500 MHz) δ 7.56 (m, 5H), 5.55 (ddd, J=0.8, 7.7, 15.5 Hz, 1H), 5.43 (ddd, J=1.0, 7.7, 15.5 Hz, 1H), 4.13 (dd, J=0.9, 4.1, 6.9 Hz, 1H), 3.51 (dd, J=6.5, 12.7 Hz, 1H), 3.33 (s, 3H), 3.25 (dd, J=7.3, 12.7 Hz, 1H), 2.89 (ddd, J=4.3, 6.1, 7.0 Hz, 1H), 2.38 (h, J=6.9 Hz, 1H), 2.03 (dh, J=4.1, 6.8 Hz, 1H), 1.51 (dqd, J=4.3, 7.5, 14.9 Hz, 1H), 1.38 (pd, J=7.3, 14.4 Hz, 1H), 1.01 (d, J=6.9 Hz, 1H), 1.00 (d, J=6.8 Hz, 1H), 0.88 (s, 9H), 0.88 (t, J=7.4 Hz, 1H), 0.03 (s, 3H), 0.00 (s, 3H); $^{13}$C NMR (CDCl$_3$, 125 MHz) δ 155.0, 135.0, 133.9, 130.4, 130.1, 129.9, 124.0, 86.3, 76.1, 57.7, 40.1, 39.3, 36.8, 26.0, 23.7, 18.3, 15.9, 14.6, 9.7, −3.8, −4.7; HR-ESI-MS m/z calcd. for $C_{25}H_{42}N_4O_2SSi$ [M+Na]$^+$: 513.2690, found 513.2693.

5-(((2R,3S,6S,7S,E)-3-((tert-Butyldimethylsilyl)oxy)-7-methoxy-2,6-dimethylnon-4-en-1-yl)sulfonyl)-1-phenyl-1H-tetrazole (16)

Sulfide 15 (1.95 g, 4.0 mmol) was dissolved in EtOH (40 mL) and cooled to 0° C. In a vial, a 30% v/v solution of H$_2$O$_2$ (3.6 mL) was added to solid (NH$_4$)$_6$Mo$_7$O$_{24}$·4H$_2$O (2.45 g, 20.0 mmol) and shaken until the bubbling ceased (~5 min). This solution was then added to the cooled solution of 15 in EtOH via glass pipette. After 20 min, the mixture was warmed to rt and stirred overnight. The resulting mixture was diluted with H$_2$O (50 mL), extracted with EtOAc (3×50 mL), washed with brine (25 mL), dried over Na$_2$SO$_4$ and concentrated on a rotary evaporator. Pure sulfone 16 (1.82 g, 87%) was obtained by flash chromatography eluting with a gradient of hexanes to 2:1 hexanes/EtOAc. The remainder of the material was either the sulfide 15 ($R_f$ higher than 16), the corresponding sulfoxide ($R_f$ higher than 16) or a mixture of both. These materials were readily resubmitted to the oxidation procedure to provide additional samples of 16.

Sulfone 16: TLC (3:1 hexanes/EtOAc): $R_f$=0.66; $^1$H NMR (CDCl$_3$, 500 MHz) δ 7.68 (m, 2H), 7.61 (m, 3H), 5.61 (ddd, J=1.1, 7.9, 15.6 Hz, 1H), 5.36 (ddd, J=1.1, 7.0, 15.6 Hz, 1H), 4.18 (dd, J=4.3, 6.7 Hz, 1H), 4.07 (dd, J=3.4, 14.4 Hz, 1H), 3.46 (dd, J=9.1, 14.4 Hz, 1H), 3.34 (s, 3H), 2.90 (ddd, J=4.4, 6.0, 7.0 Hz, 1H), 2.43 (m, 1H), 2.40 (tt, J=6.5, 13.6 Hz, 1H), 1.51 (m, 1H), 1.39 (pq, J=7.3, 14.4 Hz, 1H), 1.11 (d, J=6.9 Hz, 3H), 1.02 (d, J=6.8 Hz, 3H), 0.90 (t, J=7.4 Hz, 3H), 0.89 (t, 9H), 0.06 (s, 3H), 0.03 (s, 3H); $^{13}$C NMR (CDCl$_3$, 125 MHz) δ 154.2, 136.2, 133.3, 131.6, 129.8, 128.9, 125.3, 86.2, 75.8. 58.5, 57.7, 39.3, 35.3, 26.0, 23.7, 18.3, 15.9, 15.3, 9.8, −4.0, −4.8; HR-ESI-MS m/z calcd. for $C_{25}H_{42}N_4O_4SSi$ [M+Na]$^+$: 545.2588, found 545.2587.

D. Procedures for the Component Coupling to Alkene 19.

A two-step procedure was used to prepare alkene 18 from side chain component 16 and core component 9, as shown in Scheme 3 (in the manuscript) and Scheme S3 (below). The following section provides a complete description of the synthetic procedures and spectroscopic properties of intermediates 19-18.

Scheme S3. Synthesis of epoxide 2. Preparation of 16 required 3 chromatographic purifications as the crude product 19 as shown in Scheme S1 could be used without additional purification.

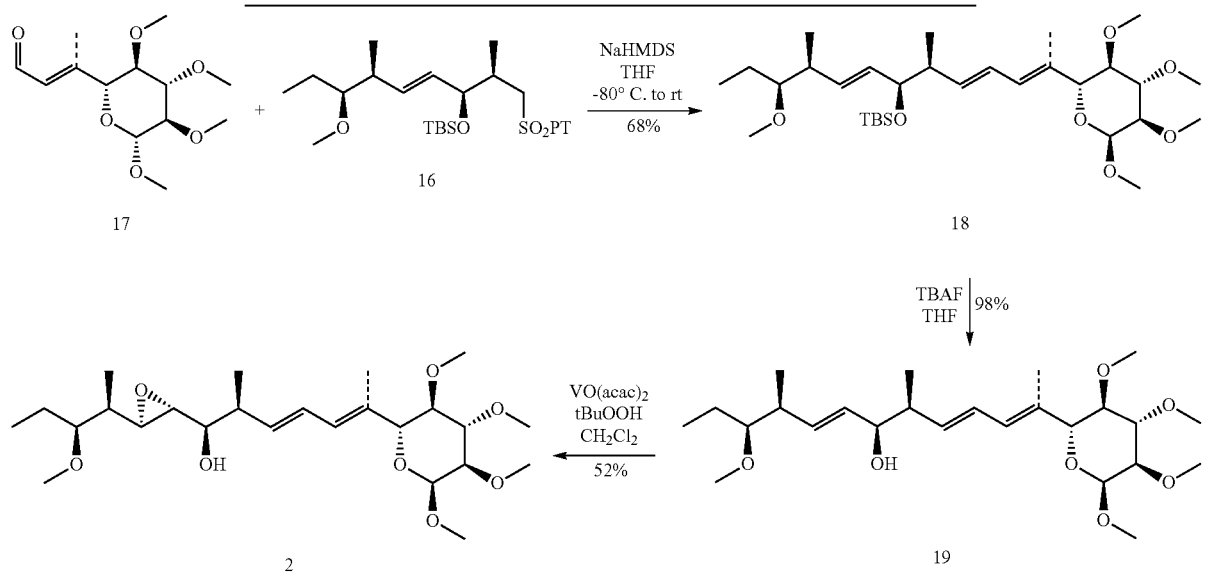

(E)-3-((2R,3R,4S,5R,6S)-3,4,5,6-Tetramethoxytetrahydro-2H-pyran-2-yl)but-2-enal (19)

Allylic alcohol 8 (468.2 mg, 1.7 mmol) was dissolved in $CH_2Cl_2$ (20 mL) and $MnO_2$ (2.21 g, 25.4 mmol) was added as a powder. The slurry was vigorously stirred at rt until TLC indicated complete conversion, typically 20-24 h. The mixture was applied to a DCVC column containing 80 g $SiO_2$. The column was washed with EtOAc (3×50 mL) and dried via rotary evaporation. The resulting product, aldehyde 19 (459.2 mg, 99% yield) was further dried via toluene azeotrope (3×10 mL) and used as is.

Aldehyde 19: TLC (1:1 hexanes/EtOAc): $R_f$=0.38; $^1$H NMR (CDCl$_3$, 500 MHz) δ 10.11 (d, J=7.8 Hz, 1H), 6.12 (d, J=7.1 Hz, 1H), 4.83 (d, J=3.6 Hz, 1H), 4.00 (d, J=9.8 Hz, 1H), 3.64 (s, 3H), 3.54 (s, 3H), 3.53 (m, 1H), 3.45 (s, 3H), 3.41 (s, 3H), 3.22 (dd, J=3.6, 9.7 Hz, 1H), 3.06 (dd, J=8.8, 9.8 Hz, 1H); 2.23 (d, J=1.4 Hz, 3H); $^{13}$C NMR (CDCl$_3$, 125 MHz) δ 191.2, 157.9, 129.5, 97.9, 83.5, 82.8, 81.8, 74.5, 61.2, 60.7, 59.3, 55.6, 14.3; HR-ESI-MS m/z calcd. for $C_{13}H_{22}O_6$[M+Na]$^+$: 297.1309, found 297.1306.

tert-Butyl(((2E,4E,6S,7S,8E,10S,11S)-11-methoxy-6,10-dimethyl-2-((2R,3R,4S,5R,6S)-3,4,5,6-tetramethoxytetrahydro-2H-pyran-2-yl)trideca-2,4,8-trien-7-yl)oxy)dimethylsilane (18)

Highly dry THF for this procedure was required and was distilled fresh from Na benzophenone ketyl prior to use. Sulfone 16 (568.4 mg, 1.09 mmol) was dissolved in freshly distilled THF (30 mL) and cooled to −78° C. A 2 M solution of NaHMDS in THF (572.0 mL, 1.14 mmol) was added in a drop wise fashion. After 1 h at −78° C., freshly prepared and dried aldehyde 19 (328.2 mg, 1.19 mmol) was added in THF (15 mL). The solution was warmed to rt over 1.5 h and stirred overnight. The resulting mixture was diluted with satd. NH$_4$Cl (50 mL), extracted with EtOAc (3×200 mL), washed with brine (25 mL), dried over Na$_2$SO$_4$ and concentrated on a rotary evaporator. Pure alkene 18 (423.1 mg, 68%) was obtained by flash chromatography eluting with a gradient of hexanes to 1:1 hexanes/EtOAc. This was accompanied by ~11% of the chromatographically isolable cis-C8, C9 isomer of 18 indicating that the reaction occurred with ~6:1 ratio of trans:cis.

Alkene 18: TLC (1:1 hexanes/EtOAc): $R_f$=0.62; $^1$H NMR (CDCl$_3$, 500 MHz) δ 6.22 (ddd, J=1.2, 10.8, 15.8 Hz, 1H), 6.08 (dd, J=1.5, 10.7 Hz, 1H), 5.69 (dd, J=7.6, 15.2 Hz, 1H), 5.38 (m, 2H), 4.79 (d, J=3.6 Hz, 1H), 3.90 (dd, J=5.5, 6.4 Hz, 1H), 3.85 (d, J=9.8 Hz, 1H), 3.62 (s, 3H), 3.52 (s, 3H), 3.49 (m, 1H), 3.41 (s, 3H), 3.39 (s, 3H), 3.33 (s, 3H), 3.19 (dd, J=3.6, 9.6 Hz, 1H), 3.07 (dd, J=8.8, 9.8 Hz, 1H), 2.86 (dt, J=4.3, 6.7 Hz, 1H), 2.31 (m, 2H), 1.79 (d, J=1.3 Hz, 3H), 1.52 (m, 1H), 1.38 (pd, J=7.4, 14.2 Hz, 1H), 1.00 (d, J=6.8 Hz, 6H), 0.88 (s, 9H), 0.87 (t, J=7.4 Hz, 3H), 0.02 (s, 3H), −0.01 (s, 3H); $^{13}$C NMR (CDCl$_3$, 125 MHz) δ 138.7, 134.1, 131.8, 131.3, 130.5, 125.4, 97.6, 86.3, 83.4, 82.0, 81.9, 77.8, 76.2, 61.2, 60.2, 59.2, 57.7, 55.2, 44.2, 39.7, 26.0, 23.7, 18.4, 16.4, 15.5, 12.7, 9.4, −3.9, −4.6; HR-ESI-MS m/z calcd. for $C_{31}H_{58}O_7Si$ [M+Na]$^+$: 593.3844, found 593.3846.

E. Procedures for Synthesis of Epoxides 2 and 20.

A two-step procedure was used to convert alkene 19 to the targeted epoxide 2 or 20. The following section provides a complete description of the synthetic procedures and spectroscopic properties of intermediates 19 and epoxide 2, and the corresponding epoxide isomer 20.

(2E,4E,6S,7S,8E,10S,11S)-11-methoxy-6,10-dimethyl-2-((2R,3R,4S,5R,6S)-3,4,5,6-tetramethoxytetrahydro-2H-pyran-2-yl)trideca-2,4,8-trien-7-ol (19)

Alkene 18 (79.2 mg, 0.14 mmol) was dissolved in wet THF (8 mL) in an Oakridge 15 mL Teflon tube (Nalgene). Solid TBAF (108.8 mg, 0.41 mmol) was added and the mixture was stirred at rt until TLC analysis showed complete conversion (typically 5-6 h). NH$_4$Cl (5 mL) was added and the resulting mixture was extracted with EtOAc (3×25 mL). The combined organic phases were washed with brine (10 mL), dried over Na$_2$SO$_4$ and concentrated on a rotary evaporator. Pure alkene 19 (54.2 mg, 86%) was obtained by flash chromatography eluting with a gradient of hexanes to 1:1 hexanes/EtOAc.

Alcohol 19: TLC (1:1 hexanes/EtOAc): $R_f=0.41$; $^1$H NMR (CDCl$_3$, 500 MHz) δ 6.33 (ddd, J=1.1, 10.9, 15.2 Hz, 1H), 6.10 (dd, J=1.6, 10.7 Hz, 1H), 5.64 (dd, J=8.2, 15.2 Hz, 1H), 5.58 (dd, J=7.9, 15.5 Hz, 1H), 5.45 (dd, J=6.9, 15.5 Hz, 1H), 4.79 (d, J=3.6 Hz, 1H), 3.97 (m, 2H), 3.85 (d, J=9.8 Hz, 1H), 3.62 (s, 3H), 3.52 (s, 3H), 3.49 (m, 1H), 3.41 (s, 3H), 3.38 (s, 3H), 3.34 (s, 3H), 3.19 (dd, J=3.6, 9.6 Hz, 1H), 3.08 (dd, J=8.8, 9.8 Hz, 1H), 2.89 (dt, J=4.1, 6.6 Hz, 1H), 2.43 (m, 1H), 2.37 (m, 1H), 1.80 (d, J=1.3 Hz, 1H), 1.52 (dqd, J=4.1, 7.4, 14.8 Hz, 1H), 1.38 (pd, J=7.3, 14.4 Hz, 1H), 1.03 (d, J=6.8 Hz, 3H), 1.01 (d, J=6.8 Hz, 3H), 0.88 (t, J=7.4 Hz, 3H); $^{13}$C NMR (CDCl$_3$, 125 MHz) δ 136.9, 135.4, 132.5, 130.2, 130.0, 127.0, 97.6, 86.3, 83.4, 82.0, 81.9, 76.4, 76.1, 61.1, 60.3, 59.2, 57.7, 55.3, 43.5, 39.5, 23.7, 16.3, 15.8, 12.8, 9.6; HR-ESI-MS m/z calcd. for $C_{25}H_{44}O_7[M+Na]^+$: 479.2979, found 479.2981.

(1R,2S,3E,5E)-1-((2R,3R)-3-((2R,3S)-3-methoxypentan-2-yl)oxiran-2-yl)-2-methyl-6-((2R,3R,4S,5R,6S)-3,4,5,6-tetramethoxytetrahydro-2H-pyran-2-yl)hepta-3,5-dien-1-ol (2)

Alkene 18 (42.1 mg, 73.8 μmol) was dissolved in CH$_2$Cl$_2$ (2 mL) in a 2 dram vial equipped with a Teflon cap. Solid VO(acac)$_2$ (58.7 mg, 221.4 μmol) was added and the mixture was cooled to −78° C. A solution of 5.5 M solution t-BuOOH in hexanes (58.7 μL, 332.0 μmol) was added and the mixture was warmed for 2 h over −20° C. The flask was then stored at −20° C. for 6 h at which point dimethylsulfide (100 μL) was added. After 15 min at −20° C., the mixture was warmed to rt and stirred for an additional 30 min. The resulting contents were flushed through a pad of SiO$_2$ (10 g) flushing with EtOAc (20 mL), and concentrated on a rotary evaporator. Epoxide 2 (22.8 mg, 52%) was obtained by flash chromatography eluting with a gradient of hexanes to 1:1 hexanes/EtOAc, followed by pTLC in a tank containing 2:1 hexanes/EtOAc.

Epoxide 2: TLC (1:1 hexanes/EtOAc): $R_f=0.39$; $^1$H NMR (C$_6$D$_6$, 500 MHz) δ 6.45 (ddd, J=1.1, 10.9, 15.1 Hz, 1H), 6.30 (dd, J=1.1, 11.0 Hz, 1H), 5.66 (dd, J=8.5, 15.1 Hz, 1H), 4.68 (d, J=3.6 Hz, 1H), 4.16 (d, J=9.7 Hz, 1H), 3.84 (dd, J=8.7, 9.6 Hz, 1H), 3.62 (s, 3H), 3.36 (s, 3H), 3.26 (s, 3H), 3.21 (m, 3H), 3.15 (s, 3H), 3.11 (s, 3H), 2.89 (dd, J=2.3, 6.8 Hz, 1H), 2.85 (dd, J=2.3, 4.6 Hz, 1H), 2.82 (td, J=4.8, 7.4 Hz, 1H), 2.42 (h, J=7.6 Hz 1H), 1.85 (d, J=1.3 Hz, 3H), 1.74 (bs, 1H), 1.55 (dt, J=4.3, 6.9 Hz, 1H), 1.48 (qd, J=7.3, 14.6 Hz, 1H), 1.36 (m, 1H), 1.14 (d, J=6.9 Hz, 3H), 1.00 (d, J=6.8 Hz, 3H), 0.84 (t, J=7.4 Hz, 3H); $^{13}$C NMR (C$_6$D$_6$, 125 MHz) δ 136.3, 133.2, 129.4, 126.6, 97.7, 83.5, 83.4, 82.2, 82.2, 76.2, 71.7, 60.6, 59.7, 58.8, 57.7, 57.2, 56.7, 54.6, 41.7, 38.7, 23.5, 16.2, 12.4, 10.4, 9.6; HR-ESI-MS m/z calcd. for $C_{25}H_{44}O_8[M+Na]^+$: 495.2928, found 495.2926.

F. Biological Assays and Screens.

Primary Chronic Lymphocytic Leukemia (CLL) Cells Sampling and Cell Culture.

Peripheral blood mononuclear cells (PBMC) from CLL patients were obtained from the CLL Research Consortium (CRC) tissue bank. This protocol was approved by the institutional review board (IRB) of the University of California, San Diego. Blood samples were taken from two CLL patients after written informed consent for blood sample collection and confirmation of diagnosis for CLL diseases, The PBMCs were separated from heparinized venous blood by density gradient centrifugation using Ficoll-Hypaque media (GE Healthcare). The samples with >95% positively for leukemic B cells was confirmed by staining for CD5 and CD19 followed by assessment using flow cytometry. CLL-B cells were maintained in RPMI 1640 medium supplemented with 10% FBS, 2 mM L-glutamine, and 100 U/mL of penicillin and 100 μg/mL of streptomycin at 37° C. in an atmosphere containing 5% CO$_2$.

In Vitro Cytotoxicity Analyses.

The CLL-B cells ($3\times10^5$ cells) were treated for 48 h with 10, 100, 300, and 1000 nM of 1a, 1b, 2 or 19 at 37° C. in an atmosphere containing 5% CO$_2$. Fludarabine (F-ara-A) dosed at 10 μM was used as a control. The cells were centrifuged and labeled with CD19/CD5/DiOC6 and subjected to flow cytometry. The data was analyzed using FlowJo software. In order to discriminate the compound specific-induced apoptosis versus background spontaneous cell death from in vitro culture conditions, we calculated the percentage of specific induced apoptosis (% SIA) using the following formula: % SIA=[(compound induced apoptosis−media only spontaneous apoptosis)/(100−media only spontaneous apoptosis)]×100. The dose-response curves were plotted to determine IC$_{50}$ values using the GraphPad Prism version 6.0c software.

Reverse Transcriptase PCR (RT-PCR) Analyses:

CLL-B ($5\times10^6$ cells/well) were treated with a given dose of compound from a DMSO stock solution over 4 h. RNA isolation and cDNA preparation, PCR reaction was performed in 20 μL of reaction volume as described previously.[53] PCR conditions give by incubation at 94° C. for 3 min; 35 cycles of 94° C. for 30 s, 55-60° C. (annealing temperature: 55° C. for GAPDH, 53.6° C. for RNU6A, 58° C. for DNAJB1, 54° C. for SF3A1, 55° C. for PRPF4, 55° C. for ARF4, and 55° C. for U2AF2) for 30 s, and 72° C. for 1 min; followed by 72° C. for 5 min. PCR products were separated on a 2% agarose gel and stained with ethidium bromide. Details of the primers used for RT-PCR are provided in Table 1.

Quantitative Reverse Transcription-PCR (qRT-PCR):

cDNA was prepared using identical methods as used for RT-PCR analysis. The amount of unspliced RNA for different genes was determined using Power SYBR Green PCR master mix (Applied Biosystems) by qRT-PCR using specific primers designed for detection of the intron of each gene (Table 2). The qPCR was performed using 5 pM of each primer on 20 ng of the obtained cDNA. PCR conditions were as follows: one cycle of 50° C. for 2 min (UDG Incubation), one cycle of 95° C. for 10 min (UDG Inactivation), followed by 95° C. for 15 sec; 60° C. for 30 s for 40 cycles and adding a step for dissociation using a 7900 HT Fast Real Time PCR System (Applied Biosystems). Unspliced RNA levels were calculated using 2-ΔΔCT method.[54] GAPDH was used as a control for normalization.

TABLE 1

RT-PCR forward (FP) and reverse (FP) primers as defined by the exon, sequence and annealing temperature (Ta).

| Primer | Direction | Exon | 5' Sequence 3' | SEQ ID NO: | Ta |
|---|---|---|---|---|---|
| DNAJB1 | FP | Exon 2 | GAACCAAAATCACTTTCCCCAAGGAAGG | 1 | 58 |
|  | RP | Exon 3 | AATGAGGTCCCCACGTTTCTCGGGTGT | 2 |  |
| SF3A1 | FP | Exon 6 | GGCCTATGCTCAGATCGACT | 3 | 54 |
|  | RP | Exon 7 | ATCAGACTCGACCTCCATC | 4 |  |
| PRPF4 | FP | Exon 8 | GAGTGGGCTTTGCAAGCTCT | 5 | 55 |
|  | RP | Exon 9 | CTGTCGAGACTCCAAAGCTT | 6 |  |
| ARF4 | FP | Exon 2 | GATTGGATGCTGCTGGCAA | 7 | 55 |
|  | RP | Exon 3 | CACCAACATCCCATACTGTG | 8 |  |
| U2AF2 | FP | Exon 4 | AGGTCCGTAAATACTGGGAC | 9 | 55 |
|  | RP | Exon 5 | CTCAGTGATGCCAAAGGGGA | 10 |  |
| GAPDH | FP | Exon 2 | TGGATATTGTTGCCATCATGA | 11 | 55 |
|  | RP | Exon 3 | TGGAATCATATTGGAACATGT | 12 |  |
| RNU6A | FP | Intronless | CGCTTCGGCAGCACATATAC | 13 | 53.6 |
|  | RP | Intronless | GAATTTGCGTGTCATCCTT | 14 |  |
| H2A | FP | Intronless | ATGGCTGCGGTCCTCGAGTAT | 15 | 61.0 |
|  | RP | Intronless | TCAGTTCCTCGTTGCGGA | 16 |  |

TABLE 2

Sequences of the qRT-PCR primers used in this study.

qRT-PCR primers

| Primer | Location | 5' Sequence 3' | SEQ ID NO: |
|---|---|---|---|
| DNAJB1-FP | Intron 2 | GGCCTGATGGGTCTTATCTATGG | 19 |
| DNAJB1-RP | Intron 2 | TTAGATGGAAGCTGGCTCAAGAG | 18 |
| RIOK3-FP | Intron 3 | CCTTATTGTGACAACTTCATTGAG | 19 |
| RIOK3-RP | Intron 3 | TGAAGATTTACTTAGGAGCACA | 20 |
| SF3A1-FP | Intron 6 | GGTGTTCCCAGAGAGCAGTAG | 21 |
| SF3A1-RP | Intron 6 | GCTGGGGCCATGTCTGTTTT | 22 |
| PRPF4-FP | Intron 8 | TGCTTGACACTCAGACCCCA | 23 |
| PRPF4-RP | Intron 8 | AAAATGCCAGAGTGTGACTGC | 24 |
| ARF4-FP | Intron 2 | GTAAGAAAGTTTACAGATGACTT | 25 |
| ARF4-RP | Intron 2 | AGATAATCAACATGCTTAACAAA | 26 |
| U2AF2-FP | Intron 4 | TCTCCGTCAGTCATTCCCCT | 27 |
| U2AF2-RP | Intron 4 | TCATTCCCCTGTCAACCACG | 28 |
| GAPDH-FP | Exon 3 | TGGTCACCAGGGCTGCTT | 29 |
| GAPDH-RP | Exon 4 | AGCTTCCCGTTCTCAGCCTT | 30 |

FP: forward primer;
RP reverse primer

Tables of NMR Results.

TABLE 3

NMR data (1H 500 MHz, 13C 100 MHz, CDCl3) for alkene 18

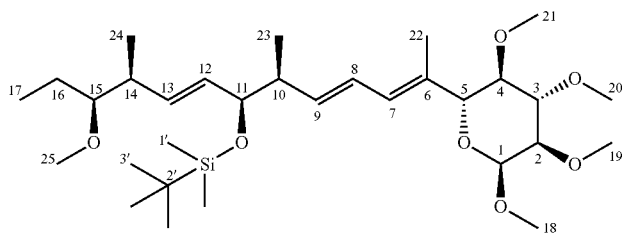 [SMILES: CC[C@H](OC)[C@@H](C)/C=C/[C@H](O[Si](C)(C)C(C)(C)C)[C@@H](C)/C=C/C=C(\C)[C@H]1O[C@H](OC)[C@H](OC)[C@@H](OC)[C@@H]1OC]

18

| No. | $\delta_H$ (J in Hz) | $\delta_C$, type | gCOSY | HMBC |
|---|---|---|---|---|
| 1 | 4.79 d (3.6) | 97.6, CH | 2 | 2, 5, 18 |
| 2 | 3.19 dd (3.6, 9.6) | 81.9, CH | 1, 3 | 3, 19 |
| 3 | 3.49 m | 83.4, CH | 2, 4 | 2, 4, 20 |
| 4 | 3.07 dd (8.8, 9.8) | 82.0, CH | 3, 5 | 3, 5, 6, 21 |
| 5 | 3.85 d (9.8) | 76.2, CH | 4 | 4, 6, 22 |
| 6 |  | 131.3, C |  |  |
| 7 | 6.08 dd (1.5, 10.7) | 130.5, CH | 8, 22 | 5, 8, 9, 22 |
| 8 | 6.22 ddd (1.2, 10.8, 15.2) | 125.4, CH | 7, 9 | 7, 10 |
| 9 | 5.69 dd (7.6, 15.2) | 138.7, CH | 8, 10 | 7, 10, 11, 23 |
| 10 | 2.31 m | 44.2, CH | 9, 11, 23 | 8, 9, 11, 23 |
| 11 | 3.90 (5.5, 6.4) | 77.8, CH | 10, 12 | 9, 10, 12, 13, 23 |
| 12 | 5.38 m | 131.8, CH | 11, 13 | 11, 14 |
| 13 | 5.38 m | 134.1, CH | 12, 14 | 11, 14, 24 |
| 14 | 2.31 m | 39.7, CH | 13, 15, 24 | 12, 13, 15, 16, 24 |
| 15 | 2.86 dt (4.3, 6.7) | 86.3, CH | 14, 16 | 13, 19, 24, 25 |
| 16a | 1.52 m | 23.7, CH$_2$ | 15, 16b, 19 | 14, 19 |
| 16b | 1.38 pd (7.4, 14.2) |  | 15, 16a, 19 | 14, 15, 19 |
| 19 | 0.87 t (7.4) | 9.4, CH$_3$ | 16a, 16b | 15, 16 |
| 18[a] | 3.39 s | 55.2, CH$_3$ |  | 1 |
| 19[a] | 3.41 s | 60.2, CH$_3$ |  | 2 |
| 20[a] | 3.62 s | 61.2, CH$_3$ |  | 3 |
| 21[b] | 3.52 s | 59.2, CH$_3$ |  | 4 |
| 22 | 1.79 d (1.3) | 12.7, CH$_3$ | 7 | 5, 6, 7, 8 |
| 23 | 1.00 d (6.8) | 15.5, CH$_3$ | 10 | 9, 10, 11 |
| 24 | 1.00 d (6.8) | 16.4, CH$_3$ | 14 | 13, 14, 15 |
| 25[c] | 3.33 s | 57.7, CH$_3$ |  | 15 |
| 1a' | 0.02 s | −4.6, CH$_3$ |  |  |
| 1b' | −0.01 s | −3.9, CH$_3$ |  |  |
| 2' |  | 18.4, C |  |  |
| 3' | 0.88 s | 26.0, CH$_3$ |  |  |

[a]Protons and carbons at 18 and 20 were assigned by $^1$H, $^{13}$C HMBC data.
[b]Protons and carbons at 19 and 21 were assigned by $^1$H, $^{13}$C HMBC data. However, they could not be unambiguously established due to the close proximity of C2 and C4.
[c]The assignment of the protons and carbons at 25 was further confirmed by the fact that the chemical shifts of protons and carbons at 18, 19, 20 and 21 were comparable to that in precursors such as allylic alcohol 8.

TABLE 4

NMR data (1H 500 MHz, 13C 100 MHz, CDCl3) for alcohol 19

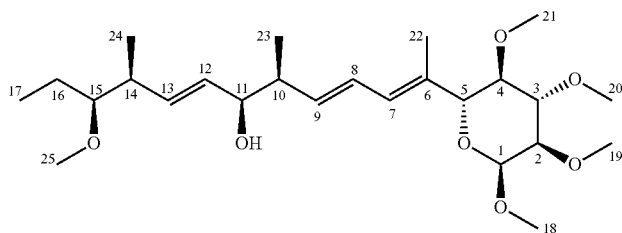

19

| No. | $\delta_H$ (J in Hz) | $\delta_C$, type | gCOSY | HMBC |
|---|---|---|---|---|
| 1 | 4.79 d (3.6) | 97.6, CH | 2 | 2, 5, 18 |
| 2 | 3.19 dd (3.6, 9.6) | 81.9, CH | 1, 3 | 3, 19 |
| 3 | 3.49 m | 83.4, CH | 2, 4 | 2, 4, 20 |
| 4 | 3.08 dd (8.6, 9.8) | 82.0, CH | 3, 5 | 3, 5, 6, 21 |
| 5 | 3.85 d (9.8) | 76.1, CH | 4 | 4, 6, 7, 22 |

TABLE 4-continued

NMR data (1H 500 MHz, 13C 100 MHz, CDCl3) for alcohol 19

19

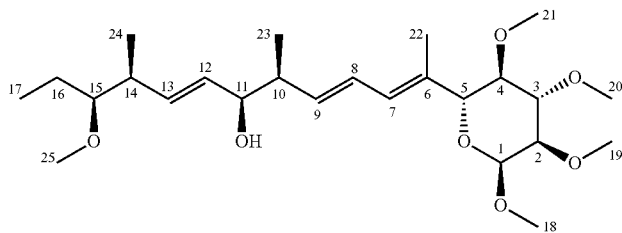 [SMILES: CC[C@H](OC)[C@@H](C)/C=C/[C@H](O)[C@@H](C)/C=C/C=C(\C)[C@H]1O[C@H](OC)[C@H](OC)[C@@H](OC)[C@@H]1OC]

| No. | δ$_H$ (J in Hz) | δC, type | gCOSY | HMBC |
|---|---|---|---|---|
| 6 |  | 130.2, C |  |  |
| 7 | 6.10 dd (1.6, 10.7) | 130.0, CH | 8, 22 | 5, 8, 9, 22 |
| 8 | 6.33 ddd (1.1, 10.9, 15.2) | 127.0, CH | 7, 9 | 7, 10 |
| 9 | 5.64 dd (8.2, 15.2) | 136.9, CH | 8, 10 | 7, 10, 11, 23 |
| 10 | 2.43 m | 43.5, CH | 9, 11, 23 | 8, 9, 11, 23 |
| 11 | 3.97 m | 76.4, CH | 10, 12 | 9 |
| 11-OH | 3.97 m |  |  | 11 |
| 12 | 5.45 dd (6.9, 15.5) | 132.5, CH | 11, 13 | 11, 13, 14 |
| 13 | 5.58 dt (7.9, 15.5) | 135.4, CH | 12, 14 | 11, 12, 14, 24 |
| 14 | 2.37 m | 39.5, CH | 13, 15, 24 | 12, 13, 15, 16, 24 |
| 15 | 2.89 dt (4.1, 6.6) | 86.3, CH | 14, 16 | 13, 19, 24, 25 |
| 16a | 1.52 dqd (4.2, 7.4, 14.8) | 23.7, CH$_2$ | 15, 16b, 19 | 19 |
| 16b | 1.39 pd (7.3, 14.4) |  | 15, 16a, 19 | 14, 15, 19 |
| 19 | 0.88 t (7.4) | 9.6, CH$_3$ |  | 15, 16 |
| 18a | 3.38 s | 57.7, CH$_3$ | 16a, 16b | 1 |
| 19a | 3.41 s | 60.3, CH$_3$ |  | 2 |
| 20a | 3.62 s | 61.1, CH$_3$ |  | 3 |
| 21a | 3.52 s | 59.2, CH$_3$ |  | 4 |
| 22 | 1.80 d (1.3) | 12.8, CH$_3$ | 7 | 5, 6, 7, 8 |
| 23 | 1.03 d (6.8) | 16.3, CH$_3$ | 10 | 9, 10, 11 |
| 24 | 1.01 d (6.8) | 15.8, CH$_3$ | 14 | 13, 14, 15 |
| 25b | 3.34 s | 55.3, CH$_3$ |  | 15 |

[a]Protons at carbons at 18, 19, 20 and 21 were assigned by $^1$H, $^{13}$C HMBC data.
[b]The assignment of the protons and carbons at 25 was further confirmed by the fact that the chemical shifts of protons and carbons at 18, 19, 20 and 21 were comparable to that in precursors such as allylic alcohol 8.

TABLE 5

NMR data (1H 500 MHz, 13C 100 MHz, C6D6) for epoxide 2

2

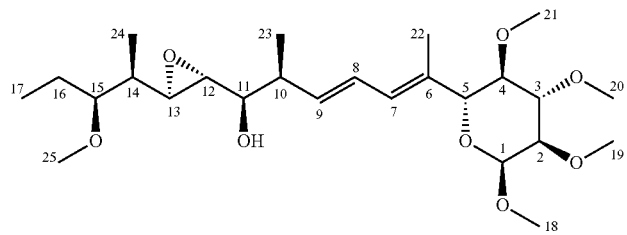

| No. | δ$_H$ (J in Hz) | δC, type | gCOSY | HMBC |
|---|---|---|---|---|
| 1 | 4.68 d (3.6) | 97.7, CH | 2 | 2, 5, 18 |
| 2 | 3.21 m | 82.2, CH[b] | 1, 3 | 3, 19 |
| 3 | 3.84 dd (8.7, 9.6) | 83.4, CH | 2, 4 | 2, 4, 20 |
| 4 | 3.21 m | 82.2, CH[b] | 3, 5 | 3, 5, 6, 21 |
| 5 | 4.16 d (9.7) | 76.2, CH | 4 | 4, 6, 7, 22 |
| 6 |  | 133.2, C |  |  |
| 7 | 6.30 dd (1.1, 11.0) | 129.4, CH | 8, 22 | 5, 8, 9, 22 |
| 8 | 6.45 ddd (1.1, 10.9, 15.1) | 126.6, CH | 7, 9 | 6, 7, 10 |
| 9 | 5.66 dd (8.5, 15.1) | 136.3, CH | 8, 10 | 7, 10, 11, 23 |
| 10 | 2.42 h (7.6) | 41.7, CH | 9, 11, 23 | 8, 9, 11, 12, 23 |
| 11 | 3.21 m | 71.7, CH | 10, 12 | 9 |
| 11-OH | 1.74 m |  |  | 9, 11 |
| 12 | 2.85 dd (2.3, 4.6) | 58.8, CH | 11[c] | 11 |

TABLE 5-continued

NMR data (1H 500 MHz, 13C 100 MHz, C6D6) for epoxide 2

2

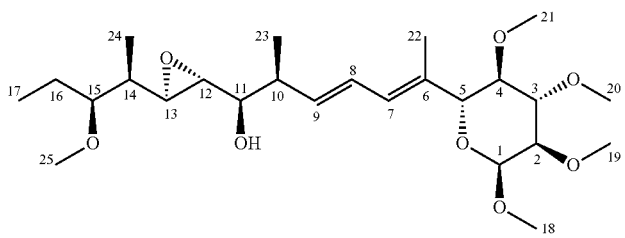

| No. | $\delta_H$ (J in Hz) | $\delta$C, type | gCOSY | HMBC |
|---|---|---|---|---|
| 13 | 2.89 dd (2.3, 6.8) | 57.7, CH | 14[c] | 12, 24 |
| 14 | 1.55 dt (4.3, 6.9) | 38.7, CH | 13, 15, 24 | 13, 24 |
| 15 | 2.82 td (4.8, 7.4) | 83.5, CH | 14, 16 | 13, 19, 24, 25 |
| 16[a] | 1.48 qd (7.3, 14.6) | 23.5, $CH_2$ | 15, 16b, 19 | 14, 15, 19 |
| 16[b] | 1.36 m | | 15, 16a, 19 | 15, 19 |
| 19 | 0.84 t (7.4) | 9.6, $CH_3$ | 16a, 16b | 15, 16 |
| 18[a] | 3.15 s | 54.6, $CH_3$ | | 1 |
| 19[a] | 3.26 s | 57.2, $CH_3$ | | 2 |
| 20[a] | 3.62 s | 60.6, $CH_3$ | | 3 |
| 21[a] | 3.36 s | 59.7, $CH_3$ | | 4 |
| 22 | 1.85 d (1.3) | 12.4, $CH_3$ | 7 | 5, 6, 7 |
| 23 | 1.14 d (6.9) | 16.2, $CH_3$ | 10 | 9, 10, 11 |
| 24 | 1.00 d (6.8) | 10.4, $CH_3$ | 14 | 13, 14, 15 |
| 25[b] | 3.11 s | 56.7, $CH_3$ | | 15 |

[a]Protons at carbons at 18, 19, 20 and 21 were assigned by $^1$H, $^{13}$C HMBC data.
[b]Protons at carbons 2 and 4 were assigned by $^1$H, $^{13}$C HMBC data.
[c]The gCOSY peak for 12, 13 was not identified due to the proximity of protons at C12 and C13.

CONCLUSION

We describe herein the preparation of a carbohydrate-derived spliceosome inhibitor 2 in a total of 22 steps, including 12 longest linear steps from common building blocks (auxiliary 11, D-glucose and propionaldehyde). Complete in vitro and in vivo pharmacological analyses can be conducted, and this improved stability along with its improved solubility in aqueous buffers suggests an important advance in optimization of splice modulators.

Overall, this development offers several medicinal chemical benefits. First, it demonstrates that the pyran or macrolide core commonly associated with the known spliceosome inhibitors can be replaced with materials directly available from monosaccharides in the chiral pool. Second, it provides a means to prepare highly stable materials that lack rapid degradation and/or metabolic instability. Third, the use of a carbohydrate motif offers ready access to explore the SAR contained within the core unit (macrolide of 1a-1b or pyran in 1c, FIG. 1). Here, one can envision application of the described route to provide derivatives with expanded functionality at the anomeric C1 center, stereoisomers at C1-C4 positions, as well as explore the use of deoxygenated materials and alternative ethers at C1-C4. While to date there has been no structural information on the complex of any established splice modulator with the Sf3b component of the spliceosome, the subsequent integration of a rational design could deliver a carbohydrate-derived splice modulator with enhanced binding and reduced pharmacological risk.

REFERENCES

[1] (a) Kotake, Y.; Sagane, K.; Owa, T.; Mimori-Kiyosue, Y.; Shimizu, H.; Uesugi, M.; Ishihama, Y.; Iwata, M.; Mizui Y. Nat. Chem. Biol. 2007, 3, 570; (b) Kaida, D.; Motoyoshi, H.; Tashiro, E.; Nojima, T.; Hagiwara, M.; Ishigami, K.; Watanabe, H.; Kitahara, T.; Yoshida, T.; Nakajima, H.; Tani, T.; Horinouchi, S.; Yoshida M. Nat. Chem. Biol. 2007, 3, 576; (c) Hasegawa, M.; Miura, T.; Kuzuya, K.; Inoue, A.; Won, K. S.; Horinouchi, S.; Yoshida, T.; Kunoh, T.; Koseki, K.; Mino, K.; Sasaki, R.; Yoshida, M.; Mizukami, T. ACS Chem. Biol. 2011, 6, 229; (d) Bonnal, S.; Vigevani, L.; Valcarcel, J. Nat. Rev. Drug Discovery 2012, 11, 847; [2] Seki-Asano, M.; Okazaki, T.; Yamagishi, M.; Sakai, N.; Taka-yama, Y.; Hanada, K.; Morimoto, S.; Takatsuki, A.; Mizoue K. J. Antibiot. (Tokyo). 1994, 47, 1395; [3] (a) Mizui, Y.; Sakai, T.; Iwata, M.; Uenaka, T.; Okamoto, K.; Shimizu, H.; Yamori, T.; Yoshimatsu, K.; Asada, M. J. Antibiot (To-kyo). 2004, 57, 188. (b) Asai, N.; Kotake, Y.; Niijima, J.; Fukuda, Y.; Uehara, T.; Sakai, T. J. Antibiot (Tokyo). 2007, 60, 364; [4] Salient examples of this family also include spliceostatin A, FR901465, meayamycin, and herboxadiene (GEX1A, 1c), as described within the following: (a) Miller-Wideman, M.; Makkar, N.; Tran, M.; Isaac, B.; Biest, N.; Stonard, R. J. Antibiot (Tokyo). 1992, 45, 914. (b) Sakai, Y; Yoshida, T., Ochiai, K.; Uosaki, Y., Saitoh, Y.; Tanaka, F.; Akiyama, T.; Akinaga, S.; Mizukami, T. J. Antibiot (Tokyo). 2002, 55, 855. (c) Liu, X.; Biswas, S.; Berg, M. G.; Antapli, C. M.; Xie, F.; Wang, Q.; Tang, M. C.; Tang, G. L.; Zhang, L.; Dreyfuss, G.; Cheng, Y. Q. J. Nat. Prod. 2013, 76, 685; (d) Nakajima, H.; Sato, B.; Fujita, T.; Takase, S.; Terano, H.; Okuhara M. J. Antibiot (Tokyo). 1996, 49, 1196-203; (e) Meng, F.; McGrath, K. P.; Hoveyda, A. H. Nature 2014, 513, 367; [5] For reports on the clinical trials on E7101, consult: (a) Hong, D. S., Kurzrock, R.; Naing, A.; Wheler, J. J.; Falchook, G. S.; Schiffman, J. S.; Faulkner, N.; Pilat, M. J.; O'Brien, J.; LoRusso, P. Invest. New Drugs. 2014, 32, 436; (b) Dehm, S. M. Clin. Cancer Res. 2013, 19, 6064; [6] The instability of many of the natural product splicing inhibitor, see: (a) Villa, R.; Kashyap, M. K.; Kumar, D.; Kipps, T. J.; Castro, J. E.; La Clair, J. J.; Burkart, M. D. J. Med. Chem. 2013, 56, 6576. (b) Lagisetti, C.; Palacios, G.; Goronga, T.; Freeman, B.; Caufield, W.; Webb, T. R. J. Med. Chem. 2013, 56, 10033; (c) Albert, B. J.; Sivaramakrishnan, A.; Naka, T.; Czaicki, N. L.; Koide, K. J. Am. Chem. Soc. 2007, 129, 2648; [7] Lagisetti, C.; Pourpak, A.; Jiang, Q.; Cui, X.; Goronga, T.; Morris, S. W.; Webb, T. R. J. Med. Chem. 2008, 51, 6220; [8] (a) Convertini, P.; Shen, M.; Potter, P. M.; Palacios, G.; Lagisetti, C.; de la Grange, P.; Horbinski, C.; Fondufe-Mittendorf, Y. N.; Webb, T. R.; Stamm, S. Nucleic Acids Res. 2014, 42, 4947. (b) Webb, T. R.; Joyner, A. S.; Potter, P. M. Drug Discov. Today. 2013, 18, 43. (c) Fan, L.; Lagisetti, C.; Edwards, C. C.; Webb, T. R.; Potter, P. M. ACS Chem. Biol. 2011, 6, 582-9. (d) Lagisetti, C.; Palacios, G.; Goronga, T.; Freeman, B.; Caufield, W.; Webb, T. R. J. Med. Chem. 2013, 56, 10033; [9] Lagisetti, C.; Yermolina, M. V.; Sharma, L. K.; Palacios, G.; Prigaro, B. J.; Webb, T. R. ACS Chem. Biol. 2014, 9, 643; [10] Kanada, R. M.; Itoh, D.; Nagai, M.; Niijima, J.; Asai, N.; Mi-zui, Y.; Abe, S.; Kotake, Y. Angew. Chem. Int. Ed. Engl. 2007, 46, 4350; [11] Arai, K.; Buonamici, S.; Chan, B.; Corson, L.; Endo, A.; Gerard, B.; Hao, M. H.; Karr, C.; Kira, K.; Lee, L.; Liu, X.; Lowe, J. T.; Luo, T.; Marcaurelle, L. A.; Mizui, Y.; Nevalainen, M.; O'Shea, M. W.; Park, E. S.; Perino, S. A.; Prajapati, S.; Shan, M.; Smith, P. G.; Tivitmahaisoon, P.; Wang, J. Y.; Warmuth, M.; Wu, K. M.; Yu, L.; Zhang, H.; Zheng, G. Z.; Keaney, G. F. Org. Lett. 2014, 16, 5560; [12] (a) He, H.; Ratnayake, A. S.; Janso, J. E.; He, M.; Yang, H. Y.; Loganzo, F.; Shor, B.; O'Donnell, C. J.; Koehn, F. E. J. Nat. Prod. 2014, 77, 1864-70. (b) Eustaquio, A. S.; Janso, J. E.; Ratnayake, A. S.; O'Donnell, C. J.; Koehn, F. E. Proc. Natl. Acad. Sci. USA. 2014 111, E3376; [13] (a) Ghosh, A. K.; Veitschegger, A. M.; Sheri, V. R.; Effen-berger, K. A.; Prichard, B. E.; Jurica, M. S. Org. Lett. 2014, 16, 6200. (b) Ghosh, A. K.; Chen, Z. H.; Effenberger, K. A.; Jurica, M. S. J. Org. Chem. 2014, 79, 5697. (c) Ghosh, A. K.; Ma, N.; Effenberger, K. A.; Jurica, M. S. Org. Lett. 2014, 16, 3154-7. (d) Effenberger, K. A.; Anderson, D. D.; Bray, W. M.; Prichard, B. E.; Ma, N.; Adams, M. S.; Ghosh, A. K.; Jurica, M. S. J. Biol. Chem. 2014, 289, 1938; [14] (a) Larrayoz, M.; Blakemore, S. J.; Dobson, R. C.; Blunt, M. D.; Rose-Zerilli, M. J.; Walewska, R.; Duncombe, A.; Oscier, D.; Koide, K.; Forconi, F.; Packham, G.; Yoshida, M.; Cragg, M. S.; Strefford, J. C.; Steele, A. J. Leukemia. 2016, 30, 351. (b) Schreiber, C. A.; Sakuma, T.; Izumiya, Y.; Holditch, S. J.; Hickey, R. D.; Bres-sin, R. K.; Basu, U.; Koide, K.; Asokan, A.; Ikeda, Y. PLoS Pathog. 2015, 11, e1005082. (c) Gao, Y.; Trivedi, S.; Ferris, R. L.; Koide K. Sci. Rep. 2014, 4, 6098. (d) Gao, Y.; Koide, K. ACS Chem. Biol. 2013, 8, 895; (e) Gao, Y.; Vogt, A; Forsyth, C. J.; Koide, K. Chembi-ochem. 2013, 14, 49; (f) Visconte, V.; Rogers, H. J.; Singh, J.; Bar-nard, J.; Bupathi, M.; Traina, F.; McMahon, J.; Makishima, H.; Szpurka, H.; Jankowska, A.; Jerez, A.; Sekeres, M. A.; Sauntharara-jah, Y.; Advani, A. S.; Copelan, E.; Koseki, H.; Isono, K.; Padgett, R. A.; Osman, S.; Koide, K.; O'Keefe, C.; Maciejewski, J. P.; Tiu, R. V. Blood. 2012, 120, 3193; (g) Osman, S.; Albert, B. J.; Wang, Y.; Li, M.; Czaicki, N. L.; Koide K. Chemistry 2011, 19, 895. (h) Albert, B. J.; McPherson, P. A.; O'Brien, K.; Czaicki, N. L.; Destefino, V.; Osman, S.; Li, M.; Day, B. W.; Grabowski, P. J.; Moore, M. J.; Vogt, A.; Koide K. Mol. Cancer Ther. 2009, 8, 2308; [15] (a) Kashyap, M. K.; Kumar, D.; Villa, R.; La Clair, J. J.; Ben-ner, C.; Sasik, R.; Jones, H.; Ghia, E. M.; Rassenti, L. Z.; Kipps, T. J.; Burkart, M. D.; Castro, J. E. Haematologica. 2015, 100, 945. (b) Villa, R.; Mandel, A. L.; Jones, B. D.; La Clair, J. J.; Burkart, M. D. Org. Lett. 2012, 14, 5396; [16] (a) Ernst, B.; Magnani, J. L. Nat. Rev. Drug Discov. 2009, 8, 661. (b) Jensen, K. J.; Brask, J. Biopolymers 2005, 80, 747. (c) Schweizer, F. Angew. Chem. Int. Ed. Engl. 2002, 41, 231; [19] Structures were generated by positioning the atoms within the molecule using the known NOE correlations and minimizing with MM2 energy minimization. Efforts are now underway to complete a detailed solution structure of 1a, 1b and 2; [18] Yan, C.; Hang, J.; Wan, R.; Huang, M.; Wong, C. C.; Shi, Y; Science 2015, 349, 1182; [19] (a) Noel, A.; Delpech, B.; Crich, D. Org. Lett. 2012, 14, 4138. (b) Collins, D. J.; Hibberd, A. I.; Skelton, B. W.; White, A. H. Aust. J. Chem., 1998, 51, 671. (b) Molina P. I.; Bueno M. M.; Galbis, J. A. Carbohydr. Res., 2003, 338, 549. (c) Matwiejuk, M.; Thiem, J. Chem. Comm., 2011, 47, 8379; [20] For instance, the first clinical lead, E-7101, bears a carbamate in place of the C29-C30 acetate, see: Eskens, F. A.; Ramos, F. J.; Burger, H.; O'Brien, J. P.; Piera, A.; de Jonge, M. J.; Mizui, Y.; Wiemer, E. A.; Carreras, M. J.; Baselga, J.; Tabernero J. Clin. Cancer Res. 2013, 19, 6296; [21] (a) Nunes, C. D.; Vaz, P. D.; Felix, V.; Veiros, L. F.; Moniz, T.; Rangel, M.; Realista, S.; Mourato, A. C.; Calhorda, M. J. Dalton Trans. 2015, 44, 5125. (b) Rodriguez-Berrios, R. R.; Torres, G.; Prieto, J. A. Tetrahedron. 2011, 67, 830; [22] Dalisay, D. S.; Molinski, T. F. J. Nat. Prod. 2009, 72, 739; [S1] Noel, A.; Delpech, B.; Crich, D. Org. Lett. 2012, 14, 4138; [S2] Villa, R.; Mandel, A. L.; Jones, B. D.; La Clair, J. J.; Burkart, M. D. Org. Lett. 2012, 14, 5396; [S3] Kashyap, M. K.; Kumar, D.; Villa, R.; La Clair, J. J.; Benner, C.; Sasik, R.; Jones, H.; Ghia, E. M.; Rassenti, L. Z.; Kipps, T. J.; Burkart, M. D.; Castro, J. E. Haematologica. 2015, 100, 945; [S4] Livak, K. J., Schmittgen, T. D. Methods. 2001, 25, 402.

Example 2 Synthesis of Carbohydrate-Derived Splice Modulators Q1-Q10

Compounds in Embodiments Q1-Q10 were synthesized in similar manner as described above (e.g., Schemes 1-3) and confirmed by proton and carbon NMR and high-resolution mass spectrometry.

What is claimed is:

1. A compound with structure of Formula (I):

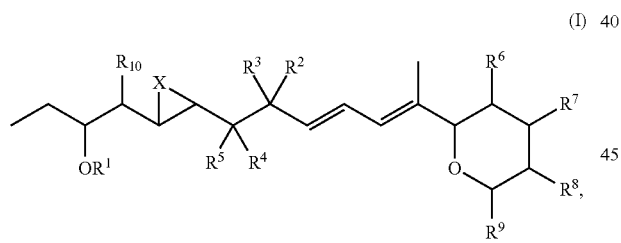

wherein,

X is —O— or —C($R^{26}$)($R^{27}$)—;

$R^{26}$ is hydrogen, halogen, substituted or unsubstituted alkyl, substituted or unsubstituted aryl, —OR$^{28}$, —OC(O)R$^{28}$, —OC(O)OR$^{28}$, or —OC(O)NR$^{28}$R$^{29}$;

$R^{27}$ is hydrogen, halogen, substituted or unsubstituted alkyl, substituted or unsubstituted aryl, —OR$^{30}$, —OC(O)R$^{30}$, —OC(O)OR$^{30}$, or —OC(O)NR$^{30}$R$^{31}$;

$R^1$ is hydrogen, substituted or unsubstituted alkyl, —C(O)R$^{11}$, or —C(O)OR$^{11}$;

$R^2$ is hydrogen, halogen, substituted or unsubstituted alkyl, —OR$^{12}$, —OC(O)R$^{12}$, —OC(O)OR$^{12}$, or —OC(O)NR$^{12}$R$^{13}$;

$R^3$ is hydrogen, halogen, substituted or unsubstituted alkyl, —OR$^{14}$, —OC(O)R$^{14}$, —OC(O)OR$^{14}$, or —OC(O)NR$^{14}$R$^{15}$;

$R^4$ is hydrogen, halogen, substituted or unsubstituted alkyl, —OR$^{16}$, —OC(O)R$^{16}$, —OC(O)OR$^{16}$, or —OC(O)N$^{16}$R$^{17}$;

$R^5$ is hydrogen, halogen, substituted or unsubstituted alkyl, —OR$^{18}$, —OC(O)R$^{18}$, —OC(O)OR$^{18}$, or —OC(O)NR$^{18}$R$^{19}$;

$R^6$ is hydrogen, —OR$^{20}$, —C(O)R$^{20}$, —C(O)OR$^{20}$, —OC(O)R$^{20}$, or —OC(O)OR$^{20}$;

$R^7$ is hydrogen, —OR$^{21}$, —C(O)R$^{21}$, —C(O)OR$^{21}$, —OC(O)R$^{21}$, or —OC(O)OR$^{21}$;

$R^8$ is hydrogen, —OR$^{22}$, —C(O)R$^{22}$, —C(O)OR$^{22}$, —OC(O)R$^{22}$, or —OC(O)OR$^{22}$;

$R^9$ is hydrogen, —OR$^{23}$, —C(O)R$^{23}$, —C(O)OR$^{23}$, —OC(O)R$^{23}$, or —OC(O)OR$^{23}$;

$R^{10}$ is hydrogen, substituted or unsubstituted alkyl, —OR$^{24}$, —OC(O)R$^{24}$, —OC(O)OR$^{24}$, or —OC(O)NR$^{24}$R$^{25}$; and $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{28}$, $R^{29}$, $R^{30}$, and $R^{31}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

2. The compound of claim 1, wherein:

X is —O—;

$R^1$ is hydrogen or unsubstituted $C_1$-$C_4$ alkyl; and $R^{10}$ is hydrogen or unsubstituted $C_1$-$C_4$ alkyl.

3. The compound of claim 2, the compound having a structure of Formula (IIA):

(IIA)

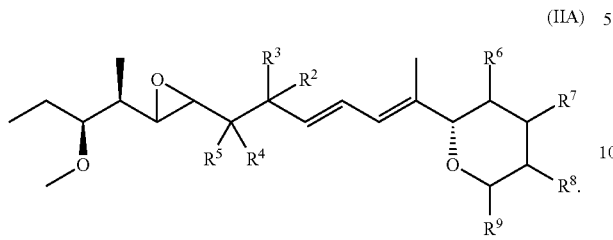

4. The compound of claim 2, the compound having a structure of Formula (IIB):

(IIB)

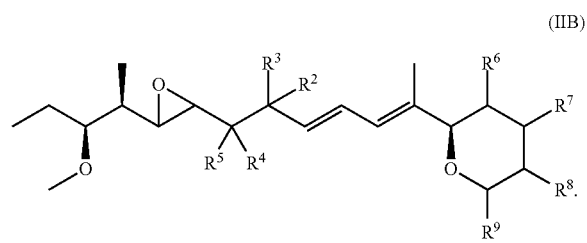

5. The compound of claim 1, wherein:
X is —C($R^{26}$)($R^{27}$)—;
$R^1$ is hydrogen or unsubstituted $C_1$-$C_4$ alkyl; and
$R^{10}$ is hydrogen or unsubstituted $C_1$-$C_4$ alkyl.

6. The compound of claim 5, wherein:
$R^1$ is hydrogen or —$CH_3$; and
$R^{10}$ is hydrogen or —$CH_3$.

7. The compound of claim 6, the compound having a structure of Formula (IIIA):

(IIIA)

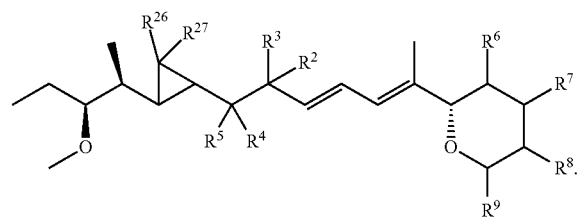

8. The compound of claim 6, the compound having a structure of Formula (IIIB):

(IIIB)

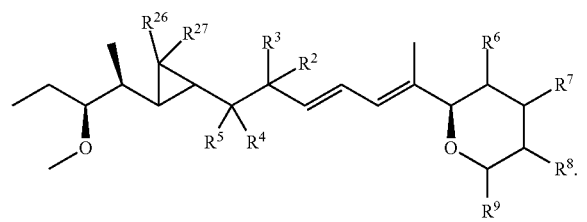

9. The compound of claim 1, wherein:
one of $R^4$ and $R^5$ is hydrogen and the other one of $R^4$ and $R^5$ is —OH,
wherein a chiral carbon where $R^4$ and $R^5$ are attached has (S) or (R) stereochemistry.

10. The compound of claim 9, wherein one of $R^2$ and $R^3$ is hydrogen and the other one of $R^2$ and $R^3$ is —$CH_3$,
wherein a chiral carbon where $R^2$ and $R^3$ are attached has (S) or (R) stereochemistry.

11. The compound of claim 10, wherein:
$R^6$ is hydrogen, —$OR^{20}$ or —C(O)$OR^{20}$;
$R^7$ is hydrogen, —$OR^{21}$ or —C(O)$OR^{21}$;
$R^8$ is hydrogen, —$OR^{22}$ or —C(O)$OR^{22}$;
$R^9$ is hydrogen, —$OR^{23}$ or —C(O)$OR^{23}$; and
$R^{20}$, $R^{21}$, $R^{22}$, and $R^{23}$ are each independently hydrogen or unsubstituted $C_1$-$C_4$ alkyl.

12. The compound of claim 11, wherein $R^{20}$, $R^{21}$, $R^{22}$, and $R^{23}$ are each independently hydrogen or —$CH_3$.

13. The compound of claim 11, wherein:
$R^6$ is —$OCH_3$;
$R^7$ is hydrogen or —$OCH_3$;
$R^8$ is hydrogen or —$OCH_3$; and
$R^9$ is —$OCH_3$.

14. The compound of claim 1, wherein the compound is selected from:

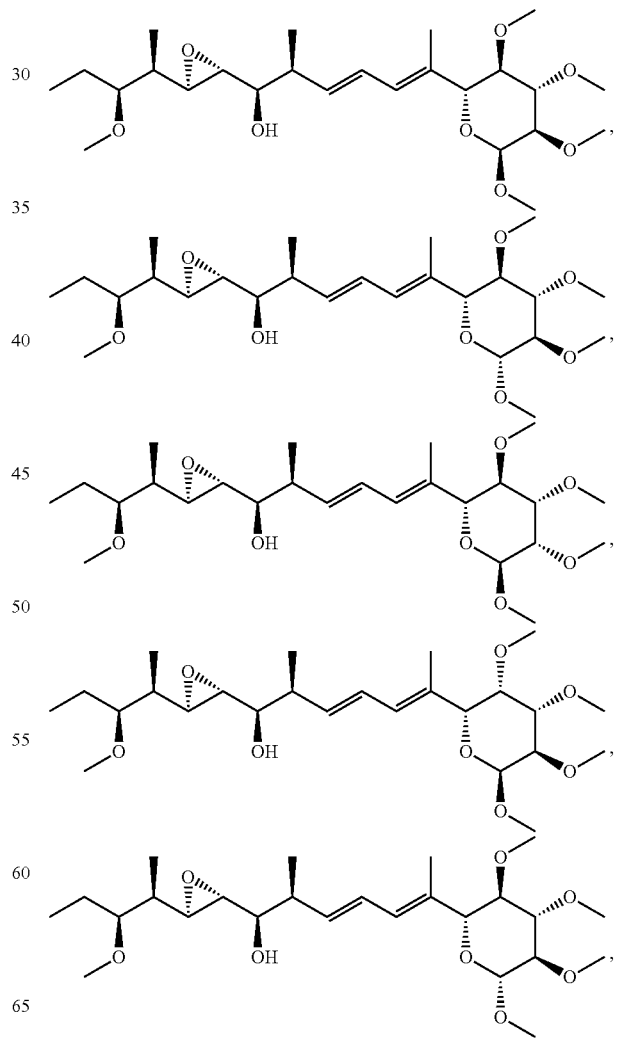

143
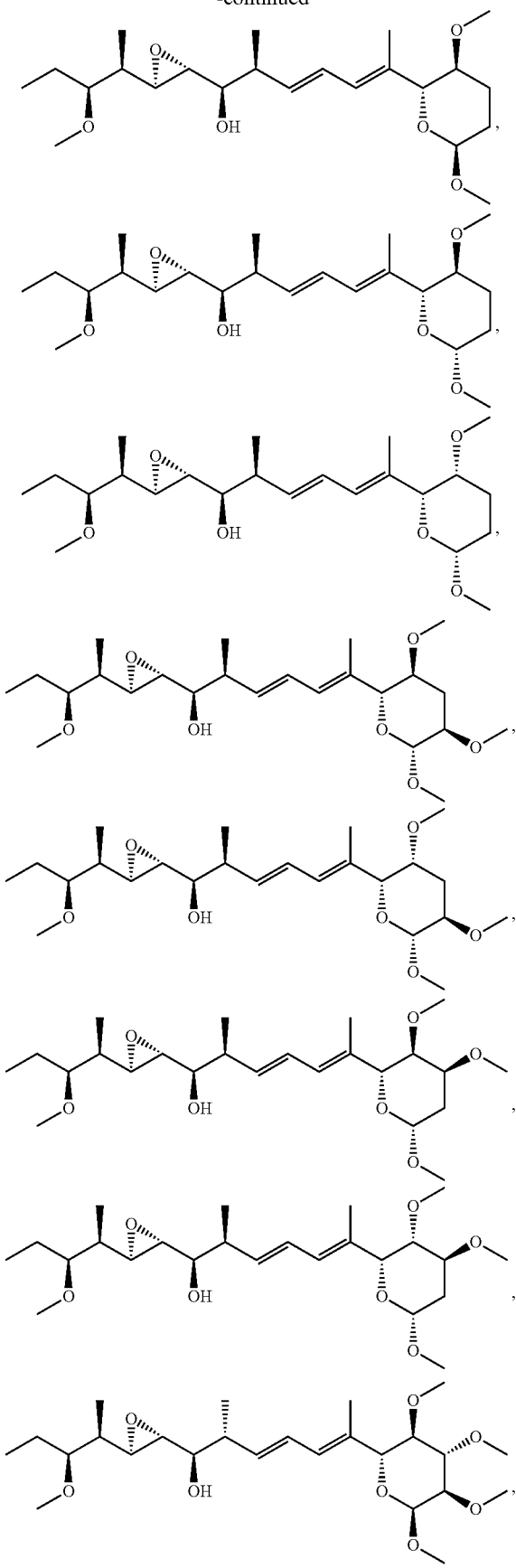
144
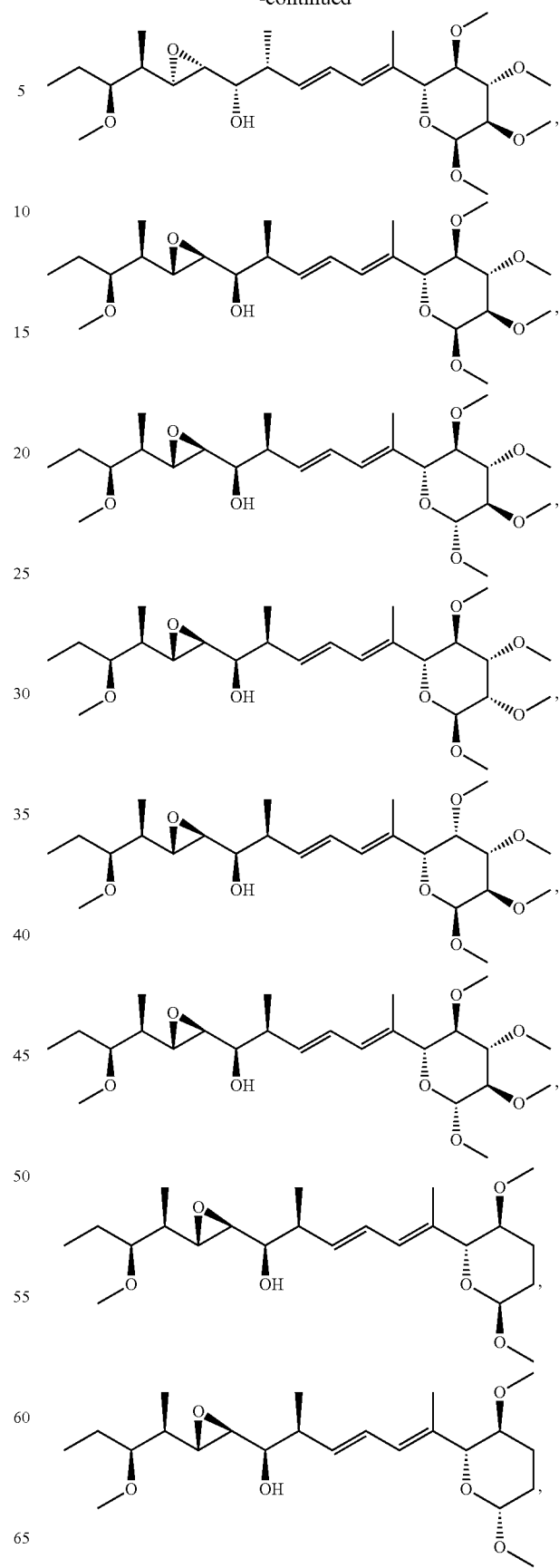

145
-continued
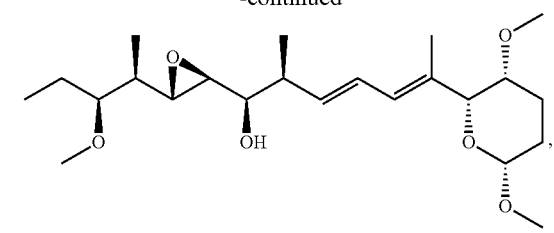,
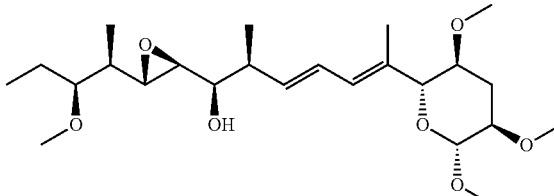,
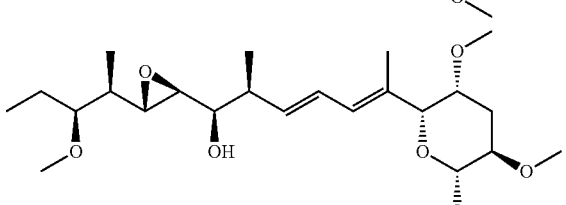,
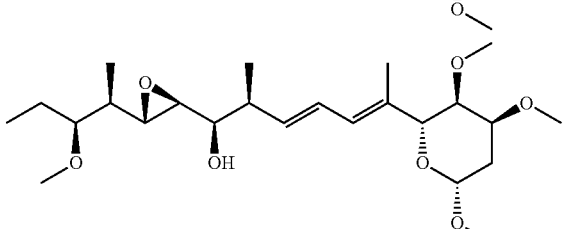,
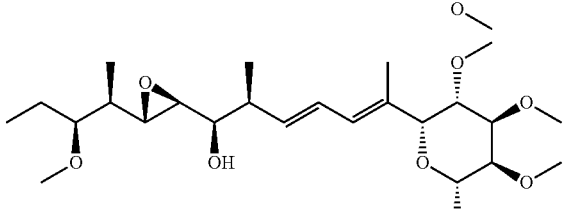,
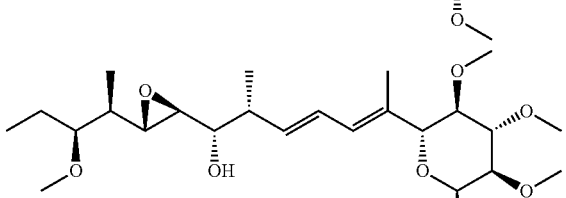,
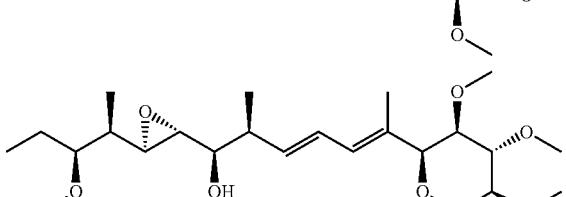,
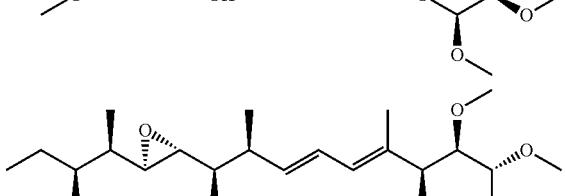,
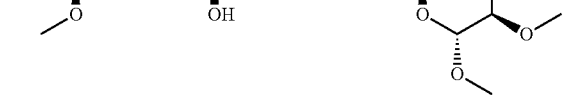,
146
-continued
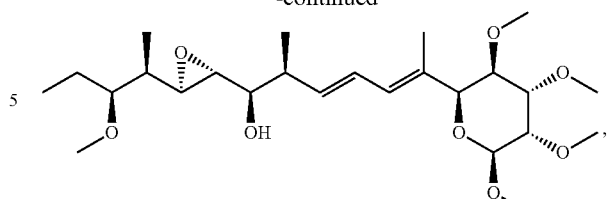;
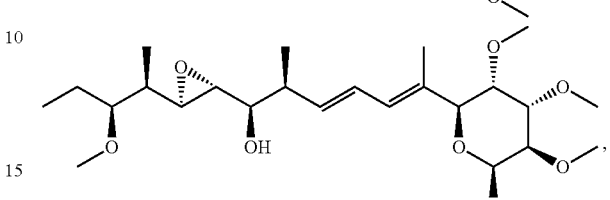,
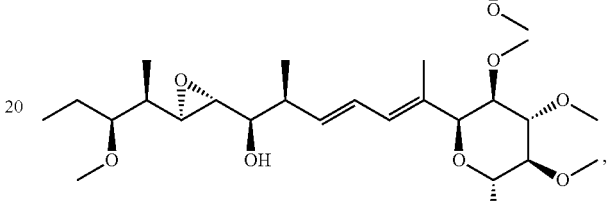,
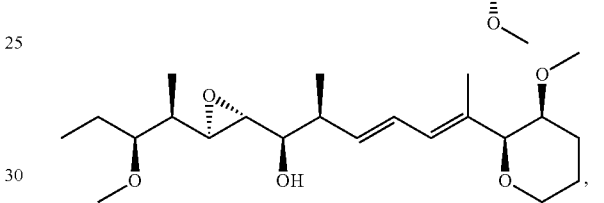,
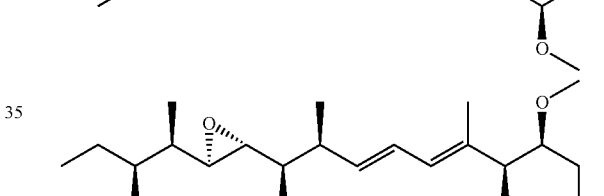,
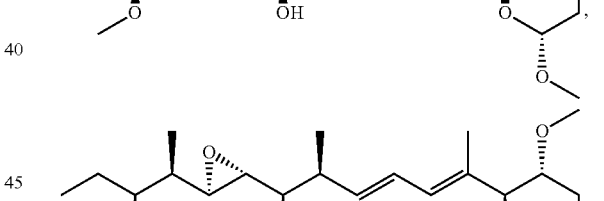,
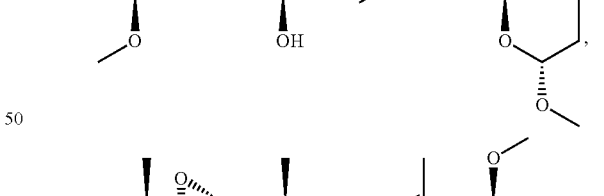,
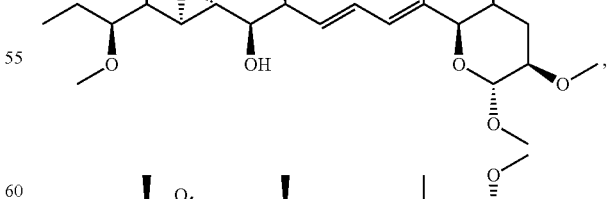,
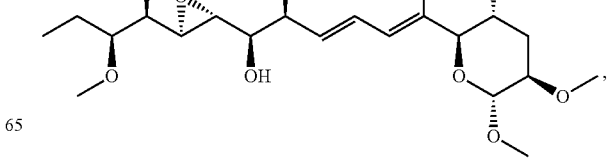, 147
-continued
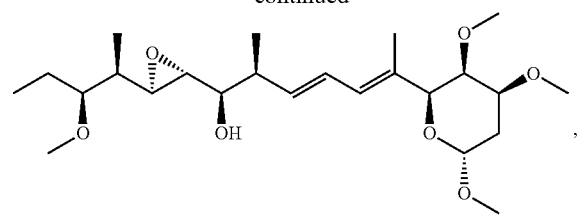,
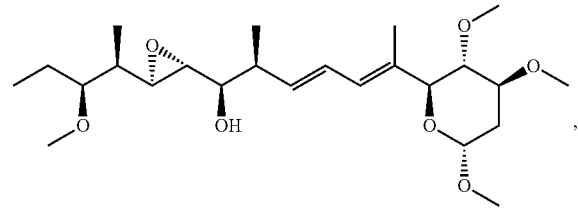,
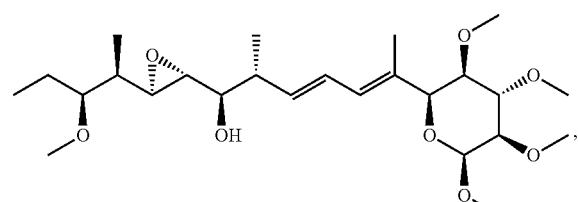,
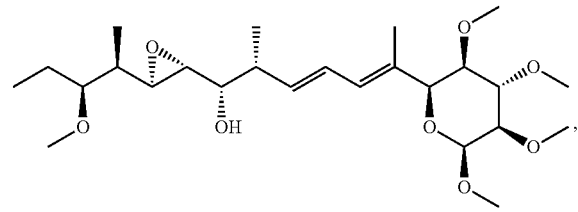,
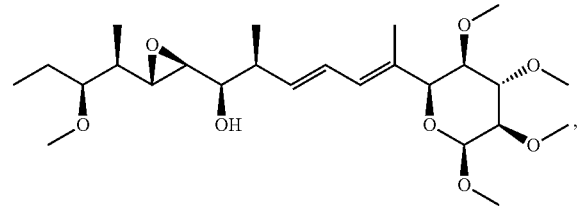,
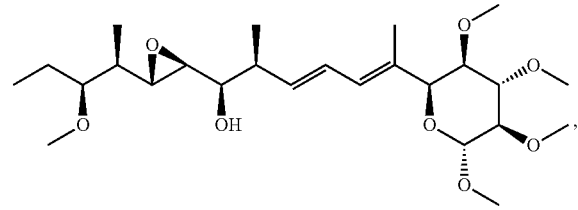,
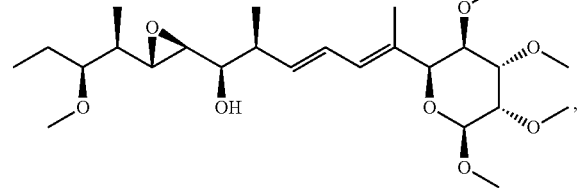,
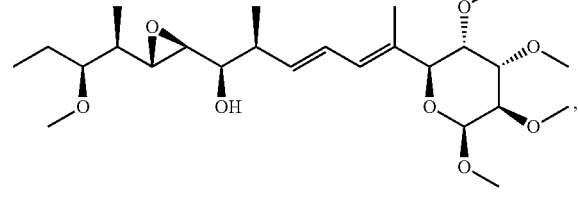,
148
-continued
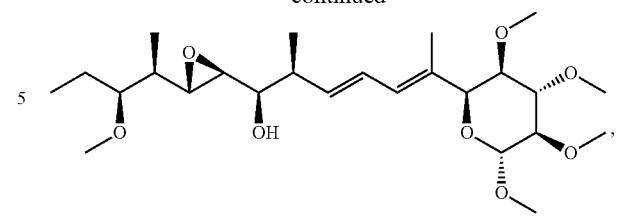,
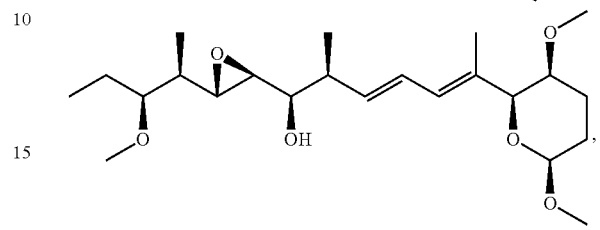,
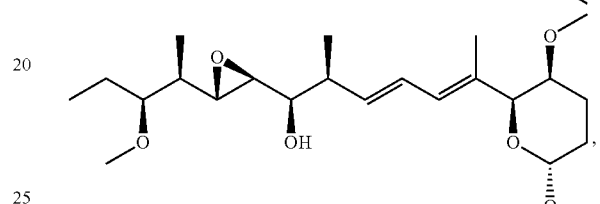,
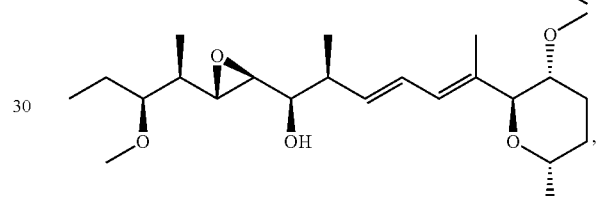,
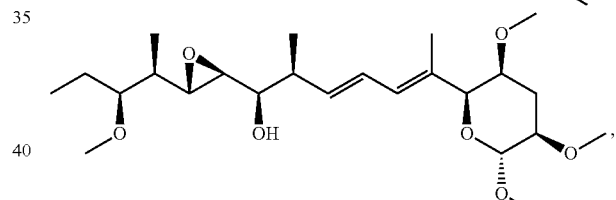,
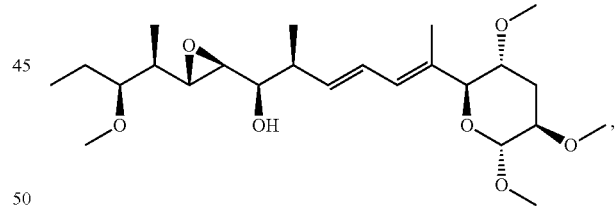,
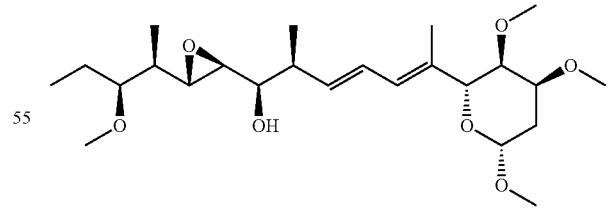,
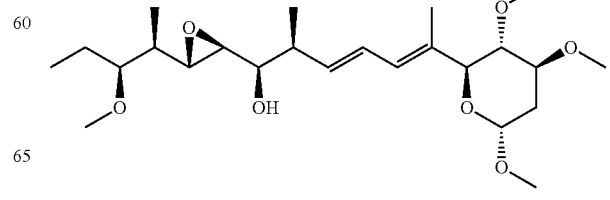,

149
-continued
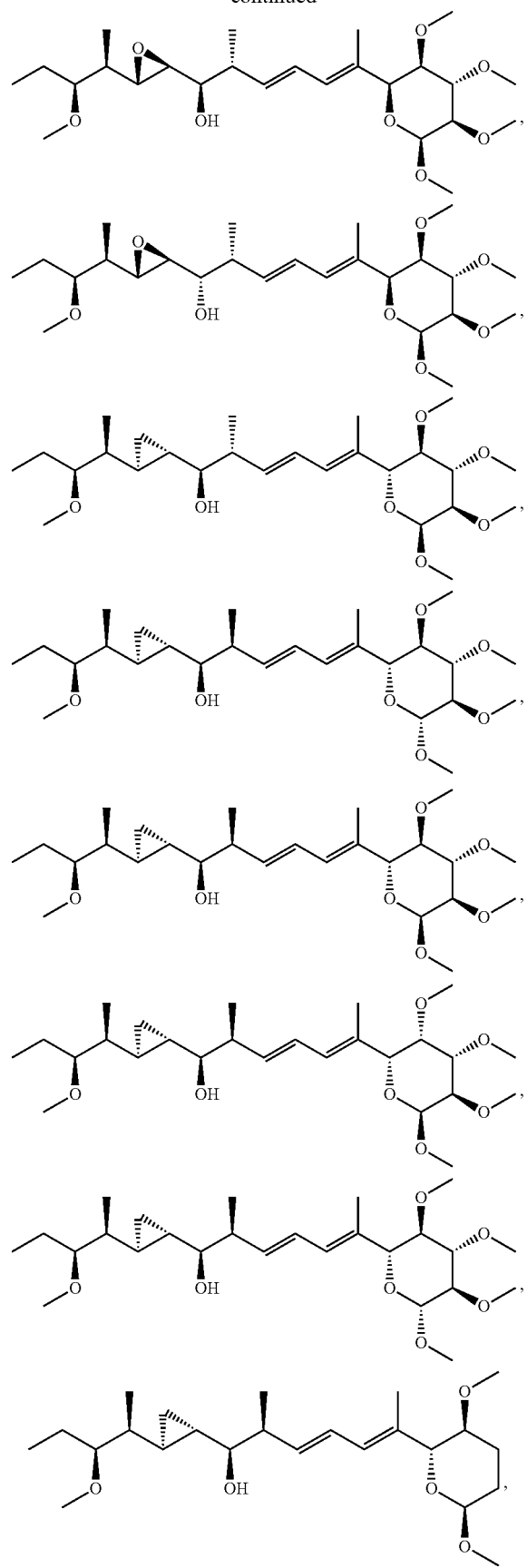
150
-continued
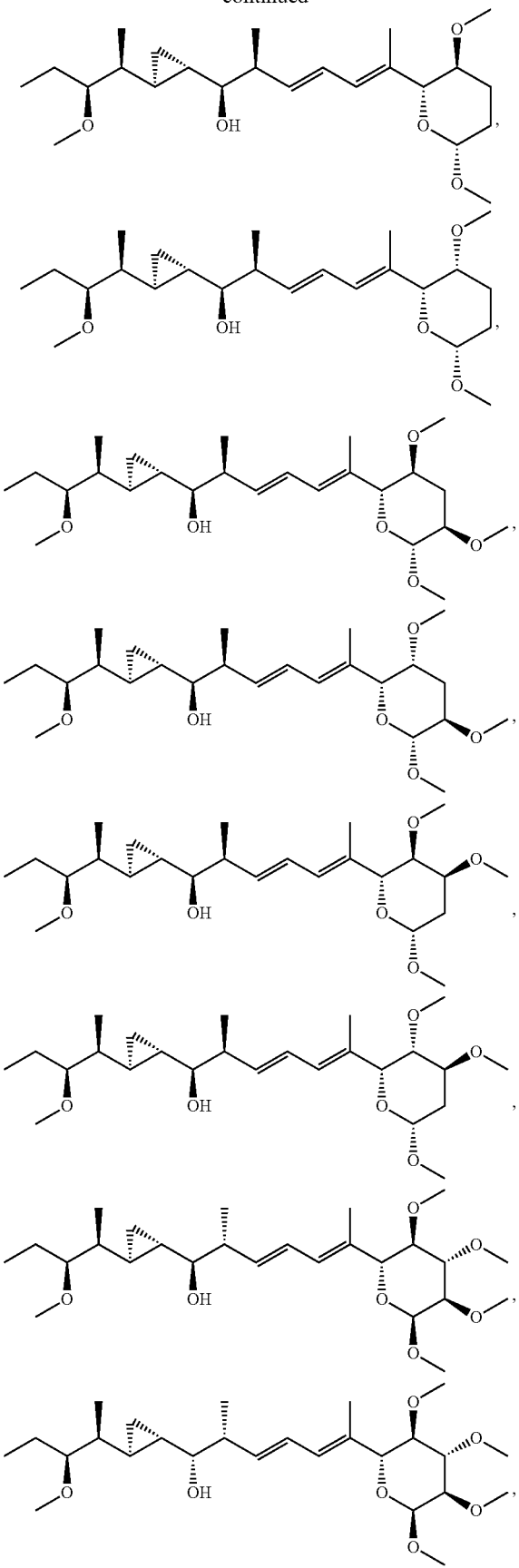

151
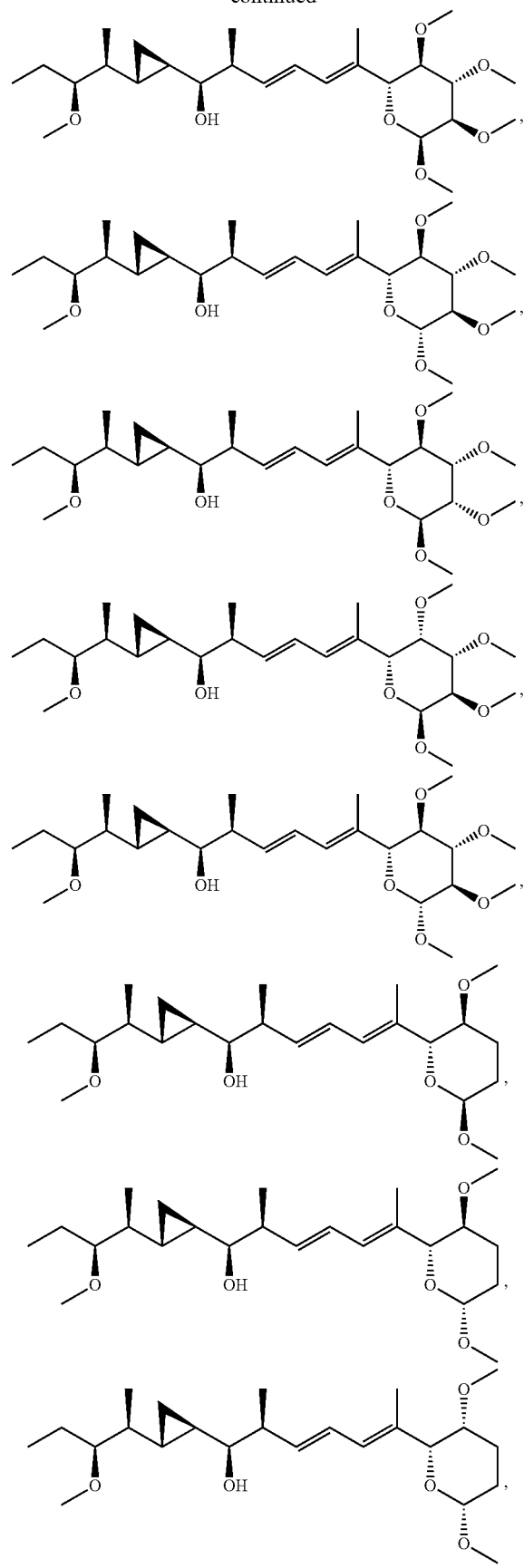
152
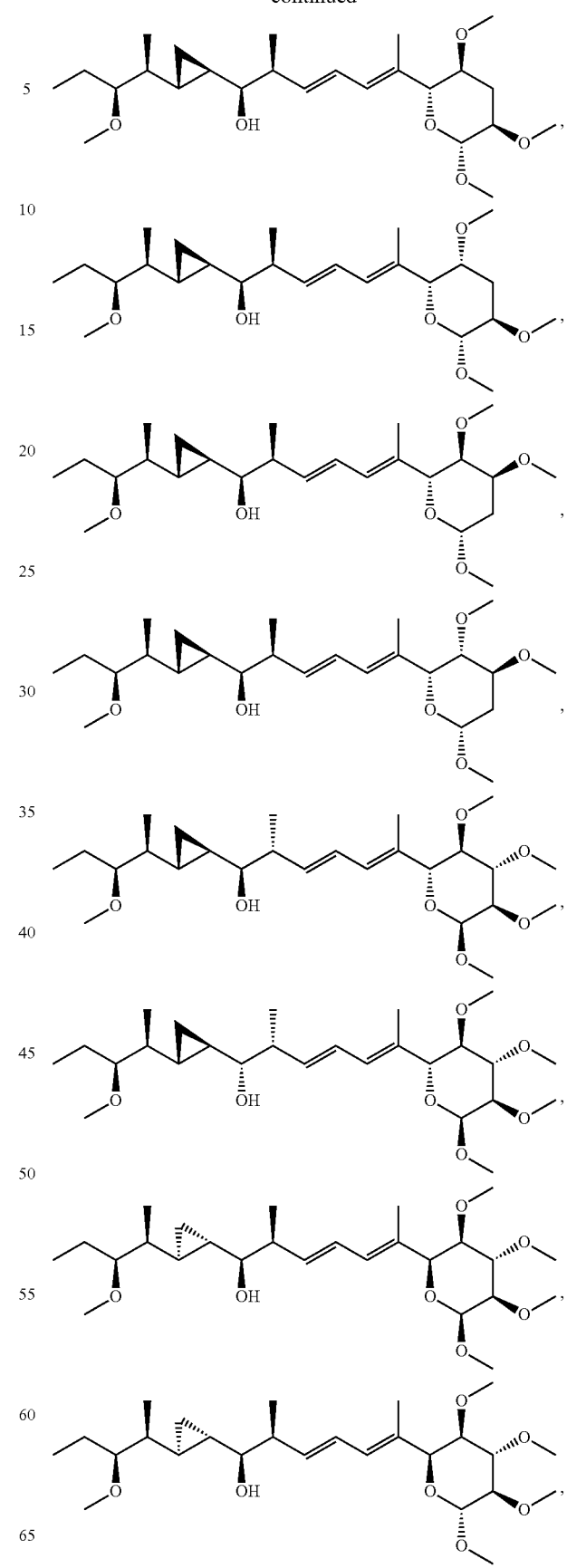

153
-continued
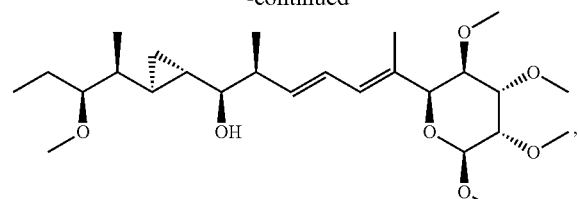
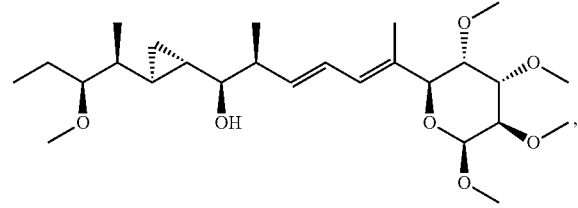
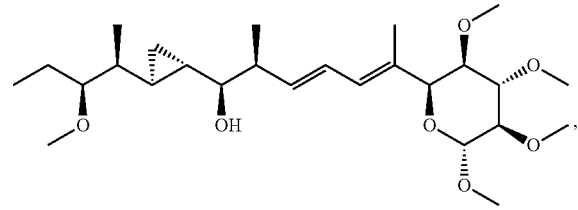
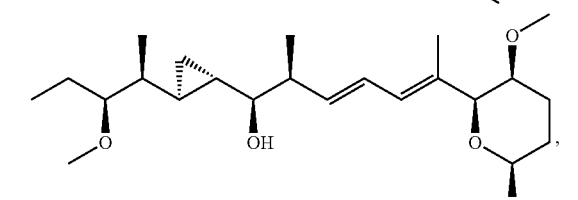
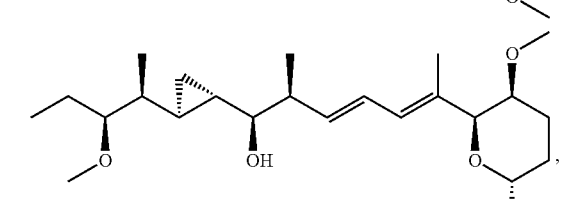
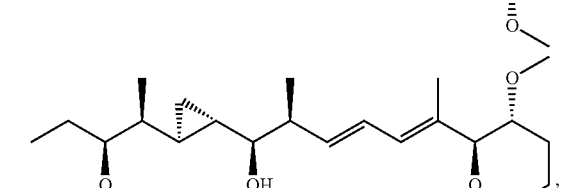
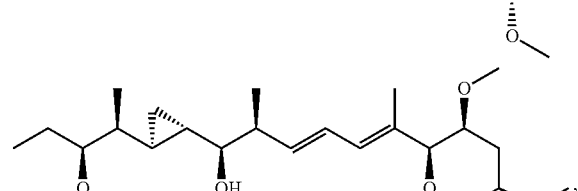
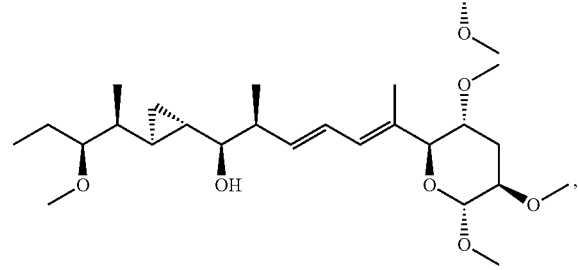
154
-continued
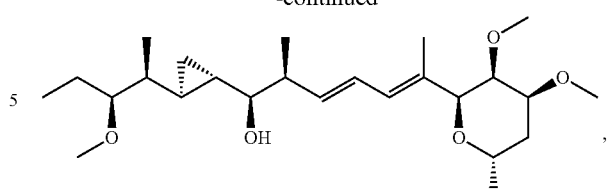
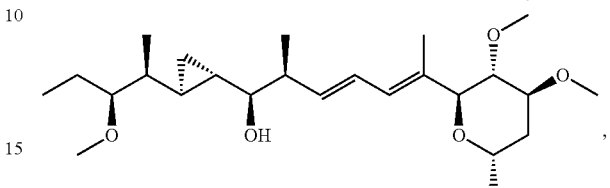
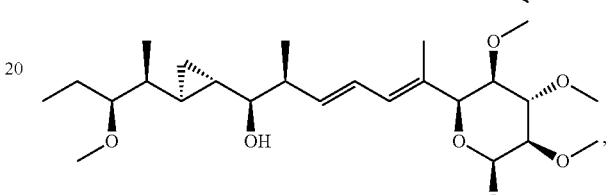
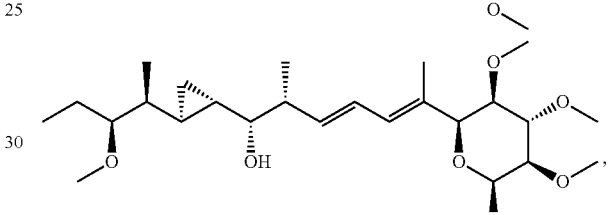
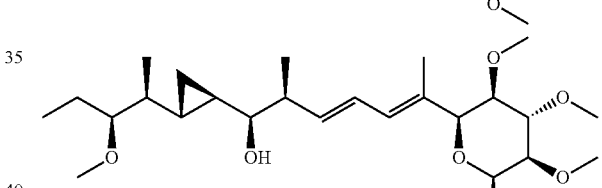
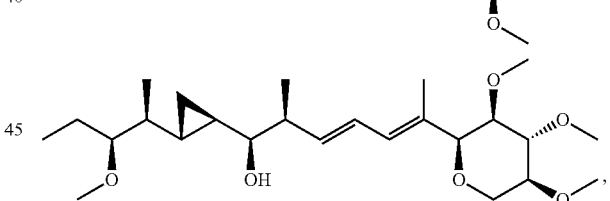
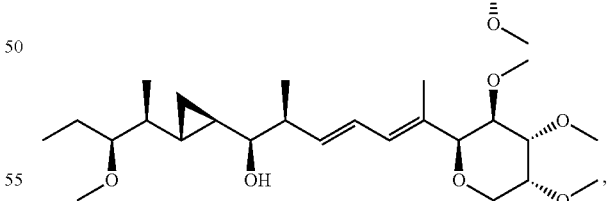
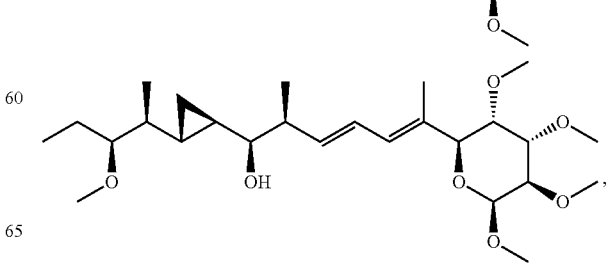

155
-continued
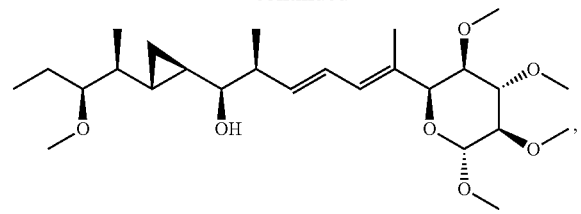
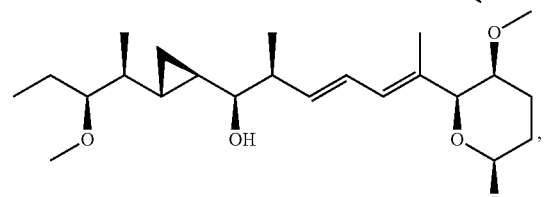
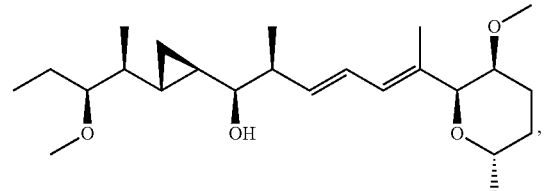
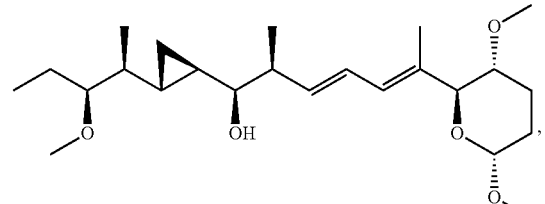
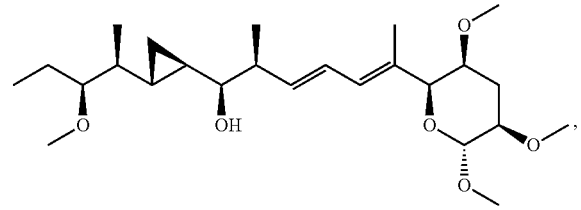
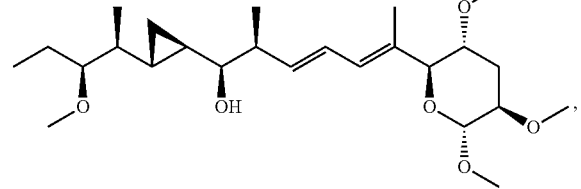
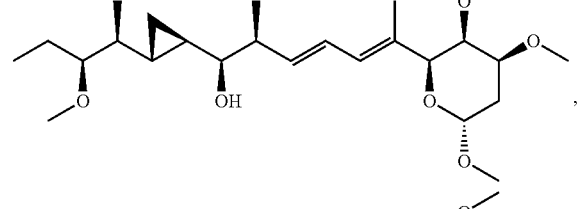
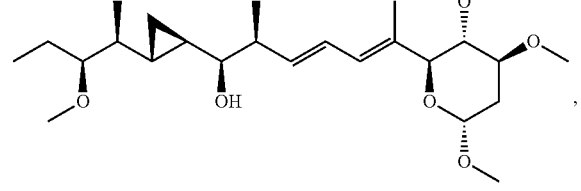
156
-continued
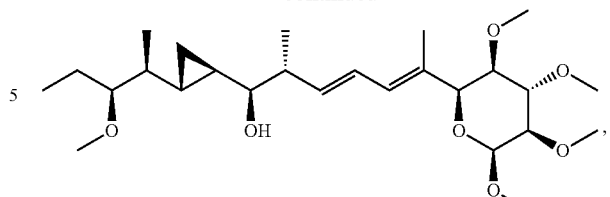
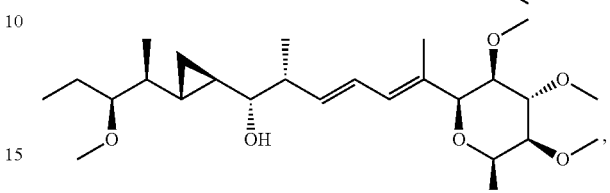
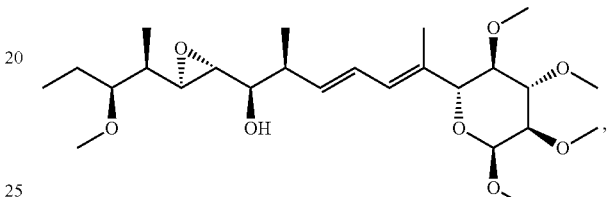
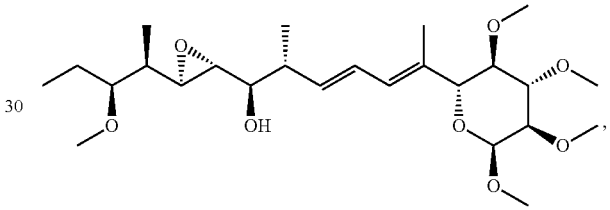
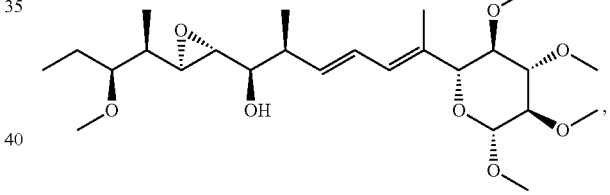
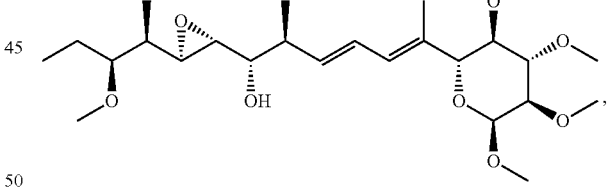
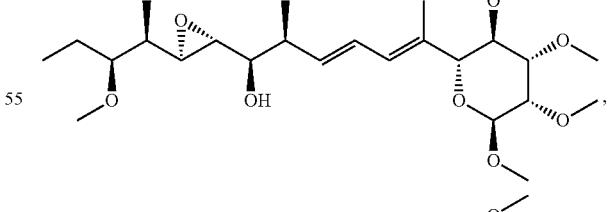
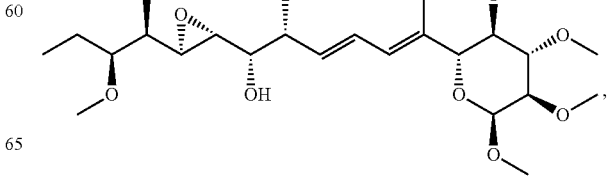

157
-continued

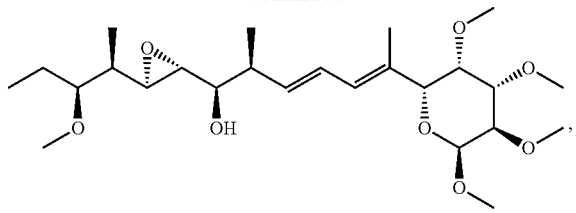

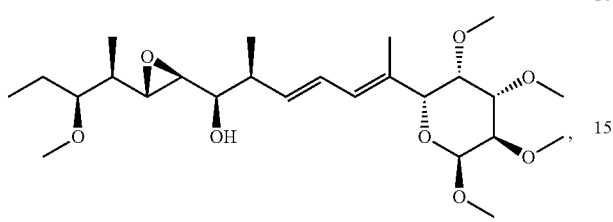

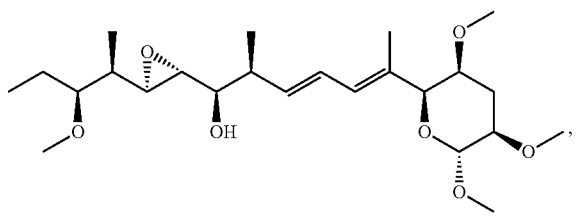

158
-continued

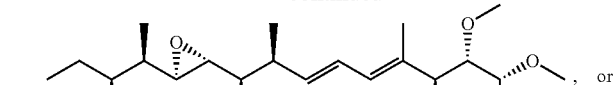

15. A pharmaceutical composition comprising a compound of claim 1 and a pharmaceutically acceptable excipient.

16. A method of treating cancer, the method comprising administering to a subject in need thereof a therapeutically effective amount of a compound of claim 1.

17. The method of claim 16, wherein the cancer is leukemia, lymphoma, metastatic cancer, or bone cancer.

18. The method of claim 16, wherein the cancer is chronic lymphocytic leukemia (CLL).

* * * * *

SEQUENCE LISTING

<160> NUMBER OF SEQ ID NOS: 30

<210> SEQ ID NO 1
<211> LENGTH: 28
<212> TYPE: DNA
<213> ORGANISM: Artificial Sequence -continued

```
<220> FEATURE:
<223> OTHER INFORMATION: Synthetic polynucleotide

<400> SEQUENCE: 1
gaaccaaaat cactttcccc aaggaagg                                      28

<210> SEQ ID NO 2
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 2
aatgaggtcc ccacgtttct cgggtgt                                       27

<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 3
ggcctatgct cagatcgact                                               20

<210> SEQ ID NO 4
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 4
atcagactcg acctccatc                                                19

<210> SEQ ID NO 5
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 5
gagtgggctt tgcaagctct                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6
ctgtcgagac tccaaagctt                                               20

<210> SEQ ID NO 7
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 7
gattggatgc tgctggcaa                                                19
```

```
<210> SEQ ID NO 8
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 8
caccaacatc ccatactgtg                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 9
aggtccgtaa atactgggac                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 10
ctcagtgatg ccaaagggga                                               20

<210> SEQ ID NO 11
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 11
tggatattgt tgccatcatg a                                             21

<210> SEQ ID NO 12
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 12
tggaatcata ttggaacatg t                                             21

<210> SEQ ID NO 13
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 13
cgcttcggca gcacatatac                                               20

<210> SEQ ID NO 14
<211> LENGTH: 19
<212> TYPE: DNA
<213> ORGANISM: Artificial Sequence
<220> FEATURE:
<223> OTHER INFORMATION: Synthetic polynucleotide
```

<400> SEQUENCE: 14
gaatttgcgt gtcatcctt                                                          19

<210> SEQ ID NO 15
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 15
atggctgcgg tcctcgagta t                                                       21

<210> SEQ ID NO 16
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 16
tcagttcctc gttgcgga                                                           18

<210> SEQ ID NO 17
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 17
ggcctgatgg gtcttatcta tgg                                                     23

<210> SEQ ID NO 18
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 18
ttagatggaa gctggctcaa gag                                                     23

<210> SEQ ID NO 19
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 19
ccttattgtg acaacttcat tgag                                                    24

<210> SEQ ID NO 20
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 20
tgaagattta cttaggagca ca                                                      22

<210> SEQ ID NO 21

<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 21
ggtgttccca gagagcagta g                                              21

<210> SEQ ID NO 22
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 22
gctggggcca tgtctgtttt                                                20

<210> SEQ ID NO 23
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 23
tgcttgacac tcagacccca                                                20

<210> SEQ ID NO 24
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 24
aaaatgccag agtgtgactg c                                              21

<210> SEQ ID NO 25
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 25
gtaagaaagt ttacagatga ctt                                            23

<210> SEQ ID NO 26
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 26
agataatcaa catgcttaac aaa                                            23

<210> SEQ ID NO 27
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 27

```
tctccgtcag tcattccct                                           20

<210> SEQ ID NO 28
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 28 tcattccct gtcaaccacg                                           20

<210> SEQ ID NO 29
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 29
tggtcaccag ggctgctt                                            18

<210> SEQ ID NO 30
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 30
agcttcccgt tctcagcctt                                          20
```